US011627742B2

(12) United States Patent
Broglie et al.

(10) Patent No.: US 11,627,742 B2
(45) Date of Patent: Apr. 18, 2023

(54) COMPOSITIONS AND METHODS TO CONTROL INSECT PESTS

(71) Applicant: CORTEVA AGRISCIENCE LLC, Indianapolis, IN (US)

(72) Inventors: Karen E Broglie, Landenberg, PA (US); Kevin Andrew Kriss, Wilmington, DE (US); Albert L Lu, West Des Moines, IA (US); Mani Muthalagi, Hockessin, DE (US); James Kevin Presnail, Minneapolis, MN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

(21) Appl. No.: 16/806,222

(22) Filed: Mar. 2, 2020

(65) Prior Publication Data

US 2020/0196609 A1 Jun. 25, 2020

Related U.S. Application Data

(62) Division of application No. 15/597,207, filed on May 17, 2017, now abandoned, which is a division of application No. 13/791,596, filed on Mar. 8, 2013, now Pat. No. 9,686,995, which is a division of application No. 12/868,994, filed on Aug. 26, 2010, now abandoned.

(60) Provisional application No. 61/330,484, filed on May 3, 2010, provisional application No. 61/237,880, filed on Aug. 28, 2009.

(51) Int. Cl.
| | |
|---|---|
| *C12N 15/82* | (2006.01) |
| *C12N 15/113* | (2010.01) |
| *A01N 63/60* | (2020.01) |
| *A01N 63/00* | (2020.01) |
| *A01N 57/16* | (2006.01) |
| *A01N 65/20* | (2009.01) |
| *A01N 65/44* | (2009.01) |

(52) U.S. Cl.
CPC .............. *A01N 63/60* (2020.01); *A01N 57/16* (2013.01); *A01N 63/00* (2013.01); *A01N 65/20* (2013.01); *A01N 65/44* (2013.01); *C12N 15/113* (2013.01); *C12N 15/8218* (2013.01); *C12N 15/8286* (2013.01); *C12N 2310/11* (2013.01); *C12N 2310/531* (2013.01); *Y02A 40/146* (2018.01)

(58) Field of Classification Search
None
See application file for complete search history.

(56) References Cited

U.S. PATENT DOCUMENTS

| 9,107,417 B2 | 8/2015 | Broglie et al. |
| 9,238,822 B2* | 1/2016 | Baum ................ C12N 15/8286 |
| 2004/0187170 A1 | 9/2004 | Plaetinck et al. |
| 2006/0272049 A1 | 11/2006 | Waterhouse et al. |
| 2007/0050860 A1 | 3/2007 | Andersen et al. |
| 2012/0164205 A1 | 6/2012 | Baum et al. |

FOREIGN PATENT DOCUMENTS

| WO | 2004061087 | 7/2004 |
| WO | 2005110068 A2 | 11/2005 |
| WO | 2007035650 A2 | 3/2007 |

OTHER PUBLICATIONS

Takahashi et al (Biol. Chem., 2002, 383: 1263-1266) (Year: 2002).*
Davy et al (EMBO reports, 2001, 2(9): 821-828) (Year: 2001).*
Baum et al, "Control of coleopteran insect pests through RNA interference," Nature Biotechnology, vol. 25 No. 11, (Nov. 1997), pp. 1322-1326 and 1 page of Supplementary Tables and 15 pages of Supplementary Figures.
International Search Report for International Application No. PCT/US2010/046762 completed Nov. 9, 2010.
International Search Report for International Application No. PCT/US2010/046762 completed Jan. 20, 2011.
Written Opinion for International Application No. PCT/US2008/087954 completed Jan. 20, 2011.
Yan et al., Plant Physiology, vol. 141: 1508-1518 (2006).
Thomas et al., The Plant Journal, vol. 25 (4): 417-425 (2001).
Bird et al, Biotechnology and Genetic Engineering Reviews, vol. 9: 207-227 (1991).
Takahashi etal (Biol. Chem., 383: 1263-1266).
Davy et al. (EMBO reports, 2001, 2(9): 821-828).

* cited by examiner

*Primary Examiner* — Jason Deveau Rosen

(57) ABSTRACT

Methods and compositions are provided which employ a silencing element that, when ingested by a pest, such as a Coleopteran plant pest or a *Diabarotica* plant pest, decrease the expression of a target sequence in the pest. In specific embodiments, the decrease in expression of the target sequence controls the pest and thereby the methods and compositions are capable of limiting damage to a plant. The present invention provides various target polynucleotides set forth in any one of SEQ ID NOS: 1-236 or active variants and fragments thereof, wherein a decrease in expression of one or more the sequences in the target pest controls the pest (i.e., has insecticidal activity). Further provided are silencing elements which when ingested by the pest decrease the level of the target polypeptide and thereby control the pest. In specific embodiment, the pest is *D. virgifera virgifera, D. barberi, D. speciosa,* or *D. undecimpunctata howardi*. Plants, plant part, bacteria and other host cells comprising the silencing elements or an active variant or fragment thereof of the invention are also provided.

28 Claims, 2 Drawing Sheets

Specification includes a Sequence Listing.

T0 Test of first RNAi candidates in SFX germplasm

Missing Rows 440

Means Comparisons

Comparisons for all pairs using Tukey-Kramer HSD

| Construct | Gene | # events | Priority | Grouping | mean |
|---|---|---|---|---|---|
| Control | | 6 | | A | 2.16 |
| PHP41121 | SEQ ID NO: 8 RIBOSOMAL PROTEIN S10E | 1 | 17 | AB | 1 |
| PHP41134 | SEQ ID NO: 26 RIBOSOMAL PROTEIN | 7 | 29 | B | 0.89 |
| PHP41127 | SEQ ID NO: 17 27kD PROTEINASE | 22 | 44 | B | 0.81 |
| PHP41130 | SEQ ID NO: 28 Nucleoplasmin-like | 4 | 12 | B | 0.75 |
| PHP41118 | SEQ ID NO: 10 NO HITS | 8 | 26 | B | 0.72 |

COMPOSITIONS AND METHODS TO CONTROL INSECT PESTS

CROSS-REFERENCE TO RELATED APPLICATIONS

This application is a divisional application of U.S. Non Provisional application Ser. No. 15/597,207, filed on May 17, 2017; which is a divisional application of U.S. Non Provisional Application Ser. No. 13/791,596, filed on Mar. 8, 2013; which is a continuation of U.S. Non Provisional application Ser. No. 12/868,994, filed on Aug. 26, 2010; which claims the benefit of U.S. Provisional Application No. 61/330,484, filed on May 3, 2010 and U.S. Provisional Application No. 61/237,880, filed Aug. 28, 2009, the contents of which are herein incorporated by reference in their entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 3150USDIV2_SEQLIST.txt, a creation date of Aug. 25, 2010 and a size of 306 Kb. The sequence listing filed via EFS-Web is part of the specification and is hereby incorporated in its entirety by reference herein.

FIELD OF THE INVENTION

The present invention relates generally to methods of molecular biology and gene silencing to control pests.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including *Lepidoptera, Diptera, Coleoptera, Hemiptera*, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences. Thus, there is an immediate need for alternative methods to control pests.

BRIEF SUMMARY OF THE INVENTION

Methods and compositions are provided which employ a silencing element that, when ingested by a pest, such as Coleopteran plant pest including a *Diabarotica* plant pest, is capable of decreasing the expression of a target sequence in the pest. In specific embodiments, the decrease in expression of the target sequence controls the pest and thereby the methods and compositions are capable of limiting damage to a plant. The present invention provides various target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or active variants or fragments thereof, wherein a decrease in expression of one or more the sequences in the target pest controls the pest (i.e., has insecticidal activity). Further provided are silencing elements, which when ingested by the pest, decrease the level of expression of one or more of the target polynucleotides. Plants, plant parts, plant cells, bacteria and other host cells comprising the silencing elements or an active variant or fragment thereof are also provided.

In another embodiment, a method for controlling a pest, such as a Coleopteran plant pest or a *Diabarotica* plant pest, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part a silencing element of the invention. When the plant expressing the silencing element is ingested by the pest, the level of the target sequence is decreased and the pest is controlled.

DETAILED DESCRIPTION OF THE INVENTION

Figure 1:
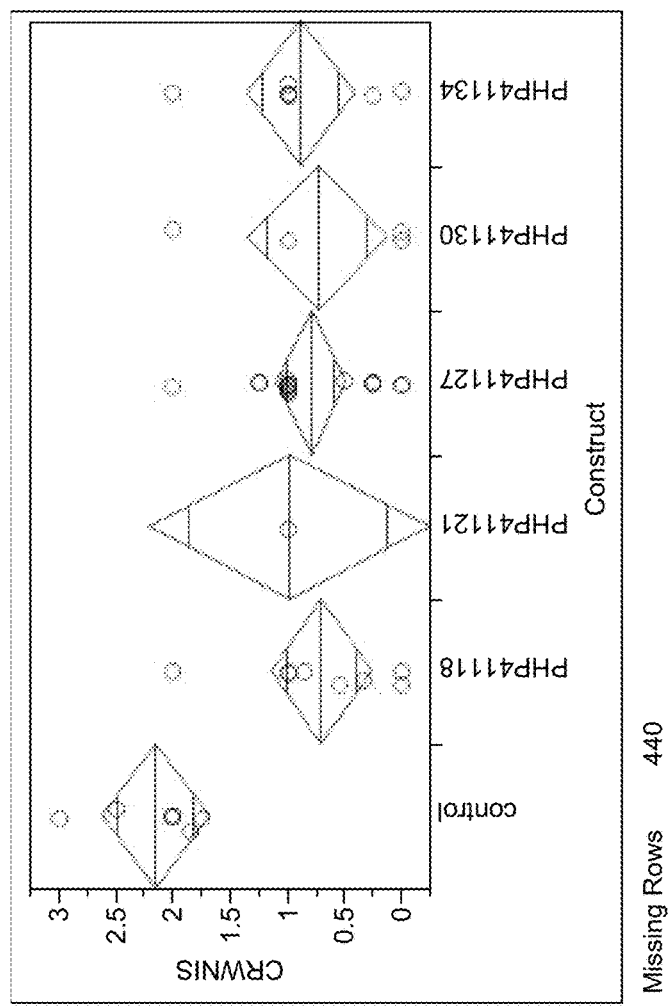
FIG. 1 shows a corn rootworm whole plant assay. The data demonstrates that expression of SEQ ID NO: 8 (clone idv1c.pk001.e9.f); SEQ ID NO: 26 (clone idv1c.pk003.p13.f); SEQ ID NO:17 (clone idv1c.pk003.f9.f); SEQ ID NO:28 (clone idv1c.pk004.d17.p); and SEQ ID NO:10 (clone idv1c.pk001.n1.f) as a hairpin in a maize plant produces a maize plant, which when ingested by corn root worm, has insecticidal activity. CRWNIS refers to corn root worm nodal injury score.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Frequently, RNAi discovery methods rely on evaluation of known classes of sensitive genes (transcription factors, housekeeping genes etc.). In contrast, the target polynucleotide set forth herein were identified based solely on high throughput screens of all singletons and representatives of all gene clusters from a cDNA library of neonate western corn rootworms. This screen allowed for the discovery of many novel sequences, many of which have extremely low or no homology to known sequences. This method provided the advantage of having no built in bias to genes that are frequently highly conserved across taxa. As a result, many novel targets for RNAi as well as known genes not previously shown to be sensitive to RNAi have been identified.

As such, methods and compositions are provided which employ a silencing element that, when ingested by a pest, such as a Coleopteran plant pest or a *Diabrotica* plant pest, is capable of decreasing the expression of a target sequence in the pest. In specific embodiments, the decrease in expression of the target sequence controls the pest and thereby the methods and compositions are capable of limiting damage to a plant or plant part. The present invention provides target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, or 236, or active variants and fragments thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. Silencing elements designed in view of these target polynucleotides are provided which, when ingested by the pest, decrease the expression of one or more of the target sequences and thereby controls the pest (i.e., has insecticidal activity).

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to control pests, particularly, Coleopteran plant pest or a *Diabrotica* plant pest.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also Baum et al. (2007) *Nature Biotech* 11:1322-1326 and WO 2007/035650 which proved both whole plant feeding assays and corn root feeding assays. Both of these references are herein incorporated by reference in their entirety. See, also the examples below.

The invention is drawn to compositions and methods for protecting plants from a plant pest, such as Coleopteran plant pests or *Diabarotica* plant pests or inducing resistance in a plant to a plant pest, such as Coleopteran plant pests or *Diabarotica* plant pests. As used herein "Coleopteran plant pest" is used to refer to any member of the Coleoptera order.

As used herein, the term "*Diabarotica* plant pest" is used to refer to any member of the *Diabrotica* genus. Accordingly, the compositions and methods are also useful in protecting plants against any *Diabarotica* plant pest including, for example, *Diabrotica adelpha; Diabrotica amecameca; Diabrotica balteata; Diabrotica barberi; Diabrotica biannularis; Diabrotica cristata; Diabrotica decempunctata; Diabrotica dissimilis; Diabrotica lemniscata; Diabrotica limitata* (including, for example, *Diabrotica limitata quindecimpuncata); Diabrotica longicornis; Diabrotica nummularis; Diabrotica porracea; Diabrotica scutellata; Diabrotica sexmaculata; Diabrotica speciosa* (including, for example, *Diabrotica speciosa* speciosa); *Diabrotica tibialis; Diabrotica undecimpunctata* (including, for example, *Diabrotica undecimpunctata duodecimnotata; Diabrotica* undecimpunctata howardi (spotted cucumber beetle); *Diabrotica undecimpunctata undecimpunctata* (western spotted cucumber beetle)); *Diabrotica virgifera* (including, for example, *Diabrotica virgifera virgifera* (western corn rootworm) and *Diabrotica virgifera zeae* (Mexican corn rootworm)); *Diabrotica viridula; Diabrotica wartensis; Diabrotica* sp. JJG335; *Diabrotica* sp. JJG336; *Diabrotica* sp. JJG341; *Diabrotica* sp. JJG356; *Diabrotica* sp. JJG362; and, *Diabrotica* sp. JJG365.

In specific embodiments, the *Diabarotica* plant pest comprises *D. virgifera virgifera, D. barberi, D. speciosa* or *D. undecimpunctata howardi*.

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance, the target sequence can be essential for growth and development. While the target sequence can be expressed in any tissue of the pest, in specific embodiments, the sequences targeted for suppression in the pest are expressed in cells of the gut tissue of the pest, cells in the midgut of the pest, and cells lining the gut lumen or the midgut. Such target sequences can be involved in, for example, gut cell metabolism, growth or differentiation. Non-limiting examples of target sequences of the invention include a polynucleotide set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, or 236 or variants and fragments thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. As exemplified elsewhere herein, decreasing the level of expression of one or more of these target sequences in a Coleopteran plant pest or a *Diabarotica* plant pest controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprise one or more silencing elements to the same or different target polynucleotides. The silencing element can be produced in vivo (i.e., in a host cell such as a plant or microorganism) or in vitro.

In specific embodiments, the target sequence is not endogenous to the plant. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a siRNA, a amiRNA, a miRNA, or a hairpin suppression element. Non-limiting examples of silencing elements that can be employed to decrease expression of these target Coleopteran plant pest sequences or *Diabarotica* plant pest sequences comprise fragments and variants of the sense or antisense sequence or consists of the sense or antisense sequence of the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or a biologically active variant or fragment thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. The silencing element can further comprise additional sequences that advantageously effect transcription and/or the stability of a resulting transcript. For example, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end. As discussed in further detail below, enhancer suppressor elements can also be employed in conjunction with the silencing elements disclosed herein.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 16, 17, 18, 19, 20, 22, 25, 30, 50, 100, 150, 200, 250, 300, 350, 400, 450, 500, 600, 700, 900, 1000, 1100, 1200, 1300 nucleotides or longer of the target polynucleotides set forth in any of SEQ ID NO:1-106. In other embodiments, the sense suppression element can be, for example, about 15-25, 19-35, 19-50, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides set forth in any of SEQ ID NO:1-236.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 16, 17, 18, 19, 20, 22, 25, 50, 100, 200, 300, 400, 450 nucleotides or greater of the sequence set forth in any of SEQ ID NO:1-236 may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference.

iii. Double Stranded RNA Suppression Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional dsRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In another embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 19, 18, 17, 16, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 475, 450, 425, 400, 375, 350, 325, 300, 250, 225, 200, 175, 150, 125, 100, 75, 60, 50, 40, 30, 25, 22, 20, 19, 18, 17, 16, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 10 to about 20 nucleotides, about 19 to about 50 nucleotides, about 50 nucleotides to about 100 nucleotides, about 100 nucleotides to about 150 nucleotides, about 100 nucleotides to about 300 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides, about 600 nt, about 700 nt, about 800 nt, about 900 nt, about 1000 nt, about 1100 nt, about 1200 nt, 1300 nt, 1400 nt, 1500 nt, 1600 nt, 1700 nt, 1800 nt, 1900 nt, 2000 nt or longer. In other embodiments, the length of the first and/or the third segment comprises at least 10-19 nucleotides, 10-20 nucleotides; 19-35 nucleotides, 20-35 nucleotides; 30-45 nucleotides; 40-50 nucleotides; 50-100 nucleotides; 100-300 nucleotides; about 500-700 nucleotides; about 700-900 nucleotides; about 900-1100 nucleotides; about 1300-1500 nucleotides; about 1500-1700 nucleotides; about 1700-1900 nucleotides; about 1900-2100 nucleotides; about 2100-2300 nucleotides; or about 2300-2500 nucleotides. See, for example, International Publication No. WO 0200904. In non-limiting examples the first stem of the hairpin comprises nucleotides 1-380 of SEQ ID NO: 45; nucleotides 1-266 of SEQ ID NO:50; nucleotides 1-675 of SEQ ID NO:37; or nucleotides 1-132 of SEQ ID NO: 40 or active variants and fragments thereof. In specific embodiments, the first and the third segment comprise at least 20 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 19-35 nucleotides, about 20-35 nucleotides, about 25-50 nucleotides, about 19 to 75 nucleotides, about 20 to 75 nucleotides, about 40-90 nucleotides about 15-100 nucleotides 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides or longer. In other embodiments, the length of the first and/or the third segment comprises at least 10-20 nucleotides, at least 10-19 nucleotides, 20-35 nucleotides, 30-45 nucleotides, 40-50 nucleotides, 50-100 nucleotides, or about 100-300 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments, a domain of the silencing element shares sufficient homology to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J* 19(19):5194-5201.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). miRNAs are regulatory agents comprising about 19 ribonucleotides which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

When expressing an miRNA, it is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA is present in a duplex, the two strands being referred to as the miRNA (the strand that will eventually basepair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18:2237-2242 and Guo et al. (2005) *Plant Cell* 17:1376-1386).

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, US Application Publication 2007-0130653, entitled "Methods and Compositions for Gene Silencing", herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 19 nucleotides, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide employed in the invention. Alternatively, fragments of a nucleotide sequence may range from 1-50, 25-75, 75-125, 50-100, 125-175, 175-225, 100-150, 100-300, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NO: 1-236. Methods to assay for the activity of a desired silencing element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as a silencing element will retain the ability to reduce expression of the target polynucleotide and, in some embodiments, thereby control a pest of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity." (a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A method is further provided for identifying a silencing element from the target polynucleotides set froth in SEQ ID NO:1-236. Such methods comprise obtaining a candidate fragment of any one of SEQ ID NO:1-236 which is of sufficient length to act as a silencing element and thereby reduce the expression of the target polynucleotide and/or control a desired pest; expressing said candidate polynucleotide fragment in an appropriate expression cassette to produce a candidate silencing element and determining is said candidate polynucleotide fragment has the activity of a silencing element and thereby reduce the expression of the target polynucleotide and/or controls a desired pest. Methods of identifying such candidate fragments based on the desired pathway for suppression are known. For example, various bioinformatics programs can be employed to identify the region of the target polynucleotides that could be exploited to generate a silencing element. See, for example, Elbahir et al. (2001) *Genes and Development* 15:188-200, Schwartz et al. (2003) *Cell* 115:199-208, Khvorova et al. (2003) *Cell* 115:209-216. See also, siRNA at Whitehead (jura.wi.mit.edu/bioc/siRNAext/) which calculates the binding energies for both sense and antisense siRNAs. See, also genscript.com/ssl-bin/app/rnai?op=known; Block-iT™ RNAi designer from Invitrogen and GenScript siRNA Construct Builder.

V. DNA Constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element or in specific embodiments employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. In other embodiment, the double stranded RNA is expressed from a suppression cassette. Such a cassette can comprise two convergent promoters that drive transcription of an operably linked silencing element. "Convergent promoters" refers to promoters that are oriented on either terminus of the operably linked silencing element such that each promoter drives transcription of the silencing element in opposite directions, yielding two transcripts. In such embodiments, the convergent promoters allow for the transcription of the sense and anti-sense strand and thus allow for the formation of a dsRNA.

The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes*(Kiyokawa et al. (1994) *Plant Physiology* 104:801-02; Pandolfini et al. (2003) *BioMedCentral (BMC) Biotechnology* 3:7, (website designated as: biomedcentral.com/1472-6750/3/7); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or Commelina yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J.* 1 Exp. Botany 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultr1; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Cherry promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11): 1779-86), Rice (RSs1) (Shi, T. Wang et al. (1994). *J. Exp. Bot.* 45(274): 623-631) and maize sucrose synthese −1 promoters (Yang., N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196(3):564-70. At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc.*

Natl. Acad. Sci. USA 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element can be provided as an external composition such as a spray or powder to the plant, plant part, seed, a pest, or an area of cultivation. In another example, a plant is transformed with a DNA construct or expression cassette for expression of at least one silencing element. In either composition, the silencing element, when ingested by an insect, can reduce the level of a target pest sequence and thereby control the pest (i.e., a Coleopteran plant pest including a *Diabarotica* plant pest, such as, *D. virgifera virgifera, D. barberi*, or *D. undecimpunctata howardi*). It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition. Various insecticidal formulations can also be found in, for example, US Publications 2008/0275115, 2008/0242174, 2008/0027143, 2005/0042245, and 2004/0127520, each of which is herein incorporated by reference.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Envinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes*, fungi, particularly yeast, e.g., *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* ($3^{rd}$ ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include *Enterobacteriaceae*, such as *Escherichia, Envinia, Shigella, Salmonella,* and *Proteus*; Bacillaceae; Rhizobiceae, such as *Rhizobium*; Spirillaceae, such as *Photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutant before application.

The compositions (including the transformed microorganisms) can be applied to the environment of an insect pest (such as a Coleoptera plant pest or a *Diabarotica* plant pest) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polynucleotide into a plant. "Introducing" is intended to mean presenting to the plant the polynucleotide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. raga, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), *Citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), Hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. *Leguminous* plants include beans and peas. Beans include guar, locust bean, fenugreek, soybean, garden beans, cowpea, mungbean, lima bean, fava bean, lentils, chickpea, etc.

VIII. Methods of Use

The methods of the invention comprise methods for controlling a pest (i.e., a Coleopteran plant pest, including a *Diabarotica* plant pest, such as, *D. virgifera virgifera, D. barberi*, or *D. undecimpunctata* howardi). The method comprises feeding to a pest a composition comprising a silencing element of the invention, wherein said silencing element, when ingested by a pest (i.e., a Coleopteran plant pest including a *Diabarotica* plant pest, such as, *D. virgifera virgifera, D. barberi*, or *D. undecimpunctata* howardi), reduces the level of a target polynucleotide of the pest and thereby controls the pest. The pest can be fed the silencing element in a variety of ways. For example, in one embodiment, the polynucleotide comprising the silencing element is introduced into a plant. As the Coleopteran plant pest or *Diabarotica* plant pest feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In specific embodiments, the silencing element is expressed in the roots, stalk or stem, leaf including pedicel, xylem and phloem, fruit or reproductive tissue, silk, flowers and all parts therein or any combination thereof.

In another method, a composition comprising at least one silencing element of the invention is applied to a plant. In such embodiments, the silencing element can be formulated in an agronomically suitable and/or environmentally acceptable carrier, which is preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5.602,321; beta-ketothiolase, polyhydroxybutyrate synthase, and acetoacetyl-CoA reductase (Schubert et al. (1988) J. Bacteriol. 170:5837-5847) facilitate expression of polyhydroxy-alkanoates (PHAs)); the disclosures of which are herein incorporated by reference. One could also combine the polynucleotides of the present invention with polynucleotides providing agronomic traits such as male sterility (e.g., see U.S. Pat. No. 5.583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. application Ser. No. 12/351,093, entitled "*Compositions and Methods for the Suppression of Target Polynucleotides*", filed Jan. 9, 2009 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a polynucleotide set forth in SEQ ID NO: 1-236 or an active variant or fragment thereof.

It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the invention have an improved loading of RNAi into the phloem of the plant than would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

The following examples are offered by way of illustration and not by way of limitation.

EXPERIMENTAL

Example 1

In Vitro Transcript dsRNA Screening Method

A cDNA library was produced from neonate western corn rootworm larvae by standard methods. A selected cDNA clone containing an expressed sequence tag is amplified in a PCR using universal primers to the plasmid backbone and flanking the EST insert. The universal primers also contain T7 RNA polymerase sites. 1 ul of the PCR reaction is used as the template for an in vitro transcription (IVT) reaction to produce long double stranded RNAs. Following enzymatic digestion and removal of the DNA template and single stranded RNA, the IVT reaction products are incorporated into artificial insect diet as described below.

Insect Bioassays 2.5 ul of the IVT reaction are added to a given well of a 96 well microtiter plate. 25 ul of molten lowmelt Western corn rootworm diet are added to the sample and shaken on an orbital shaker to mix the sample and diet. Once the diet has solidified, neonate rootworms are added to the well. An average of 5 neonates is added to each well. After the plate is infested, the plate is sealed with mylar and a single hole in punched in the mylar over each well to allow air exchange. 4 replicate wells are produced for each sample. The assay is scored for activity 7 days post infestation. The possible scores are dead, severely stunted (little or now growth but alive), stunted (growth to second instar but not equivalent to controls), or no activity. Samples demonstrating mortality or severe stunting were advanced to confirmation. Primary assays and confirmation assays were performed with the southern corn rootworm.

Following confirmation, a simple dose response assay was performed with both southern and western corn rootworms. Samples for dose response assays were produced in the same manner with the following modification; samples were further purified using column purification prior to enzymatic treatment. Samples were also normalized to 0.5 ug/ul and all samples were evaluated by gel electrophoresis. Dose response assays were performed with the following rates; 50, 25, 12, 6, 3, and 1.5 ppm Example 2

Sequences Having Insecticidal Activity

DNA sequences which encode double stranded RNAs which were shown to have insecticidal activity against corn rootworms using the assay described in Example 1 are set forth below. Non-limiting examples of target polynucleotides are set forth below in Table 1.

TABLE 1

| |
|---|
| SEQ ID NO: 1 |
| >iwm2c.pk005.e.1.fis1 |
| SEQ ID NO: 2 |
| >iwm2c.pk004.b13.fis1 |
| SEQ ID NO: 3 |
| >iwm2s.pk003.o1.f.fis1 |
| SEQ ID NO: 4 |
| >iwm2c.pk002.e24.fis1 |
| SEQ ID NO: 5 |
| >iwm2c.pk002.e24.fis1 |
| SEQ ID NO: 6 |
| >iwm2c.pk011.n17.fis1 |
| SEQ ID NO: 7 |
| >idv1c.pk001.d14.f.fis1 |
| SEQ ID NO: 8 |
| >idv1c.pk001.e9.f.fis1 |
| SEQ ID NO: 9 |
| >idv1c.pk001.m5.f.fis1 |
| SEQ ID NO: 10 |
| >idv1c.pk001.n1.f.fis1 |

TABLE 1-continued

SEQ ID NO: 11
>idv1c.pk002.c5.f.fis1
SEQ ID NO: 12
>idv1c.pk002.f20.f.fis1
SEQ ID NO: 13
>idv1c.pk002.j17.f.fis1
SEQ ID NO: 14
>idv1c.pk002.n13.f.fis1
SEQ ID NO: 15
>idv1c.pk003.d6.f.fis1
SEQ ID NO: 16
>idv1c.pk003.f8.f.fis1
SEQ ID NO: 17
>idv1c.pk003.f9.f.fis1
SEQ ID NO: 18
>idy1c.pk003.j4.f.fis1
SEQ ID NO: 19
>idy1c.pk003.j6.f.fis1
SEQ ID NO: 20
>idv1c.pk003.j20.f.fis1
SEQ ID NO: 21
>idy1c.pk003.l1.f.fis1
SEQ ID NO: 22
>idy1c.pk003.m1.f.fis1
SEQ ID NO: 23
>idv1c.pk003.m10.f.fis1
SEQ ID NO: 24
>idv1c.pk003.o13.f.fis1
SEQ ID NO: 25
>idv1c.pk003.o22.f.fis1
SEQ ID NO: 26
>idv1c.pk003.p13.f.fis1
SEQ ID NO: 27
>idv1c.pk004.b12.f.fis1
SEQ ID NO: 28
>idv1c.pk004.d17.f.fis1
SEQ ID NO: 29
>idv1c.pk004.f20.f.fis1
SEQ ID NO: 30
>idv1c.pk004.k5.f.fis1
SEQ ID NO: 31
>idv1c.pk004.l15.f.fis1
SEQ ID NO: 32
>idv1c.pk004.n6.f.fis1
SEQ ID NO: 33
>idv1c.pk004.o4.f.fis1
SEQ ID NO: 34
>idv1c.pk004.o9.f.fis1
SEQ ID NO: 35
>idv1c.pk004.p1.f.fis1
SEQ ID NO: 36
>idv1c.pk013.a15.f.fis1
SEQ ID NO: 37
>idv1c.pk013.b11.f.fis1
SEQ ID NO: 38
>idv1c.pk013.c21.f.fis1
SEQ ID NO: 39
>idv1c.pk013.d22.f.fis1
SEQ ID NO: 40
>idv1c.pk013.h1.f.fis1
SEQ ID NO: 41
>idv1c.pk013.h14.f.fis1
SEQ ID NO: 42
>idv1c.pk013.k1.f.fis1
SEQ ID NO: 43
>idv1c.pk014.a19.f.fis1
SEQ ID NO: 44
>idv1c.pk014.b9.f.fis1
SEQ ID NO: 45
>idv1c.pk014.b17.f.fis1
SEQ ID NO: 46
>idv1c.pk014.c14.f.fis1
SEQ ID NO: 47
>idv1c.pk014.d11.f.fis1
SEQ ID NO: 48
>idv1c.pk014.f3.f.fis1
SEQ ID NO: 49
>idv1c.pk014.j2.f.fis1
SEQ ID NO: 50
>idv1c.pk014.k23.f.fis1

TABLE 1-continued

SEQ ID NO: 51
>idv1c.pk014.m5.f.fis1
SEQ ID NO: 52
>idv1c.pk014.m13.f.fis1
SEQ ID NO: 53
>idv1c.pk014.n16.f.fis1
SEQ ID NO: 54
>idv1c.pk014.n23.f.fis1
SEQ ID NO: 55
>idv1c.pk014.o1.f.fis1
SEQ ID NO: 56
>idv1c.pk015.a16.f.fis1
SEQ ID NO: 57
>idv1c.pk015.b8.f.fis1
SEQ ID NO: 58
>idv1c.pk015.g10.f.fis1
SEQ ID NO: 59
>idv1c.pk015.l13.f.fis1
SEQ ID NO: 60
>idv1c.pk015.n19.f.fis1
SEQ ID NO: 61
>idv1c.pk015.p2.f.fis1
SEQ ID NO: 62
>idv1c.pk016.a9.f.fis1
SEQ ID NO: 63
>idv1c.pk016.f12.f.fis1
SEQ ID NO: 64
>idv1c.pk016.f21.f.fis1
SEQ ID NO: 65
>idv1c.pk016.h15.f.fis1
SEQ ID NO: 66
>idv1c.pk016.h19.f.fis1
SEQ ID NO: 67
>idv1c.pk016.j12.f.fis1
SEQ ID NO: 68
>idv1c.pk016.j15.f.fis1
SEQ ID NO: 69
>idv1c.pk016.k9.f.fis1
SEQ ID NO: 70
>idv1c.pk016.p18.f.fis1
SEQ ID NO: 71
>idv1c.pk017.c3.f.fis1
SEQ ID NO: 72
>idv1c.pk017.d14.f.fis1
SEQ ID NO: 73
>idv1c.pk017.e22.f.fis1
SEQ ID NO: 74
>idv1c.pk017.f1.f.fis1
SEQ ID NO: 75
>idv1c.pk017.h14.f.fis1
SEQ ID NO: 76
>idv1c.pk017.n19.f.fis1
SEQ ID NO: 77
>idv1c.pk017.p2.f.fis1
SEQ ID NO: 78
>idv1c.pk018.a5.f.fis1
SEQ ID NO: 79
>idv1c.pk018.c11.f.fis1
SEQ ID NO: 80
>idv1c.pk018.d5.f.fis1
SEQ ID NO: 81
>idv1c.pk018.d14.f.fis1
SEQ ID NO: 82
>idv1c.pk018.e10.f.fis1
SEQ ID NO: 83
>idv1c.pk018.e20.f.fis1
SEQ ID NO: 84
>idv1c.pk018.f19.f.fis1
SEQ ID NO: 85
>idv1c.pk018.f22.f.fis1
SEQ ID NO: 86
>idv1c.pk018.g20.f.fis1
SEQ ID NO: 87
>idv1c.pk018.h21.f.fis1
SEQ ID NO: 88
>idv1c.pk018.m5.f.fis1
SEQ ID NO: 89
>idv1c.pk019.c4.f.fis1
SEQ ID NO: 90
>idv1c.pk019.i5.f.fis1

TABLE 1-continued

SEQ ID NO: 91
>idv1c.pk019.k3.f.fis1
SEQ ID NO: 92
>idv1c.pk019.17.f.fis1
SEQ ID NO: 93
>idv1c.pk020.a8.f.fis1
SEQ ID NO: 94
>idv1c.pk020.b11.f.fis1
SEQ ID NO: 95
>idv1c.pk020.g17.f.fis1
SEQ ID NO: 96
>idv1c.pk020.i7.f.fis1
SEQ ID NO: 97
>idv1c.pk020.i24.f.fis1
SEQ ID NO: 98
>idv1c.pk020.k19.f.fis1
SEQ ID NO: 99
>idv1c.pk020.l3.f.fis1
SEQ ID NO: 100
>idv1c.pk020.p23.f.fis1
SEQ ID NO: 101
>idv1c.pk021.c21.f.fis1
SEQ ID NO: 102
>idv1c.pk021.d22.f.fis1
SEQ ID NO: 103
>idv1c.pk021.g16.f.fis1
SEQ ID NO: 104
>idv1c.pk021.h12.f.fis1
SEQ ID NO: 105
>idv1c.pk021.m20.f.fis1
SEQ ID NO: 106
>idv1c.pk004.j11.f.fis1
SEQ ID NO: 107
>idv1c.pk001.o20.f
SEQ ID NO: 108
>idv1c.pk002.a20.f
SEQ ID NO: 109
>idv1c.pk002.c15.f
SEQ ID NO: 110
>idv1c.pk002.i21.f
SEQ ID NO: 111
>idv1c.pk024.b23.f
SEQ ID NO: 112
>idv1c.pk024.e1.f
SEQ ID NO: 113
>idv1c.pk024.e24.f
SEQ ID NO: 114
>idv1c.pk024.k17.f
SEQ ID NO: 115
>idv1c.pk024.m13.f
SEQ ID NO: 116
>idv1c.pk024.n1.f
SEQ ID NO: 117
>idv1c.pk024.o3.f
SEQ ID NO: 118
>idv1c.pk025.a4.f
SEQ ID NO: 119
>idv1c.pk025.c5.f
SEQ ID NO: 120
>idv1c.pk025.c23.f
SEQ ID NO: 121
>idv1c.pk025.d18.f
SEQ ID NO: 122
>idv1c.pk025.d20.f
SEQ ID NO: 123
>idv1c.pk025.f24.f
SEQ ID NO: 124
>idv1c.pk025.j20.f
SEQ ID NO: 125
>idv1c.pk025.l10.f
SEQ ID NO: 126
>idv1c.pk026.a16.f
SEQ ID NO: 127
>idv1c.pk026.b23.f
SEQ ID NO: 128
>idv1c.pk026.d22.f
SEQ ID NO: 129
>idv1c.pk026.e6.f
SEQ ID NO: 130
>idv1c.pk026.g12.f TABLE 1-continued SEQ ID NO: 131
>idv1c.pk026.h15.f
SEQ ID NO: 132
>idv1c.pk026.i12.f
SEQ ID NO: 133
>idv1c.pk026.j18.f
SEQ ID NO: 134
>idv1c.pk026.k13.f
SEQ ID NO: 135
>idv1c.pk027.b21.f
SEQ ID NO: 136
>idv1c.pk027.c7.f
SEQ ID NO: 137
>idv1c.pk027.k4.f
SEQ ID NO: 138
>idv1c.pk027.p21.f
SEQ ID NO: 139
>idv1c.pk028.b7.f
SEQ ID NO: 140
>idv1c.pk028.c22.f
SEQ ID NO: 141
>idv1c.pk028.h6.f
SEQ ID NO: 142
>idv1c.pk028.i16.f
SEQ ID NO: 143
>idv1c.pk028.m11.f
SEQ ID NO: 144
>idv1c.pk028.o18.f
SEQ ID NO: 145
>idv1c.pk029.a17.f
SEQ ID NO: 146
>idv1c.pk029.d16.f
SEQ ID NO: 147
>idv1c.pk029.i22.f
SEQ ID NO: 148
>idv1c.pk029.j20.f
SEQ ID NO: 149
>idv1c.pk029.k11.f
SEQ ID NO: 150
>idv1c.pk029.l22.f
SEQ ID NO: 151
>idv1c.pk030.e10.f
SEQ ID NO: 152
>idv1c.pk030.e21.f
SEQ ID NO: 153
>idv1c.pk030.h13.f
SEQ ID NO: 154
>idv1c.pk030.h23.f
SEQ ID NO: 155
>idv1c.pk030.l9.f
SEQ ID NO: 156
>idv1c.pk030.m22.f
SEQ ID NO: 157
>idv1c.pk030.o7.f
SEQ ID NO: 158
>idv1c.pk031.a11.f
SEQ ID NO: 159
>idv1c.pk031.e16.f
SEQ ID NO: 160
>idv1c.pk031.g2.f
SEQ ID NO: 161
>idv1c.pk031.g22.f
SEQ ID NO: 162
>idv1c.pk031.i13.f
SEQ ID NO: 163
>idv1c.pk031.m3.f
SEQ ID NO: 164
>idv1c.pk032.b4.f
SEQ ID NO: 165
>idv1c.pk032.e16.f
SEQ ID NO: 166
>idv1c.pk032.f14.f
SEQ ID NO: 167
>idv1c.pk032.m9.f
SEQ ID NO: 168
>idv1c.pk033.a15.f
SEQ ID NO: 169
>idv1c.pk033.b14.f
SEQ ID NO: 170
>idv1c.pk033.m3.f TABLE 1-continued SEQ ID NO: 171
>idv1c.pk033.n10.f
SEQ ID NO: 172
>idv1c.pk033.n18.f
SEQ ID NO: 173
>idv1c.pk034.e8.f
SEQ ID NO: 174
>idv1c.pk034.p24.f
SEQ ID NO: 175
>idv1c.pk035.f21.f
SEQ ID NO: 176
>idv1c.pk035.g1.f
SEQ ID NO: 177
>idv1c.pk035.h19.f
SEQ ID NO: 178
>idv1c.pk035.j4.f
SEQ ID NO: 179
>idy1c.pk035.m1.f
SEQ ID NO: 180
>idv1c.pk035.o13.f
SEQ ID NO: 181
>idv1c.pk036.a14.f
SEQ ID NO: 182
>idv1c.pk036.e18.f
SEQ ID NO: 183
>idv1c.pk036.f4.f
SEQ ID NO: 184
>idv1c.pk036.f9.f
SEQ ID NO: 185
>idv1c.pk036.i17.f
SEQ ID NO: 186
>idv1c.pk036.i20.f
SEQ ID NO: 187
>idv1c.pk036.k23.f
SEQ ID NO: 188
>idv1c.pk034.k22.f
SEQ ID NO: 189
>idv1c.pk002.c7.f
SEQ ID NO: 190
>idv1c.pk002.f18.f
SEQ ID NO: 191
>idv1c.pk002.i23.f
SEQ ID NO: 192
>idv1c.pk002.j24.f
SEQ ID NO: 193
>idv1c.pk002.m16.f
SEQ ID NO: 194
>idv1c.pk002.n13.f
SEQ ID NO: 195
>idv1c.pk024.c7.f
SEQ ID NO: 196
>idv1c. pk024.j15.f
SEQ ID NO: 197
>idv1c.pk025.b17.f
SEQ ID NO: 198
>idv1c.pk025.f3.f
SEQ ID NO: 199
>idv1c.pk025.i8.f
SEQ ID NO: 200
>idv1c.pk025.l17.f
SEQ ID NO: 201
>idv1c.pk025.o24.f
SEQ ID NO: 202
>idv1c.pk025.p9.f
SEQ ID NO: 203
>idv1c.pk026.f20.f
SEQ ID NO: 204
>idv1c.pk026.p8.f
SEQ ID NO: 205
>idv1c.pk026.p22.f
SEQ ID NO: 206
>idv1c.pk027.a14.f
SEQ ID NO: 207
>idv1c.pk027.g7.f
SEQ ID NO: 208
>idv1c.pk027.k23.f
SEQ ID NO: 209
>idv1c.pk028.b17.f
SEQ ID NO: 210
>idv1c.pk028.f11.f TABLE 1-continued SEQ ID NO: 211
>idv1c.pk029.c3.f
SEQ ID NO: 212
>idv1c.pk029.f5.f
SEQ ID NO: 213
>idv1c.pk029.j4.f
SEQ ID NO: 214
>idv1c.pk030.b23.f
SEQ ID NO: 215
>idv1c.pk030.f9.f
SEQ ID NO: 216
>idv1c.pk030.g11.f
SEQ ID NO: 217
>idv1c.pk031.c20.f
SEQ ID NO: 218
>idv 1 c.pk031.d1.f
SEQ ID NO: 219
>idv1c.pk031.j1.f
SEQ ID NO: 220
>idv1c.pk031.j6.f
SEQ ID NO: 221
>idv1c.pk031.p16.f
SEQ ID NO: 222
>idv1c.pk032.a16.f
SEQ ID NO: 223
>idv1c.pk032.f11.f
SEQ ID NO: 224
>idv1c.pk032.i21.f
SEQ ID NO: 225
>idv1c.pk032.n18.f
SEQ ID NO: 226
>idv1c.pk032.p5.f
SEQ ID NO: 227
>idv1c.pk033.d24.f
SEQ ID NO: 228
>idv1c.pk033.j21.f
SEQ ID NO: 229
>idv1c.pk033.o9.f
SEQ ID NO: 230
>idv1c.pk033.p15.f
SEQ ID NO: 231
>idv1c.pk033.p16.f
SEQ ID NO: 232
>idv1c.pk034.i2.f
SEQ ID NO: 233
>idv1c.pk034.j6.f
SEQ ID NO: 234
>idv1c.pk035.i17.f
SEQ ID NO: 235
>idv1c.pk035.k18.f
SEQ ID NO: 236
>idv1c.pk036.i19.f
SEQ ID NO: 237
Construct expressing SEQ ID NO: 8 as a hairpin RNA. The construct comprises: UBI1ZM promoter 5'UTR and 1$^{st}$ intron operably linked to SEQ ID NO: 8 operably linked to the ADH1 intron operably linked to the complement of SEQ ID NO: 8.
SEQ ID NO: 238
Construct expressing SEQ ID NO: 26 as a hairpin RNA. The construct comprises: UBI1ZM promoter 5'UTR and 1$^{st}$ intron operably linked to SEQ ID NO: 26 operably linked to the ADH1 intron operably linked to the complement of SEQ ID NO: 26.
SEQ ID NO: 239
Construct expressing SEQ ID NO: 17 as a hairpin RNA. The construct comprises: UBI1ZM promoter 5'UTR and 1$^{st}$ intron operably linked to SEQ ID NO: 17 operably linked to the ADH1 intron operably linked to the complement of SEQ ID NO: 17.
SEQ ID NO: 240
Construct expressing SEQ ID NO: 28 as a hairpin RNA. The construct comprises: UBI1ZM promoter 5'UTR and 1$^{st}$ intron operably linked to SEQ ID NO: 28 operably linked to the ADH1 intron operably linked to the complement of SEQ ID NO: 28.
SEQ ID NO: 241
Construct expressing SEQ ID NO: 28 as a hairpin RNA. The construct comprises: UBI1ZM promoter 5'UTR and 1$^{st}$ intron operably linked to SEQ ID NO: 28 operably linked to the ADH1 intron operably linked to the complement of SEQ ID NO: 28.
SEQ ID NO: 242
Construct expressing SEQ ID NO: 13 as a hairpin RNA. The construct comprises: UBI1ZM promoter 5'UTR and 1$^{st}$ intron operably linked to SEQ ID NO: 13 operably linked to the ADH1 intron operably linked to the complement of SEQ ID NO: 13.
SEQ ID NO: 243

TABLE 1-continued

Construct expressing SEQ ID NO: 40 as a hairpin RNA. The construct comprises: UBI1ZM promoter 5'UTR and 1$^{st}$ intron operably linked to SEQ ID NO: 40 operably linked to the ADH1 intron operably linked to the complement of SEQ ID NO: 40.
SEQ ID NO: 244
Construct expressing SEQ ID NO: 72 as a hairpin RNA. The construct comprises: UBI1ZM promoter 5'UTR and 1$^{st}$ intron operably linked to SEQ ID NO: 72 operably linked to the ADH1 intron operably linked to the complement of SEQ ID NO: 72.
SEQ ID NO: 245
Construct expressing SEQ ID NO: 73 as a hairpin RNA. The construct comprises: UBI1ZM promoter 5'UTR and 1$^{st}$ intron operably linked to SEQ ID NO: 73 operably linked to the ADH1 intron operably linked to the complement of SEQ ID NO: 73
SEQ ID NO: 246
Construct expressing SEQ ID NO: 15 as a hairpin RNA. The construct comprises: UBI1ZM promoter 5'UTR and 1$^{st}$ intron operably linked to SEQ ID NO: 15 operably linked to the ADH1 intron operably linked to the complement of SEQ ID NO: 15.
SEQ ID NO: 247
Construct expressing SEQ ID NO: 18 as a hairpin RNA. The construct comprises: UBI1ZM promoter 5'UTR and 1$^{st}$ intron operably linked to SEQ ID NO: 18 operably linked to the ADH1 intron operably linked to the complement of SEQ ID NO: 18.
SEQ ID NO: 248
Construct expressing nt 1-380 of SEQ ID NO: 45 as a hairpin RNA. The construct comprises: UBI1ZM promoter 5'UTR and 1$^{st}$ intron operably linked to nt 1-380 of SEQ ID NO: 45 operably linked to the ADH1 intron operably linked to the complement of nt 1-380 of SEQ ID NO: 45.
SEQ ID NO: 249
Construct expressing nt 1-675 of SEQ ID NO: 37 as a hairpin RNA. The construct comprises: UBI1ZM promoter 5'UTR and 1$^{st}$ intron operably linked to nt 1-675 of SEQ ID NO: 37 operably linked to the ADH1 intron operably linked to the complement of nt 1-675 of SEQ ID NO: 37.
SEQ ID NO: 250
Construct expressing SEQ ID NO: 29 as a hairpin RNA. The construct comprises: UBI1ZM promoter 5'UTR and 1$^{st}$ intron operably linked to SEQ ID NO: 29 operably linked to the ADH1 intron operably linked to the complement of SEQ ID NO: 29.
SEQ ID NO: 251
Construct expressing nt 1-266 of SEQ ID NO: 50 as a hairpin RNA. The construct comprises: UBI1ZM promoter 5'UTR and 1$^{st}$ intron operably linked to nt 1-266 of SEQ ID NO: 50 operably linked to the ADH1 intron operably linked to the complement of 1-266 of SEQ ID NO: 50.
SEQ ID NO: 252
Construct expressing nt 16-585 of SEQ ID NO: 47 as a hairpin RNA. The construct comprises: UBI1ZM promoter 5'UTR and 1$^{st}$ intron operably linked to nt 16-585 of SEQ ID NO: 47 operably linked to the ADH1 intron operably linked to the complement of nt 16-585 of
SEQ ID NO: 47.

Example 3

Transformation of Maize

Immature maize embryos from greenhouse donor plants are bombarded with a plasmid containing the silencing element of the invention operably linked to either a tissue specific, tissue selective, or constitutive promoter and the selectable marker gene PAT (Wohlleben et al. (1988) *Gene* 70:25-37), which confers resistance to the herbicide Biala- phos. In one embodiment, the constructs will express a long double stranded RNA of the target sequence set forth in table 1. Such a construct can be linked to the dMMB promoter. Alternatively, the selectable marker gene is provided on a separate plasmid. Transformation is performed as follows. Media recipes follow below.
Preparation of Target Tissue The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to either the tissue specific, tissue selective, or constitutive promoter is made. This plasmid DNA plus plasmid DNA containing a PAT selectable marker is precipitated onto 1.1 μm (average diameter) tungsten pellets using a CaCl$_2$ precipitation procedure as follows: 100 μl prepared tungsten particles in water; 10 μl (1 μg) DNA in Tris EDTA buffer (1 μg total DNA); 100 μl 2.5 M CaCl$_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/ DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity.

Plants are monitored and scored for the appropriate marker, such as the control of a Coleoptera plant pest, such as a *Diabarotica* plant pest and have insecticidal activity. For example, to plant roots are fed to western corn rootworm larvae (WCR, *Diabrotica virgifera*). Transgenic corn roots are handed-off in Petri dishes with MSOD medium containing antibiotics and glyphosate for in vitro selection. Two WCR larvae are infested per root in each dish with a fine tip paintbrush. The dishes are sealed with Parafilm to prevent the larvae from escaping. The assays are placed into a 27° C. 60% RH Percival incubator incomplete darkness. Contamination and larval quality are monitored. After six days of feeding on root tissue, the larvae are transferred to WCR diet in a 96 well plate. The larvae are allowed to feed on the diet for eight days making the full assay fourteen days long. Larval mass and survivorship are recorded for analysis. A one-way ANOVA analysis and a Dunnett's test is performed on the larval mass data to look for statistical significance compared to an untransformed negative control. WCR larvae stunting is measured after feeding on two events and compared to growth of larvae fed on negative control plants.

In other assays, transgenic corn plants ($R_0$) generated are planted into 10-inch pots containing Metromix soil after reaching an appropriate size. When plants reach the V4 growth stage, approximately 1000 Western corn rootworm (WCR, *Diabrotica virgifera*) eggs are infested into the root zone. Non-transgenic corn of the same genotype is infested at a similar growth stage to serve as a negative control. Eggs are pre-incubated so hatch occurs within 24 hours of infestation. Larvae are allowed to feed on the root systems for 3 weeks. Plants are removed from the soil and washed so that the roots can be evaluated for larval feeding. Root damage is rated using a Node Injury Scale (NIS) to score the level of damage where a 0 indicates no damage, a 1 indicates that one node of roots is pruned to within 1.5 inches, a 2 indicates that 2 nodes are pruned, while a 3 indicates that 3 nodes are pruned. Because the plants being used for evaluation are directly out of tissue culture after transformation and because transformation events are unique, only a single plant is evaluated per event at this time. The plants in the assay that present signs or symptoms of larval feeding indicate that a successful infestation is obtained. Negative control plant roots are moderately to severely damaged averaging whereas roots of the transgenic plants provide substantial control of larval feeding, with about 0.2 or less on the Node Injury Scale.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 4

*Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Such as a construct can, for example, express a long double stranded RNA of the target sequence set forth in table 1. Such a construct can be linked to the dMMB promoter. Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants. Assays for insecticidal activity can be performed as described above in Example, 5.

Example 5

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the examples above by the method of particle gun bombardment (Klein et al. (1987) Nature, 327:70).

Soybean Embryogenic Suspension Culture Initiation

Soybean cultures are initiated twice each month with 5-7 days between each initiation. Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (Bio-Whitaker Molecular Applications) and the DNA fragments containing silencing element of interest are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the appropriate marker or the ability of the plant, when injected with the silencing elements, to control the Coleopteran plant pest or the *Diabarotica* plant pest.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot.

Media Recipes

| SB 196-FN Lite liquid proliferation medium (per liter)- | |
|---|---|
| MS FeEDTA-100x Stock 1 | 10 ml |
| MS Sulfate-100x Stock 2 | 10 ml |
| FN Lite Halides-100x Stock 3 | 10 ml |
| FN Lite P, B, Mo-100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2 SO 4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | Na$_2$ EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL—Cat #11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat #11117-066); 1 ml B5 vitamins 1000× stock; 60 g maltose; 750 mg MgCl$_2$ hexahydrate; 5 g activated charcoal; pH 5.7; and, 2 g gelrite.

SB 103 solid medium (per liter) comprises: 1 pkg. MS salts (Gibco/BRL—Cat #11117-066); 1 ml B5 vitamins 1000× stock; 60 g maltose; 750 mg MgCl$_2$ hexahydrate; pH 5.7; and, 2 g gelrite.

SB 71-4 solid medium (per liter) comprises: 1 bottle Gamborg's B5 salts w/ sucrose (Gibco/BRL—Cat #21153-036); pH 5.7; and, 5 g TC agar.

2,4-D stock is obtained premade from Phytotech cat #D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide Example 6

Expression of Silencing Elements in Maize

The silencing elements set forth in SEQ ID NO: 8, 26, 17, 28 and 10 were expressed in a maize plant as hairpins and the plant was tested for insecticidal activity against corn root worms. The sequences set forth in SEQ ID NO: 8, 26, 17, 28 and 10 were engineered to be expressed as a hairpin. The constructs comprised the following components: the maize ubiquitin promoter/5'UTR/1$^{st}$ intron operably linked SEQ ID NO:8, 26, 17, 28 or 10::ADH1 intron::complement of SEQ ID NO:8, 26, 17, 28 and 10. Plasmids PHP41121, PHP41134, PHP41127, PHP41130, PHP41118 were generated as summarized below in Table 2.

TABLE 2

| SEQ ID NO of silencing element | SEQ ID NO of construct w/ promoter and silencing element | Clone name of silencing element | Sequence homology of the silencing element | Plasmid name |
|---|---|---|---|---|
| 8 | 237 | idvlc.pk001.e9.f | Ribosomal protein s10E | PHP41121 |
| 26 | 238 | idvlc.ph003.p13.f | Ribosomal protein | PHP41134 |
| 17 | 239 | idvlc.pk003.f9.f | 27 kD proteinase | PHP41127 |
| 28 | 240 | idvlc.pk004.d17.f | Tribolium | PHP41130 |
| 10 | 241 | idvlc.pk001.n1.f | No hits | PHP41118 |

Maize plants were transformed with Plasmids PHP41121, PHP41134, PHP41127, PHP41130, PHP41118 and plants expressing the silencing elements denoted in Table 2 were transplanted from 272V plates into greenhouse flats containing Fafard Superfine potting mix. Approximately 10 to 14 days after transplant, plants (now at growth stage V2-V3) were transplanted into treepots containing Fafard Superfine potting mix. At 14 days post greenhouse send date, plants were infested with 100 eggs of western corn root worms (WCRW)/plant. For later sets, a second infestation of 100 eggs WCRW/plant was done 14 days after the first infestation and scoring was at 14 days after the second infestation. 21 days post infestation, plants were scored using CRWNIS. Those plants with a score of ≤0.5 are transplanted into large pots containing SB300 for seed. As shown in FIG. 1, each of SEQ ID NO: 8, 26, 17, 28 and 10 had insecticidal activity.

Example 7

Insect Bioassays 2.5 ul of an in-vitro transcription reaction which synthesized one of the sequences set forth in SEQ ID NO: 107-236 were added to a given well of a 96 well microtiter plate. 25 ul of molten lowmelt western corn rootworm diet were added to the sample and shaken on an orbital shaker to mix the sample and diet. Once the diet had solidified, neonate rootworms were added to the well. An average of 5 neonates were added to each well. After the plate was infested, the plate was sealed with mylar and a single hole was punched in the mylar over each well to allow air exchange. 4 replicate wells were produced for each sample. The assay was scored for activity 7 days post infestation. Table 3 provides insecticidal bioassay data employing the southern corn rootworm. The possible scores are dead (D), severely stunted (SS; little or no growth but alive), stunted (S; growth to second instar but not equivalent to controls), contaminated (c), or no activity.

Following confirmation, a simple dose response assay was performed with both southern and western corn rootworms. See, Tables 4 and 5 below. Samples for dose response assays were produced in the same manner described above with the following modification: samples were further purified using column purification prior to enzymatic treatment. Samples were also normalized to 0.5 ug/ul and all samples were evaluated by gel electrophoresis. Dose response assays were performed with the following rates: crude, 0.5, 0.25, 0.0125 ppm, and 0.125 dilutions (equivalent to 51, 25, 12.5 and 6 ppm).

TABLE 3

Insecticidal Bioassay Data Against Southern Corn Root Worm

| Clone name | | | | | |
|---|---|---|---|---|---|
| idv1c.pk001.o20.f | S | S | S | S | S |
| idv1c.pk002.a20.f | S | S | S | S | S |
| idv1c.pk002.c7.f | SS | SS | SS | SS | SS |
| idv1c.pk002.c15.f | S | S | S | S | S |
| idv1c.pk002.f18.f | SS | SS | S | SS | SS |
| idv1c.pk002.i21.f | S | S | S | S | S |
| idv1c.pk002.i23.f | SS | SS | SS | SS | SS |
| idv1c.pk002.j24.f | SS | SS | SS | SS | SS |
| idv1c.pk002.m16.f | SS | SS | SS | SS | SS |
| idv1c.pk002.n13.f | SS | SS | SS | SS | SS |
| idv1c.pk024.b23.f | S | S | S | S | S |
| idv1c.pk024.c7.f | SS | SS | D | SS | SS |
| idv1c.pk024.e1.f | S | S | S | S | S |
| idv1c.pk024.e24.f | S | S | S | S | S |
| idv1c.pk024.j15.f | SS | SS | SS | SS | SS |
| idv1c.pk024.k17.f | S | S | S | S | S |
| idv1c.pk024.m13.f | S | S | S | S | S |
| idv1c.pk024.n1.f | S | S | S | S | S |
| idv1c.pk024.o3.f | S | S | S | S | S |
| idv1c.pk025.a4.f | S | S | S | S | S |
| idv1c.pk025.b17.f | SS | SS | SS | SS | SS |
| idv1c.pk025.c5.f | S | S | S | S | S |
| idv1c.pk025.c23.f | S | SS | S | S | S |
| idv1c.pk025.d18.f | S | S | S | S | S |
| idv1c.pk025.d20.f | S | S | S | S | S |
| idv1c.pk025.f3.f | SS | SS | SS | SS | SS |
| idv1c.pk025.f24.f | S | S | S | S | S |
| idv1c.pk025.i8.f | SS | SS | SS | S | SS |
| idv1c.pk025.j20.f | S | S | S | S | S |
| idv1c.pk025.l10.f | S | S | S | S | S |
| idv1c.pk025.l17.f | SS | S | SS | SS | SS |
| idv1c.pk025.o24.f | SS | SS | SS | SS | SS |
| idv1c.pk025.p9.f | SS | SS | S | SS | SS |
| idv1c.pk026.a16.f | S | S | S | S | S |
| idv1c.pk026.b23.f | S | S | S | S | S |
| idv1c.pk026.d22.f | S | S | S | S | S |
| idv1c.pk026.e6.f | S | S | S | S | S |
| idv1c.pk026.f20.f | SS | SS | SS | SS | SS |
| idv1c.pk026.g12.f | S | S | S | S | S |
| idv1c.pk026.h15.f | S | S | S | S | S |
| idv1c.pk026.i12.f | S | S | S | S | S |
| idv1c.pk026.j18.f | S | S | S | S | S |
| idv1c.pk026.k13.f | S | S | S | S | S |
| idv1c.pk026.p8.f | S | SS | S | S | SS |
| idv1c.pk026.p22.f | SS | SS | SS | SS | SS |
| idv1c.pk027.a14.f | SS | SS | SS | SS | SS |
| idv1c.pk027.b21.f | S | S | S | S | S |
| idv1c.pk027.c7.f | S | S | S | S | S |
| idv1c.pk027.g7.f | SS | SS | SS | SS | SS |
| idv1c.pk027.k4.f | S | S | S | S | S |
| idv1c.pk027.k23.f | SS | SS | SS | SS | SS |
| idv1c.pk027.p21.f | S | S | S | S | S |
| idv1c.pk028.b7.f | S | S | S | S | S |
| idv1c.pk028.b17.f | S | SS | SS | S | SS |
| idv1c.pk028.c22.f | S | S | S | S | S |
| idv1c.pk028.f11.f | SS | SS | SS | SS | SS |
| idv1c.pk028.h6.f | S | S | S | S | S |
| idv1c.pk028.i16.f | S | S | S | S | S |
| idv1c.pk028.m11.f | S | S | S | S | S |
| idv1c.pk028.o18.f | S | S | S | S | S |
| idv1c.pk029.a17.f | S | S | S | S | S |
| idv1c.pk029.c3.f | SS | SS | SS | SS | SS |
| idv1c.pk029.d16.f | S | S | S | S | S |
| idv1c.pk029.f5.f | SS | SS | S | SS | SS |
| idv1c.pk029.i22.f | S | S | S | S | S |
| idv1c.pk029.j4.f | SS | SS | SS | SS | SS |
| idv1c.pk029.j20.f | S | S | S | S | S |
| idv1c.pk029.k11.f | S | S | S | S | S |
| idv1c.pk029.l22.f | S | S | S | S | S |

TABLE 3-continued

Insecticidal Bioassay Data Against Southern Corn Root Worm

| Clone name | | | | | |
|---|---|---|---|---|---|
| idv1c.pk030.b23.f | SS | SS | SS | SS | SS |
| idv1c.pk030.e10.f | S | S | S | S | S |
| idv1c.pk030.e21.f | S | S | S | S | S |
| idv1c.pk030.f9.f | SS | SS | SS | SS | SS |
| idv1c.pk030.g11.f | SS | SS | SS | SS | SS |
| idv1c.pk030.h13.f | S | S | S | S | S |
| idv1c.pk030.h23.f | S | S | S | S | S |
| idv1c.pk030.l9.f | S | S | S | S | S |
| idv1c.pk030.m22.f | S | S | S | S | S |
| idv1c.pk030.o7.f | S | S | S | S | S |
| idv1c.pk031.a11.f | S | S | S | S | S |
| idv1c.pk031.c20.f | SS | SS | SS | SS | SS |
| idv1c.pk031.d1.f | SS | SS | SS | SS | SS |
| idv1c.pk031.e16.f | S | S | S | S | S |
| idv1c.pk031.g2.f | S | S | S | S | S |
| idv1c.pk031.g22.f | S | S | S | S | S |
| idv1c.pk031.i13.f | S | S | S | S | S |
| idv1c.pk031.j1.f | SS | SS | SS | SS | SS |
| idv1c.pk031.j6.f | SS | SS | SS | SS | SS |
| idv1c.pk031.m3.f | S | S | S | S | S |
| idv1c.pk031.p16.f | SS | SS | SS | SS | SS |
| idv1c.pk032.a16.f | SS | SS | SS | SS | SS |
| idv1c.pk032.b4.f | S | S | S | S | S |
| idv1c.pk032.e16.f | S | S | S | S | S |
| idv1c.pk032.f11.f | SS | SS | SS | SS | SS |
| idv1c.pk032.f14.f | S | S | S | S | S |
| idv1c.pk032.i21.f | SS | SS | SS | SS | SS |
| idv1c.pk032.m9.f | S | S | S | S | S |
| idv1c.pk032.n18.f | SS | SS | SS | SS | SS |
| idv1c.pk032.p5.f | SS | SS | SS | SS | SS |
| idv1c.pk033.a15.f | S | S | S | S | S |
| idv1c.pk033.b14.f | S | S | S | S | S |
| idv1c.pk033.d24.f | SS | SS | SS | SS | SS |
| idv1c.pk033.j21.f | SS | SS | SS | SS | SS |
| idv1c.pk033.m3.f | S | S | S | S | S |
| idv1c.pk033.n10.f | S | S | S | S | S |
| idv1c.pk033.n18.f | S | S | S | S | S |
| idv1c.pk033.o9.f | SS | SS | SS | SS | SS |
| idv1c.pk033.p15.f | SS | SS | SS | SS | SS |
| idv1c.pk033.p16.f | SS | SS | SS | SS | SS |
| idv1c.pk034.e8.f | S | S | S | S | S |
| idv1c.pk034.i2.f | SS | SS | SS | SS | SS |
| idv1c.pk034.j6.f | SS | SS | SS | SS | SS |
| idv1c.pk034.p24.f | S | S | S | S | S |
| idv1c.pk035.f21.f | S | S | S | S | S |
| idv1c.pk035.g1.f | S | S | S | S | S |
| idv1c.pk035.h19.f | S | S | S | S | S |
| idv1c.pk035.i17.f | SS | SS | SS | SS | SS |
| idv1c.pk035.j4.f | S | S | S | S | S |
| idv1c.pk035.k18.f | SS | SS | SS | SS | SS |
| idv1c.pk035.m1.f | S | S | S | S | S |
| idv1c.pk035.o13.f | S | S | S | S | S |
| idv1c.pk036.a14.f | S | S | S | S | S |
| idv1c.pk036.e18.f | S | S | S | S | S |
| idv1c.pk036.f4.f | S | S | S | S | S |
| idv1c.pk036.f9.f | S | S | S | S | S |
| idv1c.pk036.i17.f | S | S | S | S | S |
| idv1c.pk036.i19.f | SS | SS | SS | SS | SS |
| idv1c.pk036.i20.f | S | S | S | S | S |
| idv1c.pk036.k23.f | S | S | S | S | S |

*columns in Table 3 represent replicate wells 1, 2, 3, and 4 and the average.

TABLE 4

Insect Bioassays Against Southern and Western Corn Root Worm.

| Clone name | Seq id | SCRW | | | | WCRW | | | | SCRW 2 | | | |
|---|---|---|---|---|---|---|---|---|---|---|---|---|---|
| | | Crude | 0.5 | 0.25 | 0.125 | Crude | 0.5 | 0.25 | 0.125 | Crude | 0.5 | 0.25 | 0.125 |
| idv1c.pk034.k22.f | DNA directed polymerase regulatory; prolactin;binding element | SS | S | S | S | D | D | S | S | SS | S | S | S |
| idv1c.pk002.c7.f | | SS | S | N | N | S | S | N | N | SS | N | N | N |
| idv1c.pk002.f18.f | cadherin like | S | N | N | N | S | N | N | N | S | N | N | N |
| idv1c.pk002.i23.f | mitochondrial NADH dehydrogenase Fe-S protein | S | N | N | N | S | S | S | S | S | S | N | N |
| idv1c.pk002.j24.f | Human DNA sequence from clone RPS-858M22 | S | S | N | N | N | N | N | N | S | S | N | N |
| idv1c.pk002.m16.f | conserved hypothetical protein | SS | N | N | N | SS | N | N | N | SS | S | N | N |
| idv1c.pk002.n13.f | 16s ribosomal RNA gene | S | N | N | N | SS | SS | N | N | S | S | N | N |
| idv1c.pk024.c7.f | conserved hypothetical protein | SS | S | N | N | SS | SS | N | N | SS | S | N | N |
| idv1c.pk024.j15.f | | SS | N | N | N | N | N | N | N | SS | N | N | N |
| idv1c.pk025.b17.f | cadherin like | SS | S | N | N | SS | SS | S | N | SS | S | N | N |
| idv1c.pk025.f3.f | alpha tubulin | SS | SS | S | S | SS | SS | N | N | SS | SS | S | S |
| idv1c.pk025.i8.f | chromaffin granule amine transporter | SS | S | S | S | SS | SS | SS | S | SS | S | N | S |
| idv1c.pk025.l17.f | Cytochrome b561 domain-containing protein 2 | S | S | N | N | S | S | N | N | S | S | N | N |
| idv1c.pk025.o24.f | ATP-dependent RNA helicase | N | N | N | N | SS | S | N | N | S | N | N | N |
| idv1c.pk025.p9.f | conserved insect hypothetical protein | S | N | N | N | N | N | N | N | S | N | N | N |
| idv1c.pk026.f20.f | NADH-ubiquinone oxidoreductase 24 kDa subunit | S | S | N | N | SS | N | N | N | S | S | N | N |
| idv1c.pk026.p8.f | Sec61 gamma subunit alpha | SS | N | N | N | SS | SS | S | S | SS | S | S | N |
| idv1c.pk026.p22.f | no hits | S | N | N | N | SS | S | N | N | S | N | N | N |
| idv1c.pk027.a14.f | conserved insect sequence | S | N | N | N | N | N | N | N | S | N | N | N |
| idv1c.pk027.g7.f | conserved hypothetical protein | SS | SS | S | S | S | S | S | S | SS | SS | S | S |
| idv1c.pk027.k23.f | low homology to zebrafish sequence | SS | N | N | N | SS | S | S | S | SS | N | N | N |
| idv1c.pk028.b17.f | highly similar to conserved drosophila sequence | SS | S | N | N | SS | SS | SS | SS | SS | S | N | N |
| idv1c.pk028.f11.f | | S | S | N | N | S | N | N | N | S | S | N | N |
| idv1c.pk029.c3.f | dynein heavy chain of insects | SS | N | N | N | S | S | S | S | SS | N | N | N |
| idv1c.pk029.f5.f | COP9 complex homolog subunit 6 | SS | S | N | N | SS | SS | SS | SS | SS | S | N | N |
| idv1c.pk029.j4.f | acyl-coa dehydrogenase | S | S | S | S | SS | SS | S | S | S | S | S | S |
| idv1c.pk030.b23.f | Lancl1 protein [Tribolium castaneum] | SS | S | N | N | SS | SS | SS | S | SS | S | S | N |
| idv1c.pk030.f9.f | no hits | S | N | N | N | S | N | N | N | S | S | N | N |
| idv1c.pk030.g11.f | aspartate aminotransferase | SS | SS | S | S | SS | N | N | N | SS | SS | S | S |
| idv1c.pk031.c20.f | low-density lipoprotein receptor, | SS | S | N | N | SS | SS | N | N | SS | S | N | N |
| idv1c.pk031.d1.f | chaperonin | SS | S | S | N | SS | SS | SS | S | SS | S | S | N |
| idv1c.pk031.j1.f | 1,4-dihydroxy-2-naphthoate octaprenyltransferase | S | N | N | N | N | N | N | N | S | N | N | N |
| idv1c.pk031.j6.f | no hits | S | N | N | N | SS | SS | SS | N | S | N | N | N |
| idv1c.pk031.p16.f | ribosomal protein S12 | S | S | S | S | SS | SS | SS | SS | S | S | S | S |
| idv1c.pk032.a16.f | DEAD box ATP-dependent RNA helicase | S | S | S | S | SS | SS | N | N | S | S | S | S |
| idv1c.pk032.f11.f | ribosomal protein L4e | SS | SS | SS | S | SS | SS | SS | N | SS | SS | SS | S |
| idv1c.pk032.i21.f | conserved hypothetical protein similar to p01-like | SS | S | S | S | SS | SS | S | N | SS | S | S | S |

TABLE 4-continued

Insect Bioassays Against Southern and Western Corn Root Worm.

| Clone name | Seq id | SCRW | | | | WCRW | | | | SCRW 2 | | | |
| --- | --- | --- | --- | --- | --- | --- | --- | --- | --- | --- | --- | --- | --- |
| | | Crude | 0.5 | 0.25 | 0.125 | Crude | 0.5 | 0.25 | 0.125 | Crude | 0.5 | 0.25 | 0.125 |
| idv1c.pk032.n18.f | protein | S | S | S | S | SS | SS | S | S | SS | S | S | S |
| idv1c.pk032.p5.f | no hits | S | S | S | S | SS | SS | S | N | S | S | S | S |
| idv1c.pk033.d24.f | sodium pump alpha subunit; | SS | S | N | N | N | N | N | N | SS | SS | S | N |
| idv1c.pk033.j21.f | proteasome subunit alpha type 6 | SS | S | S | N | SS | SS | SS | S | SS | S | S | N |
| idv1c.pk033.o9.f | similar to Uncharacterized protein ZK1236.4 [Acyrthosiphon pisum] | S | S | S | N | S | S | N | N | S | S | S | N |
| idv1c.pk033.p15.f | ribosomal protein L35Ae | SS | SS | S | N | S | S | N | N | SS | SS | SS | N |
| idv1c.pk033.p16.f | similar to ribosomal protein L10Ae | S | S | S | S | S | S | S | S | S | S | S | S |
| idv1c.pk034.i2.f | cadherin-like gene | S | N | N | N | SS | SS | SS | N | SS | S | N | N |
| idv1c.pk034.j6.f | conserved hypothetical protein | SS | S | N | N | S | S | S | N | SS | S | S | N |
| idv1c.pk035.j17.f | ryanodine receptor-like protein castaneum | N | N | N | N | SS | SS | N | N | S | N | N | N |
| idv1c.pk035.k18.f | conserved hypothetical protein | S | N | N | N | SS | S | N | N | S | N | N | N |
| idv1c.pk036.i19.f | predicted protein | SS | S | N | N | SS | S | S | N | SS | SS | SS | S |

TABLE 5

Insect Bioassays Against Southern and Western Corn Root Worm.

| Clone name | 1° assay result | 1st Confirmation | 2nd Confirmation | SCRW dose response #1 | | | | SCRW does response #2 | | | |
| --- | --- | --- | --- | --- | --- | --- | --- | --- | --- | --- | --- |
| | | | | Crude | 0.5 | 0.25 | 0.125 | Crude | 0.5 | 0.25 | 0.125 |
| idy1c.pk001.o20.f | S | SS | SS | S | N | N | N | S | N | N | N |
| idy1c.pk002.a20.f | S | SS | SS | S | N | N | N | N | N | N | N |
| idy1c.pk002.c15.f | S | S | N | SS | S | N | N | SS | SS | S | N |
| idy1c.pk002.i21.f | S | SS | SS | SS | S | N | N | SS | S | S | S |
| idy1c.pk024.b23.f | S | SS | SS | SS | N | N | N | S | S | N | N |
| idy1c.pk024.e1.f | S | S | S | S | S | N | N | S | S | N | N |
| idy1c.pk024.e24.f | S | S | S | S | S | N | N | S | N | N | N |
| idy1c.pk024.k17.f | S | S | S | SS | N | N | N | SS | SS | N | N |
| idy1c.pk024.m13.f | S | S | S | S | N | N | N | S | S | N | N |
| idy1c.pk024.n1.f | S | S | S | S | S | S | S | S | S | N | N |
| idy1c.pk024.o3.f | S | SS | SS | S | S | S | S | N | N | N | N |
| idy1c.pk025.a4.f | S | SS | S | S | S | N | N | S | S | N | N |
| idy1c.pk025.c5.f | S | N | N | N | N | N | N | S | N | N | N |
| idy1c.pk025.c231 | S | N | N | S | N | N | N | S | N | N | N |
| idy1c.pk025.d18.f | S | S | N | SS | SS | N | N | SS | SS | S | N |
| idy1c.pk025.d20.f | S | S | S | S | S | S | S | S | S | N | N |
| idy1c.pk025.f24.f | S | SS | SS | S | S | S | S | S | S | S | N |
| idy1c.pk025.j20.f | S | SS | SS | S | N | N | N | S | S | N | N |
| idy1c.pk025.l10.f | S | S | S | S | N | N | N | S | N | N | N |
| idy1c.pk026.a16.f | S | SS | SS | S | N | N | N | S | N | N | N |
| idy1c.pk026.b23.f | S | S | S | S | N | N | N | N | N | N | N |
| idy1c.pk026.d22.f | S | S | S | N | N | N | N | N | N | N | N |
| idy1c.pk026.e6.f | S | S | S | S | N | N | N | S | N | N | N |
| idy1c.pk026.g12.f | S | S | S | SS | S | N | N | SS | SS | N | N |
| idy1c.pk026.h15.f | S | N | N | S | N | N | N | N | N | N | N |
| idy1c.pk026.i12.f | S | N | N | N | N | N | N | N | N | N | N |
| idy1c.pk026.j18.f | S | S | N | S | N | N | SS | N | N | N | N |
| idy1c.pk026.k13.f | S | SS | SS | S | S | S | S | S | S | S | N |
| idy1c.pk027.b21.f | S | N | N | S | N | N | N | N | N | N | N |
| idy1c.pk027.c7.f | S | N | N | N | N | N | N | N | N | N | N |
| idy1c.pk027.k4.f | S | SS | SS | SS | N | N | N | SS | S | N | N |
| idy1c.pk027.p21.f | S | SS | SS | SS | N | N | N | SS | N | N | N |
| idy1c.pk028.b7.f | S | SS | SS | S | N | N | N | N | N | N | N |
| idy1c.pk028.c221 | S | SS | SS | SS | N | N | N | SS | S | N | N |
| idy1c.pk028.h6.f | S | SS | SS | SS | N | N | N | SS | N | N | N |
| idy1c.pk028.i16.f | S | N | N | S | N | N | N | S | N | N | N |

TABLE 5-continued

Insect Bioassays Against Southern and Western Corn Root Worm.

| Clone name | 1° assay result | 1st Confirmation | 2nd Confirmation | Crude | SCRW dose response #1 0.5 | 0.25 | 0.125 | Crude | SCRW dose response #2 0.5 | 0.25 | 0.125 |
|---|---|---|---|---|---|---|---|---|---|---|---|
| idy1c.pk028.m11.f | S | N | N | S | N | N | N | S | N | N | N |
| idy1c.pk028.o18.f | S | S | SS | S | S | S | S | S | S | S | N |
| idy1c.pk029.a17.f | S | S | S | S | S | S | S | S | N | N | N |
| idy1c.pk029.d16.f | S | S | S | S | S | S | S | S | S | S | S |
| idy1c.pk029.i22.f | S | S | S | SS | SS | S | S | SS | SS | S | N |
| idy1c.pk029.j20.f | S | S | 5 | SS | SS | 5 | 5 | SS | 5 | 5 | 5 |
| idy1c.pk029.k11.f | S | N | N | SS | S | S | N | SS | S | S | S |
| idy1c.pk029.l22.f | S | S | SS | S | S | N | N | S | N | N | N |
| idy1c.pk030.e10.f | S | S | S | SS | S | S | S | SS | S | S | S |
| idy1c.pk030.e21.f | S | S | S | SS | S | S | S | SS | SS | S | S |
| idy1c.pk030.h13.f | S | S | S | S | S | S | S | SS | S | S | S |
| idy1c.pk030.h23.f | S | SS | S | SS | SS | S | S | SS | S | S | N |
| idy1c.pk030.l9.f | S | N | N | S | N | N | N | S | N | N | N |
| idy1c.pk030.m22.f | S | N | N | S | N | N | N | S | N | N | N |
| idy1c.pk030.o7.f | S | S | SS | SS | S | N | N | SS | S | N | N |
| idy1c.pk031.a11.f | S | S | S | SS | S | S | S | SS | S | S | S |
| idy1c.pk031.e16.f | S | S | S | S | N | N | N | N | N | N | N |
| idy1c.pk031.g2.f | S | SS | SS | SS | S | S | N | SS | S | S | N |
| idy1c.pk031.g22.f | S | S | S | SS | N | N | N | SS | S | N | N |
| idy1c.pk031.i13.f | S | SS | SS | SS | S | S | S | SS | N | N | N |
| idy1c.pk031.m3.f | S | S | S | SS | S | S | N | SS | S | S | N |
| idy1c.pk032.b4.f | S | S | S | SS | S | N | N | SS | S | N | N |
| idy1c.pk032.e16.f | S | S | S | S | S | S | S | S | S | N | N |
| idy1c.pk032.f14.f | S | N | N | S | N | N | N | S | N | N | N |
| idy1c.pk032.m9.f | S | SS | SS | SS | N | N | N | SS | S | N | N |
| idy1c.pk033.a15.f | S | N | N | N | N | N | N | S | N | N | N |
| idy1c.pk033.b14.f | S | N | N | S | N | N | N | S | N | N | N |
| idy1c.pk033.m3.f | S | S | S | SS | N | N | N | SS | N | N | N |
| idy1c.pk033.n10.f | S | SS | SS | S | S | S | S | S | S | N | N |
| idy1c.pk033.n18.f | S | SS | SS | S | N | N | N | S | N | N | N |
| idy1c.pk034.e8.f | S | S | S | S | N | N | N | S | N | N | N |
| idy1c.pk034.p24.f | S | S | N | S | S | S | N | S | N | N | N |
| idy1c.pk035.f21.f | S | S | S | S | S | S | S | S | S | S | N |
| idy1c.pk035.g1.f | S | S | N | S | N | N | N | S | N | N | N |
| idy1c.pk035.h19.f | S | SS | SS | S | N | N | N | N | N | N | N |
| idy1c.pk035.j4.f | S | SS | SS | SS | S | S | S | SS | SS | S | S |
| idy1c.pk035.m1.f | S | S | S | S | S | S | S | S | S | S | N |
| idy1c.pk035.o13.f | S | S | S | S | N | N | S | N | N | N | N |
| idy1c.pk036.a14.f | S | S | N | SS | 5 | 5 | N | SS | 5 | 5 | N |
| idy1c.pk036.e18.f | S | S | S | S | S | S | N | S | S | S | N |
| idy1c.pk036.f4.f | S | S | S | S | S | S | S | S | S | N | N |
| idy1c.pk036.f9.f | S | S | S | SS | S | S | S | SS | S | S | N |
| idy1c.pk036.i17.f | S | S | S | S | S | S | S | S | S | S | S |
| idy1c.pk036.i20.f | S | S | S | SS | SS | N | N | SS | SS | S | N |
| idy1c.pk036.k23.f | S | S | S | S | S | N | N | S | S | S | N |

Example 8

Expression of Silencing Elements in Maize

The silencing elements set forth in SEQ ID NO: 13, 40, 72 and 73 were expressed in a maize plant as hairpins and the plants were tested for insecticidal activity against corn root worms. The sequences set forth in SEQ ID NO: 13, 40, 72 and 73 were engineered to be expressed as a hairpin. The constructs comprised the following components: the maize ubiquitin promoter/5'UTR/1$^{st}$ intron operably linked to one of SEQ ID NO: 13, 40, 72 and 73::the ADH1 intron:: complement of the corresponding SEQ ID NO. Plasmids PHP41136, PHP41567, PHP41992, PHP42000 were generated as summarized below in Table 6. PHP19288 was a control plasmid which lacked a silencing element.

TABLE 6

| SEQ ID NO of silencing element | SEQ ID NO of construct w/ promoter and silencing element | Clone name of silencing element | Plasmid name |
|---|---|---|---|
| 13 | 242 | idv1c.pk002.j17.f | PHP41136 |
| 40 | 243 | idv1c.pk013.h1.f | PHP41567 |
| 72 | 244 | idv1c.pk017.d14.f | PHP41992 |
| 73 | 245 | idv1c.pk017.e22.f | PHP42000 |

Maize plants were transformed with plasmids PHP41136, PHP41567, PHP41992, PHP42000, and PHP19288 (control lacking silencing element) and plants expressing the silencing elements denoted in Table 6 were transplanted from 272V plates into greenhouse flats containing Fafard Superfine potting mix. Plants were infected (100 eggs per plant) 14 days post greenhouse send date and a second infestation (150 eggs per plant) was performed 14 days later. The scoring for insecticidal activity was done 14 days later (28 days post first infection). Each of SEQ ID NO: 13, 40, 72 and 73 had insecticidal activity in this assay.

Figure 2:
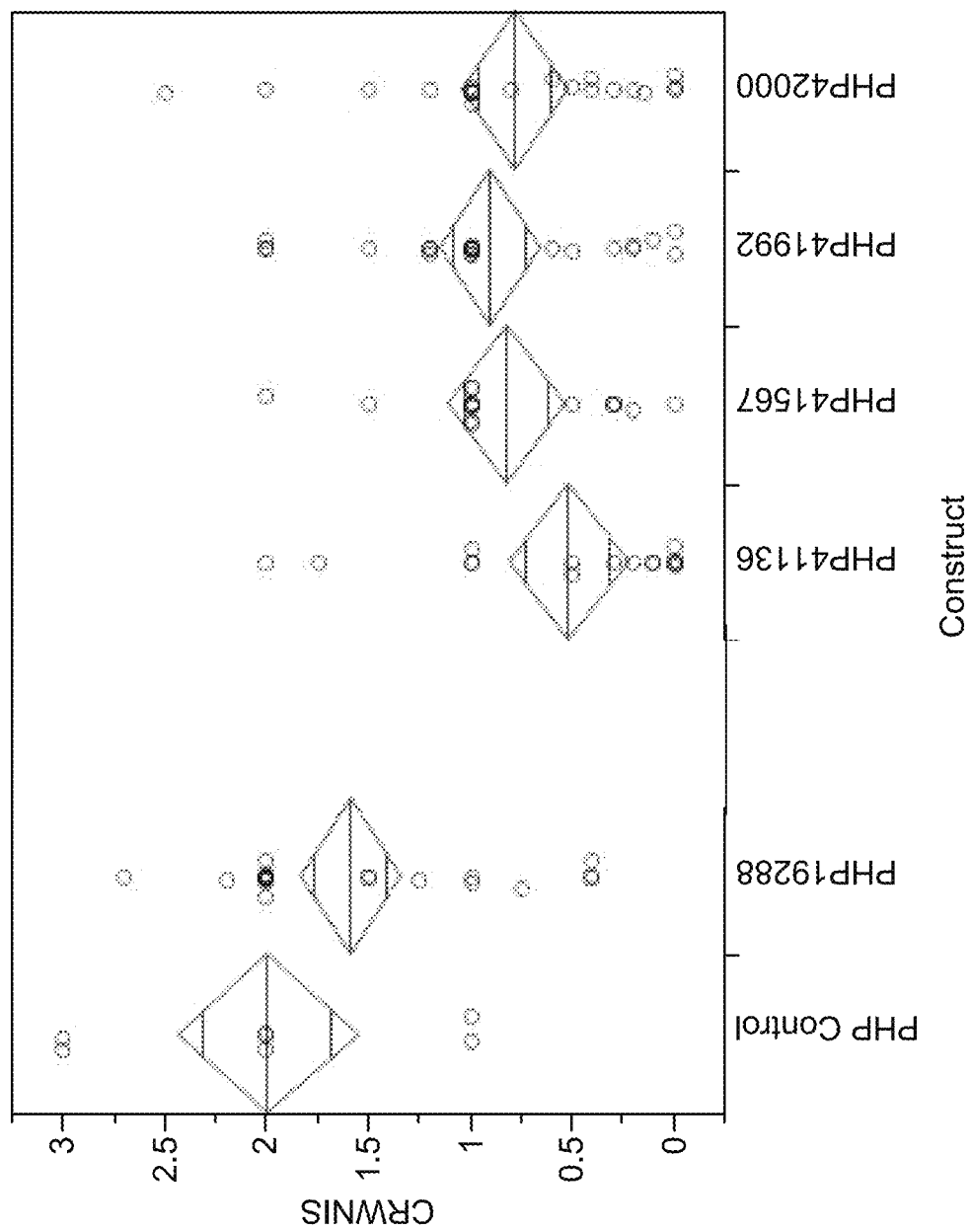
FIG. 2 shows a corn rootworm whole plant assay. The data demonstrates that expression of SEQ ID NO: 13 (clone idv1c.pk002.j17.f); SEQ ID NO: 40 (clone idv1c.pk013.h1.f); SEQ ID NO:72 (clone idv1c.pk017.d14.f); and SEQ ID NO:73 (clone idv1c.pk017.e22.f) as a hairpin in a maize plant produces a maize plant, which when ingested by corn root worm, has insecticidal activity. CRWNIS refers to corn root worm nodal injury score. PHP19288 is a control plasmid lacking the silencing element.

As shown in FIG. 2, significant efficacy was shown with the PHP41136, PHP41567, PHP41992, and PHP42000 constructs. No significant difference between PHP41136 and the PHP positive control was seen. Table 7 provides a summary of the data shown in FIG. 2.

TABLE 7

| Oneway Anova | |
|---|---|
| Summary of Fit | |
| Rsquare | 0.440885 |
| Adj Rsquare | 0.412145 |
| Root Mean Square Error | 0.654125 |
| Mean of Response | 1.270885 |
| Observations (or Sum Wgts) | 226 |

| Analysis of Variance | | | | |
|---|---|---|---|---|
| Source | DF | Sum of Squares | Mean Square | F Ratio | Prob > F |
| Construct | 11 | 72.20360 | 6.56396 | 15.3407 | <.0001* |
| Error | 214 | 91.56622 | 0.42788 | | |
| C. Total | 225 | 163.76982 | | | |

| Means for Oneway Anova | | | | | |
|---|---|---|---|---|---|
| Level | Number | Mean | Std Error | Lower 95% | Upper 95% |
| PHP Control | 20 | 1.96000 | 0.14627 | 1.672 | 2.2483 |
| PHP19288 | 22 | 1.59545 | 0.13946 | 1.321 | 1.8703 |
| PHP41136 | 16 | 0.52813 | 0.16353 | 0.206 | 0.8505 |
| PHP41567 | 17 | 0.82941 | 0.15865 | 0.517 | 1.1421 |
| PHP41992 | 23 | 0.91304 | 0.13639 | 0.644 | 1.1819 |
| PHP42000 | 21 | 0.78810 | 0.14274 | 0.507 | 1.0695 |

Std Error uses a pooled estimate of error variance

Example 9

Insect Bioassays 2.5 μl of an in-vitro transcription reaction which synthesized one of the sequences set forth in SEQ ID NO: 13, 40, 72 and 73 was added to a given well of a 96 well microtiter plate. 25 ul of molten lowmelt western corn rootworm diet were added to the sample and shaken on an orbital shaker to mix the sample and diet. Once the diet solidified, neonate rootworms were added to the well. An average of 5 neonates was added to each well. After the plate was infested, the plate was sealed with mylar and a single hole was punched in the mylar over each well to allow air exchange. 4 replicate wells were produced for each sample. The assay was scored for activity 7 days post infestation. Dose response assays were performed with the following rates: 50, 25, 12.5, 6.5, 3.2, and 1.5 ppm. Table 8 provides insecticidal bioassay data employing the southern corn rootworm. The possible scores are dead (D), severely stunted (SS; little or no growth but alive), stunted (S; growth to second instar but not equivalent to controls), contaminated (c), or no activity.

TABLE 8

Comparison of T0 activity and dsRNA assay results

| | SCRW | | | | | | WCRW equivalent to 5 ng/cm2 | | | | | | | T0 Gene |
|---|---|---|---|---|---|---|---|---|---|---|---|---|---|---|
| Gene id | 50 ppm | 25 ppm | 12.5 ppm | 6.5 ppm | 3.2 ppm | 1.5 ppm | 50 ppm | 25 ppm | 12.5 ppm | 6.5 ppm | 3.2 ppm | 1.5 ppm | PHP# | testing results |
| Proteosome subunit alpha type 3 | SS | SS | SS | | | | SS | SS | SS | SS | SS | SS | 41136 | good |
| Low homology to sea urchin reverse transcriptase | N | N | N | N | N | N | SS | SS | SS | SS | SS | SS | 41129 | poor |
| Mosquito conserved hypo. Prot. | SS | SS | SS | SS | SS | SS | SS | SS | SS | SS | SS | SS | 41124 | poor |
| Syntaxin | ss | ss | ss | N | N | N | N | N | N | N | N | N | 41558 | poor |
| Ribosomal protein L27E | SS | SS | SS | SS | SS | SS | S | S | N | N | N | N | 41567 | good |
| No hits | SS | SS | S | N | N | N | S | N | N | N | N | N | 41549 | poor |
| Proteosome beta subunit | SS | SS | SS | SS | SS | SS | S | S | S | S | N | N | 41999 | poor |
| Cadherin like | S | S | S | S | S | S | SS | SS | SS | SS | S | S | 41992 | good |
| Ribosome biogenesis regulatory homolog | S | S | N | N | N | N | SS | SS | SS | SS | S | S | 42000 | good |

Example 10

Expression of Silencing Elements in Maize

The silencing elements set forth in the various SEQ ID NOs denoted in Table 9 were expressed in a maize plant (via the FASTcom high thoughput screening methods) as hairpins and the various plants were tested for insecticidal activity against corn root worms. The sequences set forth in the SEQ ID NOs denoted in Table 9 were engineered to be expressed as a hairpin. The constructs comprised the following components: the maize ubiquitin promoter/5'UTR/ 1$^{st}$ intron operably linked SEQ ID NO set forth in Table 9::ADH1 intron::complement of the SEQ ID NO: set forth in Table 9. The various plasmids having these silencing expression constructs were generated as summarized below in Table 9.

TABLE 9

| Row Labels | SEQ ID NO making up one stem of the hairpin | Clone name of silencing element | SEQ ID NO of full length expression vector | Weak Pass | # pass | % tested | % rtPCR (+) | % actives of rtPCR + | Diet assay activity |
|---|---|---|---|---|---|---|---|---|---|
| PHP44742 | nt 1-380 of SEQ ID NO: 45 | idy1c.pk014.b17.f | 248 | 100.0% | 0.0% | 19 | 90 | 100 | s |
| PHP44107 | 8 | idy1c.pk001.e9.f | 237 | 94.7% | 0.0% | 19 | 95 | 100 | ss |
| PHP44118 | 15 | idy1c.pk003.d6.f | 246 | 55.0% | 10.0% | 20 | 70 | 100 | s |
| PHP44747 | nt 1-266 of SEQ ID NO: 50 | idy1c.pk014.k23.f | 251 | 40.0% | 13.3% | 15 | 67 | 50 | ss |
| PHP44116 | 18 | idy1c.pk003.j4.f | 247 | 31.6% | 10.5% | 19 | 25 | 100 | ss |
| PHP44109 | 29 | idy1c.pk004.f20.f | 250 | 30.0% | 10.0% | 20 | 58 | 63 | SS |
| PHP44750 | nt 1-675 of SEQ ID NO: 37 | idy1c.pk013.b11.f | 249 | 30.0% | 0.0% | 10 | 50 | 33 | s |
| PHP44119 | 9 | idy1c.pk001.m5.f |  | 26.3% | 0.0% | 19 | No data | No data | ss |
| PHP44117 | 14 | idy1c.pk002.n13.f |  | 26.3% | 5.3% | 19 | 0 | 0 | s |
| PHP44744 | nt 1-132 of SEQ ID NO: 40 | idy1c.pk013.h1.f | 243 | 21.1% | 5.3% | 19 | 68 | 38 | s |
| PHP44748 | nt 16-585 of SEQ ID NO: 47 | idy1c.pk014.d11.f | 252 | 17.6% | 5.9% | 17 | 83 | 25 | s |
| PHP44211 | 54 | idy1c.pk014.n23.f |  | 15.0% | 0.0% | 20 | No data | No data | s |
| PHP44208 | 32 | idy1c.pk004.n6.f |  | 12.5% | 25.0% | 8 | No data | No data | s |
| PHP45641 | 92 | idy1c.pk019.l7.f |  | 12.5% | 0.0% | 8 | 50 | 12 | s |
| PHP44115 | 12 | idy1c.pk002.f20.f |  | 10.0% | 10.0% | 20 | No data | No data | ss |
| PHP44122 | 27 | idy1c.pk004.b12.f |  | 10.0% | 0.0% | 20 | No data | No data | ss |
| PHP44120 | 25 | idy1c.pk003.o22.f |  | 10.0% | 15.0% | 20 | No data | No data | s |
| PHP44121 | 21 | idy1c.pk003.l1.f |  | 10.0% | 5.0% | 20 | No data | No data | s |
| PHP44746 | 46 | idy1c.pk014.c14.f |  | 9.1% | 18.2% | 11 | 40 | 25 | s |
| PHP44976 | 66 | idy1c.pk016.h19.f |  | 7.7% | 0.0% | 13 | 92 | 8 | ss |
| PHP44213 | 23 | idy1c.pk003.m10.f |  | 5.6% | 0.0% | 18 | No data | No data | s |
| PHP44113 | 26 | idy1c.pk003.p13.f |  | 5.3% | 5.3% | 19 | No data | No data | ss |
| PHP44114 | 24 | idy1c.pk003.o13.f |  | 5.3% | 5.3% | 19 | No data | No data | s |
| PHP44745 | 33 | idy1c.pk004.o4.f |  | 5.3% | 0.0% | 19 | 76 | 0 | s |
| PHP44210 | 11 | idy1c.pk002.c5.f |  | 5.0% | 0.0% | 20 | No data | No data | ss |
| PHP44106 | 10 | idy1c.pk001.n1.f |  | 5.0% | 15.0% | 20 | No data | No data | s |
| PHP44112 | 28 | idy1c.pk004.d17.f |  | 0.0% | 0.0% | 17 | No data | No data | ss |
| PHP44216 | 20 | idy1c.pk003.j20.f |  | 0.0% | 0.0% | 12 | No data | No data | ss |
| PHP44220 | 13 | idv1c.pk002.j17.f |  | 0.0% | 0.0% | 20 | No data | No data | ss |
| PHP44209 | 56 | idy1c.pk015.a16.f |  | 0.0% | 0.0% | 14 | No data | No data | s |
| PHP44212 | 38 | idy1c.pk013.c21.f |  | 0.0% | 0.0% | 20 | No data | No data | s |
| PHP44215 | 39 | idy1c.pk013.d22.f |  | 0.0% | 0.0% | 18 | No data | No data | s |
| PHP44217 | 53 | idy1c.pk014.n16.f |  | 0.0% | 0.0% | 13 | No data | No data | s |
| PHP44221 | 48 | idy1c.pk014.f3.f |  | 0.0% | 0.0% | 10 | No data | No data | s |
| PHP44743 | 48 | idy1c.pk013.k1.f |  | 0.0% | 0.0% | 20 | 37 | 0 | s |
| PHP44756 | 49 | idy1c.pk014.j2.f |  | 0.0% | 0.0% | 20 | 0 | 0 | s |
| PHP44757 | 61 | idy1c.pk015.p2.f |  | 0.0% | 0.0% | 20 | 80 | 0 | s |
| PHP44975 | 65 | idy1c.pk016.h15.f |  | 0.0% | 0.0% | 5 | 31 | 0 | s |
| PHP44977 | 68 | idy1c.pk016.j15.f |  | 0.0% | 0.0% | 6 | 30 | 0 | s |
| PHP44982 | 75 | idy1c.pk017.h14.f |  | 0.0% | 0.0% | 11 | 55 | 0 | s |
| PHP44989 | 84 | idy1c.pk018.fl9.f |  | 0.0% | 0.0% | 9 | 45 | 0 | s |
| PHP44991 | 87 | idy1c.pk018.h21.f |  | 0.0% | 0.0% | 12 | 60 | 0 | s |
| PHP44992 | 91 | idy1c.pk019.k3.f |  | 0.0% | 0.0% | 5 | 25 | 0 | s |
| PHP45629 | 99 | idy1c.pk020.l3.f |  | 0.0% | 0.0% | 13 | 80 | 0 | s |
| PHP45635 | 104 | idy1c.pk021.h12.f |  | 0.0% | 0.0% | 6 | 30 | 0 | s |
| PHP45636 | 98 | idy1c.pk020.k19.f |  | 0.0% | 0.0% | 14 | 70 | 0 | s |
| PHP45638 | 97 | idy1c.pk020.i24.f |  | 0.0% | 0.0% | 7 | 35 | 0 | s |
| PHP45640 | 95 | idy1c.pk020.g17.f |  | 0.0% | 0.0% | 15 | 75 | 0 | s |
| PHP44111 | 17 | idy1c.pk003.f9.f |  | 0.0% | 0.0% | 19 | No data | No data | s |
| PHP44204 | 16 | idy1c.pk003.f8.f |  | 0.0% | 0.0% | 20 | No data | No data | s |
| PHP44205 | 34 | idy1c.pk004.o9.f |  | 0.0% | 0.0% | 13 | No data | No data | s |
| PHP44206 | 43 | idy1c.pk014.a19.f |  | 0.0% | 0.0% | 17 | No data | No data | s |
| PHP44207 | 22 | idy1c.pk003.m1.f |  | 0.0% | 0.0% | 20 | No data | No data | s |
| PHP44214 | 41 | idy1c.pk013.h14.f |  | 0.0% | 0.0% | 18 | No data | No data | s |

-continued

| Row Labels | SEQ ID NO making up one stem of the hairpin | Clone name of silencing element | SEQ ID NO of full length expression vector | Pass | Weak pass | # tested | % rtPCR (+) | % actives of rtPCR + | Diet assay activity |
|---|---|---|---|---|---|---|---|---|---|
| PHP44218 | 19 | idy1c.pk003.j6.f | | 0.0% | 0.0% | 20 | No data | No data | s |
| PHP44219 | 52 | idy1c.pk014.m13.f | | 0.0% | 0.0% | 20 | No data | No data | s |
| PHP44222 | 31 | idy1c.pk004.l15.f | | 0.0% | 5.6% | 18 | No data | No data | s |
| PHP44223 | 36 | idy1c.pk013.a15.f | | 0.0% | 5.3% | 19 | No data | No data | s |
| PHP44739 | 44 | idy1c.pk014.b9.f | | 0.0% | 0.0% | 4 | 0 | No data | s |
| PHP44741 | 51 | idy1c.pk014.m5.f | | 0.0% | 0.0% | 3 | 0 | 0 | s |
| PHP44749 | 57 | idy1c.pk015.b8.f | | 0.0% | 0.0% | 3 | 0 | 0 | s |
| PHP44752 | 60 | idy1c.pk015.n19.f | | 0.0% | 0.0% | 10 | 70 | 0 | s |
| PHP44753 | 71 | idy1c.pk017.c3.f | | 0.0% | 0.0% | 19 | 85 | 0 | s |
| PHP44973 | 59 | idy1c.pk015.l13.f | | no data | no data | 0 | 24 | No data | s |
| PHP44978 | 69 | idy1c.pk016.k9.f | | no data | no data | 0 | 10 | No data | s |
| PHP45630 | 102 | idy1c.pk021.d22.f | | no data | no data | 0 | 5 | No data | s |
| PHP45631 | 105 | idy1c.pk021.m20.f | | no data | no data | 0 | 30 | No data | s |
| PHP45637 | 96 | idy1c.pk020.17.f | | no data | no data | 0 | 15 | No data | s |
| PHP45639 | 94 | idy1c.pk020.b11.f | | no data | no data | 0 | 15 | No data | s |

Maize plants were transformed with PHP plasmids and plants expressing the silencing elements denoted in Table 9 were transplanted from 272V plates into greenhouse flats containing Fafard Superfine potting mix. Approximately 10 to 14 days after transplant, plants (now at growth stage V2-V3) were transplanted into treepots containing Fafard Superfine potting mix. At 14 days post greenhouse send date, plants were infested with 100 eggs of western corn root worms (WCRW)/plant. For later sets, a second infestation of 100 eggs WCRW/plant was done 14 days after the first infestation and scoring was at 14 days after the second infestation. 21 days post infestation, plants were scored using CRWNIS. Those plants with a score of ≤0.5 are transplanted into large pots containing SB300 for seed. "Pass" as denoted in Table 9 is a Nodal injury score of 0.2 to 0. "Weak pass" as denoted in Table 9 is a score from >0.2 to 0.75 which was the cut off for advancing an event. "% rtPCR" as denoted in Table 9 is the percent of the 20 events with demonstrated expression of the hairpin as determined by rtPCR. "% actives of rtPCR" as denoted in Table 9 is the percent of rtPCR positives that also passed the CRWNIS test. So this last number could be 100% even if only 10 of 20 events were rtPCR positive if all 10 also passed the CRWNIS test. The "diet assay activity" summarizes the data previously presented herein denoting either stunted (s) or severely stunted (ss) activity when the hairpins mixed with the CRW diet and fed directly to the bugs.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide comprising a heterologous promoter operably linked to a polynucleotide sequence encoding a double stranded RNA, wherein the double stranded RNA targets a Coleopteran plant pest target sequence, and wherein the Coleopteran plant pest target sequence comprises:

(a) the nucleotide sequence comprising SEQ ID NO: 73 or the full length complement thereof; or (b) the nucleotide sequence comprising at least 90% sequence identity to SEQ ID NO: 73 or the full length complement thereof; and wherein said double stranded RNA has insecticidal activity against a Coleopteran plant pest.

2. The isolated polynucleotide of claim 1, wherein said Coleopteran plant pest is a *Diabrotica* plant pest.

3. An expression cassette comprising the polynucleotide of claim 1.

4. The expression cassette of claim 3, wherein said double stranded RNA comprises a hairpin RNA.

5. The expression cassette of claim 3, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the polynucleotide.

6. A host cell comprising a heterologous expression cassette of claim 3.

7. A plant cell having stably incorporated into its genome a heterologous polynucleotide encoding a double stranded RNA, wherein the double stranded RNA targets a Coleopteran plant pest target nucleotide sequence, wherein the Coleopteran plant pest target nucleotide sequence comprises:

a) the nucleotide sequence as set forth in SEQ ID NO: 73 or the full length complement thereof; or, b) a nucleotide sequence comprising at least 90% sequence identity to SEQ ID NO: 73 or the full length complement thereof;

wherein the double stranded RNA, when ingested by a Coleopteran plant pest, reduces the level of a target sequence in said Coleopteran plant pest and thereby controls the Coleopteran plant pest.

8. The plant cell of claim 7, wherein the Coleopteran plant pest is a *Diabrotica* plant pest.

9. The plant cell of claim 7, wherein said plant cell comprises an expression cassette capable of expressing the heterologous polynucleotide encoding the dsRNA.

10. The plant cell of claim 7, wherein said double stranded RNA is a hairpin RNA.

11. The plant cell of claim 7, wherein said heterologous polynucleotide is operably linked to a heterologous promoter.

12. The plant cell of claim 7, wherein said plant cell is from a monocot.

13. The plant cell of claim 12, wherein said monocot is maize, barley, millet, wheat or rice.

14. The plant cell of claim 7, wherein said plant cell is from a dicot.

15. The plant cell of claim 14, wherein said plant cell is soybean, canola, alfalfa, sunflower, safflower, tobacco, *Arabidopsis*, or cotton.

16. A plant or plant part comprising a plant cell of claim 7.

17. A transgenic seed comprising the heterologous polynucleotide comprising the double stranded RNA of claim 7.

18. A method for controlling a Coleopteran plant pest comprising feeding to a Coleopteran plant pest a composition comprising a double stranded RNA, wherein said double stranded RNA targets a Coleopteran plant pest having a nucleotide sequence comprising at least 90% sequence identity to SEQ ID NO: 73, or the full length complement thereof, and wherein said double stranded RNA has insecticidal activity against said Coleopteran plant pest.

19. The method of claim 18, wherein said Coleopteran plant pest is a *Diabrotica* plant pest.

20. The method of claim 19, wherein said *Diabrotica* plant pest is *D. virgifera virgifera, D. speciosa, D. barberi*, or *D. undecimpunctata howardi.*

* * * * *

21. The method of claim 18, wherein said composition comprises a plant or plant part having stably incorporated into its genome a polynucleotide encoding the double stranded RNA.

22. The method of claim 18, wherein said double stranded RNA comprises a hairpin RNA.

23. The method of claim 21, wherein said polynucleotide is operably linked to a heterologous promoter.

24. The method of claim 21, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the double stranded RNA.

25. The method of claim 21, wherein said plant is a monocot.

26. The method of claim 25, wherein said monocot is maize, barley, millet, wheat or rice.

27. The method of claim 21, wherein said plant is a dicot.

28. The method of claim 27, wherein said plant is soybean, canola, alfalfa, sunflower, safflower, tobacco, *Arabidopsis*, or cotton.

* * * * *

SEQUENCE LISTING

```
<160> NUMBER OF SEQ ID NOS: 252

<210> SEQ ID NO 1
<211> LENGTH: 1442
<212> TYPE: DNA
<213> ORGANISM: Diabrotica virgifera virgifera
<220> FEATURE:
<221> NAME/KEY: misc_feature
<222> LOCATION: 189, 190, 191, 192, 193, 194, 195, 196, 197, 198, 199,
      200, 201, 202, 203, 204, 205, 206, 207, 208, 209, 210, 211, 212,
      213, 214, 215, 216, 217, 218, 219, 220, 221, 222, 223, 224,
      225, 226, 227, 228
<223> OTHER INFORMATION: n = A,T,C or G

<400> SEQUENCE: 1
gcacgaggcg tcaagcaagg ccagtcagtg aaaaattacc tgccaaccat cctctgctta         60
caggacagcg tgtacttgat gctcttttcc catgtgtaca gggtggtact actgccattc        120
ccggagcttt cggttgtgga aaaactgtaa tttcacaatc tctttccaaa tattccaact        180
ctgatgtcnn nnnnnnnnn nnnnnnnnnn nnnnnnnnn nnnnnnnct gaagtattga        240
```

```
gagatttccc tgaattgact gttgaaattg acgggcacac tgaatctatt atgaaacgta      300
ccgcattggt cgccaacaca tctaacatgc ctgtagctgc tcgtgaagct tctatctata      360
ctggtattac tcttcctgaa tacttccgtg atatgggtta caacgtatct atgatggctg      420
actcgacatc acgttgggcc gaagctttga gagaaatttc aggtcgtttg gctgaaatgc      480
ctgccgattc cggttatccg gcttacttag gtgcccgttt ggcttccttc tacgaacgtg      540
ctggtcgcgt taaatgttta ggtaatccag acagagaagg atccgtttca attgtaggag      600
ccgtatcacc tcctggtggt gatttctcag atcctgttac cactgctact cttggtattg      660
tacaggtgtt ctggggtttg acaagaaaac ttgcccaacg taagcacttc ccttcagtag      720
actggcttgg atcatattcc aaatatttaa gagcattgga cgacttttat gacaaaaact      780
tccaagagtt tattcctctt agaaccaaag ttaaggaaat tcttcaggaa gaagatgatc      840
tagccgaaat tgtgcagctg gtaggtaaag catctctggc agaaacggac aaaatcacct      900
tggaaattgc caggcttctt aaagaagatt tcttgcaaca aaactcatac tcttcttatg      960
acagattctg tccattctat aaaactgtcg gtatgttgag aaacatgatc ggtttgtacg     1020
acatggcgag acacgctgta gaatcaaccg cacaatcaga aataagatca cttggaacg      1080 taataagaga ttcaatgagt ggaattttat atcaacttag cagtatgaaa tttaaggatc     1140
ccgtaaaaga tggtgaagct aaaatcaagg cagattttga tcaattatat gaagatattc     1200
agcaggcctt cagaaactta agagattaaa tcttttaag gaattttcc tattttgttc      1260 atcagtgtaa gtttaaaaat atagcgatat ttatcaaaaa gaataataag gcctctatcc      1320
ctcacttctg tgaatattaa tatggccgta ctaaagatag taactaaaga taggttttct      1380
cttttttgat attatcctgt acaaaataaa ttatgtaaat tgttaaaaaa aaaaaaaaaa      1440
aa                                                                     1442

<210> SEQ ID NO 2
<211> LENGTH: 1098
<212> TYPE: DNA
<213> ORGANISM: Diabrotica virgifera virgifera

<400> SEQUENCE: 2
gcccaacgta agcacttccc ttcagtagac tggcttggat catattccaa atatttaaga       60
gcattggacg acttttatga caaaaacttc aagagtttta ttcctcttag aaccaaagtt      120
aaggaaattc ttcaggaaga agatgatcta gccgaaattg tgcagctggt aggtaaagca      180
tctctggcag aaacggacaa aatcaccttg gaaattgcca ggcttcttaa gaagatttc       240 ttgcaacaaa actcatactc ttcttatgac agattctgtc cattctataa aactgtcggt      300
atgttgagaa acatgatcgg tttgtacgac atggcgagac acgctgtaga atcaaccgca      360
caatcagaaa taagatcac ttggaacgta taagagatt caatgagtgg aattttatat        420
caacttagca gtatgaaatt taaggatccc gtaaaagatg gtgaagctaa atcaaggca       480 gattttgatc aattatatga agatattcag caggccttca gaaacttaga agattaaatc      540
tttttaagga attttcccta ttttgttcat cagtgtaagt ttaaaaatat agcgatattt      600
atcaaaaaga ataataaggc ctctatccct cacttctgtg aatattaata tggccgtact      660
aatgatagta actaaagata ggttttctct ttttgatat tatcctgtac aaaataaatt       720
atgtaaattg ttgaatatgt gtatagtttt tttgggtgag ggtacagtgc ttattaaata      780
ctttttaaac atttttccg ccattccaat tactattaag ttttttcgtt ttaatacttt       840
tttaaatata caggtgctta atatcgttta tattttcagt attacttggt tttcttcatg      900
```

| | | |
|---|---|---|
| taaattgttt taaatttttc ttttaccctt ttaatcttgt atattacatt acccaattaa | 960 |
| agttaattgt acagattaag ataaacgagt atcttataac atctattaga ttgttagaat | 1020 |
| caataaatgt agtgtaattg ttctgttttg aacaaataaa tgcatcatta ttgttgttta | 1080 |
| aaaaaaaaaa aaaaaaaa | 1098 |

<210> SEQ ID NO 3
<211> LENGTH: 1766
<212> TYPE: DNA
<213> ORGANISM: Diabrotica virgifera virgifera

<400> SEQUENCE: 3

| | | |
|---|---|---|
| tttttatccc gtgagatatt tttgcagtcc ttttaataaa attcttcata attcaccatg | 60 |
| aagggctgcg ttttcaacat cgacaacggt tatttggaag gcctgtgtcg tggctttaaa | 120 |
| tgtgggatcc tgaaacaatc cgattatttg aatttggtcc agtgtgaaac tcttgaagat | 180 |
| ttaaaactgc acttgcaagg cactgactat ggaactttt tggccaatga accttcacct | 240 |
| ttgtcagtat ccgtcatcga ttcaagactt cgagaaaaac tcgtgattga gttccagcac | 300 |
| atgcgtaacc aagcagtaga gcctctctcg acatttatgg acttcattac ctacagttac | 360 |
| atgatcgaca acataatttt gcttattaca ggaactcttc accagagacc aatcagtgaa | 420 |
| ttaatcccta atgtcaccc tctaggtagc ttcgagcaaa tggaagccat ccacgtagct | 480 |
| gctactccag ctgagttata caacgctgta ttggtggaca ccaccttgc tccattcttc | 540 |
| gttgattgca tcagtgaaca agatttggat gaaatgaaca ttgaaattat cagaaacacc | 600 |
| ttatacaaag cttacttgga agcatttat accttctgca aggaaattgg aggtactact | 660 |
| gccgatagca tgtgtgaaat tttggctttt gaggcagata gacgtgctat tattattact | 720 |
| atcaactcgt ttggcactga attaagcaaa gatgaccgtg ctaagttgta ccctcgctgt | 780 |
| ggaagactca accccgatgg tttggctgct ctagtgagag ccgaggacta cgaccaagtt | 840 |
| aaagcagttg ctgaatacta cgctgaatat tccaaactgt ttgaaggagc tggcaacaac | 900 |
| ccgggagaca aaacattgga agacaaattc tttgaatacg aagtacgtct taacatcaat | 960 |
| gctttcatgc aacagtttca ctttggggtg ttctactctt acttgaaatt gaaggaacag | 1020 |
| gaatgcagaa atattgtatg gattgctgaa tgtgtagctc aaaaacacag ggctaaaatc | 1080 |
| gataactaca tcccaatatt ctaaggaat ttcttgtttg cactattgtt tgcattccat | 1140 |
| ttggctcatt tagttcttag tgtcagtaag tggaattatc aaaagtatca gttttatga | 1200 |
| tcagatgta ctattcagac cttcagacaa atccagttag tacaatgttt tcgtttcaca | 1260 |
| tttattatca actacatctt tcagtcgtcc aagattgtta tgaaattaaa tatacattaa | 1320 |
| atgtgttgat gttttaacaa tacatagcaa atccctcaaaa agaacaataa aaagactcgc | 1380 |
| agtttatttt gaaggaaaat ccattgagta ttaatgtatc ctaaaatatg taatcataaa | 1440 |
| attacatggt catatcagtt ttatcgcctt tcagaaattt gctgttacct atccttattg | 1500 |
| tttattatat ttttaatga tcggtatgtt tttgatatta ttttagtttt ctggaaataa | 1560 |
| tattgcacaa attcttagtt atctgattca acatgtatca atgctttgtt gagtcatatc | 1620 |
| ataaatatta ttatgttttc tgtgtataaa gcgtagctag gccaaaatgt tatttctgtt | 1680 |
| gtatatgtaa gaataaataa aattatatgt atctgaaaaa aaaaaaaaa aaaaaaaaa | 1740 |
| aaaaaaaaaa aaaaaaaaaa aaaaaa | 1766 |

<210> SEQ ID NO 4

```
<211> LENGTH: 1016
<212> TYPE: DNA
<213> ORGANISM: Diabrotica virgifera virgifera

<400> SEQUENCE: 4
gtgacatttg cttcagaact ttgaaactca caacacccac atatggagac ttaaaccatt      60
tggtatccct cacaatgtcc ggtgtaacca cctgtcttag gttcccaggt cagttgaatg     120
ctgatcttag aaaattggct gtcaacatgg ttcccttccc ccgtctccac ttcttcatgc     180
ccggattcgc tccactcacc tcaagaggca gccaacaata cagagcgttg acagttccag     240
agctcacaca gcaaatgttt gatgccaaga acatgatggc ggcttgtgat cccagacacg     300
gaaggtacct tacagtagct gcagtattca gaggtaggat gtcaatgaaa gaagttgacg     360
aacagatgct caacatccag aacaagaaca gcagctactt cgtcgaatgg atccccaaca     420
acgttaaaac agccgtttgt gatatcccac caagaggtct caagatgtct gccactttca     480
tcggcaactc aaccgccatc caagaattgt tcaaacgtat ctccgaacag tttacagcta     540
tgttcaggag gaaagctttc ttgcattggt acaccggaga aggtatggat gaaatggaat     600
tcacggaagc agaatccaac atgaacgact ggtatcaga ataccaacag taccaagaag      660
ccacagctga cgaagatgcc gaattcgacg aagaccagga agccgaagtc gacgagaact     720
aaatttcata cgttaatttt ggatctgaaa tcaaagcttt ataactttta tatttgtctc     780
ctctcctttt attttttatt taagcatgtt ttttgtacag tctctacatt cccgtttgta     840
aatttcgaat acactactta aattattcca agactgactt tttgttgctt gtgtttctgg     900
aatttcagga agtgtttaga tatttaacat gttttgcgaa ctgtttttttt atgaataggc     960
attaaaactg ctgccattac ttataaaaaa aaaaaaaaa aaaaaaaaaa aaaaaa        1016

<210> SEQ ID NO 5
<211> LENGTH: 1016
<212> TYPE: DNA
<213> ORGANISM: Diabrotica virgifera virgifera

<400> SEQUENCE: 5
gtgacatttg cttcagaact ttgaaactca caacacccac atatggagac ttaaaccatt      60
tggtatccct cacaatgtcc ggtgtaacca cctgtcttag gttcccaggt cagttgaatg     120
ctgatcttag aaaattggct gtcaacatgg ttcccttccc ccgtctccac ttcttcatgc     180
ccggattcgc tccactcacc tcaagaggca gccaacaata cagagcgttg acagttccag     240
agctcacaca gcaaatgttt gatgccaaga acatgatggc ggcttgtgat cccagacacg     300
gaaggtacct tacagtagct gcagtattca gaggtaggat gtcaatgaaa gaagttgacg     360
aacagatgct caacatccag aacaagaaca gcagctactt cgtcgaatgg atccccaaca     420
acgttaaaac agccgtttgt gatatcccac caagaggtct caagatgtct gccactttca     480
tcggcaactc aaccgccatc caagaattgt tcaaacgtat ctccgaacag tttacagcta     540
tgttcaggag gaaagctttc ttgcattggt acaccggaga aggtatggat gaaatggaat     600
tcacggaagc agaatccaac atgaacgact ggtatcaga ataccaacag taccaagaag      660
ccacagctga cgaagatgcc gaattcgacg aagaccagga agccgaagtc gacgagaact     720
aaatttcata cgttaatttt ggatctgaaa tcaaagcttt ataactttta tatttgtctc     780
ctctcctttt attttttatt taagcatgtt ttttgtacag tctctacatt cccgtttgta     840
aatttcgaat acactactta aattattcca agactgactt tttgttgctt gtgtttctgg     900
aatttcagga agtgtttaga tatttaacat gttttgcgaa ctgtttttttt atgaataggc     960
```

```
attaaaactg ctgccattac ttataaaaaa aaaaaaaaaa aaaaaaaaaa aaaaaa          1016
```

<210> SEQ ID NO 6
<211> LENGTH: 1374
<212> TYPE: DNA
<213> ORGANISM: Diabrotica virgifera virgifera

<400> SEQUENCE: 6

```
ggacaacttc gtgtttggac agtctggagc tggaaacaac tgggccaagg gacattacac    60
agaaggtgct gaattagttg attcagtatt agatgttgta aggaaagaag ctgaatcatg   120
tgattgttta caaggattcc aactcacaca ctcacttgga ggtggtactg gatcaggtat   180
gggtaccctc cttatctcaa aaatccgtga agaataccca gacagaatta tgaacacata   240
ctcagtagtc ccctcaccca agtatcaga taccgtagta gaaccataca cgccacact    300
ttcagtacat caattggtag aaaacacaga tgaaacatac tgtattgata atgaagctct   360
ctatgacatt tgcttcagaa cctttgaaact cacaacaccc acatatggag acttaaacca   420
tttggtatcc ctcacaatgt ccggtgtaac cacctgtctt aggttcccag gtcagttgaa   480
tgctgatctt agaaaattgg ctgtcaacat ggttcccttc ccccgtctcc acttcttcat   540
gcccggattc gctccactca cctcaagagg cagccaacaa tacagagcgt tgacagttcc   600
agagctcaca cagcaaatgt ttgatgccaa gaacatgatg gcggcttgtg atcccagaca   660
cggaaggtac cttacagtag ctgcagtatt cagaggtagg atgtcaatga agaagttga    720
cgaacagatg ctcaacatcc agaacaagaa cagcagctac ttcgtcgaat ggatccccaa   780
caacgttaaa acagccgttt gtgatatccc accaagaggt ctcaagatgt ctgccacttt   840
catcggcaac tcaaccgcca tccaagaatt gttcaaacgt atctctgaac agtttacagc   900
tatgttcagg aggaaagctt tcttgcattg gtacaccgga gaaggtatgg atgaaatgga   960
attcacggaa gcagaatcca acatgaacga cttggtatca gaataccaac agtaccaaga  1020
agccacagct gacgaagatg ccgaattcga cgaagaccag gaagccgaag tcgacgagaa  1080
ctaaatttca tacgttaatt ttggatctga aatcaaagct ttataacttt tatatttgtc  1140
tcctctcctt ttatttttta tttaagcatg ttttttgtac agtctctaca ttcccgtttg  1200
taaatttcga atacactact taaattattc caagactgac ttttgttgc ttgtgtttct   1260
ggaatttcag gaagtgttta gatatttaac atgttttgcg aactgttttt ttatgaatag   1320
gcattaaaac tgctgccatt acttataaaa aaaaaaaaaa aaaaaaaaaa aaaa          1374
```

<210> SEQ ID NO 7
<211> LENGTH: 1128
<212> TYPE: DNA
<213> ORGANISM: Diabrotica virgifera virgifera

<400> SEQUENCE: 7

```
ggggagttca gaatttgtga atagagattg accaaaatga aagcggcttg tattattaca    60
ctattactac ctgttgtatt aagttacaaa gctaacttaa atcctctttc aaatgagttt   120
ataaactata tcaatagcaa gcaaaacaca tgggttgctg aaagaacctt tgatgagaaa   180
ctttcaatcc aagaaataaa aaattttatta ggagcgagaa aaaggagttt aggagatgta   240
aaaggattta tgcacagtga agatattcaa gttccagatt ctttcgatgc aagggaaaac   300
tggaaagact gttcagatgt tatcagcact attgtagacc aatctgcttg tggatcttgc   360
tgggcaatgt ctgcagcatc tgcaatgagt gacagacgat gcatagtcac ccagggaaag   420
```
cttaaagtgc ctgtttctgc tgaaaattta ttgtcttgtt gcgatgactg tggatttgga 480
tgcgccggag gatatataga tgatgcatgg tcgttttggc aagagaatgg aattactaca 540
ggaggtcttt acggcagcaa ccagggttgt caatcatatt cgcttcaacc ttgtgaacat 600
catacaaatg gtactaaagt gcaatgcagt actttgaact acggcacacc ttcttgcaga 660
agcgatcaat gtgacgatac cgcactaaat tataagtccg agttaactta tgcctcaggt 720
ccagtgaatt actatactac agttcccaat atgcaaaagg aaatattgac aaatggtccg 780
atacaaactc gttttgatgt gtacagcgat ttcttcagtt acaaaagtgg tgtttatcaa 840
catgtcgctg gagattatgt aggaggacat gccgtcagag ttttaggttg ggagtagag 900 aatggagtcg cttattggtt ggctgctaat tcatggaatg aagattgggg agacaaggga 960
ttgtttaaaa taattcgcgg aacaaatgaa tgcagtttcg agaatggtat ggttgcgtca 1020
actccaagag tctaattcta aacaaaatat tggaaatagg cttaattctg gtttatttta 1080
aataaaacac ttgatcccaa aaaaaaaaaa aaaaaaaaaa aaaaaaaa 1128

<210> SEQ ID NO 8
<211> LENGTH: 600
<212> TYPE: DNA
<213> ORGANISM: Diabrotica virgifera virgifera

<400> SEQUENCE: 8
ggggctttct gatttttgac agcttctata gaagtttatc aagatgttga tgccaaaaaa 60
gaatagagta tgtatttacg aatacctctt caaagaggga gtcatggtag ctaaaaaaga 120
ttaccatgcc ccaaaacacc tcgaactaga aactatccct aaccttcaag taattaaggc 180
tttacaatca cttaaatcaa aaggttacgt aaaggaacaa ttcgcctgga ggcattatta 240
ttggtatttg actaactctg gcatcgaata cctccgcaca ttcttacact tacctggaga 300
aattgtccca tctaccttga aacgcccagc aaggacagaa accacccgtc ctagaccagc 360
tgctctcaga tctgagacat ctaaaccttc agaagaccgt gcaggataca gaaggactcc 420
tggaggccct ggagctgaca agaaagctga tgttggtcca ggaactggag atgttgagtt 480
caggcaagga ttcggacgtg gacgggcacc acaataaatt tattgataag ttaattttta 540
taaattgatc agccaataaa aagtttggtt aaaaaaaaaa aaaaaaaaaa aaaaaaaaaa 600

<210> SEQ ID NO 9
<211> LENGTH: 1874
<212> TYPE: DNA
<213> ORGANISM: Diabrotica virgifera virgifera

<400> SEQUENCE: 9 ttttttttt ttttttttt ttttttttc tttatttgtc caagtttaat ttacagatca 60
caaataatgc aatgcaagta ataagtcaat tagttattaa aaatacattg atactccaat 120
attagtatat aaaagaaaca aaacatatca aaattattta agtagtggag tccaaataga 180
ctatttcttc ttttgggctt tttctgcagc ttttgtgact tttccggcgc tgggatcttt 240
gaaggcaacg ctcttgatga ctcctactgc aacggtttgc ctcatgtcac ggacagcaaa 300
acgtccaagg ggtgggaatt cttggaatga ttctacacac atgggcttgg tgggtaccaa 360
gttgacaatg gcggcatcac cagatttgat ggctttggga ttttcttcag tggtcttacc 420
agaacgacgg tcaacctttt ctttgccaaa aggatcgata ggccgtgctt tcgcagtccc 480
tatgcatact gaacatcagg atcaagccag cttttgccct tttgctctac gcgaggtttc 540
tgtcctcgct gagctggcct taggacacct gcgttattct ttgacagacg taccgcccca 600

-continued

```
gtcaaactcc ccgcctggca gtgtcctcga atcgaatcag gctggaggta agttgacgct    660
cgaaacgaag cacacggacg ctagccgagt atccgaaagg caagccttat cggaaccacg    720
aaaccgacga acggcacaac gcaacgaaac gtcactccgt gccctcggct caagaatacc    780
gtgacagtcg cagcctcgtg agcgaacgac gcacgcgttt cgccttaccg agtaagtaaa    840
gaaacgatga agtagtggt atttcaccgg cgatgttgcc atctcccact tatgctacac     900
ctctcatgtc tccttacaat gccagactag agtcaagctc acagggtct tctttccccg     960 ctaattttc caagcccgtt cccttggcag tggtttcgct agatagtggg tagggacagt    1020
gggaatctcg ttaatccatt catgcgcgtc actaattaga tgacgaggca tttggctacc   1080
ttaagagagt catagttact cccgccgttt acccgcgctt gcttgaattt cttcactttg   1140
acattcagag cactgggcag aaatcacatt gtgtcaacac ccgctggggc catcgcaatg   1200
ctttgtttta attagacagt cggattcccc tagtccgtgc cagttctgag ctgaccgttg   1260
aatggcggcc gaagaggaca tccaagcacc cgaaagtaac tcagagcctc gcagcaagac   1320
ggttccgcgg gaggccaagg cacgggaccg aactcggatc catgaaaccc aactcgtaag   1380
aattaggctc acttcacctc acccaggccc ggcacgtcag ccatgaccca cttcctcgcc   1440
aagcccgaca cgccccgatc ctcagagcca atccttatcc cgaagttacg gatccaattt   1500
gccgacttcc cttacctaca ttattctatc gactagaggc tcttcacctt ggagacctgc   1560
tgcggatatg ggtacgaacc ggtgcgagcc tccacgtggc cctctcctgg attttcaagg   1620
ttcgaggaga agatccggac accgctgcaa ctgcggtgct cttcgcgttc caaaccatat   1680
ctccctgcta gaggattcca tggaactcga acgcttatac agaaaagaaa actcttcccg   1740
gatctctcga cgacgtctcc aggtcctttt gggttacccc gacgaactct cttgcgaggg   1800
cccgactttt tgacggttcc gctaccgggt tccggaatag gaaccggatt cccttttcgcc   1860 caatgggtgt gccc                                                    1874
```

<210> SEQ ID NO 10
<211> LENGTH: 816
<212> TYPE: DNA
<213> ORGANISM: Diabrotica virgifera virgifera

<400> SEQUENCE: 10

```
tttttttttt tttttttttt tttttttttt cagagagatt cccatcaacg taaataatca     60
gggtatttat tcacatgtcc ctacgttctt atcatcatgt aaaggagtt ttgactatac     120 atattttgaa acatttaaa tggggccctc agaacaacag tggactaagt cacaaattca    180 gcattttttag attaatatat caataaaagc agcaaaatta atcttccga ttaacaggga    240 cctacacaac ctacctctat atttggctag atgatgctac ataatttgta gctttatctc    300
ataaacataa tgaaaatatg aatgcaaaga ttgcatttat ctcaaaactt agttttttgag   360 cttatgccac tgttgctgat agcctcaaat attaacatgt tgacagacat aacatctata    420
gatgtctaat ttccattgaa acgtctagat gacatttta aaataacgaa ttgtgcatat     480
tcaaactaca tctatagatg catatgaaat atgacatgaa catacattgt cgtcatcaat    540
atgtttacaa aactcattgt ttccatattg acagtctaat tctataccc gtatctgcaa     600 aaaaacttaa tttccaattt tcgtggcaaa cgactaacaa aacagttatc catctataca    660
caaaactctg atctaaacaa aaattctag gaacctctaa taccagtcat ctaatacctc     720
gtaactgaat atctttagac ttgataagaa aaaaaaaaca gaaaaaacct acttgacaaa    780
```
tctcttggca gatacgggct attagaatta gacccc                          816

<210> SEQ ID NO 11
<211> LENGTH: 579
<212> TYPE: DNA
<213> ORGANISM: Diabrotica virgifera virgifera

<400> SEQUENCE: 11
ggggctttta catcaaaaat ttctttagct gttgtcggtt aaggaacagc ttacaaaatg    60
aaattcaaca aattagtaac cgcttcaaga agcaaaaata ggaaaaggca tttcacagcc   120
ccatcccaca tcagaagaac ccttatgtcc gcacccttgt ctaaagaact tagacaaaag   180
tacaatgtta gcactatgcc aatccgcaag gacgatgaag tacaagttgt aaggggcac    240 tacaaaggct agcaagtagg taagttgta caagtataca ggaagaaatt cgttatctac    300
attgaaagga tccagagaga aaaagccaat ggagctagtg tatatgtagg aatccaccct   360 tcaaagttg ttattgttaa acttaaaatg gacaaggaca ggaagaagat cattgacaga    420
agagccaaag gacgtttggc tgctttgggc aaagacaaag gaaaatacac tgaagaatca   480
gctgcctcag ctgtagaaac atcttaagtg taataagtaa ttttttaataa taaaataata   540 taaagttcca aaaaaaaaaa aaaaaaaaaa aaaaaaaaa                          579

<210> SEQ ID NO 12
<211> LENGTH: 585
<212> TYPE: DNA
<213> ORGANISM: Diabrotica virgifera virgifera

<400> SEQUENCE: 12
gggggctggc agtttgctgt cttaatgttg acatttttat atattggaaa aaatgtcgaa    60
agttgaattt aaacaagata tgcccccaca agggggctac aatccaatta actataaaag   120
agttccagcc aaaactttat ttggaggatg ggccttaatc gggggctacc ttggcatgac   180
tgcaggagcg gcgtatttat attatttaaa cgttaaggca gtaaaaactc gagaacttga   240
attaaagggc gccagcttag cgctgtatcc aatacttatg gctgaaagag accgtgaata   300
tatgaagcaa ttaaggagaa atagagatga agaacgtgaa ttaatgaaaa atgttgaagg   360
atggcagacg ggtacatggt atggtgaacc catctacaag actaaagaca aagatactct   420
tattcatccc ctattccatg aatattacat tcacagttct tacaaggact acactgttcg   480
tgcaaacgtt ggtttgatgt cttaaatttt tattctattg taatttagta gcgaaattta   540
aatattaaat tgtaaatatg aaaaaaaaaa aaaaaaaaa aaaaa                    585

<210> SEQ ID NO 13
<211> LENGTH: 1043
<212> TYPE: DNA
<213> ORGANISM: Diabrotica virgifera virgifera

<400> SEQUENCE: 13
ggggagtcgt caacatcaat ttcaagtttc aagaaaaagc aaatcactac gacttgccgg    60
attttgtagt agtgttaatt ttgtattaaa aaatcaaaat gagttctatt ggaactgggt   120 acgattatc agcttcccaa ttctctcctg atggaagagt atttcaagtt gaatatgcaa    180
tgaaagcagt tgaaaatagt ggcaccgtaa taggcctccg aggtacagat ggcattgtat   240
tggctgctga aaagctcatt atgtcaaaat tgcatgaacc aagtacaaat aaacgaattt   300
tcaacattga taaacacata ggaatggcat tttcaggctt aatagctgat gcaaggcaaa   360
tcgttgagat tgctagaaaa gaagcatcaa attatagaca tcaatatggt tcaaatattc   420

```
ctcttaaata cctaaatgat agagtaagca tgtacatgca tgcatacact ttatacagtg      480
ctgttagacc atttggttgc agtgtcatct tggccagtta tgaagatagt gacccatcta      540
tgtatctgat tgatccatct ggagttagct atggatactt tggatgtgct acaggtaaag      600
caaaacagtc tgcaaagact gaaatagaaa aattgaagat ggggaatcta acatgcaaag      660
aacttgttaa agaagcagcc aaaatcattt atttggtcca tgatgagctg aaggataaga      720
attttgaact ggaactttca tgggtatgca agatacgaa tggtttacat accaaagtgc       780
ctgaatcagt gtttgctgat gcagaaaaag ctgccaaaca agcaatggaa gcagattcag      840
aatcagatac agaagatatg taataactac atttagtttt taatatttcg ctgatggtgg      900
ctgttcttac aatatttcgt gtgttatgtt catatattat gtaatactgt gagaatttcc      960
atttcaagga taggtttata acttttttt ctaataaata cataacttta tgtcaaaaaa      1020
aaaaaaaaaa aaaaaaaaa aaa                                              1043

<210> SEQ ID NO 14
<211> LENGTH: 601
<212> TYPE: DNA
<213> ORGANISM: Diabrotica virgifera virgifera

<400> SEQUENCE: 14
gggataatca ttagttttt tattgaaagc tggaatgaag ggttggatga aaaaaaaaac        60
tgtctttatt taatttataa agaattttat ttttaagtta aaaagcttaa attttttaa       120 aagacgagaa gaccctatag agttttataa aattattaat aagttttttt agtattaaat      180
ttatttatat aataaattta tttaattggg gtgattaaaa aataaattta acttttttta      240
tattattata ttaattaata attttttgat ccaattttt tgattataag aataaattac       300
cttagggata acagcgtaat tttattggag agttcaaatc ggtaataaag attgcgacct      360
cgatgttgga ttaaagttta taattggtgt agcagctata ttattaagtc tgttcgactt      420
ttaaaatttt acatgatctg agtttaaacc ggtgtgagcc aggttggttt ctatctttaa      480
tttattaata tatttagta cgaaaggacc aaatatataa aataattttt atatttagat       540
aaatattaaa aaaaaaaaa aaaaaaaag caaaaaaaaa aaaaaaaaaa aaaaaaaaaa        600
a                                                                     601

<210> SEQ ID NO 15
<211> LENGTH: 913
<212> TYPE: DNA
<213> ORGANISM: Diabrotica virgifera virgifera

<400> SEQUENCE: 15
gggggcagtt atttcgactt ttcatgcttg tcataaaata aaattaaaat atatccggcg        60
aggtgttgac tagcggattt ttttagattc aacaatctta tttttataaaa taattagtta     120 aaatgatgca aacagctaat aatgcatatt atcccgatta ttccactgct ccaatgcaac      180
gtcaaattaa ccccctatgca gataatggag ggagtgtagt agcaatagca ggtgaagact      240
ttgtaataat tggtgcagat acacgtttga gtactggatt ttccatttat accagagaac      300
aaaacaaact tttcccacta tcaggcacta ctgttttggg ttgtgcagga tgttggtgtg      360
acactctaac attaaccaga atccttaaat ctcgcatgca gatgtaccaa caagagcata      420
acaaaacaat gtctacaact gcatgtgccc agatgttgtc aacctgctc tactacaaga      480 gattcttttcc ttattatata tcaaacattc tagtaggttt agataatgaa ggaaagggct      540
```

```
gtgtttacag ctatgatcct attggacatt gtgaaaaagc tacgtataga gcaggtggtt    600
cagctggagc tcttcttcag cctctgttgg acaatcaaat tggacagaag aacatgctta    660
aaacatctgg ggaacctctt agtcaggaga aagctctgtc tacccttaaa gatgtattta    720
tttctgctgc tgaaagagac atctacactg gagatagcgt acttataaat attattacta    780
aagatggagt aaaggaagag tccttccagt tgagacggga ttagaagcaa gtggttttgt    840
ttatattttc ttatgtgtaa ttcaaatata ctttctaaat aaacaaaaaa aaaaaaaaaa    900
aaaaaaaaaa aaa                                                       913
```

<210> SEQ ID NO 16
<211> LENGTH: 681
<212> TYPE: DNA
<213> ORGANISM: Diabrotica virgifera virgifera

<400> SEQUENCE: 16

```
ggggatttcg ttggtttaac gattgatagt aactataaat tcaaattaca gatcagatgt     60
atatatatat ataaacacgc aaaaatgctt ggctataaaa tgaaaatgt aactgcaata    120 ttagatgacg ttatatataa aaataaataa aatctgctgt tgatattgta gttcattagt    180
tttgaaaaat aagcagtact aactttaatc ttgtgccaaa ttagttttat tgttaatatt    240
aatattttca cccaaataag agaaatggat gacgtgcaac tgggtcctgt gagtattagc    300
atgatagaag ataattttata tttaggagga ttggcagctg cgaaaaattt ggaagtttta    360
aagaagtaca acattactca tattcttacc atagatatat gtccattacc aagaactgta    420
acagaacaaa gaaattagt taccagattt atacagttgt cagaccaacc aagagaagat    480
ttgctttcat attttgatga aacagattta tttattaatg aaggaaggga aagggaatt    540 gttttggttc attgttattt tggtgtttct agaagtgcca ctgttgttat tgcccatata    600
atgaaaaaat accagatgag ttactttgag gcatttgata tggtaaaagc tgaaaaaaaa    660
aaaaaaaaaa aaagaaaaaa a                                              681
```

<210> SEQ ID NO 17
<211> LENGTH: 1109
<212> TYPE: DNA
<213> ORGANISM: Diabrotica virgifera virgifera

<400> SEQUENCE: 17

```
gggggagtag ttgtttttat tgtgagatga tttcgaagtt caccctggtt ttcttggttt     60
gcattgtcgc accagcgata ggtgatccac cagttccaga atggagtgac acttatagcg    120
tagaaggaac tatccatttg ccttatgcag aaatagtaga gcctttccat gcttggtatg    180
atggaaaatc taaaaattcg cgcattgatt actacaatgg gacggctaag acataccaac    240
ttggaggaaa tggaaatggt gtccaactga agtagttcc attcactaca gaggaggtcc    300
taaaccaaat aacgtgcttc cagatcaatg gaactgaaga cgatccagtg actcctcaat    360
cgattttgcc agatttagaa ggatttgaat atcaaggcat acaggagtat ggagatagag    420
aactagaggt atggtttcta aaaactgtcc agttagaaaa agaaaacgaa tacactctat    480
gggttgtccg agatgagcat ggtaaagcta ttccagttaa atatgatatg agaggataca    540
attcgttatt gggaagccac tacgatcatt actatttgct atacacatcg aagtcttaca    600
ggactcacaa gattgatccc tccgttttttg aagtagaaac taatagtgaa tgcagaagtt    660
ttcctggacc cggaaatcaa catgttcaca tcatgaaccc catggccgaa tacattcgtc    720
ccgaaaaaag tgagcacgtg gactcaagct ttggcgattt tataaataac cacaacaaaa    780
```

```
attacgcaga cacaaaagaa cacgttttta gaaaagaggt tttccgtcaa aacgtcaggt    840
tcatcgaatc tgtcaaccga caaaataaag gtaagtgtta tagtagggga gcaaagtagg    900
tgtgctaaat ttgcagtcac tcgagagtta tggcgaccta ttgggttgtg attattaggt    960
cctaaaacca aaaaagtta agtaaaattt tccatttcca acaatcgttt tttccgatta    1020
tagcgtcatc tatccataat tcgaaaaaat gtctctaata aagttgcttt attttacga    1080 aaaaaaaaaa aaaaaaaaaa aaaaaaaaa                                     1109
```

<210> SEQ ID NO 18
<211> LENGTH: 400
<212> TYPE: DNA
<213> ORGANISM: Diabrotica virgifera virgifera

<400> SEQUENCE: 18

```
gggggatttt ctctagtttg caggaagcag gaatttcagt aaagaaataa gattaaaatg     60
gcagacaaag tagaaaaggt tgccagacca atgaaattcc cttacacatt cagtgcaaaa    120
attgcacaat tcccaatcaa gcactacttg aagaaccaat ggatctggaa atactatgct    180
atttctcttg tagtatgtct tccagtcttc aactcgatta gtaaactggc caactctcct    240
ggaaacgttg ctaaatgggc agagattcgc agaagagaag ctgctgaaca tcatcactaa    300
gaaaattttt tttatagtaa ttagtctgcc aattgttttg ttctaattta atttctatta    360
aatacatgta gaaaaaaaa aaaaaaaaaa aaaaaaaaa                            400
```

<210> SEQ ID NO 19
<211> LENGTH: 800
<212> TYPE: DNA
<213> ORGANISM: Diabrotica virgifera virgifera

<400> SEQUENCE: 19

```
gggaagcagt ggtatcaacg cagagtggcc attacggccg gggtagttct agcgttctag     60
ttctatagtt gttgtgtagt attttctgtg tagtttgtga tttttcctat tgtgcatttg    120
tatattttat ttatttattt atatatttac gatcagtaag aacatttac ataaattcaa    180 taagcatata gattcgtgta aaaaaatgcc aaagctatcc aaaaaaaatc aaaaaaaagt    240
aggcgctcaa caagactcgt taccgagaaa tgacagaact actgactgta cctcaaattc    300
acattcacat tctggtaatg gtgaaactac ttatcatagc gcaaattcaa attctgttgc    360
tcttgaaagt agttcatcaa atgcccaaat tcaaattagc accataccct caataaatga    420
taattcttcg ccaaacagct cctttgatca aactgcacct acaagttcaa gtttacctga    480
gggaagagta cactccgaaa gaattaattt tcgtcctaga agagccagtt tggtaacact    540
gagacgtgaa aaagtacag ctttgaggaa gacacataaa aatatgagaa aaaataaagc    600
tgtaacaagt tttaaatctt ttgctcaagc cgaaattcaa catgtatctc ttcccagcca    660
ggagaatttg aaatctcgag gatcaattgt gaatttggtc actaaaagaa aaaacacaaa    720
tgaagaatgt tcatcccatg gctcccttac agaatcagat atgggtaacc aaaaaaaaaa    780
aaaaaaaaaa aaaaaaaaa                                                 800
```

<210> SEQ ID NO 20
<211> LENGTH: 1105
<212> TYPE: DNA
<213> ORGANISM: Diabrotica virgifera virgifera

<400> SEQUENCE: 20

```
gggagcccctt atttctccta ttgctatata cgcagctgaa acatggactc tcaaaaaaat      60
caatcgaagt aagatcgaag ccttcgaaat gtaggtctac agaattattg tacccgtgtc     120
caggagagaa cacagaacca acctgtcaat tctgaaagag cttcatataa aagacaaggt     180
attaaaaaaa gtataccgac catacttaaa ttactttggt aaagtaacga ttactatacg     240
aagaggcaaa tcgttacttt gattactctg attacttcgt accaatcgta tcagagcgag     300
taacgactat tgtatctact ttgattactt cgtatcagag cgataacga ctattgtatc      360
tactttgatt actctgatta cttcgtacca atcgtatcag agcgagtaac aactattgta     420
cctactttga ttattctgat tacttcgtac caatcgtatc agagcgagta acaactattg     480
tcagggccgc gtttaggtca aatgacgccc taggcaattc tctagtagcc gcccttcaaa     540
catgtaccat ttttgcgaaa aaaaacgcaa gcagaatttt ttatttaaat aagaatgtta     600
ttgcacaaat ctcggtgttc ttcaaataat gtttagaaat gtgttaaaaa tattctttat     660
tttacatcag gcgtaatgtt acatattact attataagta tgtttgagcg tttggaactg     720
tgtccaatgc atgcgtttta atgcatgata cgtagaaatt gcctgtttgt agccgcacct     780
acttgttcga ttttaaatga gagatgcatt gaaaacatta ctcaagcact atgtgtttat     840
agctttgttt aacaataaaa aaattaattt ttagcgatgc aaataatcaa aaccggtata     900
atttgacatg cactttcaaa tgcggtaagc agaattgcta ttttattttt taatcaaaag     960
ttattcggat tcaaaaattg caattttttcg atattttgaa agttcaaccg cgtctatctc    1020
gaaaactatg catcctacga aaaaacttta acaacatttt ttgcttagaa tgacccaaaa    1080
aaaaaaaaaa aaaaaaaaaa aaaaa                                          1105

<210> SEQ ID NO 21
<211> LENGTH: 936
<212> TYPE: DNA
<213> ORGANISM: Diabrotica virgifera virgifera

<400> SEQUENCE: 21
gggggctcat tgtagtagcg ccaggcgcgg aaacgtgagt gctaaaacac agtgatcgta      60
ctagtccaaa acatcttta tattttctta cttttatatc taattgtata gtttcgttat     120
ttttattact tagaagttta tattttctca tcgttttata cgcttctggt aaggattttt     180
atacattaaa caatattact tgcttgggta agttatgttt tattttgaaa tatagcattg     240
taaccttttt taaatctttt atttttttta ttttttcttt ttctttaaca tactactgat     300
acgctgcaga ggtccatgcg ttttcaattt tttaggatct tttgataact ttttaaaat     360
gtaacacatt tagaaagacc gttgaaaagt tcgccctttt agaccgcgga ggcagtgacg    420
tagctgacag gtccgcaagg cggggggccc cgacattagg agggataagt agagatctct    480
ctagtcagag ataagtactt actttcgatc ttttcgtaat tacgtactta ctttcgatct    540
tttcgtaatt acctctgttt tccttccatt gcatgtgatc tttgtatata tttcttaata    600
ttttacagaa aacgtaagtg tgtctacaaa atgttttgca tatttgtgta aaattaatca    660
aaatatctta aaaccagtag tcaattaaaa aaatatttaa aaatgttgtg caataaacct    720
tgcggtattt actgaagtgt ttcacacctg tttgaagtta aatatcaagg tttattttt     780
ggccgggaat ttaaaggttg tggtatattt acttttaca attaataatg ggatcaactg      840
attgggtata tagggtgatc aaattatacc ttgtagttca atatcttcgt tgccagaaga    900
gatgcaggaa aaaaaaaaaa aaaaaaaaaa aaaaaa                               936
```

<210> SEQ ID NO 22
<211> LENGTH: 812
<212> TYPE: DNA
<213> ORGANISM: Diabrotica virgifera virgifera

<400> SEQUENCE: 22

| | | | | | |
|---|---|---|---|---|---|
| gggaaagcac | taaaaaatgc | aggatacaaa | tttgacattg | catatacatc | tgtccttaca | 60 |
| agagctcaga | acacacttaa | ttcaataatc | aaagaaattg | ccaagagaa | tttggaaact | 120 |
| ataaaaactt | ggagactcaa | tgaaagacat | tatggtggcc | tcactggctt | aaataaagca | 180 |
| gaaacagcag | caaaatatgg | agatgagcag | gtagctattt | ggcggcgcag | ttttgacatt | 240 |
| ccacctccac | caatggaacc | tgaccatgct | tattatgata | ccattgtaaa | agatgcccga | 300 |
| tatgctgatg | gtcctgcacc | agatcagttt | cctaaatttg | aatccttaaa | gctaacaatt | 360 |
| gagcgtactt | tacccttctg | gaatgaaact | gttgttccac | aaattaaggc | tggaaaacag | 420 |
| atcttaattg | cagcacatgg | taacagtttg | agaggaattg | taaagcatct | agaccagctt | 480 |
| actgatgacc | aaattatgca | gttgaatttg | ccaacaggaa | ttccatttgt | ctacacatta | 540 |
| gatgaaaatt | tgaaaccaat | aaagagttta | gaattcctag | gagatccaga | aactgtgaaa | 600 |
| aaggctatgg | aagctgtagc | tgcccaagga | aaagccaaat | aagcattatt | tattatttat | 660 |
| tgttttaatt | tatatcaaaa | tcattattg | ttagatattt | gatgtgtaat | gaataaatgg | 720 |
| ttaggctgaa | ttgtaaaact | cagcagaaat | gttatgtgca | agacattaaa | gcatattctt | 780 |
| ctcaaaaaaa | aaaaaaaaaa | aaaaaaaaaa | aa | | | 812 |

<210> SEQ ID NO 23
<211> LENGTH: 1127
<212> TYPE: DNA
<213> ORGANISM: Diabrotica virgifera virgifera

<400> SEQUENCE: 23

| | | | | | |
|---|---|---|---|---|---|
| gggggaagta | ttctgtagaa | aactgataag | tatattgctt | ttctcattta | tttatgtggt | 60 |
| taaatagtga | gttagtgttg | gtcaacgtag | atgataacaa | ctgaacattg | aataaactac | 120 |
| aagaataatg | ttaagcataa | aaattctgtt | atgtatgttg | ctggcacacc | aatctgcggt | 180 |
| agaagctgta | tataatgttg | gagttggacg | agccgattgc | acaggaccat | cagcagaaat | 240 |
| tactttatg | ggttatgcca | aatccggtca | gaaaggatgt | ggtatccatt | taaggcagtt | 300 |
| ttcaagagca | tttgtgatta | aagatgagaa | cactctagtt | gcatttgtga | caattgacac | 360 |
| atgtatgatg | aaccatcccc | taaaacaagc | ggtaatagat | aaattggatc | taaaatatcc | 420 |
| caatgtattt | actctaaaga | atacaattct | cagtggaaca | cacagtcaca | gcacacctgg | 480 |
| aggtttcctc | aaggatgtaa | tgttggacat | accaagctcg | ggatattgta | agaaaccttt | 540 |
| taacgcattg | gtagcaggaa | ttgtaaaatc | catagataaa | gcatacaaca | atcaagttga | 600 |
| agcaagaatc | ttttacagca | ctactacagt | aactaataca | aacaggaaca | gaagtccagc | 660 |
| tgcttacctc | tataatccag | aatcagaaag | aaaaaagtaa | gtgtaatact | agataataat | 720 |
| actttaaact | ttattaagta | taataaaatt | aataacgtac | aaaatactca | aaattaacat | 780 |
| ttatttccaa | attaccatat | aaatataatt | ttaataattc | tgggactcaa | acattgtaa | 840 |
| tttatttttg | cttattaata | ataataaatt | gtacaaataa | attctatttg | tcactctaaa | 900 |
| cacaaataag | atgttgctgt | tctttacgac | agtctcctgg | cgactagtgt | cataactttt | 960 |
| atactcgcat | tttaatggcc | atcattaata | gtggagtcaa | tggagttttt | acttaggaaa | 1020 |
| aaaatcaaac | aagagaggac | tgtttataac | ttcattcaga | aatgtatcat | aaacaacaca | 1080 |

```
tcaaaaagtt ctactccaaa aaaaaaaaaa aaaaaaaaaa aaaaaaa                  1127
```

<210> SEQ ID NO 24
<211> LENGTH: 869
<212> TYPE: DNA
<213> ORGANISM: Diabrotica virgifera virgifera

<400> SEQUENCE: 24

```
gggccaatag tcccatgaaa gcagcctacg attattacaa gaaatgttca aagacaggaa    60
attgcttgcc accagtaagc ctccttcctg gcaaccaaaa ggaaggcgaa gttcaactgc   120
aaccaatcga tctcaagaaa atccattttt taaacggagt ttatgaagcc ggaagttctg   180
ctgacttctc caggtcttcg tctgagacga atccaatgg agcctctctt gatagtgacg    240
cgtccaatgc gagatttgcg ataactggag ccaacgatga ggacaacgag gtatctccca   300
gccagaggat tccatgcaaa ggtgatggaa aagtgtgcgt gcccaaggac gcttgcgtca   360
atggtgtggt caccaaacat agaggaagcg cattgcagat caaacaaaat aattatctaa   420
gtaaacattc agatccacaa agccaggcgt tgttagaaaa tgtgaattca aaatattact   480
actacacgag aacaaaagga ttattcagga tatgttaccc aaaagaaagg ccgcctactg   540
taaagacata cttgagtcct ttggaaacgc attgtaacaa tgtaaattac tacattcccg   600
atgaaaataa cgataccaag gacttcactg acgatgcttg acaagatta catatgggac    660
gatccatgat agctctcttt atcatatcgt tcatagctgt ctttgctgcc ttctgcaccg   720
gggtcactgg atgttggaag aggtctccag gaaatattac agccactgca atacttatgc   780
tgctagcatg tttgttgagt gctggtgcta tgggtctatg gcacggagtg gaatattaca   840
aaaaaaaaaa aaaaaaaaaa aaaaaaaaa                                     869
```

<210> SEQ ID NO 25
<211> LENGTH: 569
<212> TYPE: DNA
<213> ORGANISM: Diabrotica virgifera virgifera

<400> SEQUENCE: 25

```
ggggagttcg attccggcag cggacggcga ctctgtgaaa gttgatcgct taaacgtttc    60
tacacgtggt gcacgtgctc cgtaccgaga cgacgacgaa gagaagacgc cggcgtcgcg   120
acgcgagtag acgacaacgt ggttgaacaa gtgtggaagt gccggcatgt tgcactgagt   180
gaagtgacag agttgtgcgc atgtgaggaa aggatgtcaa gggattaaag gcggcatca    240
tggtgagctg tttaaggtta gtaaattcca tactgctggc gcttgactga gaataatgag   300
taagtgttta atagtgattt aatatagttt cttgaacttt tattcaggaa agattcaagt   360
aaatgtgata cagtaggcgg tactgtagac taaagaaag ctttattta atttaggaa      420
atattatttt taatattatt ttttgatag tttttttata gatttaatt atattgaaaa     480
agttgacatg ttgtgtaatg tctggctaat tggctcggcc aaggccatca aattcactca   540
aaaaaaaaaa aaaaaaaaa aaaaaaaa                                       569
```

<210> SEQ ID NO 26
<211> LENGTH: 576
<212> TYPE: DNA
<213> ORGANISM: Diabrotica virgifera virgifera

<400> SEQUENCE: 26

```
ggggcttttt cacaatgcag gcaccaacga caaagccaaa aagagatcca atccactctg    60
tccaagtttt tggcagaaag aaatcagcta cagccgtagc ttattgcaaa agaggtagag   120
```

```
gagtcttgag ggtaaatggc agacctctca gccaagtgga gcctaaaatg ctccaagaca    180
aacttcaaga acccattctt cttcttggaa aggacaaatt ctctgctgtt gacatcagag    240
ttagagtaaa tggtggtgga catgtttccc aaatttatgc tattagacaa gctatctcaa    300
aggctttggt agcttattac caaaaatatg ttgatgaagc atcaaagaag gaattgaagg    360
atatccttat ccaatatgac cgtaccttgt tggtagccga tcccagacgc tgcgaaccca    420
agaaattcgg tggtccaggt gctcgtgccc gctaccaaaa atcttaccgt taagttcttt    480
tttagattta atgttgtgtt tcttgtatgt attaagatat caacaataaa cacaattttt    540
tcccgcaaaa aaaaaaaaaa aaaaaaaaaa aaaaaa                              576

<210> SEQ ID NO 27
<211> LENGTH: 1118
<212> TYPE: DNA
<213> ORGANISM: Diabrotica virgifera virgifera

<400> SEQUENCE: 27
ggggcaccaa ttaatccttt ttaattagta cgtgtatacc tataagaaaa atcaataaaa     60
tacatattcg atagttcgct gctgaagtga caggcaaaga gaaatgaag gtgattcttt    120 gtttactggg ggttgttacc ttagtactga gcactcccgt gtaccaggaa gacttacaga    180
aatattatcc tcaaggatca attccatgcc cattcttcaa gaaagacgcc agttttaatg    240
catcttccga tgatattaaa gtttatttta gaaacaaaga tcatcctgag agttcagtac    300
caatagacat taacgatagt tcggaagtcg atgcgttggg attttcacca aataaagata    360
caatgtttgt tgtccacggc tggcacaacg gtcacgactc gccagtctgc gatgagatat    420
ccaaagctgt cctccagaac gacgactaaa acgttttcct aatcgattgg aacaaaatcg    480
ccagcaacct ctacttagta gcttacaaag cagttccagg ggtcggtcaa ttactaggaa    540
cactcattag aaatttggtc aacaacaata aattggattt gaataaagct tctatcgttg    600
gccattcttt gggagctcat gtcgctggat tggccggagc tgaactcaac ggacgggtta    660
gtaacattgt aggtctggac cctgctctac catgcttctc atacaacgat atcagtacaa    720
gattggaccc ctccgatgca caatacgtcg aggtaataca cacatgcgca ggtttactcg    780
gttttgatgt agatattgga cactcagatt attaccctaa tggcggaaaa gatcaacccg    840
gttgcacttt ggatgttgta ggaatgtgca gacacagtag atcatattac tactatgcgg    900 aatcttttaat tagtggagga tttgctgcaa acaatgtaa ttgctacaaa gatttttaaca    960 acaatcaatg taatggagga acatccaata tgggagaata taatatcaac aaaagtgcca   1020
aaggcggata ctacctcaac acaaatagtc agtcaccata tgcccaacat tgatataaat   1080
gtataataga aaaaaaaaaa aaaaaaaaaa aaaaaaaa                           1118

<210> SEQ ID NO 28
<211> LENGTH: 955
<212> TYPE: DNA
<213> ORGANISM: Diabrotica virgifera virgifera

<400> SEQUENCE: 28
ggggattaca aactgaactc aacaacctct tttcatcttc gacccgtttg ccggcgttag     60
cttgtaaaac atttctgtta aaatcacgaa ccatccgtta aagaaatgg cagatgaata    120 tttttttgct ttaaccctca aggtaaaaa cagtgaaatc tgggatccag aagcgaaggg    180
agcagaggat taccaagggg gacacaaatt gatcattaaa caagctttgt tgggacccga    240
```

| | |
|---|---|
| agcccaagaa ggtgaagtaa atgttgtaca agtagaagct atgacgtgga aagactcagt | 300 |
| taaaatccca attgccacac taaaagccgg aggcccaaat aaccaagtat tgttagatct | 360 |
| gtcattccca gacccaccag tcacattttc acttatacaa ggtaatggac cagttcacat | 420 |
| tgtaggccat catttaattg gtagtccgat ggaagaattc gatgaaatgg atgaattaga | 480 |
| agaggaaatg ttggatgatg aagaagggga agaaggagcc gaggaagatg aggatgaaga | 540 |
| tgaacccaaa gccaaaaaag caaaatcagc gactaacgcc aagggcaaaa ctcccgtaaa | 600 |
| aaacaattca aaggctgcaa agaaataaac aagttcatct aatccccaaa ccacctcctt | 660 |
| tgtaatgtta agttagtttt ttaatgtatc tcgggagttg ttatacatcc attaacagat | 720 |
| caaccgtaac aatttctctt aaatataagt ataatatttt atgtttcttg acgtcataag | 780 |
| attttgtgaa agtttctttt attccaggtg taactcttag ttttaatgtg atcaatattt | 840 |
| ttaagctgga aacgtattta tttcctttga aatcatccaa ttttgttgta aatatgcagc | 900 |
| cctcattaaa ccatttttg tagcaaaaaa aaaaaaaaa aaaaaaaaaa aaaaa | 955 |

<210> SEQ ID NO 29
<211> LENGTH: 422
<212> TYPE: DNA
<213> ORGANISM: Diabrotica virgifera virgifera

<400> SEQUENCE: 29

| | |
|---|---|
| gggggaaata tatactacaa tgaagttttt aagatcgaca gtgtgctaca ttgccatctt | 60 |
| ggcaattctc tttaccctct gtgccgatga ggttgaagga aggagaaaaa ttttgatggg | 120 |
| gcgaaaaagc attaccagga catatcttcg tggaaatgct gttcctgcgt atgtgataat | 180 |
| aatccttgta ggaattggtc aactcatcct gggagggata ttgtacgttg cattgaggaa | 240 |
| gaagatcatt gctgcacctg taacggcatc atatgcagtg gctagacaag aaccataaat | 300 |
| tttatttgtc tagaatatta ttttctaaat atgcatcttt tttaaattat tgtctacgta | 360 |
| aataataagt ctagaaatat ataaaaattg tcaaaaaaaa aaaaaaaaaa aaaaaaaaaa | 420 |
| aa | 422 |

<210> SEQ ID NO 30
<211> LENGTH: 2911
<212> TYPE: DNA
<213> ORGANISM: Diabrotica virgifera virgifera

<400> SEQUENCE: 30

| | |
|---|---|
| gggggtgcga agctaccatc cgtgggatta tgcctgaacg cctctaaggc cgatcctttt | 60 |
| ggcttgaaga gttttcagca agaggtgtca gaaaagttac cacagggata actggcttgt | 120 |
| ggcggccaag cgttcatagc gacgtcgctt tttgatcctt cgatgtcggc tcttcctatc | 180 |
| attgcgaagc agaattcgcc aagcgttgga ttgttcaccc atagacaggg aacgtgagct | 240 |
| gggtttagac cgtcgtgaga caggttagtt ttaccctact gatgactcgt cgttgcgata | 300 |
| gtaatcctgc tcagtacgag aggaaccgca ggttcggaca tttggttgac gcacttactc | 360 |
| gagcgggtaa tggtgcgaag ctaccatccg tgggattatg cctgaacgcc tcctcaaagt | 420 |
| cacaagatga gtgtaacgcc acctacagat ctacacaaga aagaagaacc acgatagcat | 480 |
| cgacagacag tggtaatggc cgacgaccgc gacgagggaa ttttaaaata cgaaatgttg | 540 |
| taaaaggaga ggcaccaaaa agaagagtag atggttcgaa aaatcaatga aaagctagtt | 600 |
| gaacgttcag tttcttttaa aaagaaagt tttgtagatt tgaaacaac accgcacaca | 660 |
| tcttatggaa aatgtaatgt cactcaagtg caattgaatt tgcctgaata tattggtctc | 720 |

```
gaagttacaa tcatttcagg tcgttgcgcc aactctgaat ttttattaat aacggtgcat    780
attgatataa ataaaacata aaactaaaat caaatgggta tgagtgagaa aagaatgtga    840
atcggcagtt cataaatctt tctgaaagta ttaaggtctc ttatcttata gataaatgac    900
aaagcacttc tagtgatgca ccgcaaaata aaggtcaacc tcacgctcgg gtaacctgtt    960
ttcaatagcg actagactaa tagtatttgt aaataggaca gttttatgga cttcaaaatg   1020
tgattctaca atttacgcgg atattaatca aaattcggag ttggcgcagt gatgtgagat   1080
tattgtaatt tctaaacgaa tctatttatg taaattttat tgtgtttgag tgacattaca   1140
tcaaccataa gatgtgtgtg gggcccttt ggcgaatttt gccataaaaa aattaatttg   1200
gaggcttttt aactagctcc aagagttgta cagaaagata tgccgctatt aatattgttt   1260
cgcaacaaat agatcatttt gattacttaa aaaaagtaca atgaatcata ctaagttatt   1320
ttttgttgta ctatccgttg caagataatt tggatagtaa atttaaacta attcaactaa   1380
atatattaaa attttcgttc catctacttc cattttcttt tattttttt tataacgagt    1440 ggatcaacaa aatgagcatt ttttatatt ttaattgtga tttgaaagtg tattttaagt   1500
gggagatgat gatgttcgag tctattaact gtacgttact tatcacaatc tattttgtat   1560
ggattttcat acaaagaact ttagtttgtt gattattatt taataaacta catttttattt   1620 aaaatgtact gtttaacgaa tcatgtaacg atcacgctcc tgcgcagtaa acaaaatatg   1680
ttccaacaaa cagatgatcg ttcatcgcat cgtccttcca attgttccaa caaaaattgt   1740
gatcgtccaa tgacagtgtt gcgacgatca ttttagtact ctgatactat aaaaattgtg   1800
tgttggaaga aacctaatgt aactgcgcca ttttgaactc agatgtttct taggtatgcc   1860
cagggtagta gttcccttaa agaaaaaaaa gtgggaaaat gtttaggttt ctatttatta   1920
acaaatcaca tattggatgg acagtctgca tctttttttg tcagtataga taaaaaatcc   1980
tgttcttata atgctaactt gattatcaaa cgactgctaa gccttagatt gaagcctcat   2040
acgcaccaaa ctgcctaatt tagatacaaa attagccaaa ctaaatcttc gaatacccaa   2100
aacacttaaa ttattgccat ccatatgtct agtgtgtaaa gacaaccaga aaaacctgat   2160
tactgatact aggagtgtaa aatataagct gagggccctg acatctgacg agttgatgaa   2220
gaatatatct tcctatagaa actgttaaaa aaacggtaat attaaatgcg aaacacggag   2280
ctacgatgag aagaaaaaat ttggtcctct aaccactaca agaaaggtcc aaaggtgttg   2340
taatatttga tcttatacag tataactcat gatcaaacaa cgtagagagc aaatatgaga   2400
acatcaaatg tatgttaata ttccgttggg gtgagttgac ggaattaatt aaaaataagt   2460
gtaacgacga acagtaatat atttatttat tttgggtgaa caagcggcgt gttttgctta   2520
tatctcgaaa gagggttgat tgttagcgaa ccgaggattt gtctgcatcg tttgcgtgct   2580
gtgtagagac tggcctccgg accaccacct ttatgtcaac tagttttgcg gttttgagat   2640
aatgaccaga aagggccata cattctgcat ctccttttaa gaacctttttt gtattttaag   2700 aagttgacat aacgagtgtg gcactctggg catcgcaatc tattagtgtt tccttgaatg   2760
aaacattaat cacaatctgt ttaaaggata acatttcgtt tctcgaaatc aacggcatat   2820
ggtttgtata tcacatgtgg attttaaatg accaatgccg tttcattttg agaaaagcca   2880
tgaaaaaaaa aaaaaaaaaa aaaaaaaaa a                                  2911
```

<210> SEQ ID NO 31
<211> LENGTH: 1287
<212> TYPE: DNA

<213> ORGANISM: Diabrotica virgifera virgifera

<400> SEQUENCE: 31

```
gggagacaag aggcagctac tattaacgat acatcgctct ctcgttagtg ttcatatttt      60
acgtgtagtg taacagaaag tgcagttttt tattcaccat gtctaaccgc aacatccta     120
tcaaaatggg tgacttcagt gttatcgaca cggagtttag cagcatcagg gaaaggttcg    180
acgccgaaat gaggaaaatg gaagaagaaa tgaacaaatt cagatctgaa cttaccagta    240
gggaagcgaa caacttcttc agaagcacaa ccagcatgtc gtacgaatct gaaacggtga    300
ctggtggaaa taagtcttca tcgacgtcca gttcaacgac acagcaaagc agcacaggat    360
cagatttagc ccacagagca ccaagtggtg atgtcagaac atggtacgac gacctcaact    420
ctcccctaat ccaacaggac ggtaacgaaa agagcctaaa attaagattc gacgttagtc    480
agtatgctcc agaagaaatt gtagtcaaaa ctgttgataa taaactcttg gttcacgccg    540
agcacgaaga gaaaacagaa tcaaaatccg tatacagaga atacaatagg gaattcttgc    600
tgcctaaagg aacaaatccc gaacacatca agagctcatt aagtaaagat ggcgtcctca    660
ctgtcgaagc acctctccca gctatcacct caggggaaaa attaattcca atccaacatt    720
aagtaattta aaattccttg taagccttcg aagcgtttat gtccgctagt aaatactcat    780
cgattaatta tttaaaatgt aacaactcat gtgactaaca aaatttttat tttatttcat    840
ttttaaaacc tggcaacgtt gtctggcttg tttaggataa gtcacaaatt tagtgttggc    900
tctaaagtac ttactgtcta cacagcacaa gtcacaaatc gttaaataca ccataaacct    960
catgcatcgt tgccggatgg ttcaaaagct catactattt gtgactatct tcttgatggc   1020
ggtcgtaaac ttgaaggttg attaacatcc tttcacaaag cttaattatg caatgaaaat   1080
aattttttaac aactttattt gtgacaaaaa aattgaagct aatgtaaaat tgtttggtta   1140
aattcttgtg aaggtctatg gttcgatgtt caataaccag caatttcacc gtaggcgtag   1200
tgtaacaaat tgtatcatgt gtaggatatt tacgaataaa ttattttttaa tctcgttaaa   1260
aaaaaaaaaa aaaaaaaaaa aaaaaaa                                        1287
```

<210> SEQ ID NO 32
<211> LENGTH: 560
<212> TYPE: DNA
<213> ORGANISM: Diabrotica virgifera virgifera

<400> SEQUENCE: 32

```
gggatcacgt gaataaatta caatatttct tcaaaatccc ttgacgcatc cccttgtaca     60
caatactgat aacatggtat tcggtataga tgttatcggt attgtggaca ggggcgcgcg    120
ttaaggtatt ttgaagaaat attgtgattt attcacgtga tcactccgtc tgttaggtag    180
acggagttat tttatgttcg taacaggtag tctgtatttc ttttaaggca aatatttggt    240
ccgtcgttga tctattgttt ctaaaacctg cctggtattc tcccaatact ttttccgaat    300
attgatttag ccttttctct atacagtatg cggcaaaata aacagtacct actgaaatga    360
atattgaaat gtttatgatg atttatatat ctagtataca tgatatagcc ttgcaaactt    420
tattcacgac gacgcatgtt cccgataaac agatgttaaa gatgtcctct ggtcagtgac    480
ggatctacgg ggagggaaaa tgagaaaatt ttttccccta acaaggttca aaaaaaaaaa    540
aaaaaaaaaa aaaaaaaaa                                                 560
```

<210> SEQ ID NO 33
<211> LENGTH: 807

```
<212> TYPE: DNA
<213> ORGANISM: Diabrotica virgifera virgifera

<400> SEQUENCE: 33
gggggacagt tcaatatgga tccactactt tactggttca tatttgttac gttaatatgt      60
acgctaggta ttctaggaag ttacttaatg ttttctataa taagagatag ctgttttaag     120
agaaagaaac aaaaagatac tgtgatggta atatatgaac cagattttca tccagcatgt     180
ctgagtaagt tacagtatga taaacatgat gttgaagatt taacgagaat cgaaagaaat     240
tccaagacgg ggtttagaag actaagttttt caaaatgaag tatttggtaa gcagtttgaa     300
ggattattgg gtgagaaaag acaatctgtt gacaaggaaa gtgatgtgtt tgtatctacc     360
aacactcttg acaaaagcat tacatcaatt acagaagaag atgaagaatc agacgatagt     420
tttgatcgag atactgtcag cgtagacatt gaagtatcag acgaggtaag agaagtttta     480
agaaccgaaa agaagctaa gaaggtcgag aaagaaatga acaggtttgc aggtggtaca     540
aacgatttac aatattacga aatcaatgag aagtatataa aattaatgat ttctctttgt     600
gatatggaat gcagctccat cgagtgcaga aaacacaaaa acagagtttt aagttacatc     660
gagcaatgtc agaaccaact caaattaaaa tctctgaagt ctaaataatt attttatt      720 gcttggagat gtaattatta taaatatatt ttaaatataa gtttagtata aacagccaaa     780
aaaaaaaaaa aaaaaaaaaa aaaaaaa                                         807

<210> SEQ ID NO 34
<211> LENGTH: 981
<212> TYPE: DNA
<213> ORGANISM: Diabrotica virgifera virgifera

<400> SEQUENCE: 34
ggggattcta aacttttcga actaacaaac aagatggcaa ccaaattttt agttctcgcc      60
gcattcattg cagtagctaa agccggttct tatggatcag gtttcggcta cgccgcgcca     120
gctgttgtcg ctcacggatc tcacgatgcc atctctacct actccactgt gcaacatcat     180
gctccagccg tacactccta tgctgctcac gctcccctcg ttcatgctcc agttgcccat     240
tcctacgcag ctccctttggt tcaagctcca gtcgctcacg cttacgctgc tcccgttgct     300
cacgttcacg ctgaaccctc tgcaccagcc cattacgact tcgcatatgg agtaagtgac     360
ccccacaccg gagatgctaa gagccaacac gaatctcgtc gtggagatgt tgttcacgga     420
agctactccc tcgtagaatc cgatggaacc aaacgtaccg tagactacac tgctgatcca     480
caccatggat ttaatgctgt tgtacacaaa gaacctaccg tacatgctgt tgctccagtt     540
gttgccaaaa tcgtagtccc agtagcacat gctgctccag tagctcatgc tgcttatgct     600
gctccagcgg ttcatgccgc ttactctgct ccagcagttc atgctgctta ctctgctcca     660
gcagttcatg ccgcttactc tgctccagtt gtccatgctg cccacgctgc cccagttgcc     720
catgctgctt atgctggtcc agttgcccac gccgcttatg cagcaccagc tctacatgga     780
tacgctggct ctgttgctca tggttacgct gctcctttgg ctcatggtca tcatgcttat     840
gctgctcatg ctccagtcct ttcacataac ttgtggtaat tctagaaagg aaaaattgta     900
gattttgtat ataaattatt tatactgctt gcattacaat aaaagattgt ggaaaaaaaa     960
aaaaaaaaaa aaaaaaaaa a                                                981

<210> SEQ ID NO 35
<211> LENGTH: 1160
<212> TYPE: DNA
```

<213> ORGANISM: Diabrotica virgifera virgifera

<400> SEQUENCE: 35

| | | | | | |
|---|---|---|---|---|---:|
| gggagtaaaa | ttaaactgca | gtgattaaca | atgaaagttg | ttattatttt | cgcttttatc | 60 |
| tgcaatattg | catttgtagc | tcatgtttac | ccggaatact | taaaacaata | tcgctgcaag | 120 |
| gcatcttcgg | aaaattatag | tgaatgcttt | ctaaataagc | tcagaaatac | tctgccctac | 180 |
| tacgttaaag | gcattcctga | attagatata | cctccatttg | atccgtttac | actacctata | 240 |
| tacagtcgca | atgtaaacat | attgggaaac | aagattagtg | cgactttcaa | aaattcgatt | 300 |
| gtaactggac | taaggaactc | tattattcat | aatgctaagg | ttgatctgaa | taacaactat | 360 |
| gcagaaataa | gcgttactat | tccttggttg | gatatggcca | cagagtatga | tatttctggt | 420 |
| gaattctttc | aatacccact | agatgtgaag | ggtactttta | aaggaaatat | aactgacatt | 480 |
| caacttttct | caaaatctac | tctacaaact | ttcaaaaata | acggtgaaga | ttattataaa | 540 |
| tttgataaaa | taaccaaaa | agtacaaatt | ggaggaggcc | atattgaaat | aacaactaca | 600 |
| gataaagatc | ttatgccgat | agttcaaaca | atacaagaat | atttaatga | gcatcccaga | 660 |
| ggcttcttta | acttgatatt | gccattcaca | ttggaatacg | cacaagacct | actcagagaa | 720 |
| tttggcaatg | aatatttagc | caatcttcct | gcttctgaat | ggttaccgca | gtaaacataa | 780 |
| atttgaaaaa | aatagtagac | ttagtagttt | aaacaacata | gttttttagt | taaaaaaatt | 840 |
| gaccgtagta | tttaaataat | ataatgacaa | taatgttgtt | gatgatcagt | tgagatatat | 900 |
| ctatccgcta | ttctatggaa | aattccagaa | atgcaatgca | ttttgaatta | tgcccataag | 960 |
| tggagtaatt | cgttctagca | gcatatagcc | tacatgttca | aatggactga | gacccgtatc | 1020 |
| ttctgttgac | catagcaata | catacatttc | ctcgtagaac | acttttttgt | gattattatt | 1080 |
| tttactttgt | gagtattttg | tatatgtgaa | ataaaaatat | tatattttgc | aaaaaaaaaa | 1140 |
| aaaaaaaaaa | aaaaaaaaa | | | | | 1160 |

<210> SEQ ID NO 36
<211> LENGTH: 721
<212> TYPE: DNA
<213> ORGANISM: Diabrotica virgifera virgifera

<400> SEQUENCE: 36

| | | | | | |
|---|---|---|---|---|---:|
| ggggtcactt | taattgtcag | taggaactga | gtgctagttc | aaggtagacg | tacgttgacg | 60 |
| agcgtgtagc | aaagttgttc | gtttcggatt | ttgtttttcg | taggtagatt | aatatggatt | 120 |
| atagtaagac | atggctggga | ggcattaaaa | aatgcagctt | ctgtgcatgt | cttccagaaa | 180 |
| aatatagcaa | tgaatgggtt | aaaggcgcct | cacgcttctc | tgagttacct | aggacattct | 240 |
| tggtattaat | ttttctattt | tgcttcaagt | aatattgtcc | tcatggctta | gtggcgggaa | 300 |
| gcaagatcat | attagtcgcc | gtttcgcaaa | atgaagcata | tttcataaat | atctgtgggt | 360 |
| ataaagtatt | ctccaagcga | agctccagaa | tgctgcagaa | tgcaggagct | ttatagccaa | 420 |
| gtctgaagtg | aatacagagc | aatatcatta | ataagtcatg | ttcttaaatt | atttctaaaa | 480 |
| attataaaaa | ctgtcagagt | gatgatgata | gccaacttgg | atttagaaag | gaattaggaa | 540 |
| taaaagatgc | attatttact | tttaatgtga | taactcaaaa | atgcatggat | tatgtttgtg | 600 |
| aatctgcatg | tttgttactt | taatttttaa | attgtatttt | tttttaaatt | ttaaaaagca | 660 |
| tttgacaaag | taagacatga | aatattagtc | caaaaaaaaa | aaaaaaaaaa | aaaaaaaaaa | 720 |
| a | | | | | | 721 |

<210> SEQ ID NO 37
<211> LENGTH: 928
<212> TYPE: DNA
<213> ORGANISM: Diabrotica virgifera virgifera

<400> SEQUENCE: 37

| | | | | | |
|---|---|---|---|---|---|
| ggggtttagt | atgtcttaga | gcattatggt | tactcttcca | atcattggat | gatcgttctc | 60 |
| caatgcggta | tcctgtatat | taccacttaa | tacaaattgc | gaaacagaca | gaatctgtaa | 120 |
| aattagtgtt | tcaagatatc | aaccatctaa | agcaacagtt | tgccaattgc | cttccgtcta | 180 |
| atgaacagct | tcaaaagctt | tataggcttt | tacatgaagt | actggttaaa | tcaaatcaaa | 240 |
| gtgagcaggc | tgctttagtg | atgattgaac | ttcttggtac | atacactgac | aaaaatgctt | 300 |
| ctcatgccag | agaagacgcc | atccgttgca | ttgtatcagc | actagctgat | cccaacacat | 360 |
| tccttcttga | tccattgtta | tcactaaaac | ctgtcagatt | tttggagggt | gatttaatac | 420 |
| atgaccttt | aaacatcttt | gttagtgaaa | atttgtccac | ctacctcaag | ttttacaatg | 480 |
| aacataagga | atttgtgagt | gcacaaggtt | taaatcatga | acagaatatg | caaaaaatga | 540 |
| gactgctttc | cttcatgcag | cttgctgaga | gtaatcctga | aatatctttt | gatgtcatcg | 600 |
| aaaaggagtt | acagatgaaa | ccagacgaag | ttgaaagctt | tattattgaa | gtattaaaaa | 660 |
| ccaagttagt | tcgtgcaaga | atggatcaat | cttcccggaa | agtctttgtg | tccagcacaa | 720 |
| tgcacaggac | tttcggaagg | gcacaatggc | aacaactgcg | ggacttactg | cactcttgga | 780 |
| ggggaaatat | aagttctgtt | caagacggta | tgaagactat | cgccgctgct | cagctagaac | 840 |
| ttatgaacca | acaacagtaa | tgataatgaa | gttttcataa | cttttaataa | aacgttgaaa | 900 |
| aaaaaaaaaa | aaaaaaaaaa | aaaaaaaa | | | | 928 |

<210> SEQ ID NO 38
<211> LENGTH: 1339
<212> TYPE: DNA
<213> ORGANISM: Diabrotica virgifera virgifera

<400> SEQUENCE: 38

| | | | | | |
|---|---|---|---|---|---|
| ggggaatata | attaattcaa | taattagaat | tagaaatatc | tcgttggaac | agttgtagat | 60 |
| attcataatg | gagagtaact | tgggttatca | aaatgggagt | caaagtagag | aacaagactt | 120 |
| tcaaaaactg | tcgcagacca | tcggtaccag | catacagaaa | atatcacaaa | atgtgtcttc | 180 |
| tatgcagcgg | atggtcaatc | aaataggaac | ccatcaagat | tcgcctgaat | tgagaaagca | 240 |
| attacattcc | attcaacact | acacccagca | gttagtaaag | gacacaaatg | gatacatcaa | 300 |
| agaccttagc | catattccac | catctctatc | acaatccgag | cagagacaaa | ggaaaatgca | 360 |
| gagggagagg | cttcaagatg | agtacaccag | tgcattgaat | ttgtttcaaa | acgtccagag | 420 |
| aagtacagca | tacaaagaaa | aggagcaggt | caataaggct | aaggcccagg | tgtatggaga | 480 |
| accccatttta | attggatata | agtccaagga | ccaacaactc | atagaactgc | aagacaataa | 540 |
| ttcgaggcaa | atgcaaatgc | aagaggagtc | aaatctaagg | gaattagaag | aacaggaaca | 600 |
| gtcaataaga | cagttggaga | gcgacatcaa | cgatgtcaac | ctaattttca | aagaattagg | 660 |
| aacccttgtg | cacgaacagg | gcgaagtgat | agacagtatc | gaggccaacg | tggaagaac | 720 |
| caccgacttc | gtcagccaag | gtgcccaaca | actccgcgaa | gctagtacgt | tgaaaaacaa | 780 |
| agtaagaaga | agaagctga | tcatgttgat | gatcgctgct | ctagttttaa | ctatactcat | 840 |
| aataataatc | gttgtatccg | tgaaacgtta | aaatagtatt | atggtaatga | tattaaaaat | 900 |
| gtgatgattt | aaatgattgt | ggtaagtaga | taggaaatat | tcatgaacta | cacatcctta | 960 |

| | |
|---|---|
| cttattattt tatcttattt ggtgaagctc ccagttcctt aacccttttc ttggcaaacc | 1020 |
| gatataaaac tgtgaaaact ctgttttctt tatattcatg cccttctaga attatttaaa | 1080 |
| aatttatgaa ataaatattt cacctttaat ttattcctaa gtaccaaatt tgaatgtgtt | 1140 |
| acaaatttgt tacgttgcca agaataccat accccttatt accactgatg gtccatgcat | 1200 |
| tttctaaggt ttgaaccgat ttctcagaac aaagttaaaa tttcttttat ctgagttcat | 1260 |
| gggagtgctc tcgcgtcaca acacccccct atccccatta aattttagga aaaaaaaaa | 1320 |
| aaaaaaaaa aaaaaaaaa | 1339 |

<210> SEQ ID NO 39
<211> LENGTH: 533
<212> TYPE: DNA
<213> ORGANISM: Diabrotica virgifera virgifera

<400> SEQUENCE: 39

| | |
|---|---|
| ggggctttta tttccgcttg atagtcaaga aaaggtgtca agatgacatg taaaaggcgc | 60 |
| aatggagggc gctccaagca cggccgtggt cacgtaaagc cagttcgatg caccaactgt | 120 |
| gctagatgcg ttcccaagga taaggcaatc aagaagttcg tcatcagaaa cattgttgaa | 180 |
| gccgccgctg tgagagatat tactgaggca tcagtatatc aagcttacgt tctccccaag | 240 |
| ctctatgcga agctccacta ctgtgtatcc tgcgctatcc acagcaaagt tgtgcgtaat | 300 |
| agaagcaaaa aggataggag agtcagaact cctccacaga gaaactttcc tggtagggac | 360 |
| aatgctagag ttcagcaaca acaacctagg aagtaaactg tttcttagt tttacaataa | 420 |
| aatttaagaa aaaataaaaa aaaaaaaaa aaaaaaaaa aaaaaaaaa aaaaaaaaa | 480 |
| aaaaaaaaa aaaaaaaaa aagggaaaaa aaaaaaaaa aaaaaaaaa aaa | 533 |

<210> SEQ ID NO 40
<211> LENGTH: 535
<212> TYPE: DNA
<213> ORGANISM: Diabrotica virgifera virgifera

<400> SEQUENCE: 40

| | |
|---|---|
| ggggcttttt cagcagttgt caaagcactg ccacaatggg taaataatg aaatcaggaa | 60 |
| aagtcgtatt ggtcctcggg ggccgatacg ccggcagaaa agccgtagtc gtcaaaacct | 120 |
| acgatgaagg tacatcagat aaacaatacg gacatgcctt agtagctgga attgataggt | 180 |
| acccaaggaa aatccacaaa cgcatgggca aaggcaaaat gcacaagagg tccaagatca | 240 |
| agccttttat caaagtattg aactacaacc atctcatgcc cactagatac tctgtagatt | 300 |
| tggcatcaga cttgaaagtt gtacccaagg acctcaaaga tgccatgaag aggaagaagg | 360 |
| ctagattcca gacccgtgtc aaatttgagg aaaggtataa gcaaggaaag aacaaatggt | 420 |
| tcttccaaaa attgaggttc taggctgtag atttaatttt ataattgtac actttttatt | 480 |
| ttgagaataa aatgtggata aatgcaaaaa aaaaaaaaa aaaaaaaaa aaaaa | 535 |

<210> SEQ ID NO 41
<211> LENGTH: 788
<212> TYPE: DNA
<213> ORGANISM: Diabrotica virgifera virgifera

<400> SEQUENCE: 41

| | |
|---|---|
| ggggaactgt caaatataac cttaaataat atttatttac gtgtgtgtct tgtttccata | 60 |
| gttttagctt ttttctttt aatttaaaaa gatgagtgac gatagtgata actttgaata | 120 |
| tgtagacgat gagatagatg ataaaactca caataaacta gtggataacg ttttaaagt | 180 |

```
taaataaagt tcaacatgtc aaaagtgcac atagaactga agctgccact aaagtgtctg    240
aatttaatct agtaaaatcc ctttcgaata aaaatttagt gcatgttaat gaattaacga    300
gcgttttaaa gggaaggaag tctcttcagc tgtctaataa aattaaatct acaagtaata    360
tcagcaagac attgcctaaa cctctagaaa agccacaagc tgaacgtatt aaacgagctt    420
taaactatga gaaagcgaaa ttaaaattgg atagatggga agctcttgtt caggctaata    480
gatcagctgc acaattatcg ttcccttaa atagtgatga gaaagtaaag gtcattgaga    540
aacgggccat atcttacccc ttatctttca gagttaaatc ggaccttcag aaaaatttgg    600
aaaatataga ttcacaaata gaagagtatc acatagatac agtagaaaag aaagaagatg    660
aagactatcc acttacacta gaagaattaa aggaaaaaaa agaaaagaac tagccaaact    720
tcgtgcacac cagagttta aagaagcaaa agctagacaa aaaaaaaaa aaaaaaaaa    780 aaaaaaaa                                                             788

<210> SEQ ID NO 42
<211> LENGTH: 444
<212> TYPE: DNA
<213> ORGANISM: Diabrotica virgifera virgifera

<400> SEQUENCE: 42
ggggaacgaa gtggccattt cttacagata attccacatg ccaaccattc ataagataaa     60
gcaaggcatc gtcgtgttct tgttgaaact ctagtagtcg gtatgggccc actatccaat    120
ttccaataat tctaatccaa ccagtaactt tttgtgacac ttctgtatga tctccttgaa    180
tataatcagg gttgttaaca acgcaactga atatttccgt agagggcgct tcaaaaatcc    240
gtagaaatcc gtagtacaaa aatctgacag aaaatgacac ttggcagacc aaaaaaagaa    300
gaagaatgac acttgacata caaaaaaaga agaagaatga cacttgacag accaaaaaaa    360
gaagaataat gacacttgac agaccaaaaa gaagaagaat ggcacttgac acaccaaaaa    420
aaaaaaaaaa aaaaaaaaaa aaaa                                           444

<210> SEQ ID NO 43
<211> LENGTH: 472
<212> TYPE: DNA
<213> ORGANISM: Diabrotica virgifera virgifera

<400> SEQUENCE: 43
gaggtttaca tattttcaag ttgtccaaaa atatccacat gtcttcgagg taattgagat     60
ggtagtccag acctttaaaa catttttaaa ttcatttggg tgacatatat atattggtgg    120
aattgaatat gtcaaattta tttattactt caatagtata taagtcttgc agctgttacg    180
tttaaaattt gagtagctta cttaactgtc gtatttgaaa agtgtgttgg tcgaatatgc    240
gcctcgttag ttatttctag ttgcttttg taaatttgga ggatcaaaaa ataaataagc    300
ttatgattaa ttgtttatat gggaggtggg ccgcagttga aatgaaaaaa ataattttta    360
ttaacgtttc gacgcccaaa tcgggtgccg ttgtcaaaat acaaatatt attaaaataa    420 acaaagtgt tgttgctaag cgaaaaaaaa aaaaaaaaaa aaaaaaaaaa aa             472

<210> SEQ ID NO 44
<211> LENGTH: 497
<212> TYPE: DNA
<213> ORGANISM: Diabrotica virgifera virgifera

<400> SEQUENCE: 44
```

```
gggcttatt cacaattatt aaataataa atggatatga ccaattatca gtaagtgaaa      60
cagaattcat tggtataaat ttcatatctg taatccgtct acccgtaaag gaaaccagaa     120
ccaatagtat taatttattt tctgaaatac agggcatgcc tttgtttaca taatatttgc    180
atactaacct ttgaaacgtt attcctgaag atctacattt gcttctgctg ctccaactgc    240
gttgaggaca ggacagacac atttatgca atatgttaat aatactataa agtatccga     300 attaaaaaaa atattcttaa aaagcacaaa taaaacaaac aacgatcacg ccacacacga    360
caaggccggg caaggtggcc aagatgccaa gatggccgaa gtgaggtcgt tcgttggtcg    420
tttttagtca cgtgatgcca tcgtgatgcc ctctctaagc ggcatgcgaa aaaaaaaaa     480 aaaaaaaaaa aaaaaaa                                                   497

<210> SEQ ID NO 45
<211> LENGTH: 809
<212> TYPE: DNA
<213> ORGANISM: Diabrotica virgifera virgifera

<400> SEQUENCE: 45
ggggaagtaa ttctgctaaa aattttacac tcctttggat tggaggaaga attacaattt    60
tcattattaa atatctattt gaaaataaat aacaattgca caaggtgtag taaaaaggtg    120
ggtcatgaat aaaataaaat attctgggaa taaaaatagt tccattgaac ctaagttacc    180
ttagtacaaa ggtgcacata aaaaaagtta taactctttg agcttataaa ataaaaatcg    240
agaatatcga aaatatattag aggttaaaat gggcatttga cattattatg gtaggaaaat   300
ctttaaaaaa atagtagtga aattttcaca gccgataaaa attttatagg ggctttattc    360
ccttaacctc cccccccccc aaacctttat gtacgttcca gttaaattat tatttagtcc    420
tggaggggga tgtgtcacca acacgatatt ttttttcctt attctctga actaattgtg     480 ataccattag ttaaacacaa tatttctaaa acttttttgc tgactatttt gtcgatgaac    540
cagttgttat atgcggcttt ttttcacatg ttatgagagg ttattaaaat tattgttaaa    600
ttatttattt gtagttaaat gtgtaagcca gttcccacat tcaaacctgt cagaggtgag    660
ctaagatatt ggttggcgac aatgtttgtg gacatcaggg ccggttttgt ggtttttgag    720
cgccccgggc aaaataaaat ttgtcgccca ttcatacaag aatatacaaa tttactccga    780
aaaaaaaaaa aaaaaaaaaa aaaaaaaa                                       809

<210> SEQ ID NO 46
<211> LENGTH: 1728
<212> TYPE: DNA
<213> ORGANISM: Diabrotica virgifera virgifera

<400> SEQUENCE: 46
ggggagtaaa gaataattcg gtgtttaccc ttattaagtg aagttttttt actacgaagt    60
gtactgtgtg ggagacaaaa aaaaacatga agaatctgtt gttcttgttt gggtttatca    120 gtatttatc agtattgcta gccgcagatg ttcgcctggt agacttagat ccaccagaag     180
ctcaacagca aatagaacaa caggaccagt ctcttcacta tgcgccaaaa gtagaatcaa    240
atgttcccgc agtaagatat ttgggaaacg aaccctcacaa tgttctggaa gatatttact   300
tagctagaca gtatcacgga caagacggaa taggaggata cctttatgga tacaacatcc    360
cagatattgc caaactgag aaaaaagttt ctggtggaga tttaagaggg gcgtacaatt    420
acattaatga tgatggggcc gaaatcaagg tcgaatattg gacgatgga actggattcc     480 atcaaatcga taatgttcct aaaatcttac ccaagccaat tgaagagtct ccggaagtta    540
```

-continued

```
aagctgaaaa ggataagttt ctagcaagat ggcatgaaga ggccgagaga aatcaacgtc    600
cagttgcttc cccctatgat gctgatggta attacgctag cggaccatta tcgctccagg    660
gacaagctga atttaagaaa atgtttgaaa atcaaccccc aaggtcagta ctaccaacaa    720
cctagctcta gttctggagt ttaccagcaa aacggacaat atcaacccgc tggacaatac    780
caacaaactg gacaatacca acaaactgga cagtaccaac aacctggaca gtaccaacaa    840
cctggacagt atcatcaatc tggtcaaatt aaacaagttc aacaaccagg acccct tcaa    900 caaggtcaat attatcaatc atctaaatcg caatcttctg gtcagcacca acaacctggt    960
caataccaac caactgatca ataccaacaa actggtcaat accaacaacc aggtcaacaa    1020
gtttctgttc agcaattaac caatcctaat caaatcgatt acactggagc atacagtgaa    1080
agccaaaact cttacgcaaa cccaactcca aacaaaccat ctggtcaata cacgccagtt    1140
gcttcaagct ccaaccagta cagccaacaa ggaggatatc aacagcctgg acaacaccaa    1200
caaggtgcat atcaacaaag tggaacaaat cagcaaccag gatcatacca acaaggtgca    1260
taccagcaga gtggagcaaa tcaacaacca ggatcatacc aacagggtgg tcaataccac    1320
caatctggac agtaccagcc ctccgataac tcaaaatcaa accaagttga taattccggt    1380
gattacgata aaagctggga caacgagggc caatatgata aaaaatacga tgaagaagaa    1440
ggctccactg gccccccaaa gggattcttc tataagtttg attaccctgt aggaaaaatt    1500
gttcagaaag gagaaatcgc tagagttgga gatctgaaaa atgcgtatag tcaaaataaa    1560
gctgcgtacg aatcccaagt aagttcaggc cactcgggtt cagctgcttc ccaaagcagt    1620
tactcatatg gttcttaact ttaagctgtg ataatgtatt ttatagattt ttaggagaat    1680
aaaaaatata ttactttcaa aaaaaaaaaa aaaaaaaaaa aaaaaaaa    1728
```

<210> SEQ ID NO 47
<211> LENGTH: 962
<212> TYPE: DNA
<213> ORGANISM: Diabrotica virgifera virgifera

<400> SEQUENCE: 47

```
gggacggttt tacgtgggaa cagcccaaaa cactacaact aaactgacaa ccttccgtaa     60
caatatttta gaaatctttt attgacgcac tagatgcctc cttctagatt ttaagtttag    120
aaaaaacttc tgtgattggc gctctgaacc ttgagaccga cgcgattttt tgcctctctg    180
aatcggaaac attctacaga gcaaagtatc gcgtactaac aagtaactgt cgcaaaacgt    240
gcccacagat tcccgatata gaccacagtg gcgtttcaag cgttactgca attcagtgtg    300
agtcaaacgt tcagtttcaa gttagatatt actcgcacat tgtgttgtgt ttaagagaaa    360
aaataatttg gaaagagca tttctataaa cactccggac tgtattggga atggtggtca    420
tccatgcatg aaaagttctt gcaaaaacaa tatttatata ttatgtattt tatacaactc    480
atcagtgttc actggttgta aattatattt tattctaatt ttttaaccta caactctaca    540
ttccttgtta ttttaaaata atcgtcaaat taacatagaa tttgcaagaa acatgtacaa    600
tgggcattta agatctgctg ccgtttgata tagaattccc ttagtgttaa ttttattgat    660
ttgattttgt aaactgtaga tgaataatta ttgtagatga tagtttgaat gtatagattt    720
tattgtacct atgtaattta ttatgagagg ataaaacgat ctatatgttg tatacaattg    780
atttaagtaa gtttggtaga tgtattgtcc aatgtagatc gtaaaatttg gtgtaatttt    840
ttatagcata gtttattttt taaataaccc aactgatact ctattgctct attcaaattg    900
```

| | |
|---|---|
| tgcttttttt gtctaagaaa taaaatagtt gtgaaaaaaa aaaaaaaaaa aaaaaaaaaa | 960 |
| aa | 962 |

<210> SEQ ID NO 48
<211> LENGTH: 1146
<212> TYPE: DNA
<213> ORGANISM: Diabrotica virgifera virgifera

<400> SEQUENCE: 48

| | |
|---|---|
| ggggattggt gttcaagtca agtcaagttt gttgagtaaa atcaaactag tttgacttga | 60 |
| tgcatctcta atatctgcca taaattgaag gactccagta ttcaatccga atatgtttca | 120 |
| acgtaaatgt aaattctaca tgacaaaaac tcagttctta atagatggac acaacatttc | 180 |
| agcgaacatc taaatattaa cgatattgaa gaaggttaca acatagaaaa tcaacaaaat | 240 |
| ctacatcatc aactacacac tgaagaccca acaagagaag aagtatcaac tgccatccta | 300 |
| aaactcaaag acaataaagc cctgaatctg ttctgatctg tataaaaagg tggtgatcat | 360 |
| ttgcagcaat ccataaatta atagtactga tatggcagaa tgaactggat ccagaaaagg | 420 |
| gaataatacg tccgttgcat aaaaaaggtg atcaactgga ttgtaagaac tatataggca | 480 |
| ttactctact agcatctacg tataaaatct tcggcaatgt attgtttgaa agactgaaac | 540 |
| ttttcacaaa ggatattgtt ggtcaatatc aatgcggatt cactgctgga aagtcaacta | 600 |
| tacatcaaat tcaagcacat agacagattc tagaaaagtc aatagaatat aacatagata | 660 |
| cccaccatct cttcgtcgac ttcaaagcag cctatgacag tgttaaaaga actgcattat | 720 |
| ataatgcaat gattgacttt gggatcccac cgaatttggt taagttgacc caactaacaa | 780 |
| tgcaaaatgt aagctcgtgc gttagaattc aaggagaaaa ctggacattc tttgacatta | 840 |
| ataatggtct aaggtctaag acaggggggac gcgctggcgt gtctcctctt taatattcct | 900 |
| tggaaaaggc agtgagaaaa ttaaatatta gaatgaatgg aagtattttt aatagatcga | 960 |
| cgcaaattct cgcattcgct gacgatatag ttatagtggg cagaagtgtg agagacatgg | 1020 |
| tgcagtattt taaaagactt gcggacgcgg caagtgaatt aggacttgtg atacacgagg | 1080 |
| aaaaaaacaa atatatgttg gtttctaaaa actcccgaaa aaaaaaaaaa aaaaaaaaa | 1140 |
| aaaaaa | 1146 |

<210> SEQ ID NO 49
<211> LENGTH: 630
<212> TYPE: DNA
<213> ORGANISM: Diabrotica virgifera virgifera

<400> SEQUENCE: 49

| | |
|---|---|
| ggggagtcag tgttgcgatc gtccagcagt cttccaaaaa ttgacgtgtt ttctggaata | 60 |
| aacaatatgt gattgagtgc tttttaacct taaaaatcaa aaagtttctt gtgatagtga | 120 |
| agtgaaatac ttaaaataat agacaatgtt tgcgaacgga caggtagtag gtgatggtac | 180 |
| ctgggacctt cgggtttttg tcacagatct acaaacggag aggttgattc gcgtaaaagg | 240 |
| agatgtccac attggcggag tgatgttgag gctggtcgag gacctagaaa tttcaatgga | 300 |
| ttggtctgac catgcgcttt ggtggcccga taaaaatata tggctgacaa gaacaagatc | 360 |
| tactctcgac caatgcggag tccacgcaga tgccttactt cattttactc caatgcacaa | 420 |
| aattctcagg ctacaattac ccgatcttag gtatttggat atgcgggttg acttttcaat | 480 |
| caaaactttc tccgctgtag ctcaactttg caaagattta ggcttaaggc acccagaaga | 540 |
| attgtctctt tcgaagccac tggaacccaa tcatttaaaa tacaattata aagacctgcc | 600 |

```
aaaaaaaaaa aaaaaaaaaa aaaaaaaaaa                                   630
```

<210> SEQ ID NO 50
<211> LENGTH: 293
<212> TYPE: DNA
<213> ORGANISM: Diabrotica virgifera virgifera

<400> SEQUENCE: 50

```
attggtcaac agaaaactaa tagaagaaga taacttaaca aatttaattt ataaaatacc    60
tagggtaaat ttagtgggcg caaacaaacg dacattggca actataaatg aaggcatacg   120
agtaatggta cgactgggca agaatatgta tgcactacaa tgtgtaataa tgccaaacat   180
gtcacatgac atgatagtag gagtggacga attggcagaa aaacatgtag tggtagattt   240
taaaaataat acgatgaaac taacagaaaa aaaaaaaaaa aaaaaaaaaa aaa          293
```

<210> SEQ ID NO 51
<211> LENGTH: 1508
<212> TYPE: DNA
<213> ORGANISM: Diabrotica virgifera virgifera

<400> SEQUENCE: 51

```
gggtagcaga gaagaggaaa ttgtatctga tgtggtttat gaaaaaagtt gacggtgtag    60
gggttgaaaa tctcggttaa atgacacatg gcgattgaca caattaggac ttctctgctt   120
ctctttaact atttctaagt cttcatacag gtccaatttt aggaagtttt tttgtgaaat   180
attatgtaat aacgagacat cttctgggat attaagggta tgtttgtttt ttacaagatg   240
ttgagagaaa gtagaagtgt tttctctttt ggtgtgctct aaggagcgtg aagataagga   300
tctacaggtc ctacctatat atgtagcgtc acaatcagaa cattgtaatc tatacacacc   360
actacgatcc atgtagttga tagggtcttt ggaattggta agacactgtc ccagattgtt   420
gggcactttg aaagaaatat gagtattatc aactgctctt ttaagaatat atctaatgtc   480
tccagaaaga cgttcatgaa gatatggtaa ggaagcatat gagggtttga aggtcaagtc   540
tctagggaaa gcagtctctc tcaagactct aaggtgtctc ttttgaataa gtttgtagac   600
aatattagga tcgtaaccgt tgttgaacgc tatttgacga agaatattaa gttctttatc   660
atagtttgat ggtgataaag gaatagtttc aagtcaggaa tagaatcaaa ataattagt   720 aatatgtagt taacatctgc acttgaaccg ttttatcagt aacatttatt aacaccatgt   780
accgattcaa gtacatttt ttaataattg aaaaaaagga aggatatagt aagagtaata   840
atataccctt atgtttttat caccttatag taaattgtac actagacaaa ttttagttta   900
atgactccta gaatttataa aactcaaaca actttgaagc tgattatctc agaactacca   960
aaactgcact taacgctttt tacgtgtggc cccctcaatt gtaaaaccaa aatgttaatg  1020
cgggctgaat ccccgcgaca aatgaatcag aagatagtcc attctttaaa atttagagca  1080 aaaccgtga agaatggac taagagctca aagagtgcgg caatcactcc tttaggagtg  1140
tagatgccat gatgatgatg ataccttgta taaaggattt taattatttt tgtgattaat  1200
tgtacacagt cgataaaaag aaagagtata aatgccttt aaatatatta aattttactt  1260
ttccatgaaa ctttagtgtt tcaatatcta atcatgaaaa gttcaagtgt cttcaacaga  1320
atattaactt tcagatttgt aatagttttg ggattaatta ttgtattgga gattcgaatt  1380
taataattct tatccaccctt accgttaccg tccagtccgt ctgctgctac tcctattgtg  1440
ataaaagtat aaattggcaa actttatttt tcatctacaa aaaaaaaaaa aaaaaaaaa  1500
```

```
aaaaaaaa                                                             1508

<210> SEQ ID NO 52
<211> LENGTH: 631
<212> TYPE: DNA
<213> ORGANISM: Diabrotica virgifera virgifera

<400> SEQUENCE: 52
ggggaaaaag ttattttttg ataaatttcg aactgtattt gaaaattgat tctatataat    60
aaatacataa aaagattggt tttaaataaa aatggcacac aatattaaaa aactgagtgt   120
ttcaatgagt aaagcgggaa tgccatttcc agtacctaca aagattatta gatttgttag   180
gaaaggttgt actaatagac cctttttcca catagtagtt gcagatgcta gatcagatca   240
acacgaccct tcaatagaac aacttggaac tcatgatcct ttcccaaatg aacacaatga   300
aagattaaca tccttaaact tcgaaagaat tcgatattgg ttatcgcatg gagcgattgc   360
aacaaatcct gttcttgaat tattaggtct tgcaggattc tatcctattc accccaggag   420
ttatatgact gcttggagaa acaggaaaa ggcaaaacaa gcttctgaag ctgctgaaca    480
gaccaaagag gagaaaagtt aataacatgt catttacttc tgtgttgtgt gtacatttta   540
gtatgtttaa gtagctataa gtctattatt ttgtaaaaag tcattataaa catataaacg   600
caaaaaaaaa aaaaaaaaaa aaaaaaaaaa a                                  631

<210> SEQ ID NO 53
<211> LENGTH: 114
<212> TYPE: DNA
<213> ORGANISM: Diabrotica virgifera virgifera

<400> SEQUENCE: 53 ggggattttta taaatctgtt aaacaatgag ttggtcagca taagctccaa agtgttgtag    60
caatacagaa tgagtttaaa tatctaaaaa aaaaaaaaaa aaaaaaaaaa aaaa          114

<210> SEQ ID NO 54
<211> LENGTH: 597
<212> TYPE: DNA
<213> ORGANISM: Diabrotica virgifera virgifera

<400> SEQUENCE: 54
ggggtctttt ctcagtgaag ccatcttggc aaacgttagt aacgtgaaat aaaacttaaa    60 tttttttcaaa atgggtcgta tgcacgcacc aggaaaaggt attgcccagt cggcattgcc  120
atacagaagg agtgtaccaa catggttgaa agtcacacca gaagaagtaa aagaccatat   180 ttttaaacttt ggcaagaaag gcttgactcc atcacaaatt ggtgttatcc tcagggattc  240
atatggtgtt gcccaagtaa ggtttgtttc tggaaacaaa atcttgcgta tcatgaaagc   300
tatgggtctt gccctgatc taccagaaga tttgtactac cttatcaaga aggcagtagc    360
tatccgcaaa catttagaac gtaacagaaa agacaaggac agcaaattcc gtttgatttt   420
ggtagaatca cgtatccacc gtttggctag gtactacaaa accaagagcg tattggcacc   480
caactggaag tacgaatcaa gcacagcatc tgctttggtc gcttaaattg tgcttttatg   540
ttaagtttat aaaataaaaa tttctattaa aaaaaaaaaa aaaaaaaaaa aaaaaaa      597

<210> SEQ ID NO 55
<211> LENGTH: 543
<212> TYPE: DNA
<213> ORGANISM: Diabrotica virgifera virgifera

<400> SEQUENCE: 55
```

```
ggggccttt  taacgaaaaa  tcgtgtgtaa  aggtagcaca  cgaataatca  tctttaatt     60 ttccctataa  tcctttcagg  atggcaatca  gaccagttta  ccgtcctcaa  atcatcaaaa   120
agaggacaaa  gaagttcatc  aggcatcagt  ccgatagata  tggtaaactt  aagagaaact   180
ggcgtaaacc  aaagggtatt  gacaacagag  tcagaaggcg  tttcaaggga  caatatttga   240
tgccaaatat  tggttatggt  tccaattcta  agactaggca  tatgctacca  acaggtttca   300
gaaaagtttt  ggtacacaat  gtaaaagaac  ttgaagttct  ccttatgcaa  aaccgtaaat   360
attgtgcaga  aattgcacat  ggagtttcgt  caaagaaacg  caaggatatt  gtagaacgtg   420
ctcagcaatt  gagtattagg  gtcacaaatg  gaaatgctag  gttacgtagc  caagaaaatg   480
aataagctat  tattttgttt  aataaaaaat  agcaaaaaaa  aaaaaaaaa   aaaaaaaaa    540 aaa                                                                     543
```

```
<210> SEQ ID NO 56
<211> LENGTH: 1023
<212> TYPE: DNA
<213> ORGANISM: Diabrotica virgifera virgifera

<400> SEQUENCE: 56
ggggattcag  tatattggga  tttattaaag  agatttctag  cccagtgaga  agaaattcaa     60
gaaagtggcg  aggttcgagg  gaaaatttt  ttctgccgtc  aataatttt   tttctagttc    120 acccttggtg  aaccaaatta  aggacttagt  tactaaacaa  gtaagttcgt  cagataccga   180
aatgtcacag  aaagaaagtg  aatctgtgga  tgctacatca  cctcctccaa  tgctaattga   240
aaccactgag  aaatccgatg  gagtcccttc  cagatcacca  tctgatgaaa  ttagtaaact   300
aagaccagag  gaccgctcaa  gaaatcagag  cttttctatc  agaaatatgc  aggtgtccag   360
gagccaaatg  aaggaataca  gagaagcctt  tagactgttc  gacaaagacg  gtgatggcag   420
tataacaaaa  gaagaattag  gcaaggtgat  gaggtcgtta  ggacaattcg  ctcgcactga   480
agagcttaaa  caaatgcttc  aagaaataga  tatcgatggt  gatggtaatg  ttagttttga   540
agaattcgta  gatatagctt  ggtcagcaag  ctcagggcgt  gatcccgatc  acactatgtc   600
tttggaggaa  gaagaaaag   agctaagaga  tgccttccgt  gtatttgata  aacacaacag   660
aggatatatt  gtctcgtcag  atctccgagc  cgttttgcat  tgtcttggag  aagacttatc   720
tgatgaagaa  attgaagaaa  tgattaaaga  agttgatgta  gacggagatg  gacgaataga   780 ctttatgaa   ttcgttaatg  ctttgggtga  accaggcaat  gaggatagct  acgatgatga   840
cgacgatgat  tacttatcat  tttataacta  gaaaacatta  agatatatgg  ttttatgta    900 cctgtgtttc  cagagaactt  catccataat  caaataagct  gcctaataaa  caattaacct   960
aattataaag  tttaaatata  cctatgcctg  ctacaaaaaa  aaaaaaaaa   aaaaaaaaa   1020 aaa                                                                    1023
```

```
<210> SEQ ID NO 57
<211> LENGTH: 1179
<212> TYPE: DNA
<213> ORGANISM: Diabrotica virgifera virgifera

<400> SEQUENCE: 57
ggggctttat  aatttgtcgt  tgaaaagat   agggctccaa  agtcctattg  ccaacaaaaa     60
aacaacgcaa  gacattaaac  aactttttc   aagcccatct  gtatttaaaa  aaacagtgca   120 aaatgttct   gtgggactgg  tttacgggaa  tgctgggata  tctaggattg  tggaagaaac   180
```

| | |
|---|---|
| ctggaaaact attattctta ggactggata acgcaggcaa aactacccct ctacatatgc | 240 |
| tcaaggatga cagactggcc cagcatcttc ccacgttaca tcccacatca gaggagcttt | 300 |
| ccattggtaa catgaggttt acgacgttcg atttgggggg ccacgagcag gctaggagag | 360 |
| tgtggaggga ctactttcca gcagtcgatg ccatagtgtt ccttgttgat gccaacgaca | 420 |
| gctcaagatt tgtagaaagc caggaacagc taaatgccct cctctcagac gaaactctat | 480 |
| caaactgtcc aatacttatc ttaggtaata aaattgatct cccaggtgct gcttcggaag | 540 |
| atgaattacg aactagattc ggcttgtttg gccaaaccac aggcaaaggc aaagtagcca | 600 |
| gaaatgatct acccggtagg cctctagaac tatttatgtg ctctatactc aaaagacaag | 660 |
| gttatggaga aggtttccgt tggttggcac aatatatcga ttaattatgt attttttccat | 720 |
| ttcgttctgt cattgagtta ggatattaat gtttgaggaa ctattggcaa cactgcaact | 780 |
| acctgattca tttcagatct taggtacttt acataaatat ctaaatatag atgttggcaa | 840 |
| tgtaattttg aacaacagta tatacattca atgtaaatta tatattttta gttaagttac | 900 |
| cttcttaaat ggtgtttgag tggctatggt actgaaatag tttgactttt tgtgttcttc | 960 |
| gataactaaa aatgatttct tgtggaaagt tacactcaga attacatagt taacttcttt | 1020 |
| atcagcagtt gttgtcaaga tttccatttt gagacgattg ttttgtaaat taggtgggaa | 1080 |
| ttttttaaaat gttggactgt tttttaacat gcctttctca acttttgtta caaataatgt | 1140 |
| tttgtccaca aaaaaaaaaa aaaaaaaaa aaaaaaaa | 1179 |

<210> SEQ ID NO 58
<211> LENGTH: 453
<212> TYPE: DNA
<213> ORGANISM: Diabrotica virgifera virgifera

<400> SEQUENCE: 58

| | |
|---|---|
| gggggaagtt cgtggtggta ttgtccgtat ccgcctgaca ttcctgccgg cttttcaatt | 60 |
| gttttccgag ttcgcgaata cattacgtgg agtggtcgtg gatttgaaaa gttttgcgtg | 120 |
| ttttaaattt tgtgagtgaa cttcgcggcg acgatacagt tggactgtgc cgctaattgt | 180 |
| tgataactgg agataacggc tttgtaataa agtggtgaca gggatctctt cgggacgctg | 240 |
| aggaaggtat ttcaatcttg gttttgtcac ttttttgaatt tcatagtaat catttttaat | 300 |
| cgagttatga aaccttgaaa tggccatttt cgcatttttc aaattttttaa taactcgaca | 360 |
| acagtcaatt ttagagaaaa attacaaggg accttttttg ctcagaatga cccaagttat | 420 |
| ccgaaaaaaa aaaaaaaaaa aaaaaaaaaa aaa | 453 |

<210> SEQ ID NO 59
<211> LENGTH: 532
<212> TYPE: DNA
<213> ORGANISM: Diabrotica virgifera virgifera

<400> SEQUENCE: 59

| | |
|---|---|
| ggggagtggc aagtttcata tctgtgaatt tgttgtttgt tacatttttct ccggcattac | 60 |
| agataatcgt tatgaagaag ttccccttag tgctgacatt tgttgcattt ctgtggattt | 120 |
| gggaggctaa tggatttacc gcagaacaaa taaatgaaat tcgtagtatt tgtagtgaag | 180 |
| aattaaaaaa aattccacgt caaaaggtg atatgggttt tccgggaatt ccgggtgtac | 240 |
| cagctccacc atcttttggg gcaatcggac ctccaggaaa aactatatat ggtctcccag | 300 |
| gagcacccgg aatacccggt ccaatgggag ctcccggtgc ggcaggacta cccggattgc | 360 |
| caggagttaa aggtgatgta ggttcctgta gcagaaaata atttggaagt tctgagtgaa | 420 |

| | |
|---|---:|
| aatttaaaac tattcttact tttgacatat tatgtagata tttgctgttg tatcatccaa | 480 |
| ataagtatca ttagaacata caaaaaaaaa aaaaaaaaa aaaaaaaaaa aa | 532 |

<210> SEQ ID NO 60
<211> LENGTH: 707
<212> TYPE: DNA
<213> ORGANISM: Diabrotica virgifera virgifera

<400> SEQUENCE: 60

| | |
|---|---:|
| ggggacagtc accactcgac ccagtcaaca taagcatcat gaactcttac agtgtggtat | 60 |
| ttgcgtttgc attggccgct gttgttgtag ccgaaccacc ttctggctac aactacaacc | 120 |
| ggcccagcgg gggtggcggc atctccttcg ggggaagcag cctctccttg ggggtggac | 180 |
| tgtccggcgg tggtggatac acggctgtat cgtctggtgg tcaaactagc gaaggagctt | 240 |
| ccgtagaccc acagcttctc gaacaagtcc gtcaaattct gctcaaagaa aacagagct | 300 |
| cttccagcgg cggtggtcat ggtggtggtg gtggatacc aggaccatct tcccaatacg | 360 |
| gtgctccatc tcctcaatac ggagtaccca gctaccaata ccgcgtcgtt ggaatcgatc | 420 |
| tagagggaat caaacaagcc atccaagttg cccagtacaa ccaaatctca cagggaccaa | 480 |
| gctttggagg ataccccagc ggacctagtt cgataccatc cgggtcttac ggagcccctt | 540 |
| actaaggctc tagaactgat ttcagtgtga ataccatctt ttaccatctc agacgggtca | 600 |
| tgatgcattc aataccatca agtttcaacc ataccatcaa aagttgaatg tttgtataaa | 660 |
| gctttcgtag gttattcaaa aaaaaaaaaa aaaaaaaaaa aaaaaaa | 707 |

<210> SEQ ID NO 61
<211> LENGTH: 715
<212> TYPE: DNA
<213> ORGANISM: Diabrotica virgifera virgifera

<400> SEQUENCE: 61

| | |
|---|---:|
| gggacaactg tcaaatattt aactcccaac ataacctgta acctgtgtaa gatcttgatt | 60 |
| gaccaaaaaa atacaaaaat ggtcaaggct tccgagacag ggggcgtgaa gcccatgtcg | 120 |
| atagcaggtc gctttataaa cgaacgagaa cgtttactag gaatgacagc tgcagaacga | 180 |
| gactttcgca aacagtggct aaaagaccaa gaattgtccc attctgagcc gaaaaatgtc | 240 |
| cctgaaatgt ataagctac ccataatcca atcaggaggc tctacagatt tcctctggat | 300 |
| accttaggta aatgttgga gcctgttttg ggattacaga gtgcttctag agtgagatac | 360 |
| ttcaccggaa aatttctttt ggctgttgca ggtgcttacg ccttgaccta ctatgttaaa | 420 |
| tacaatacca atgactggac acgtaagaac ggaatgagaa tactcaagtc taacatatca | 480 |
| gtacatgaag gtgacccagg ctatcctaga gtatctcaaa ggagtaaacc atcagattat | 540 |
| ggtgatcgag gattcaatga taacaaatta aacttgtaat atatttatat gaaaatattt | 600 |
| agtgttcgtt ttaggatcat ttatttgttg cttgcaaatt ttaaccataa catctttgta | 660 |
| taataaagtg caagaactat tgtaagaaaa aaaaaaaaaa aaaaaaaaaa aaaaa | 715 |

<210> SEQ ID NO 62
<211> LENGTH: 1242
<212> TYPE: DNA
<213> ORGANISM: Diabrotica virgifera virgifera

<400> SEQUENCE: 62

| | |
|---|---:|
| ggggacataa aatctacaag atctacagta gatacagtgt ttcgtactac aatgataaaa | 60 |

```
aacaatctttc caaagagatg ttacaagaag tgctcttaaa attatgggaa ggtctagtca      120
aaaacgaagg ctcgcaaccc acccaaaaag gcaccctgta ttcgtaagac ctacgataga      180
cttcactcaa gaagaaacga ttctacagaa cctcattcca caaattcgag aagacattct      240
gaatgaatct ttagtttacc agaagaacac gccaacagtt agaggacatg tcgaaaacct      300
tattaatgat acagtcggag atcttaagcc aaaatttctc aactgtgctt taatagcgat      360
atacgcctac aagtatttta aacaggatca caccgaagaa gagttggtca aggctgggat      420
tttgggctgg tgctacaaat tgcaagacct cgccatgatt atcgttgatg acatactgga      480
tgaatcaaaa attcgttaca ataaacctcc cttgtatagg gtagtgggaa taaacaagc      540 tatcctagac tctataattt tagaatcagc cgctaacttc ctagttttaa aatatttttc      600
tgatcacaag catttagtta aaatccaaaa ggatctcatc ctaaacatag cgacaactac      660
gatttcacag aaacaagagc tgttaaagta tgaaatagac gaattggaag ttttttgaaaa      720 tttgattaag tcttttccgc ttttaataca tgctgttaca tctgcggtgt atttggctgg      780
tatcgatgat ccaaagatcc aatccatagt gaagaagttt tgcgtggata ttgctatatt      840
tggaaaaaga tatgatgact ttacagtatt tctagaccca aaaactattg gggaaaagga      900
caacacagat atcgttagtt ttaagataac atggatggcc atccaagtct ccaaaatggg      960 aagccccccaa cagaaaaaga ctttcatgaa acactacggt cactcagatc ctgaatcagt     1020
tgctatcatt tttgatatat acagggaact caatttagtt gaacatttcg ataaatatat     1080
gatggaattt tacgacgaca tgcttacaca aattcagaac ttgcctcctc aactgccaaa     1140 agaattttc tataatatac tagactgtgc tgtagcaaat aagatgtatg cttaataaat     1200
ttaaattatg tcgaaaaaaa aaaaaaaaaa aaaaaaaaaa aa                         1242

<210> SEQ ID NO 63
<211> LENGTH: 1950
<212> TYPE: DNA
<213> ORGANISM: Diabrotica virgifera virgifera

<400> SEQUENCE: 63 ttttttttttt tttttttttt tttttttttc gcttagcaac aacactttag tttatttag       60 taatatttg tattttgaca acggcacccg atttgggcgt cgaaacgtta ataaaattat      120 tttttcatt ttaattgtgg cttatttccc atataaataa ttaatcataa aaatgccaca      180
aggaaatagc ttcagaacaa cataaagaaa cgattgttgg aaatggaaaa ttaaattaaa      240
aatggaaagt cccccactaaa atggaaaatt ttacttttact tttttttggtg ttaggaccta      300 cccttcacaa tccaataggt ccccaaagcg ctcgagtgac tgcacattta gcatactttg      360
ctcccccacc attattgata gtcaagaaga gttattacaaa atgtgtatgc atacatatta      420
aaaaaaaaat actacgtacc aaagaaatca cgaagaagtg aaaagcaaca gtaatatcat      480
tctcaaaata agtttatcat ccacctttag ccctaaacat agattattat cgaactcatt      540
tagaatttag aatacatatt atgtaaaata aaaaaaccag tataataata aataatacat      600
tttactagtg aaagaacacc aatttgctgt tggtagtatg taattgttta ggaagatctg      660
tgtgttggag tggtttctttt ttgcacaaga acattcataa ataactcaac gggtcatcaa      720
tatgccatcg tggagaatta acagataagg aaaatcaatt tgcaaagcat acaaatcagt      780
caatgttaac ttacaggaca cgatgtgata ctcatatgtt cggttcttct acccactctt      840
ttttcacggc agaagtatgg tcagtaccgt attcagattg caaagttact tacagtacgt      900
aaatccttca ggtggacaag ttacgtactg tataacataa atatattta aaaaggtgca      960
```

```
tttttaagaa aaataaaata tttgaatcac cctattggta aaaagtaaca atatgggtct   1020
atgaagacag aataataact taattgtgta tcatatatat tcaaaacctg taaacgagct   1080
ttttatagta taacgtatta tcaatttgtt ttaaattctt tttatagtat aacgtattat   1140
caatttgttt taaattctta gaagattaca aggattccat ataaaaaatg aagatatcaa   1200
acaagtggac aaaataaaat acttaggagt ctggatcacg gaagctttaa atccgaaatc   1260
agaaattcga tcaagaatag agcaatcaag agcagccttt ttgaatatga ggaaatttct   1320
gagtaaccaa agattcaatc tgcaaatccg atatcggatg gtaacgtgtt atatccactc   1380
tattcttctt tacggtgtcg aagcttggac tgttaatgct gacttaatga gaaagctgga   1440
agcttctgag atgtggcttt ttaggagaat attgaaaata ccatggaaaa actgtttagt   1500
tttgaaatta gtttttaaat aaaaaatatt ttaaaaatta aagacaaatt attaactcat   1560
taatcataaa ctttgttttt gatttattta tggacagcct tgctacaaaa ttccctcatt   1620
ccattcattc taacagctct attgcaccaa aaactcatac tcgaacagaa gcttcaacta   1680
acacaggtta gcgcagttgg caatatggtt gttagcatta aggggcatta accttcaaat   1740
tgacaactca tttcgactga cacaaacgtc aaaatgtgac aatgtgatag ctaaatattt   1800
tggaacacat acatagaaat gataagtagg agttattaca gctgattatg aagggtacaa   1860
ttggaagggg tcctagtgga ctacaaatat cctggctgaa aaacattcgc gactggacca   1920
ggttaaacac acagacgttt ttcagagccc                                    1950
```

<210> SEQ ID NO 64
<211> LENGTH: 776
<212> TYPE: DNA
<213> ORGANISM: Diabrotica virgifera virgifera

<400> SEQUENCE: 64

```
gggtacacat aacctataaa aaaaacatta atttgattta ttttgaagtg tatatgttgc     60
agttcaagtt gattctcagt tggagttgac tccaactagt tggagtcaac tccaactgaa    120
atgagcagta aaagttgatt ttaaaaattt aaatcaactt ttactagttg gagttgactc    180
ttcctggatc gattcagtaa atgttgatta tacgagaatc gcaagtgcat ttttgatgag    240
tgtgcgtttc tttgtttgga ccgtttcaac tacttattag tatggcctgt aacgtcgccc    300
ccgttgggtg aattattctg attcgatttt ttgcacaaac ttactcaaag aaatacatcc    360
gtataacaat ccttataaca aatacacagg gtgtcacgcg gtagcgcggt cgaaaaattg    420
tttaaccaat ttttgttgac caaattcaca aaaataattt ttatctactc tatctcattt    480
atgtaaatca gcggttctca atctgtggta catgtaccac tggtggtaca aatcattatt    540
tgcggtcctg ccaaagacaa accattttca tttccaataa tgacacgagc cgtctcaccg    600
tgcctcggag agcacgttac accgtcggtc cccctgggct agtgtacatc gacactagtt    660
acttgaaaca gggttaaaga tgtaattggc gccggaactg tccgaaaggc aaaaatgcca    720
tacgatatca tatattatga aagtcggaaa aaaaaaaaaa aaaaaaaaaa aaaaaa        776
```

<210> SEQ ID NO 65
<211> LENGTH: 1191
<212> TYPE: DNA
<213> ORGANISM: Diabrotica virgifera virgifera

<400> SEQUENCE: 65

```
ggggacaagt ttttttggat ccatcaagtg ttttcaaaat ggctacacac ctagacgtgg     60
```

-continued

| | | | | | |
|---|---|---|---|---|---|
| ataaaattat | tacaaaactc | acctccaaag | aggttcggga | gagcaagaaa | atcaaactaa | 120 |
| taagcatatc | tgaatctgat | ataaaagcgt | tatgtttcaa | gtctatgagc | acatttatgt | 180 |
| cacaacccat | gctgctcgag | ctagaagcac | caatcaaagt | ttgcggtgat | atacatggac | 240 |
| aatttctcga | tttgttaaaa | ctgtttggat | ttggtggttt | tccccccgac | tcaaattact | 300 |
| tattcctcgg | agactatgta | gataggggga | aacagtctgt | agaagtcata | tgcttattgt | 360 |
| tagcatacaa | aattaaatac | cccgaaaatt | tcttcttact | gcgaggtaat | catgaagcat | 420 |
| ccgcagtatg | taagatatac | ggattttttg | atgaatgcaa | aagaagatat | agcactaaaa | 480 |
| tatttaaact | atttaccgat | gttttttaaca | cattgccggt | ggctgccatc | atagacgaca | 540 |
| aaatttctg | ctgccatgga | ggcttgagcc | cagatctctt | acatatagga | caaattcgaa | 600 |
| atattcagcg | tcctattgac | attcctattc | aaggtttact | ctgtgattta | ttgtggtctg | 660 |
| atcccagtac | cgagcctggt | tggacggaaa | atgacagagg | agtgtcattc | tcatttggtc | 720 |
| cagatgttat | taataagttt | ttaaggaaac | atgactttga | tttaatttgc | agaggtcatc | 780 |
| aggttgttga | agacggctat | gaattcttcg | ctcagagaaa | attaataacg | atattttcgg | 840 |
| ctccaaatta | ttgtggtaca | tttgacaacg | ctggagcgct | tatgtcaata | aatgaaaatc | 900 |
| ttttgtgttc | atttcagatt | ttggagccaa | caaaacatat | tgaaaaaaag | aagtgattta | 960 |
| aaaagtgaat | tagatttatt | tatggatatt | aatttaagta | ctaagtagtt | acttattgac | 1020 |
| tgttatttaa | aaacagaatc | acgtaaagta | acaaattaaa | aaaaaaaatg | taaagtattc | 1080 |
| tgctcgttac | atgctttaca | tgttatttgc | atgacctttt | acgaaattct | gttcatagtt | 1140 |
| gttaatagat | aataaagatg | caaaaaaaaa | aaaaaaaaa | aaaaaaaaaa | a | 1191 |

<210> SEQ ID NO 66
<211> LENGTH: 854
<212> TYPE: DNA
<213> ORGANISM: Diabrotica virgifera virgifera

<400> SEQUENCE: 66

| | | | | | |
|---|---|---|---|---|---|
| tttttttttt | tttttttttt | tttttttttt | atagtgtaaa | actgattttt | ttattttaat | 60 |
| atataccaaa | acataccaaa | gcttaaaaaa | taatcaatta | accttcataa | aatttgggca | 120 |
| attcatttcc | taaaacaact | cttcgttcaa | taccagcttc | agtgatgatc | cccagtctga | 180 |
| ctacacctcc | tgaagaacca | tctcttgaca | tggcaagtgc | caatgtattt | gtgacaaact | 240 |
| tcacacattc | ttccttgctc | atattgggct | tgaagttggc | atctacgtaa | ccataaacat | 300 |
| aactggaacc | tgatcctccg | attgacactt | cttgtctaac | acacatccca | ccaattggta | 360 |
| tggaatatac | ttgtccgcct | ttcttttat | cccaacctgc | taccagtata | ccagccatta | 420 |
| gcgaatctct | ataattgtag | caaagttctt | ggaaaatggc | ggcacctact | tgtactttgg | 480 |
| gttcttcacc | aagttccata | ccatgaaaat | taagatgata | agcaacaatg | tctgcaattg | 540 |
| cttgtgtatc | tgctgcagat | cctgaacgac | aacagtatat | atggtcagtg | actttggtga | 600 |
| gtttgtctgc | taccoggttt | gcaatgtagg | ccccagtagt | tgtgcgagaa | tctgctccta | 660 |
| taacaacgcc | tccatcaaac | tccgcggcca | taatagaggt | tcctgtactg | tgagcggcat | 720 |
| ctctccaatc | attaggacca | gtcattgcac | catactcagt | cataagaggc | atttttaca | 780 |
| agtttaatga | aaagaataca | agcttagaaa | aattacactt | gtaatcctgc | aatgcaatat | 840 |
| tttgccagtc | cccc | | | | | 854 |

<210> SEQ ID NO 67
<211> LENGTH: 1162

<212> TYPE: DNA
<213> ORGANISM: Diabrotica virgifera virgifera

<400> SEQUENCE: 67

```
ttttttttt ttttttttt tttttttatt ataactattt atattttagt taatacatct     60
taaatacaca gtacacatta tatacaacta ttaattcaga tttttttcta tccagtcaac   120
aaaagtagta actctggtgt agacaccggg atatcccttt tcagcgcatc taaatccata   180
ggaaaccact ccaatcagat aatatcttat aaattcacca tcaaacttgc cccaaattaa   240
tggacctcct gaatctcctt gacatgcatc ttggcggcca tccgcccgtc ctgcacatag   300
agttctctcg tcaattgttg ctttagcccc aaaggcggca gcgcattttg atgtgtcaac   360
tactggaatc tgggctattt ggagggccga acttgaaggt ccattataat atgtggctcc   420
ccaaccagca actacagctg catattttac aaaactttgt tttctgaaat tatcgtcaat   480
tggtagacat acaggccata cccaaggatt ggtgggggct ctttccaaag taagaattgc   540
gatatcactg gtgtatttca cgggactgta gtcttcgtga actttagctt tgatcaatgg   600
tatatcttct ggttctgctc catcattagg attgtttaaa tctaagtctc ctaaacgagc   660
gacatataag tctttcttgt tgtgtacaca gtgagcagct gtgagaatat gtctttctgt   720
aatgagtgtt ccgccacaca accatcttgg ctttgaaggg tccctgctat ttctataacc   780
caaattaaca atgaatggta cctcatgtaa tttggctgga attccaccta caactctaaa   840
gtttgttaca ttactaacac cacatttctc gttatttaaa acggcaccaa tgatttttgt   900
atcggttgct ggttgtgtag gttctggttc tggttctggt tctgtattgt ctgttgggca   960
acaaacatat actacagctc caaatttaca tgttgaacgt tgcagatatt ggcgcgtttc  1020
ctgattattg cttcttgttt taagcaaatt gagcatgtat ttacattcgt atatactttg  1080
acaaattcca tattcattcc tagctgtgta acagggctca ccttcttcaa cagccgcgtg  1140
agcaacacta aacaaaatcc cc                                           1162
```

<210> SEQ ID NO 68
<211> LENGTH: 1186
<212> TYPE: DNA
<213> ORGANISM: Diabrotica virgifera virgifera

<400> SEQUENCE: 68

```
ggggcaaact gtaagttatt atattttgca cgattgaaag acatttacta ttagcaaaaa     60
tgtctaaaga ccgggaattg cagatgggga tgcgatgtgt gaagtacatg atttttgtgg   120
cgaattttat gttcatgtta gttggattgt tgctgatatc aattggatat accattaagg   180
ctatctacac cgatttcgat gctttcctta gcagccatag ctacaaagca tccgacttag   240
ctatagctgt tgggttcgtc attctagtgg ttgctttgtt tggttgtgca ggagcaatta   300
aagaaagtgt tctactggtt aatctatacg ctttactact tcttgtaata gttatcctgg   360
aattgaccgt aagtatcatt gcttacaaat ccaggagtca cttggaagaa acactttctc   420
aggatatgtg gattagtatg gagtattaca tagccgatac tggatatatt tgggatgcaa   480
cacaatactc gttgcactgc tgtggagtac atggtccaaa cgactgggac agatttaaca   540
gttcagacta caatctcaca gtcatttata gttcacaaga cgactcaaca agttcagact   600
tgccacaaat aaattaccca ggagtttacc aagtaccaga gagctgctgc agaaatacca   660
aatgccaaag tatcgcttct ctttacatga gaggttgctt accgaaaatc cactatataa   720
tctcgcaaag tgctcttctg cttggagttg ggctatgtg cataacattc attcagcttc    780
```

```
tcggtgctac atttgcccat cttctggcca gatctattag aaaacttaaa acacagattg      840
aagtggaaag atcaataaga agacaacaac tgtacgagtc gcttgcgaaa tctaacacac      900
aagagaaagt tagtccagtc ctatacgtgg cagagtcttc tgaagcttaa gaattcgtcg      960
tgtgttatat ataaaaataa tgatttaaat atagatttaa atatagatta aaccattgtc     1020
catttcatta cactcatgta tattgtgtta gtgtttacag ataagttata atatatacct     1080
tttctgtttt tgtgtattct ttactaggtc tatgtatgta gattctttaa atgttaaata     1140
tagaataatt ttaactgaaa aaaaaaaaa aaaaaaaaa aaaaaa                      1186

<210> SEQ ID NO 69
<211> LENGTH: 1002
<212> TYPE: DNA
<213> ORGANISM: Diabrotica virgifera virgifera

<400> SEQUENCE: 69
tttttttttt tttttttttt tttttttttt ctttaataaa tagtatattt tgtaaatttt       60
tttatcttac ataatacaaa aaatatatac attagtttta tttatgtttt atttatattt      120
caattattat tctaattctt cttcttaaca tcgtcacctt ctggattttg gtgttttgta      180
aacgttagga atacctgttc tagactactt tgtcccaaag aatagtcttc aatattcaga      240
tcacttcgct tagctctttc taatatacca aacatagtgg accatgccat ggaagtgtcg      300
gttatataat aatacaatag ttcttgatgt ttctctctaa gatgagcata aggaaattta      360
tctttgatat acttctccag tgactctgta tctgcatgta ccagaccacc gctctctggc      420
aatttcttta gttttatggt taaggtgtat ccctccgcaa atttgttttt aagatgctgt      480
gtggatccaa gacatttgaa attgccgttc accataatgg ctattcgagt gcacaaagct      540
tcacattctt ccatgctgtg agaagttaaa acgatgcact tgccgttgtc tcgaattttg      600
cataatgaat cccacaggta acgtttcgtt gctggatcca tacctgttgt aggttcgtcc      660
aaaaatagta ctggcggatc ccctatcaac gacaaaacag tacttaactt cctcttattt      720
ccaccgctca tctctttaac tttcttgtcc aaatgacgat gaaaatcgaa gtctcgagac      780
aagaaattcg caattctttg ggttctttta aactctattc ctctgagtag gcagtacatg      840
ataattgttt ctcttgctgt catatcatcc agcaaagcgt cgaattgagg acagtagccg      900
atgtttcgtt gtacttgctt cagttgcgtt tttacactct ttccttcgat ccatgtatca      960
ccgtaagata cagtttcatc tccgctcatc attttaaatc cc                       1002

<210> SEQ ID NO 70
<211> LENGTH: 1322
<212> TYPE: DNA
<213> ORGANISM: Diabrotica virgifera virgifera

<400> SEQUENCE: 70
gggtatatga ccacattgtc aactattaga aagattctgt tgccaaaaat aattctagac       60
ttttagtagg tataatactg ttgtaaggta ttacaataca tagggtacta ctactgcttc      120
ttcttgtagt tccttatctt atcggaggtt ggcgatccgt accttattga cggctgctct      180
gaaaatatct actgagctgc aatctgcaat tataccactc tcttaggttt cttagccagg      240
atatttaatc ttttatctta tccttaattt taccttgcat tttactacaa cacaggtact      300
aaaatgtgta taccaaattg gatagtttct ttctgaggtg ttactctata tattactgtt      360
gaaatatagt ataaatatgg acatcttccg aaaacaacta gacagaatat gtatactaaa      420
ctcacagtaa agatgcacga gaaataaaca aaccaagaca cgtttaatgt tacgaggagc      480
```

```
actcccgaat cctgatttac atctatctat ctaattagcc tctttcggtc catctttgga    540
aatgaacctg aagaaaccca atcctttttc attattctct gtctgtcgct atagtcatcc    600
acctagagcc cacgtgcttc ttgatatcat ctgtccatct catttggggc ttttttctgc    660
ttagtttata ttcccatggt ctccaattta taagaatttt gttcaatcga tcttctttgt    720
gtcttatatt gtgtccggca aatctccatt tcaattttgc aacttcttgt ctaacatccc    780
taacttttgt tttcactctt acccactcgt ttcttttttt tatccattaa accttgatta    840
cacgtaacga gtattgtagc gagacagtgt tctcggccgg gtgcttgttt ggtataaaca    900
tactaacgag tacttggccg agcactcgac ccagtcatat ggcgagacag tcactcggat    960
cttgttatac atatttacta agccgagtct tcgacctccc actcttcaat cgtatactcg   1020
ccaatccact gggtatgtgt aaacaacact cgctgtgtaa ctgtacatgt taccattacc   1080
acttcatcag aggagacgac ttgtgttaat caatgttatt tgggattctc aaaaatagct   1140
aacaaatgga actcagatag gacaataaag tgtagtttaa ttctacagat aagtcacacc   1200
cgtgcttatg aaattataaa tatttggagt ataaaaataa acaaaaacgt gatgcagcat   1260
ttaaatattg ttggttttaa aacttaagga gtaaaaaaaa aaaaaaaaaa aaaaaaaaaa   1320
aa                                                                  1322
```

<210> SEQ ID NO 71
<211> LENGTH: 761
<212> TYPE: DNA
<213> ORGANISM: Diabrotica virgifera virgifera

<400> SEQUENCE: 71

```
gggggacata tggtgacata actcattcaa aatccataaa aaagtttcaa aatgagttta     60
ggagttcgta aaatattttc agtaggctca aaattagtaa gaccaagtgt ccagattgtt    120
ggtcaaagat gttgctctag cggctctaaa gatggatatt tctatgtaaa cgacaaagaa    180
cccagtatgg agtttggggc tatcacagat cgtgctgccc aaacaatgtt ctttactgaa    240
ttattcagag gatttggtgt tactttggct cacattttca aagaaccagc aactataaac    300
tatccctttg aaaagggacc tctcagtcct agattcagag gtgagcatgc cttgagaagg    360 taccccctctg gtgaagaacg ttgcatcgcc tgcaagttgt gtgaggccat ctgtcctgcc    420
caggcaatca caattgaagc agaagaacgc gcagatggct ctagaagaac cactaggtat    480
gatattgaca tgacaaaatg tatttactgt ggtttttgcc aagaggcttg tccagtcgat    540
gctatagtag aaggtcccaa ctttgagttc tctactgaga ctcatgaaga acttctctat    600
aataaagaaa agttattaaa caatggcgac aaatgggagt ctgaaatagc cagtaatatt    660
catgctgacc atttatatcg ttgaaaatat atagaaaatt gtaaaaagtt gtagaatata    720
tcttattaaa caaaaaaaaa aaaaaaaaaa aaaaaaaaaa a                        761
```

<210> SEQ ID NO 72
<211> LENGTH: 2041
<212> TYPE: DNA
<213> ORGANISM: Diabrotica virgifera virgifera

<400> SEQUENCE: 72

```
ttttttttt ttttttttt ttttttttt gataacgatt tctaaagtgg aaatcgaaat     60
gtcaaaaaaa cttaatttca aagtaaagtt atggctcatt ccaaataaaa aacagtaaat    120
ttcattgtgt atataatttt gtaatgtttt tgtattcaat caaaccaaaa ataaaccact    180
```

-continued

| | |
|---|---|
| aacaaaaaaa atagagtctt ttaccacctt ctccattaaa ggagattact tcactacaca | 240 |
| aatgctgatg gatgtggcga tgattgaaat gctcgaaacc gctacttgac caaatacgtg | 300 |
| tcgtttggtg ggtaaagctc gtaatcccga attacggaat attggaaacc aattattaac | 360 |
| aagatgcttt gatacatcac agagctatgc taaatagttg ctaatgttat tcagcaataa | 420 |
| cattatcgat gggatgactg aggtcgatat taccattgct taaacacagt attgaaaaat | 480 |
| ttgtttcata cattatttaa atagtaataa ttaaattgta taataatata cagtgatgag | 540 |
| cacgctcctc ctccttctcc tcctcagtcg tttcctcatt tctgagtgtc gtgattccct | 600 |
| ataatacgat caactatctc tttccgtcgg cttctgtcct gagcttccct catggattca | 660 |
| gagaatgttt ttccactggc ttcctgtact tggtccgtcc atcgagcagg tgagcgacct | 720 |
| ctacttctgc gctcttcaac ctttttccgaa attataagtc tctccagatt atcatcactt | 780 |
| cttgcaatat ggccgaaaaa ttttaaggcg gtggagaggc aagtagagga aagtcgagtc | 840 |
| tgaatattaa gctcttggaa gattgagtga tttgttctct gttccgtcca tgagatccga | 900 |
| agcattcttc tccagcacca catttcaaag gcgtcaatct ttttctgtc gtccgatttc | 960 |
| attgtccatg tttcggatcc ctaattaaat atgggaaaaa ttaatgcacg tactaatctt | 1020 |
| attttggtgt tcttcgacaa ggagcgatct ttccagattt tcgataatcg actcatagcg | 1080 |
| tttttggcaa tgcctattct cctacgtatt tctgtttcac aacatcctgt attactgatg | 1140 |
| taggatccta gataatcgaa ctcgttaacc acttcaaact ggtctaaggc ccgtgttgtc | 1200 |
| tgaagtgaat ttaaatattg ttattaagta tattcaaatg ggaataagc cacaatttta | 1260 |
| cctaaaaatg attttattaa cgtttcgacg cccaagtcgg gtgtcgttct caaaatacaa | 1320 |
| aataatacta aataaacaaa atggtgttg cctagtaaaa aattcttcca ataatttatt | 1380 |
| taatctgact catttatatc ggcaattcag acacgtatta tacattttaa agtagacgac | 1440 |
| tttaaaatga tattgccaat attgatgagt tgcgttcctg ggactatgaa tttaaatatt | 1500 |
| ctactatcat aattttttgtt ttttgtttat tgatcttgag accacatcta ttgctttcgg | 1560 |
| cttccactag ctgcagcaga ctggacattt cttcttcgga tgcagttatt aatggtgtat | 1620 |
| catctgcata tctgagattt gagatcttct ttcctgcgat agaaataccg ccattccatt | 1680 |
| tgtcgagtgc ttttctcatt atatattccc catataataa ccatagcgcg ctaataaaca | 1740 |
| cctatatatt tctatttcta tatctatcta tctatccttt tttcagccaa cgtctgcagt | 1800 |
| ccttcctgtt ctaccattct ccatctttaa cgtctcgtct ttccatggct tcgtacactt | 1860 |
| catccctcca cgatattcgg ggtctacctc ttcttctctt tcctattggg ctccaatccg | 1920 |
| taatctttga tatccaacctt gtatgatctg ctcttctcac atgtccatac caaattgaac | 1980 |
| gtttttcttc gatgtagttg attatgtctt gttctagtgc cattcttcgt tttatctccc | 2040 |
| c | 2041 |

<210> SEQ ID NO 73
<211> LENGTH: 523
<212> TYPE: DNA
<213> ORGANISM: Diabrotica virgifera virgifera

<400> SEQUENCE: 73

| | |
|---|---|
| gggggtgtag ctttccgcag caaaaagata ggtggttagg cattattttc taaaaaccac | 60 |
| atggatgaat tgttggcaaa ttcagcccta gaggctgaaa aatttaagcc aaccgtagta | 120 |
| aataagctta ttgatctaaa ttatgactta ggaagccttt tagcacaaga cacaaatgaa | 180 |
| tttgatacaa atttattaag gaggcagaag gaagattatt tgcttaattt agctagagat | 240 |

```
aacacccaat tactattaaa tcaaatatgg gacttaacta cagaacgcct agaagaagct      300
attgtagtga aattaccact tcaaataact ttattaccta ggatgaaacc actacctaag      360
cccaaacctt taacaaagtg ggaacagttt gccaaaacga aggtataca gaaaaagaaa       420 aaatccaagt tatcatggga ccagcaactc aaaaagtggg taccettata tggatttaag      480 cgagcacaag ctgaaaaaaa aaaaaaaaaa aaaaaaaaa aaa                         523
```

<210> SEQ ID NO 74
<211> LENGTH: 473
<212> TYPE: DNA
<213> ORGANISM: Diabrotica virgifera virgifera

<400> SEQUENCE: 74

```
gggaaagtga attcactaac tatttgagta atttaaatgt caattgacct tagtttacca       60
gagctgccta tattcaccc aaggattacc gttgtgggag tgggtggtgc tggtggaaat      120
gctgtgaata acatgatcca atccaatttg caaggagtaa attttgttgt agcaaatacc      180
gatgctcaag cgttagagaa gtcattatgc gataaaaaaa ttcaactggg tattaactta      240
accaagggtc ttggtgctgg tgccttgcct gatgttggca aaggtgcagc agaagaatca      300
atcgatgaaa ttatggagca tataaaagat agtcatatgc ttttcatcac agcaggaatg      360
ggcggtggta ctggaaccgg tgcagcaccg gtaattgcaa aagcagccag agaagcaaga      420
gccgcagtta aggatagagc gccaaaaaaa aaaaaaaaa aaaaaaaaaa aaa              473
```

<210> SEQ ID NO 75
<211> LENGTH: 409
<212> TYPE: DNA
<213> ORGANISM: Diabrotica virgifera virgifera

<400> SEQUENCE: 75

```
gggagaaatg gttactttga acaagattta gtactaccaa atgttagtgt atatattatt       60
ctgcacgcat taacaattta tggatttat agaataacta ctactgaagt taagggggtca     120 gccatattat tcagtacttt tattggcatg ttggcaatat taggggtcac agctggagcc     180
catcgtcttt gggctcatag aacttacaaa gcaaaactgc cattacgagt attttttaatg    240 ttgttgcaga cagcggccct tcagaatgat cttttcatt gggttagaga tcacagaatg      300
caccacaaat atacagacac caatgctgat cctcacaact cgaacagagg attcttcttt     360
tgtcatgttg gatggctatc aaaaaaaaaa aaaaaaaaa aaaaaaaaa                   409
```

<210> SEQ ID NO 76
<211> LENGTH: 1532
<212> TYPE: DNA
<213> ORGANISM: Diabrotica virgifera virgifera

<400> SEQUENCE: 76

```
ggggaagaaa cgtcaattga atcaactaga cggtgatgtg ttcagtaatt gaatgtaaaa       60
tttaaaataa tgttgaaatt aatcaccttc atattcataa tagtgaccgt caatgcagca     120
gaaagaatca acaataattt aatttataaa aatgtgggata gaaccataga tttaacgtca    180
cagttagtaa aaatcaccag caccataact cttgaaaatg ccggcgcaga ccctatcaag     240
aattttctac tggcggagca accaaattta gttggacaga tagcatttaa aggtgccaaa     300
gactctgcca gcaagatttt aaacgtctta acagcccaag tagaaaacca gagcgataag     360
agattccaca aagttatctt gaggcagaat ttggaaccgg gccgtactgc aacagtggtg     420
```

```
gttgaagaaa tactcattaa aagtttaatt ccatatccac atagtatttc ccagaaagag     480
aagcagttag tgaggtattt tggtaatcat tatatttata caccatacac agtggttaaa     540
caaaaaactg atgttacatt aagctctaga agtattgaaa attattctaa attgaaacca     600
gttactcaga cagatagtac aatacattat ggaccatatg gagaaattgc acctttttgct    660 gtggatgaac tgatagttca ttacgaaaac aatgctccat ttttgacagt tgtccatcta    720
gatagaacaa ttgaaatatc tcactggggt aacattgcag tggaagagca aattgaaatt    780
aaacacacag gagctacatt aaaggggcca ttttcgagat atgattacca aagagacact    840
agtagtacac atcacagtat taaatcatac actactgttt taccagccac tgctcatagc    900
atttattaca gagacagcaa tggcaacatt tctacttcag ctgtaaaaca ccgtaaggat    960
tggatagaac ttgaactgag accaagattc ccacttttg gaggttggca aagttcttat    1020
actctcggct acagtgtccc cagttaccag taccttttca aggctgaaaa tggagataat   1080
gtattagcta tgaggctcat tgaccatgtt tttgacgata tgtatgttga agaagttgtt   1140
actaacgtag ttcttcctgt tggagtcact gatatcaaaa ttcgaccacc ctatgatgtg   1200
gagagactat cagatgatgt tacttacaaa tatttggata accttgggcg taaagttata   1260
agactgaaaa agagggacct gattgaacaa cacattcaag atttggaaat tacctataaa   1320
tggcaaccac gattgttgtt acatgagcct ttgctgttat cgttggcact ctttattttg   1380
tttgtagctg taattatctg ggtccgattg gacttttcac ttgcagtgcc tgagcacagc   1440
aaaagagaat aacttttgt acatctatat taacattttt tgttaaataa attatgagat    1500 tgaaaaaaa aaaaaaaaa aaaaaaaaaa aa                                    1532
```

<210> SEQ ID NO 77
<211> LENGTH: 107
<212> TYPE: DNA
<213> ORGANISM: Diabrotica virgifera virgifera

<400> SEQUENCE: 77

```
ggggatgact tcaatctttg gctatcgagg gccaacgagg aagaacgaga aagaggtggt      60
aaccatggtg acgtaagaaa aaaaaaaaaa aaaaaaaaa aaaaaaa                   107
```

<210> SEQ ID NO 78
<211> LENGTH: 985
<212> TYPE: DNA
<213> ORGANISM: Diabrotica virgifera virgifera

<400> SEQUENCE: 78

```
ggggattgaa aggtggtacc gggactgggt gagaggctag ctagatacat acctacctca     60
tgtctctttt taactaactc ttcttgtatg tgtacgctat tttaaggctt tatgcgcaca    120
ttgatatctt gtagtgctat tataggattt tgtttatttt tcattaaaaa tgggtagaag    180
acaaaataaa taccaagatg tatccgagga tctaccggaa agaggacctg tggagagtct    240
gatctactgg cgtgatccca agaaatctgg tccagtcttt ggaggagtcc tcgtagttct    300
actcgctctc acatatttct ctctaatcag tgtggtagcg tacgtttcac tcatcgccct    360
cggcgtcact ttagcttta ggatttacaa aagtattgta caagctgttc aaaagactgg     420
tgatggacat ccattcaaag aatatctgga acttagaaga ttattcttgg tcgaagattt    480
ggtagattcc atcaaattcg cagtattgtt atgactctt acctatgtgg gagcgtggtt    540
caacggaatg actctaatta ttctcgcttg ggtcgccctc ttcactcttc caaaagttta    600
cgaagtgaat aagactcaaa tcgatgccaa tttggagatt gttcggacaa aattggctga    660
```

```
aattacttca aagataaagg cagcaatacc gatgggcaag aaagccgaag aaaagaagga    720
acaatagatt taacaacatc tatcagacta tattactata catatattaa tttattgttg    780
tttctttatt ccattaaacg ttcttatgta atgtttctaa atataattag tgtacatata    840
taagatgtta ttttaatgtt tttttatttg aattttttga tgttatttat ttcttgtaat    900
acatagagtc gaagaagaat atagaattta acataataaa tgtgttgcag agaaataaaa    960
aaaaaaaaaa aaaaaaaaaa aaaaa                                          985
```

<210> SEQ ID NO 79
<211> LENGTH: 1829
<212> TYPE: DNA
<213> ORGANISM: Diabrotica virgifera virgifera

<400> SEQUENCE: 79

```
gggggtatat atcaatgata ttacatatcg acctacgttt cacttaatgt tttgatttga     60
cttgtttgca aataaatcat gacgtttgtg caaagatata atggaacagc tatgaaataa    120
ctaaaccaca ttcaaatagc aaattcccaa ctaaactcct ggacaaaatt aacgcaccac    180
tttaattaat ctaatatttt acaatatgaa cacaaaataa aactaagtta cactggaata    240
ataataataa acacctacaa ataagtccaa catgacttta tcatgacctt aatttgcctt    300
atgtttcttt aaaaatttgt ttttgccgga aatgcgtaaa taagctagca taactctaaa    360
ttgcaaaaag aaaaaaatca gtaaagtaac acaataaatt gcatctgggt caacaataat    420
accgtgtagg cccacctaca cggagactgc atttatgcgt caaagcatgc ttgatatcaa    480
atgttcaaca aaagcttgcg gaatattctc ccattcttca ataacggcct caatgagttg    540
gttgtgattg acaatagggg gtctacaact tctaatcttt ttttgagata gttcgataga    600
tgctctatag attgatgtcc ggactgttag gtggccactc taataataga atatcaatat    660
catgtaggta accaataaac tgtcgagcca catgaggacg agcgttgtct tgcatgaata    720
aaaaattagg tccaagaaac ggagcaaaaa gcattacatt ttcgacaata atgttgtcta    780
agtaataatg ggcattcata gacctcgtac gtatggggac caactccata cgagcttaaa    840
aacaaattcc ccccaaaaca ttttagagcc accaccaaag gtagtttagg agagatattg    900
cagctggcaa acctttctcc tcgccttcgc cagacttcgc cagcttttag gcgttgtaca    960
ggacttatat tatacataca cgtaaaattt tcttttttatt aataatatag tgaaatgcat   1020
aatatatagt tattttggga taaattagga ttaattattt ttaatacaat tagtaaatta   1080
ggtctagttt ttcgtaatat tcatttcaag aagcatttac ttgacaagtt acttgatatt   1140
ttaactactg ttacattttta tttttttttga aaataaatga actttgattt aaatacctag   1200
atagaacttt taaaaagtgt ttacgatttt tatttacata ataactattt ttaactcaat   1260
gcgagtacat atatacataa atctattttt aacttgaacg gatcaaaatg ttatatcagg   1320
cttttatttg gcataaagta tattacattg tggttacctg accctgaaat tacgagtcag   1380
aaatacatac atcaggaatt tgctgaatag agttttacgc attacataag acataaaaaa   1440
tgactgaaat tacacactag gaaaggtgaa ttagaattta atggaattac gataatgaag   1500
aattttgaga atatattgaa ataatattat tgaaaatata agaaacgaca aacaaatcaa   1560
cgttttaaag aagaagaaag gaaaatacaa acatgatgga caagaataag tttcacggaa   1620
aatatgagtt ccgatattat gggaccgatg aatcaagatt tagagaattt tttacaaagg   1680
acaagacaaa gagaagaatc ctaaaaagga aaataaaaaa aaaacatga agataacaaa   1740
```

| | |
|---|---|
| gaaaataaaa ttatttatgt acaaggatat acaagaattt ttatacaatg attttaagaa | 1800 |
| aaaaaaaaaa aaaaaaaaaa aaaaaaaaa | 1829 |

<210> SEQ ID NO 80
<211> LENGTH: 1307
<212> TYPE: DNA
<213> ORGANISM: Diabrotica virgifera virgifera

<400> SEQUENCE: 80

| | |
|---|---|
| gggaataaaa aatttatttt atttatattt ttatttatttt taaaataata aaatattttt | 60 |
| tagtaaaagt aaagaaaaat tttatttaat gatagttaat tagtattgtg agagaatatt | 120 |
| ttattttat aaaagaaaaa tttattttt gtaccttgtg tatcagggat tattaattaa | 180 |
| taattatata tttattattt tcgaatttaa aagagctaaa aaaattaaaa ttttttattgt | 240 |
| aaaataaata ttttaaataa ttttttttgta atgaaatgtt attcgttttt aaatatatct | 300 |
| aattttttaa gaaataaatt aaatttattt attaacaata tatttataat taaatatttt | 360 |
| tatattatta atattaaata ttttttaggga tgagcttaaa aataaaatttt tattaaaatt | 420 |
| taattttttaa ataaaaatta ggattaaaaa ttttcatatt ttaaaatatg ttattattta | 480 |
| ttttttatata ttattatttt tatttttta taattttttta ttaaaatata aatttaaatt | 540 |
| atttaaattt agtaatgatg ataatattag tattaaaaaa ttgtatattt agtaaaaata | 600 |
| tataggttta ataaaggaat tcggcaacat ttttttcacc tgtttattaa aaacatgtct | 660 |
| ttttgtatta aatataaagt ctcgcctgcc cactgattaa tttgaatggc cgcggtattt | 720 |
| tgaccgtgct aaggtagcat aatcattagt ttttttttatt gaaagctgga atgaagggtt | 780 |
| ggatgaaaaa aaaactgtct ttattttaatt tataaagaat tttatttta agttaaaaag | 840 |
| cttaaatttt tttaaaagac gagaagaccc tatagagtt tataaaatta ttaataagtt | 900 |
| ttttagtat taaattttatt tatataataa atttatttaa ttggggtgat taaaaaaataa | 960 |
| atttaacttc ttttatatta ttatattaat taataatttt ttgatccaat tttttttgatt | 1020 |
| ataagaataa attaccttag ggataacagc gtaatttat tggagagttc aaatcgataa | 1080 |
| taaagattgc gacctcgatg ttggattaaa gtttataatt ggtgtagcag ctatattatt | 1140 |
| aagtctgttc gactttttaaa attttacatg atctgagttt aaaccggtgt gagccaggtt | 1200 |
| ggtttctatc tttaatttat taatatattt tagtacgaaa ggaccaaata tataaaataa | 1260 |
| tttttatatt tagacaaaaa aaaaaaaaaa aaaaaaaaaa aaaaaaa | 1307 |

<210> SEQ ID NO 81
<211> LENGTH: 730
<212> TYPE: DNA
<213> ORGANISM: Diabrotica virgifera virgifera

<400> SEQUENCE: 81

| | |
|---|---|
| ggggattctt ttgtgaatgt ttgcttcgcg ttctcccgtt taccgttccg tgttgacacc | 60 |
| gtagaatatt gactgatctg tagtttgaat tatttttaa aaacaatgat gtgttcatga | 120 |
| actattttct ttgttaatgt gtaaatgttg caacaagctg atctaaaata gagagcaatg | 180 |
| gaatctgcga tggaacagtg cgagaccaag cctttggaaa ctctatcaag tacattaaag | 240 |
| atgtttgaca cttttaaatc tacggaagaa gaccatgaat cagacgagga aagctttcat | 300 |
| cttccgttat taggatgtga tgatgaagcg gaaaacggca tggaaatatc tgaactaaac | 360 |
| gaagaagatg aagatgccat actaaataag ttcgacacac gcgatgaagg aatggacgtg | 420 |
| gatgaatgca gcaacaaaaa agacagcgat gtttctaaaa acaatgttgt agatgaagtt | 480 |

```
aaacttagtg aagaagaggc aaagctagat ggtatagata atttaaataa agataatcgg    540
atagataatt taaatggaga tgatgaatta ttaggaaata atgagatttt agaagataaa    600
acaacagaaa gtacccctga tgataccgaa aataaaatcg aaaatgaaat aaatgaaact    660
gagcctggtt gtgaagaaga ctcaaaagag accaatatta ccaaaaaaaa aaaaaaaaaa    720
aaaaaaaaaa                                                           730

<210> SEQ ID NO 82
<211> LENGTH: 1761
<212> TYPE: DNA
<213> ORGANISM: Diabrotica virgifera virgifera

<400> SEQUENCE: 82
ggggagtgaa tgagctttca ttcgtttcgg cgagggatta gattttgtac tcgtgaattg     60
ggtcaggtta tttggcgcca tgaatcttct tggaaaagct ctcgtttttg tattgatggg    120
taagtacaca ggaaaattgc taagaaaat tttgagcgtt cggttgggag ttgttagact     180
gaaaatatta aacagcttac atagcaacac ttacacgact ataactatta ttttaagctt    240
tttataaatc cttaaaaacg ttcaaacata aaataaaata ttggtattga taacggtata    300
ttatattttg cattttttgc tttaagctaa ttgatggaaa tagtatccat atgttttagt    360
cttttaatgc cctattatac ctgttgcata actttatata atttagaaat atcttatcgt    420
gatcattttc tgtttaatcc tgtccaggga ataaaatttt tcttgggact ttcaataatg    480
caggtatctg acaactttt tagttatgta ttgtagaccg atagaaagaa aacctgcctt    540
gtatcctgtc gagtgttcgg agctgccttt taattattac tattaacaat ttagtgcaaa    600
aaacgcgatt ttttttcgat tttaacacta aattaaaaaa atagatttc cagaatattg    660 aaaaagcttc aaaatggaga ttttttaaag tgaaaatctt ttttttgacag atacttgcat    720 tatttatttg cttgtttccc tttagtaatc accttaatat gaaatttaaa aaaacttatt    780
ttttgacgtt gttttgcaac attttcattc acctttataa aaatgttgtt tagctcttta    840
cttttaactg ccgaattttg ttgcatgttt tgttgaattt tgattgtttt gtgtgaaaat    900
ttgaaacata aacgggcttt tgaatttgat gactgctggt gaagtaggta ttgagactta    960
gtttcttatt ttacacatag ctattaacaa tattggtatt gaatgataga taaaagtttt   1020 tcttttacc acagtcagat tttttataca agtgtactat tttgacggta tacaccacag    1080
tgacggtata caccattta ccacagttag attttttata caagtgtact attttgacgg    1140
tacacatgtt catataggta tcatctttct tcttagcttt ctatagtcca tgtatgggca   1200
tggcctcctc taactgattc catcaatctg tatcctaagc aacttacttt caatttgttc   1260
tggctattgt cagagataac tagaagaaga atccgaataa cttcggcagc agtatgaaga   1320
ctgggtgttg tgttgaaaaa caaacagata tcagtataaa gaaaatgata ttcaacaact   1380
agttgtattc tgccagttat gatctatgga gcggaaacta cgacacttac agagttatca   1440
gccaacagat taaaacacc acgcagggcc ttgaaacgag ctatgtctgt gagagaacat   1500
aatatatgaa atgaggacgt gaaaagcagg gcgaatgtgc aagatgtaat tggaagaact   1560
gcccatatga actggaactg ggtaggacac ttggcatggc aaaacaacga aaggtgaacg   1620
agaaacattg tactttggag accacgcgag ttcattcaga gtagtagaag aagaccagaa   1680
aaatactggc tagcgacat caaagcaaaa gtgggagaca ctggcaccaa caaaaaaaaa   1740
aaaaaaaaaa aaaaaaaaa a                                              1761
```

<210> SEQ ID NO 83
<211> LENGTH: 557
<212> TYPE: DNA
<213> ORGANISM: Diabrotica virgifera virgifera

<400> SEQUENCE: 83

| | | | | | |
|---|---|---|---|---|---|
| gggggaggtat | tctgagtttg | ggtattttaa | attgataaag | tagctagtta | agtaagaaga | 60 |
| caaaatgtat | aaagtagctg | ttttagtttg | cttccttatt | gcagcaataa | atgctagccc | 120 |
| atacggaact | tatgggcatc | aggataaaca | tgtccaacca | gttcctcatg | ttcctgacca | 180 |
| tccccacggc | tcccatggcc | atgaggaaca | cggcggatat | ggtcctcatc | atggtggtca | 240 |
| ccaagattat | acgcacggtt | ctcatggtca | tgaggaacac | ggcgaacatg | gttctcacca | 300 |
| cggtggtcac | caagattata | cgtacggttc | tcatggtcat | gagcaacacg | gcgaacatgg | 360 |
| ttcacaccat | ggtggtcaac | atcccggtgc | atacggtcct | catggtcatg | agcaagagca | 420 |
| ccaacatgag | tctcaccata | cgtacggtgg | acacgcatat | taataattgt | tataatgtaa | 480 |
| catgtttgac | tgttctttaa | atttaaataa | ataataatat | aaattgcaaa | aaaaaaaaaa | 540 |
| aaaaaaaaaa | aaaaaaa | | | | | 557 |

<210> SEQ ID NO 84
<211> LENGTH: 486
<212> TYPE: DNA
<213> ORGANISM: Diabrotica virgifera virgifera

<400> SEQUENCE: 84

| | | | | | |
|---|---|---|---|---|---|
| gggataagaa | attggaatta | agcccaaatt | ctctcgaaac | aattttttgtc | gtaacattat | 60 |
| gctgtaataa | ctgttgaaaa | gtaatggtgg | aaattcggta | tttttagata | tttatattaa | 120 |
| ataataattc | gtaggtgaat | gcaagttatt | atctagaaaa | tttgaaggta | acaatatagt | 180 |
| ttcattagaa | tcatttcagt | aactcttttc | gcaattttg | tcttaaaaat | aattgagaaa | 240 |
| cgctgtaggg | ttaaaaattt | aagttacaag | aagttagatt | ttaggtgtag | gcttaatgtt | 300 |
| ttgttttaaa | tactgctctg | gatggtgcag | tgaagatgaa | cgtaaaaaga | aagtaagccc | 360 |
| aaattctcaa | ttgaaaaatt | tttactttca | tattcgctgt | ggcattgagt | tgatgtgaag | 420 |
| aaatggtgga | ataaaaattt | ataattgtat | atatacaaaa | aaaaaaaaaa | aaaaaaaaaa | 480 |
| aaaaaa | | | | | | 486 |

<210> SEQ ID NO 85
<211> LENGTH: 492
<212> TYPE: DNA
<213> ORGANISM: Diabrotica virgifera virgifera

<400> SEQUENCE: 85

| | | | | | |
|---|---|---|---|---|---|
| ggggattttt | tagacatttt | gatattttgt | cggtatacac | gtttcgtgtc | tcaagactta | 60 |
| aaaatgcgtt | acgtggctgc | ttacttattg | gccgttttgg | gcggcaaagc | ctctcccaat | 120 |
| gctgcagatc | ttgaaaaaat | cttgggatct | gtaggtgttg | aagctgaagg | agaaagagta | 180 |
| aagaaagtca | tcagcgagct | cagtggcaag | tctgttgaag | aactcattgc | tcaaggtcgt | 240 |
| gaaaagttga | gctccatgcc | agttggtggt | ggtgccccag | ctgctgccgg | aggtgccgct | 300 |
| gctgctgctc | cagctgctga | agaaaagaaa | gaggccaaga | aggaagaaaa | gaaggttgaa | 360 |
| tctgaatcag | aagacgacga | catgggcttt | gctctattcg | actagactca | ttagttgtaa | 420 |
| gatcaacctt | gttttgtacc | ttaatatata | ttttttaagt | caaaaaaaaa | aaaaaaaaaa | 480 |
| aaaaaaaaaa | aa | | | | | 492 |

<210> SEQ ID NO 86
<211> LENGTH: 444
<212> TYPE: DNA
<213> ORGANISM: Diabrotica virgifera virgifera

<400> SEQUENCE: 86

```
gggagcactg ataaaaaaga tggtgtcgtc acttcgctta acatgaaatt ctgtctattt      60
taatatagaa gtctatggga agaacctgga caagagatta tgtccagcag tgaattaaaa     120
tgaccatatt aattactgac agttttttta agaaatgttt ttttagtagt agtgtttata     180
atttaaatgt ctttggtgtt tggaaattgg cctacacatt gtcccatgta cctatgtgaa     240
acccacgata aaaatatcc catatgtttt tgtacaaatt acaactgtag ctataattct      300
tctatttgac tgatcacatc ctttgacata aagaaaaaac ttaaccttga ttatgatcta     360
ttcttaaacg aagcaacatt atttatttat acctatcgct tcttatagtc ttacaaaaaa     420
aaaaaaaaaa aaaaaaaaaa aaaa                                            444
```

<210> SEQ ID NO 87
<211> LENGTH: 340
<212> TYPE: DNA
<213> ORGANISM: Diabrotica virgifera virgifera

<400> SEQUENCE: 87

```
gggcattcac aaaattaggc ataacgtata tgttactagg tctcaaattg cacctaaatt      60
tcctaaaaac attagtgaat tccatacgtt attaaattct gaagaaataa aaactaatag     120
ggggaacgtt ttcttataaa aaatgacgat aataatcaga tcatgttctc gtgtgaaagc     180
aattttttgg atttaagaca aatatcgaca ttttatattg acggcacttt tgaatactgt     240
ctaagacagc gattctcaat ctgtggtaca tgtacaactg gtgtacaat tcattacttg     300
cggtggtaca caaaaaaaaa aaaaaaaaaa aaaaaaaaaa                           340
```

<210> SEQ ID NO 88
<211> LENGTH: 1447
<212> TYPE: DNA
<213> ORGANISM: Diabrotica virgifera virgifera

<400> SEQUENCE: 88

```
tttttttttt tttttttttt ttttttttttt cttagtacta gataggattt atttatctgc     60
ccagttacaa aatagttata gtaagtaaat ataacaaata ataaataatt ataaggtgtt    120
ataagatctt aaaagtctgt ctggcagtta caaccacggt cgcatattat ttaagaactg    180
caaagatgta aacacagtac aaacaacatg aaaaatagct tattaggtat gaattgatta    240
aatagcttag aagcacttgc ggtggacaat tcctgggccg gattcgtcgt attcttgttt    300
ggagatccac atctgttgga aggtggagag ggaggccaag atggatccac cgatccagac    360
ggagtatttc cttctgggg gagcgatgat cttgatcttg atggtggatg gagcaagggc    420
ggtgatttcc ttttgcattc tgtcggcaat acctgggtac atggtggtac ctccggagag    480
aacagtgttg gcgtacaagt ccttacggat atcaacgtcg cacttcatga tggagttgta    540
tacggtttcg tggataccgc aagattccat acccaagaag gaaggttgga agagggcttc    600
tgggcaacgg aatctttcgt taccaatggt gatgacttgt ccatcaggca attcgtagct    660
cttttcgagg gaggtggaag cagcagcggt ggccatttcc tgttcgaagt cgagggcgac    720
atagcagagt ttttctttga tgtcacggac aatttccctt tcagcggtgg tggtgaatga    780
```

| | | |
|---|---|---|
| gtaacctctt tcagtaagaa tcttcatgag gtagtcggtc aagtcacgac cggccaagtc | 840 | |
| caaacggagg atggcgtggg gaagagcgta accttcgtag attgggacgg tgtgggtgac | 900 | |
| accatctccg gagtccaata caataccagt ggtacgacca gaagcgtaca aggagagtac | 960 | |
| ggcttggatg gctacataca tggcgggtgt gttgaaggtt tcaaacatga tttgggtcat | 1020 | |
| cttttctctg tttgccttgg ggttgagtgg agcttcagtg aggaggactg ggtgttcttc | 1080 | |
| tggagctaca cggagttcat tgtagaaggt gtgatgccag attttttcca tatcatccca | 1140 | |
| gttggtgatg ataccgtgtt caatggggta tttcaatgtg aggatacctc ttttgctttg | 1200 | |
| ggcttcatct cctacgtatg agtcttttg tcccatacca accatgacac cttgatgcct | 1260 | |
| tgggcgaccg acgattgagg ggaagacggc acggggtgcg tcatctccgg cgaatccagc | 1320 | |
| tttgcacata ccggatccat tgtcaacgac aagagccgca acatcgtcgt cacacatgtt | 1380 | |
| gtcttttgtg gttgatcact gctcactaga cagaaaaaca cagctaataa gcttgaatgc | 1440 | |
| gaccccc | 1447 | |

<210> SEQ ID NO 89
<211> LENGTH: 1444
<212> TYPE: DNA
<213> ORGANISM: Diabrotica virgifera virgifera

<400> SEQUENCE: 89

| | | |
|---|---|---|
| gggagtcgca ttcaagctta ttagctgtgt ttttctgtct agtgagcagt gatcaaccac | 60 | |
| aaaagacaac atgtgtgacg acgatgttgc ggctcttgtc gttgacaatg gatccggtat | 120 | |
| gtgcaaagct ggattcgccg gagatgacgc accccgtgcc gtcttcccct caatcgtcgg | 180 | |
| tcgcccaagg catcaaggtg tcatggttgg tatgggacaa aaagactcat acgtaggaga | 240 | |
| tgaagcccaa agcaaaagag gtatcctcac attgaaatac cccattgaac acggtatcat | 300 | |
| caccaactgg gatgatatgg aaaaaatctg gcatcacacc ttctacaatg aactccgtgt | 360 | |
| agctccagaa gaacacccag tcctcctcac tgaagctcca ctcaacccca aggcaaacag | 420 | |
| agaaaagatg acccaaatca tgtttgaaac cttcaacaca cccgccatgt atgtagccat | 480 | |
| ccaagccgta ctctccttgt acgcttctgg tcgtaccact ggtattgtat tggactccgg | 540 | |
| agatggtgtc acccacaccg tcccaatcta cgaaggttac gctcttcccc acgccatcct | 600 | |
| ccgtttggac ttgccggtc gtgacttgac cgactacctc atgaagattc ttactgaaag | 660 | |
| aggttactca ttcaccacca ccgctgaaag ggaaatcgtc cgtgacatca agaaaaact | 720 | |
| ctgctatgtc gccctcgact tcgaacagga aatggccacc gctgctgctt ccacctccct | 780 | |
| cgaaaagagc tacgaattgc ctgatggaca agtcatcacc attggtaacg aaagattccg | 840 | |
| ttgcccagaa gccctcttcc aaccttcctt cttgggtatg gaatcttgcg gtatccacga | 900 | |
| aaccgtatac aactccatca tgaagtgcga cgttgatatc cgtaaggact tgtacgccaa | 960 | |
| cactgttctc tccggaggta ccaccatgta cccaggtatt gccgacagaa tgcaaaagga | 1020 | |
| aatcaccgcc cttgctccat ccaccatcaa gatcaggatc atcgctcccc cagaaaggaa | 1080 | |
| atattccgtc tggatcggtg gatccatctt ggcctccctc tccaccttcc aacagatgtg | 1140 | |
| gatctccaaa caagaatacg acgaatccgg cccaggaatt gtccaccgca gtgcttcta | 1200 | |
| agctatttaa tcaattcata cctaataagc tattttcat gttgtttgta ctgtgtttac | 1260 | |
| atctttgcag ttcttaaata atatgcgacc gtggttgtaa ctgccagaca gacttttaag | 1320 | |
| atcttataac accttataat tatttattat ttgttatatt tacttactat aactattttg | 1380 | |
| taactgggca ggtaaataaa tcctatctag tacgcaaaaa aaaaaaaaaa aaaaaaaaa | 1440 | | aaaa 1444

<210> SEQ ID NO 90
<211> LENGTH: 993
<212> TYPE: DNA
<213> ORGANISM: Diabrotica virgifera virgifera

<400> SEQUENCE: 90

```
ggggagttcc tgtctagttt tgttgctgaa tgttatactc gtagaattga ttgaatcgaa      60
aaaaatattt aaaatgaaat ttaaattttc cgctgatgat gtaattgctg agaaaagaac     120
aacacaagga aatataaatc ttattaaacg atggctgttt gcagccgatg aaaaatatgt     180
accatctaaa ttatcagatg aattcatagt tctgtttcta ttgtcttgta acaatgacat     240
tgatgtgact aaaaagacta ttactgccta ctataaatta aggaaagacg cacctgaact     300
gtttgatgac agaacttccg agagagaaga tattcagaaa gccttaaaca cactgagaat     360
ggtaagcata ccaaatcgga cagacgaaaa ctatcaagta gtgtatctta gtctaaaaga     420
tacagatagc agtaactttg aactgaatcc cgttatgaaa gcctcattaa tgctaataga     480
tatagaacac cacaatagcc caccagatgg agttatgttt ctagctgata tgaaagggtt     540
cgggttttta cacgcgttta aattgaatcc aatctcgtta aagaaatatt tcaattatct     600
tggagaagga ataccaactc agttcaaagg aatgcattta atgaacggaa attatttcgt     660
ggatcaattg ttgagcattc ttaaggtgtt tatggcttca gaccttataa agagggtaat     720
catccatcaa gtaggctgga atccggaaga agcattccca aaaaaatgtt taccaaaaga     780
acttggagga gacctagaat cagaagacgt actttgtgaa cggacattac cgctgttcaa     840
ggatcgggaa tattttggaa aggcggaaga ggaactaagg aaaagtgtac ttaaataaaa     900
atgcgttaca tgtaatagta ttaaggaatt acaattattt ttggaataaa tatttatagt     960
gccaaaaaaa aaaaaaaaa aaaaaaaaaa aaa                                   993
```

<210> SEQ ID NO 91
<211> LENGTH: 989
<212> TYPE: DNA
<213> ORGANISM: Diabrotica virgifera virgifera

<400> SEQUENCE: 91

```
tttttttttt tttttttttt tttttttttt ctccttccgt attaaatcga tcagttcttt      60
agctctcctt acttttctt cccctgacag ttctgcttct gcctcttctt tagtgtctgt     120
agtttctttt tctgttttaa cttcttcaga ttctgtatct actttaactt ctttatcctc     180
cttattttcc tcggctaccg taacttcttt acctttcgta cttctgcgt tctcttcttt     240
tgctggttct tcttcttttg ctggttctgt atgcgtttct gacggactcg gttgctcttc     300
gggggtttta tcttcggatg atttttcaat ttctgtttcg gagggctca attcttcttc     360
ggggggactt tcttcggacg tattcagagc attattatca ctttcgactc gtggtgtctc     420
accagcttgt tcatgtgcca ggaagttttc tgattcagct gaaatagaat gaactggggc     480
tgtactgaat cctgccctgt tcaagacatc atccacttta gcagaaactg tttctaaatt     540
agtacttcct gtaatgatat ctaaaggaac acccttctga ccaataaaat atatcgaggg     600
tacactcggt tctttataaa tttcgctaaa ctgctggtga gctgtagagc ccgcaattac     660
tttgatagct acaaagtgat cttgttccag ttttttctcca aggtcgccat tattgatgag     720
gtctgttatt ttttgtgact tttcgtcagt accttcaata tacactacaa aaacggctcc     780
```

| | |
|---|---|
| tttcgattta gaaaaagcaa ccgcatcggc tatttctcca ctgtaccact tcattttaaa | 840 |
| aaaaaataag ttagtttaga cttttacaac aataaaatac tagcagactt ctaacaatta | 900 |
| aaaaagtaca catcagttat cgcaactaca aacacaaaat acaattttaa acgtcaccgt | 960 |
| caccggtcac aatctgtcat gtactcccc | 989 |

<210> SEQ ID NO 92
<211> LENGTH: 817
<212> TYPE: DNA
<213> ORGANISM: Diabrotica virgifera virgifera

<400> SEQUENCE: 92

| | |
|---|---|
| ggggatggcc ttttccggtt cacgccgtcg ttcagcaaga gcttgcgatt tttattttg | 60 |
| aaaaatagag agtattctct aatatttaag gacagcatgg aagacgattg ggctgtggat | 120 |
| aatcagagtg gtggagttgt cgccccaaaa attgcagaac tacctgaaat taagttgttc | 180 |
| gctagatgga actgcgatga tgtccaagtt tcagacatgt cccttcagga ctacattgca | 240 |
| gtgaaagaaa aaaatgcaaa gtatttaccc aattcagctg gtagatatgc tgcaaaaggg | 300 |
| ttccgtaaag cacaatgccc aatcgttgag aggttaacaa actctctaat gatgcatgga | 360 |
| cgtaacaatg gtaaaaaatt gatggctgtc agaattgtta aacatgcttt tgaaattatc | 420 |
| catttactaa ctggagaaaa tccattacag attttagttt ctgctattat caattcagga | 480 |
| cctagagaag attctactcg tattggtaga gctggtactg taagaagaca agctgttgat | 540 |
| gtgtcaccct tgagaagggt taaccaagca atttggttgc tctgcacagg tgctagggaa | 600 |
| gcagcattcc gtaatattaa aactattgct gaatgtttgg ctgatgaatt aatcaatgct | 660 |
| gccaagggat catcaaattc atatgctatc aaaagaagg atgaacttga acgtgtagcc | 720 |
| aaatccaacc gttaaattta tttctcattt tatattttat ttccaataat aaatatggat | 780 |
| aaaacacaaa aaaaaaaaa aaaaaaaaa aaaaaaa | 817 |

<210> SEQ ID NO 93
<211> LENGTH: 1186
<212> TYPE: DNA
<213> ORGANISM: Diabrotica virgifera virgifera

<400> SEQUENCE: 93

| | |
|---|---|
| tttttttttt tttttttttt tttttttttc gcaatgcgga gacaaattta taaaaagagg | 60 |
| acttgtgcaa atattgctg aacatgtcaa aagaaccaac agaaattgtg ccatccactc | 120 |
| cctatattaa ccaaaacagc agtacaaaga aattaacgtt tatttaaata atatctaagg | 180 |
| attttttctta ataaaatgac aacacagtgt caaatctata agcgctaata tatttataa | 240 |
| cttttttctaa gtttggaccc aaaagtgtat actgtaaatg tttatgttta tatacagtgt | 300 |
| gtcatttaaa gtagaaacat ccctgtaaca tttgaaatcc ttaaacattt caagagtttt | 360 |
| tttaataccg tgtgtttact tttaaattag atatagatag gaatacatcc aatacatggc | 420 |
| aacactgctt cctcgtttcc cacacctgag tcgcgccaat tgactcagtc attcgtcgat | 480 |
| tctacagtag caatgcaact tattctcata aaaaatgttg ccgattttag cgattccttt | 540 |
| agtctcctat ccctaatcga aaactaaacg tatggtaaag taataaaaga ggtaattcgg | 600 |
| gacaacattt aaagggttca tttaaagtac catatcataa tcatcatcat cagcctgttt | 660 |
| taaatccagt gcaggacata agcctctcct gtttgtatcc agaggccgtg cctctcctgt | 720 |
| acggttttgt gtagtatgga tccaattttt cgttatcttt catcatcttc caatcgtgta | 780 |
| ggtggtcttc ctctctttcg gttatctgtt cttggtatcc attcagttaa cttgcgtgtt | 840 |

| | |
|---|---|
| caccttctat ctttcatcct tgccatgtgg ccagtccatc tccattttag tctgcaagct | 900 |
| ctctccacaa aatctgtaac tctagttttg tttcgtagat cttcatttgt gatcttgtct | 960 |
| tttatttta ctcctatcat tgaacgattc attttcttg tgctattctt agttttaaag | 1020 |
| cattcttttt gcagacagag tttctggatc ataggtcatt actggcagaa cagactgatc | 1080 |
| gaagactttt actctttaga ttaatcggta cattgctgcc tttaaatacg tttttaacag | 1140 |
| ctccatatgc tgcccatcca tgtgctattc ttcttgatac atcccc | 1186 |

<210> SEQ ID NO 94
<211> LENGTH: 1033
<212> TYPE: DNA
<213> ORGANISM: Diabrotica virgifera virgifera

<400> SEQUENCE: 94

| | |
|---|---|
| tttttttttt tttttttttt tttttttttg cgtagtctga cattgcgacc aggttttgta | 60 |
| gacgtcttga actattttg ttatttttta attgttgaaa tctaaataga gcggattgaa | 120 |
| tattatcatt tactaccctg tgacaataat attattattg tcacaaaaca gtaaacaata | 180 |
| atattctcat tccaatgttc gaacaacaat gaatgttaat atagaccagg actaatctgt | 240 |
| aaaaattcgg atggcattaa aatttttgca gataaagtta ggtgacacct ttagtaataa | 300 |
| taattgaccc atgctccctc tcaaacataa ccggaacatt aataaaaaat caaatatttt | 360 |
| aaaaattcag aaaaagatcc attttttttct gctttctttg cttatagctt taaaacggtt | 420 |
| cgttctggaa caaatccgta cagaaacaaa acagagacaa ttgaatcatg tatgatgtac | 480 |
| gaccggtcaa aaatgtctta aggtattacc ttttctgcaa aatagcaata aacacaaaat | 540 |
| aaggggcaa acacgcgtg ttgttattca atgtctctta accactttgg tggcagttag | 600 |
| aaccttagta atccgcttag aaaattctta tagcttagtt aaatggtcta ccaaatttca | 660 |
| ctaaaatcga cctaacagat tctgcataat aaatttgcaa tataaatgtt tttaaaaaag | 720 |
| ttcaaatttc aaaatctttc tgaacaaaaa gtagacaatt tagtagttgg ctaattttc | 780 |
| cacatacaaa aaggcactcc acccatctaa tacaccccac agcatcaaaa tcggaccatc | 840 |
| taaggggcct cagcaatgtt tcaaaaatac taacaacttt ccggctcata aacaaatagc | 900 |
| tttgtttaat aataaaaaaa taataatttt tagcaacgca ataattaat accggtatag | 960 |
| tttgacttaa tcttttaaat gctgtcagca gaattgctat tttatttttt aatcaaaagt | 1020 |
| tatcctcgtt ccc | 1033 |

<210> SEQ ID NO 95
<211> LENGTH: 551
<212> TYPE: DNA
<213> ORGANISM: Diabrotica virgifera virgifera

<400> SEQUENCE: 95

| | |
|---|---|
| ggggacatta atttcaagcc taggttctgg agaatattaa ttaacatttc ctgcggtatt | 60 |
| gttggatgaa cattagataa gagaagacgt tccgatggag tgactaatct acgtgttaga | 120 |
| agtacttcat tatttatttt tatggatcct accttattta gaaagtcatc aactacagct | 180 |
| ttacttgaaa gataaacgca tactcggtta ttagagattc ttgatgaata aataatattt | 240 |
| tctggtttgga cgagtggtcc tagttgcaaa agataatctt gcaattttgc gccattaatt | 300 |
| gaactgaaga tgatggcttg ttctttcact ggtaattttg gagtagtttg ttgagatgca | 360 |
| atagtagagt acattagagt gttttgagaa gtggtaggag tttccattgt tgataaagta | 420 |

```
ttattcatca tttaatgtta cttgaacgat ttattataaa catatttagt tagggttata    480
atatgtatgt tgtgactggc tgaatcacta atgtgtatgc caaaaaaaaa aaaaaaaaa     540 aaaaaaaaaa a                                                          551
```

<210> SEQ ID NO 96
<211> LENGTH: 1050
<212> TYPE: DNA
<213> ORGANISM: Diabrotica virgifera virgifera

<400> SEQUENCE: 96

```
ggggagaatt tatgaatata ggtaagcctt aatacactaa tttaagagtt taataattgt     60
atattatttt caaaaatgtt ttaagtgtgt gactttgtag agatattgtt ctgtgatctg    120
agcaggtttt gcacttgact ttttgagaat tgctacaaag gtcgattgca gcaattgtca    180
ggcgattgtg gaagtctgat atgataaatt aggagttcaa ccattacata aatatcatct    240
tcatcaatga gttttaataa ttcgatgtgc acatcttctg gtccagtaac tttgctatct    300
ttagtgttct tgatgacata gatgacttct tctcgtaata atggtggttg atatcctcta    360
tggtttctag tgacagtttt tctctttcct cattaattaa ttcttgaatg taattgatcc    420
agtgacacat tctctccaat tatatcagta ataattcatc atataacaat tcatcatatt    480
tccttcatca tttttgatgt tatttctatt aaaaatgtcc gtacctacat tatcctcctc    540
ctcctccccct atcctttatc cttcgtaagg atgtggtgac gttatggtat ttgacgaatg    600
gtttctatcc attcttctct ctcttgggcg cggtgtgctg cctcagacag agagtaaccg    660
gtggcgcatt ttatttggtc tgaccatcgg agtggctatc ttcctcgagt tcttttaccc    720
tctaccttgc cttcaaccac caacctctcc atgccttctc ttcgtctggt aatgtgtcca    780
aagtacctca atatattttg gttgatgatg gtggtaagcc tagtgttgat gtcgagttct    840
gataatattg agatatttgt gcgatgtgct acattatcca tattacactt aattaaatgc    900
acttttaaaa cattttttttt tataataatt atgtaggtcg tttttttaat ttatcattaa    960
gctctaatca agttgagaga agccgaacct cagctatgta tctaatatta tacagtatgg   1020
tacaaaaaaa aaaaaaaaaa aaaaaaaaaa                                    1050
```

<210> SEQ ID NO 97
<211> LENGTH: 1391
<212> TYPE: DNA
<213> ORGANISM: Diabrotica virgifera virgifera

<400> SEQUENCE: 97

```
gggggaaaaa atgtttggat acaatgtatg tatacaagtg ggctttgatg atgtgttatt     60
gtgttttaag tgctaaaaat atttttttat attatgttca caaaaaaaag catgtgtgtt    120
ggtgacattg ttaatcctcc tgtcagttaa gtcctttatt catcttaaac aataaacttt    180
taaaacatga gcttcaaaaa agagcataaa tgattattat tttaatgctt ttcaaaatgg    240
ggttttagat gtacacgata tatattatgt tttgcataaa tgatactttt attatatttt    300
tattatttgg tcttacttta ttgtagttat ttttttgata ttttttttgtt cttactttgt    360
tatttttttg tagattgtta atttgcaact aaacgatcta cttataatag cgttagtaca    420
aattaacaaa acgaaaccta atatctacca cgagttactc ggttaagacc atacagaaat    480
aaataaattg cttaattgca attaaaacag ccgtcaaaaa tgataagaaa attaagaaaa    540
acaatatttt ttctaataat aaagtaataa aggcagtttt tgttttttatt ctattcagag    600
ttggaccacc atctccatat agctatttca gcatcccatg catctttagt gaagctatgc    660
```

```
agtcacaact ctgaagcgaa tattaacaac cctgaatatt taagggaaac catcgcgata    720
caatgattcc accttttgag acgcaatcta gcgacatctc tcgcaaaacg aggaaaacaa    780
cgaaaagccc tagatacaaa gtttactact ttttaaacaa ttagaataat tgaaataaaa    840
atataataaa caatatttta aatccacgaa tttcgttaat aaactgcttt ctggctgcat    900
cctgtatatc tggctatttta tatttagctt aatatttttt ctcttttaat atttggttca    960
agatatagag tgtttagaaa caaaattaca ctaagggcgc tcgcaaacac agccacttgt   1020
ggccgccacc ggtggcagtg ctgactgagg tttgtatgta ttttaaatgg attcggccca   1080
cacactatgt ttccggtgat cttcgagcga caagccacga caagctatgg cggtggccgt   1140
ttctggctac atgaagtcgg tggcgatcac aaaacagcca ttcgtccaga gagagaaaga   1200
gttaaaacaa catcataaga aagagcttgg atacaaaaat aggctaccag aatatatgaa   1260
ataaatagtc ggtctgttta gccatgaaga ggaaatggat gaagaacaac tacggaaaca   1320
aactgtaact cctaacttca aaattaaaac accatgtatt gaaaaaaaaa aaaaaaaaa    1380 aaaaaaaaa a                                                        1391
```

<210> SEQ ID NO 98
<211> LENGTH: 515
<212> TYPE: DNA
<213> ORGANISM: Diabrotica virgifera virgifera

<400> SEQUENCE: 98

```
ggggcttact tacctgtaaa cgaatcattc ggtttcactg ctgatttacg ttccaacact     60
ggaggtcagg ccttcccaca atcagtcttc gatcactggc aaatcttacc tggtggccca    120
atggaaccca gtaccaaacc ctatggaatt gtgcaggaca cacgtaaaag aaagggtctt    180
aaagaaggac ttccagacct ggcacaatat ctggataaat tataaacaac taagaaactt    240
aatttatgta cagattattt aataaaatta tttcaattta ctcaacggtt tttatagtta    300
attgtatttt tgatattttt attctgataa gttttcagtt ctctcaaatt gatggcaaca    360
ctagaaatga aataaactaa ataatctgac taatatttta tgtttgctat atatatttt     420 gttaacagtc cagatatttg tatatttatt aatttgacat caaaagtaaa tctgatgaaa    480
cattgaaaaa aaaaaaaaaa aaaaaaaaaa aaaaa                                515
```

<210> SEQ ID NO 99
<211> LENGTH: 580
<212> TYPE: DNA
<213> ORGANISM: Diabrotica virgifera virgifera

<400> SEQUENCE: 99

```
ggggatgtta tacattactg aatattgttt gcttaagtaa taataataat acaaaagagt     60
catcatgaag ttcttggttt tcagcttggt ctttgctgtt tactatgcaa atgcagctat    120
tactcccgaa caagctgaga agatcaaaag tttccacaaa gaatgtcttc cagaatccgg    180
agttaatccc gaattggttc aaaaggcaag acaaggagat ttcgccaatg acgacaagct    240
aaaagcacat atcttctgcg tctccaagaa gatcggtttc caaaacgatg ccggtgaaat    300
tcaagtggaa gttctcaaag ccaaagtggg tgctgcctta agatccag ctcttgctgc     360 ccaattgatc ggcacctgtg ctaagcaaca agcaaatgga cccgaaacag cctttgaaac    420
cataaaatgc tatcacgaaa agacaccaat tcatcttagt attatttaaa tattttgatt    480
ttgttataat ataaaaaact tcttttttgaa gagttgttat aaaataaatt ttttatcatt    540
```

```
atatgtacag aaaaaaaaaa aaaaaaaaaa aaaaaaaaa                         580

<210> SEQ ID NO 100
<211> LENGTH: 913
<212> TYPE: DNA
<213> ORGANISM: Diabrotica virgifera virgifera

<400> SEQUENCE: 100 gggagtgtc  aacaatgatt  tatagcagat  atctgtggat  tgtgtgtgta  gtgttatcac    60
tattttatca  gacaaattgt  gaatgcccta  aaatatatac  tcgcaatgaa  tggagcgctc   120
gaaaagcatt  aagtaccaga  ccgttaagag  aagatcctcc  accatatgtg  gttgtccatc   180
attcggccac  tcgctcatgt  ttttcagttg  aagattgttc  aaaacttgta  aaaagcatcc   240
aagattacca  tatagatcac  aatggatggg  atgatattgg  ttacaacttt  ttgattggtg   300
gtgatggaac  tatatacgaa  ggtagaggat  atggtttaca  tggtgcgcat  tctattccat   360
acaacgcaag  aagcttaggg  gtttgccttt  taggaagttt  taaagatacg  aatcctccta   420
atgtacaact  gaaagcattg  gaagactttt  tgtcttgtgc  agcagctgat  cacaaaatta   480
ttgcagatta  tcaccttatc  ggacatcggc  aagctgataa  aacagaatgt  cccggggatc   540
gagtgcatgc  agttatcgaa  aaatggcctc  attttgaagc  caatccacaa  gatgcttccc   600
caaagaaact  gtaaacatag  cgaagttacc  ttttctctta  tggaataaac  acctctctat   660
cgcaatgttt  ttagattaca  attattaata  catgtaaata  tttaaaagac  tgtatatcta   720
ctcatacttt  aaagatgtgc  gaaaatatat  cactatcttt  aaaaaaaaaa  aaaaaaaaaa   780
aaaaaaaaaa  aaaaaaaaaa  aaaaaaaaaa  aaaaaaaaaa  aaaaaaaaaa  aaaaaaaaaa   840
aaaaaaaaaa  aaaaaaaaaa  aaaaaaaaaa  aaaaaaaaaa  aaaaaaaaaa  aaaaaaaaaa   900
aaaaaaaaaa  aaa                                                         913

<210> SEQ ID NO 101
<211> LENGTH: 569
<212> TYPE: DNA
<213> ORGANISM: Diabrotica virgifera virgifera

<400> SEQUENCE: 101
ggggaggcgg  tcgacatgtt  tttttttttt  tttttttttt  ttttacattt  atccacattt    60
tattctcaaa  ataaaaagtg  tacaattata  aaattaaatc  tacagcctag  aacctcaatt   120
tttggaagaa  ccatttgttc  tttccttgct  tataccttcc  ctcaaatttg  acacgggtct   180
ggaatctagc  cttcttcctc  ttcatggcat  ctttgaggtc  cttgggtaca  actttcaagt   240
ctgatgccaa  atctacagag  tatctagtgg  gcatgagatg  gttgtagttc  aatactttga   300
taaaaggctt  gatcttggac  ctcttgtgca  ttttgccttt  gcccatgcgt  ttgtggatttt  360 tccttgggta  cctatcaatt  ccagctacta  aggcatgtcc  gtattgttta  tctgatgtac   420
cttcatcgta  ggttttgacg  actacggctt  tcggccggc  gtatcggccc  ccgaggacca   480
atacgacttt  tcctgatttc  attatttttac  ccattgtggc  agtgctttga  caactgctga   540
aaaaaaaaaa  aaaaaaaaaa  aaaaaaaaa                                       569

<210> SEQ ID NO 102
<211> LENGTH: 1350
<212> TYPE: DNA
<213> ORGANISM: Diabrotica virgifera virgifera

<400> SEQUENCE: 102
tttttttttt  tttttttttt  tttttttttt  gaactaaaaa  tgaaaataca  tttttgggct    60
```

```
acgtaatatt cctatcagct cttttacagc tggaatgttg tatgtgctgc tcattattac     120
tgcgttcagc ggttttttat tcttgtcaat ttaatacatg atatttaaaa aaaaaaagta     180
tatttacaaa ccttagggtt ttggaaaata atatgtacag tagatattac tctatgggca     240
gtaagttgcc atatatgaaa gtcatggata tttacaatat ctggaaagtg attcaataac     300
tggatcttca gtgtgtcgat gtctatcgtg tcaggcacag tctgtagaag aatcaggcag     360
ctttctttca tatatggata acttaagaac attatcaaag ttgaagatat tatcgccatg     420
ataggatcta tatattttgc agtatctttg tcagtaaaat atactaggag agcgcatatt     480
acaaccaaaa tacaaccgtt tacatctctg gccatttccc aaaatccctg cctttgtttt     540
tgatggccga tcataggatg gatagttttg cttctggata atcgtcttgc gccttgctgc     600
aaagactggt caactactat tttacttaaa actacatttc cgctttctgt tacataaaga     660
aaacttcctt ggtggaatgt atatccacca atcaacaggt agcatactcc gttgagtaat     720
aaaccacatg ctcctaaaca taaaacagat atggaatgat gcatctcgtc atgatggtcg     780 atatgaaccaa atgtctgaca tgcttcaaca aaaatagaaa aacttaacga agctaagaac     840
acacaacata ttaacataaa tatgacatca gttctggccc agccaaatgt atttttttagc    900 ttcttttctt ggttggacct ggttacggac gctttcgtct tcttatggtc atggcacttg     960
gccgggttgg atgttaactc ttctcctata cttcgctttt cgcttggtgc ctttttcatt    1020
tcgaatactt gtttcggagt atcttttcca tacttaatag ttaaaataca tcctcccaat   1080
gccataatat tacacaaagt gtggtaagag tccattaata gtgtcagagc atgagtgggg   1140
tgacttacaa ttagttctaa taagaaaaag gcgatggtca agcctagtac cacgtacagc   1200
tgaaaaggtt gcatccttct tacccattct ttcattgcca tggttgaact attcagagca   1260
cacgtctgaa cgctaggaat atcttaattg aatattttcc actgaacact gcaactatac   1320
tgtagaaact gtcaggtgtc gactgtcccc                                     1350
```

<210> SEQ ID NO 103
<211> LENGTH: 991
<212> TYPE: DNA
<213> ORGANISM: Diabrotica virgifera virgifera

<400> SEQUENCE: 103

```
tttttttttt tttttttttt tttttttttc ttaattacaa atatttacta attttcttat      60
tattatcagt caaattacaa aacaaattct attttttgctc atcaatgggc ttaaagtgat    120
ttagtaaatt tacggtccaa tctccttcaa cccctttttgt aaattctctg ataaatctat    180
agttgcaaat cgaaattttt tgttgatatt caggtagcat tcccatattt aagggaggtt    240
cttcacctct agatctcatt ccagctaaac ctttcaaaga atggtaaacc atggttattt    300
cgacgaatcg ttttttgttct ttgccttctt cttcgttaaa tataacacca acctgatatg    360
gaaatgaaaa atatatgtca tctacactag ttgctatctg ctcccttttga ctcatggaca    420 tcatagatat tgcttttttgt agactaccga taatgtcatt tgttactaga ccgtctaatg    480
atttaatatc accttcagac aatttatgtg atactacctc cactgctttt ttagaagcac    540
ttacaaaatc tggaagatta aattcttgat ctaaataggg cctaatgata aaggtagcaa    600
gaataaaatt tcttatagtt ttaaataaag aaggccaaac aaatatggga gagtctggca   660
gtaatggagg taatttgttt gaaggagaac ttggatcatc tgaataccat cttctttgat    720
taaggcctga atttaaggat ttgttatttaa aaaatatga aggctgcttg gtacaaaaac    780
```

-continued

```
ttgcatgttt acataagaaa tgatttgtta ttgtactatt aaatttacac aaatttaaat      840
tactataatt tcgcacattt ctgaacaaaa cgttaatatt cattttatca ttttaatata      900
aatcaacaaa gtcaaaagta ctaaaatatt ctaaaatttt agatttttta ggttctgtcc      960
tgtcacggtt ctgtcctgtc acctactccc c                                    991
```

<210> SEQ ID NO 104
<211> LENGTH: 445
<212> TYPE: DNA
<213> ORGANISM: Diabrotica virgifera virgifera

<400> SEQUENCE: 104

```
ggggagtatt cacttgatct tcaaggtaga ttaacgcaag tagaaatcta aaacatgtct      60
ggacgtggta agggaggcaa agttaaggga aaagcaaagt cccgatcaaa tcgtgctggt     120
ttacaatttc ctgtaggtcg tattcatcgt ttattgagaa aaggaaatta tgccgaaaga     180
gttggtgctg gagctcctgt atacttggca gctgttatgg aatatttagc tgctgaagtt     240
ttggaattgg caggaaatgc agctagagat aacaaaaaga cccgtataat tcctagacat     300
ttacaattgg ccataagaaa tgacgaggaa ttgaacaaat tactgtcagg agttaccatc     360
gcccaaggtg gagtattgcc taatatacaa gcagtacttt tacctaaaaa gacccaaaaa     420
aaaaaaaaaa aaaaaaaaa aaaaa                                            445
```

<210> SEQ ID NO 105
<211> LENGTH: 2235
<212> TYPE: DNA
<213> ORGANISM: Diabrotica virgifera virgifera

<400> SEQUENCE: 105

```
ggggcagtgc tttagaggcc acgaagcaat ttctaggata gacgaacgac gctcgcgacg      60
acgcgctgcg acgcacacga caaaaaaata cacaatacga caccacgcgc cattttgcca     120
ttttctgtgt gtgcagtgaa gtgaagtgct actaaaatct tcaaaattca acccttctaa     180
gaaggccgat ttcatgtgtt ctatatcgaa gtaaagagc aatagcatgg gagtggcaga      240
ggatttcgct cccagcttca cgcaaaagcc tcaattgagg caggaggacg atggaaacaa     300
actcattttc gaatgccagt tactggctgc tccgaaaccg gaaatcgaat ggtttcgaag     360
cgatatacca ctttcagaag acagtaggac taattttaaa attcaatcca taggcaccaa     420
caaattttta gtagtactcg aattagatga tgttattgaa accgacgctg gcctttacaa     480
ggtcaaagcg aaaatacca tgggggaaat agcagcctcc atcaatctca acttcagccc      540
catggacgaa ccaaaagaaa aacaaataga cggcctagca cccactttg cgaagaaacc      600 agctattcgc caagaagatg atggcaaaaa attattattc gaatgtagga cacaggccga     660
tccccgtcca acggtcagtt ggtcccacaa tggcaacgct gttagcgaag gtccacgtca     720
caagttgagg atagataaag atggccattc atattttgcg acccttgaaa taatcgatgt     780
cacggtagag gatgctggca aatacaaggt gaccgcaaaa aatgacttgg agaaagtaa      840 cgccacaatc agccttaact ttgacagtgg agatagcgct gatggctttg cgccttcttt     900
ccttgagaaa cccaaaatca tacctaatga gagtggcact cttattacta tgaaatgtaa     960
atgcaaagct aaacctaaac ctgacgtcac gtggttccgc ggaaccacag ccgtcaagga    1020
atcttccaaa attaaaatcc agatcgttga tctcgaagaa gacaaattcg aactgtcctt    1080
agaaatcaag gatccatcgg cagctgatgg gggtacttac agatgccatg tgaagaacga    1140
atacggagaa agtaatgcaa atctgaacct aaatatcgaa gcagaaccag aaccagaagg    1200
```

```
agaaggacca acgttcgtcg aaaaacccag gataacctct cacgatggag gcaaactcgt    1260
tgtcatggag tgtaaagttc gtgctaatcc taaacccact atagtttggt acagagaaag    1320
caaagaagtc acagaatcat ccaaaattaa gatcagtatt aaacaaacag aagaagatat    1380
atattacgtc aaattggaac tcaatgatcc ggggattgat gactctggct tgtacaaatg    1440
caatataagg aacacacttg gtgaactcaa cgccaacctc accttaaaca tcgagattat    1500
tcctgttatc aaagaaaaac ccaaagttat taaaatcatt aagaagaaaa ctgttattgt    1560
tgaatgtaaa gttctcagca agtttgcacc tgattgtaca tggtttaagg aaagcgatgc    1620
cgttaaagaa gattcaagac atactgttca cgttgaccaa gttaaagacg gcgaatttac    1680
tgttaaactc gaaattaatg aagttgagaa aaaagacaaa ggtatgtaca aattggttgc    1740
taaaaacgaa aagggtgagg caacttcaca agtcgttgaa gtcactgagt tacctccaga    1800
ggagaaaccc aaaggagaca agccgaaact gaccaaacta accaatatcg ttactgacga    1860
aggaaaatca gttgatttta taacttctct caaaatcgaa gacaaaacag tcaaaatcac    1920
atggtacaag aacaccactg tgataaccga atcttcagaa atcaaaatct cttttgatgg    1980
cactgtgacg cgacttagca ttagtaaatg taaagtatca cattccgcta catacaagtg    2040
cgttgccaaa aacgaatttg gcgaagacga aataagcgct acacttaaag taaacgaagc    2100
taaagaggaa gatgaagaag aagaagaatc cgaagaggag gttatcgaag aaaagaaaga    2160
ggaaaagaaa gtagaaaaga aagaagaaaa acaggaaaag aaagcaaaaa aaaaaaaaaa    2220
aaaaaaaaaa aaaaa    2235

<210> SEQ ID NO 106
<211> LENGTH: 1148
<212> TYPE: DNA
<213> ORGANISM: Diabrotica virgifera virgifera

<400> SEQUENCE: 106
ggggagagta gatagtaagt aagtgaatgt acgttgtgaa tgacggaagc cggtttgtta     60
cagagaggag gatggagtcc aacacgataa cgttgacgag attttcttg gcggaacaac    120 aaaaatttcc agaagccaca ggtgaattga cccagctgct gacttctatt caaacagctg    180
ttaaggttat cagtagcgcc gttagaagag ctggtattac caaattgttt ggtaccgtag    240
gtgaaacaaa tgtacaggga gaagaagtta aaaagttgga cgtattggcc aacgaattat    300
ttatcaatat gcttaagtca tcttatacag tagcattgct tatatctgaa gaaaatgaaa    360
caattttgga ggtagagact gaacaccgag gaaagtatat agtagccttc gatccattag    420
atggttcctc gaatatcgac tgtctggtat cgataggttc aattttcgcc atttacagaa    480
aatccgacaa cacagttcca gccctcgatg acacactaat gtccggaagg aatgtagtag    540
cagccggata tgcgctttat ggcagtgcaa ctatgctggt catatcttct ggatctggtg    600
tgcatggttt catgctggat gccaccatag gagaatttgt tttgactgaa cacaacatgc    660
ggattccgaa aaaaaggaaa aatctactct ataaacgaag ggtactacca cgaatgggat    720
gatgccataa gagaatacgt cgatgccaag aaagatcctt ctaaggggaa agcctatggt    780
gccaggtacg taggttctat ggtcgcagat gttcacagaa ctattaaata tggaggaatc    840 ttttatacc ctgcaacgaa gtcttcccct aagggcaagc ttagactgat gtacgaatgt    900
gttccgatgg ccttttttgct cgaccaagca ggaggattag ctactgatgg caagattaat    960
atattagata tcaaacctac taaccaccat cagagaagtc ctattttct ggggtctata   1020
```

```
gaagatgtag aggaggttca aagttatatc aataaacatt gtgaatgtaa aaaataggtt    1080
aagagatttg tttcaataaa gtttattatt agttatacaa aaaaaaaaaa aaaaaaaaaa    1140
aaaaaaaa                                                             1148

<210> SEQ ID NO 107
<211> LENGTH: 574
<212> TYPE: DNA
<213> ORGANISM: Diabrotica virgifera virgifera

<400> SEQUENCE: 107
ggggagttat ttttgattat ttttacgtat attatacagt cttaaagttt ggcttcaccc      60
tgtagtagta gttttcccta attctgacct gttttttta ttgtttctaa attcccaatt     120
ttgtgtcagt gcacttttc cacaaatctt tttacataaa agaccttatt aacaagaatt     180
tatattaact ataaacgaaa ataagatttt tttctgatac aatgtttgtt gttttgtttc    240
tttttgcaac acgttttatt ctttgctata acttaaaaat gggctattca ttagatacca    300
attttttcat ttaagtccct ttttattttt tcatatcaat gatttgttat tgcgaaaata    360
ttcttagaaa tgaattatat aataaaaaaa acaataaaac taatgttaac cgtcttgatt    420
ttcgcaaaaa tatgggttca tcattttatc tttcggaagg actaaccgaa aaattataca    480
tctactttgc attcggagta ttgtaagaaa aacatgcatt cgttacagta gtaccagcta    540
tacaagagat tcattatgat tcagctctgc gggg                                574

<210> SEQ ID NO 108
<211> LENGTH: 725
<212> TYPE: DNA
<213> ORGANISM: Diabrotica virgifera virgifera

<400> SEQUENCE: 108
gggagtgagg cttattgtta acaaactggc aaaaaaataa ttaaaactaa acaaatttga      60
tgaaaaatgt tcataaaagg tatatttcgt tgattgggaa gaatagtatg atatttcaaa    120
aacatcaagt ttacagaaaa gacaattaaa gattgagatg ggttacaaga ttggattact    180
taagcaatac aatattaaat atgcttttca tcagaataat taaaacatac agtattaact    240
gacaatatgg gtgttacatc caattcatac accaccccca actcatattt tcatcccca     300 ttttgagtta taatactttt ctctataaaa attttgtact atttcacaat tataaggtta    360
ttagggacaa taaaacgaaa cagtttaaat gttttattag agtttaaata acaatgaatg    420
aaaaaaatcg cagttatagt acaataacaa tataaaaaaa attaaaaatt tgggcccgcc    480
taaaaaaaaa ggttctacaa gttacaaccg ctacattttt ttttctttc aaaagagag     540 agcaggccag ctttctttt ttcacttatt cccactttct tcttgtaagc ttgttttaga    600
gtaacgtcac gtgctgatgg aagtttgctt tgaagaacgt ttatggtgtt aaattcctgt    660
tctttgtatg acttatatag taggtgacta gggattagat tacatctttt ttcccgattt    720
ttatc                                                                725

<210> SEQ ID NO 109
<211> LENGTH: 725
<212> TYPE: DNA
<213> ORGANISM: Diabrotica virgifera virgifera

<400> SEQUENCE: 109
ggggagtgtg ccacgggatc ggattgaggg tgattgtact gtttgtgtag aacattagtt      60
taataaaatg gcagccgtag taaacttgta caattatttt tataacttag cagatcccag    120
```

-continued

```
agtgaaaaac tggtttatga tggaaaatcc cttcccaact ttaggaataa ttggagtata      180
cctattatta gtcctgcaaa tcctgccaaa ctttatgaaa ataggaaac ccttcgaact       240 aacgaagata attagattat ataatatatt tcaagtagtg gcctgtattg gtataatgta      300
cagtatcctg acgtcaggct ggattcaagg agaaatatat attggttgtt ctccaattga      360
ttactccaac aaaccaaatc ccgtcaaact cctgggtgca ttctactggc tctatttgtt      420 aaaggtgta gaactgatcg agactatatt cttcgctcta cgaaagaaaa acaaccagat       480
aacaggcctc cacatctacc accatggatc tacgttcttt ttggcatgga ttgggtgcaa      540
attcattgga ggtggtatgg cttctattcc tcccttcgtt aactcattca tacatgtact      600
aatgtacaca tattactact tgtcttcttt gggacctgaa tggcaaaaga agctgcaacc      660
atggaaacca aggcttacta tgttgcaaat gatacaattc accctcctca taattcactc      720
tctga                                                                 725
```

<210> SEQ ID NO 110
<211> LENGTH: 508
<212> TYPE: DNA
<213> ORGANISM: Diabrotica virgifera virgifera
<220> FEATURE:
<221> NAME/KEY: misc_feature
<222> LOCATION: 439
<223> OTHER INFORMATION: n = A,T,C or G

<400> SEQUENCE: 110

```
ggggagtgtt acgacgcgaa cggtgccaag cgctgctgta aagttgcgtg cttttctgaa      60
aaaactttcg atttgcgtgc cgcgaaaaag cgagttgtca cagacaattt tgttttgtgg      120
tgaatattcg gcggattgcg taatttgtcg attggttttt ggtgtttttt tgtgtgtgcg      180
acagagtaac tattttattg gattgtgttt tgaagattac tcagctttat cggaacctct      240
gagaggaaag tctagtattc gagcaggtcg aatggagttc ttctacaccg aaaaaaacca      300
gtgaattgtg ttttaaagtg tgcgttttg tcgatttcca atttcctctg cggcgtataa      360
tttctattgg ctacattatc tatacagttt gtgtttgtgc tttgtaccag atttccaatc      420
acttagccat gtttggagng gaataattaa aaggtgagtt tgaattttt ttacattatc       480 tcttctacaa aaggaacaat agaagctc                                        508
```

<210> SEQ ID NO 111
<211> LENGTH: 623
<212> TYPE: DNA
<213> ORGANISM: Diabrotica virgifera virgifera

<400> SEQUENCE: 111

```
ggggatatca aacgccaaaa gacgtttata aacatattta atgcataaat acatcctact      60
aaactatatt ttccataaaa tctacaataa ataagttata taaactttac acgcccatct      120
gcttcttcca agatgacgtc accatctttt tcactcacaa aaatatcaca atctacaaat      180
caccaaacat ctccaaaata tcggttttat ccaaactatt tctgatattt catatcgtat      240
atttcagtta tcgcaagtgt tgagaacctc aatagcaaaa tagatttgcg ggccttattt      300
ttcacttcaa aatgtctgct aaccagtata ctattagaga gattgtggac tatcagtcta      360
cccataatgc aagtagtgcc gatgacgaaa atgacaccgc atcggacgaa gaacaagtac      420
ccattatgta ccaatacgaa atggtgggcc cattggaaag gacagtaaag cgacgaggcc      480
atcttcctaa agaagcggtt aaaattctaa aaaattggtt atacgaacac agattcaatg      540
```

```
catatcctac ggaaattgaa aaacagattt tgtcacaaga aacgaacctg acggttcttc    600
aaatcagcaa ttggtttata aac                                           623
```

```
<210> SEQ ID NO 112
<211> LENGTH: 625
<212> TYPE: DNA
<213> ORGANISM: Diabrotica virgifera virgifera

<400> SEQUENCE: 112
gggtttgttt gaattttttcc gaaacaatgc atgttttcgt tctaattgca ctcccctaca    60
tagttacagg ttattgaagc gctattatag tcgaggcaat aaagcagtaa aaagatcaaa   120
acccgccaaa tttttgcagt tggatgaatc tcaatgaaat attttgcatt cgattcgtaa   180
gagacttagg aaacttcgta aacaaaaatg atgatgaccg aatgtaaatt gcataattga   240
tttgcaaaaa tgtaaacata atgtgtataa gtcgtatttt ataatgaata acgtcataat   300
tgggaggaca aaaactgaaa cgatttacaa tataccgctc caagttgtaa atcctcatag   360
ttaacattgt atttgtgttt gactagatca ttaacgaata cggaaataat caaataaaca   420
acttgtttcg aacatggtaa atgttatgtg taaaattatc attttactta aattttttta   480
aacctaatgt gcatcagcgg tatttttaaa tttataacgt cataattgga gtaaaaaaaa   540
tgcaacatgt taaatataca gcaccaggta gtacaaattt tgtctagacc ttatagacct   600
tatattatag accttagcat agtta                                        625
```

```
<210> SEQ ID NO 113
<211> LENGTH: 664
<212> TYPE: DNA
<213> ORGANISM: Diabrotica virgifera virgifera

<400> SEQUENCE: 113
gaggagttca ctttgggatt gtattcctga atattaaccg gtagtgccag gtgacagtgt    60
ttaattaaat atccagaaaa aatgccaggc ccttcaagac ctctgtggca gtagccgga   120 aagcgtgatc cagaacaaga acgcgaagct caagcatgga tcgaagctgt cacaggaatg   180
aggtttcctc caggagttcc atacgaagat tgtcttaggg acggtattct cctttgcaca   240 tgatgaacc gtttggcacc tggaatcatc caaaaaatca acacatctgg tggagactat   300
aaaatgatgg ataacttgaa ccaattccaa aaagcttgtg tgaaatacgg tgttcccgat   360
gtagatcttt tccaaacaac tgacctgtgg gacaggaaaa gcatcgtttt agtcacaact   420 accattttttg ctctaggtcg cacctgttac aaacaccctg aatggcgcgg tccttttcttg   480 ggacccagac catctgaaga aaacaggaga gacttcagcg acgaacaatt aagagctggt   540
gaagctatta ttggactcca agctggccaa aacagaggtg ccactcaagc tgggcagaac   600
tttggtgctt ctagaaaaat cattttggga aaataaacaa acattcgaag agacatattg   660
aatc                                                              664
```

```
<210> SEQ ID NO 114
<211> LENGTH: 656
<212> TYPE: DNA
<213> ORGANISM: Diabrotica virgifera virgifera

<400> SEQUENCE: 114
gggtaagaat gcagcagcta gcaataaggg cgaagtagtc tgcagaagca ttttttctttc    60 tagagctcct taaacatca ttcacgattc attaatacca gttttcattt ttttttaaat   120
atgtagtctt tttattgaaa cattttcaaa tcaaaatttc tagaaaacgg tgtgttttac   180
```

```
tgacttaatc aagagtacct tctaatacta gaataccgca caatttaata atccagtgtt      240
agaaatgttt aaaattaaa gacaaaaaaa ttatccgata aaattacagt tatcctacca      300
aaaacggacg cctacgatcg gtactaggaa ttcacagtag ggcttttcat tcacagaagc      360
tcgaaacaaa tgacaatcga tgaaaagcct tattaatgga atcaatttat ctccgggaga      420
taaacaggca taccagtttt ccattttttca aaatagaagc gttctggagg tattaaagat      480
aactagttat aagacgccaa cgtccaagag ctctagttcc cttaggaagc aatttcgaac      540
tacttgaatt aggttaaaaa caggagagtt tctggacacc ctgtataaga aagacaccag      600
gaatattttc acgaatacga caaccagtgg agctaagagt tgaatctttt gtcacg         656
```

<210> SEQ ID NO 115
<211> LENGTH: 185
<212> TYPE: DNA
<213> ORGANISM: Diabrotica virgifera virgifera

<400> SEQUENCE: 115

```
gggatgtcaa atcataaaaa tcatccttat catttagtag atattagacc atgacccttta      60 ttaggagctt ttagagcaat attaacaata ttaggaataa ttaaatgatt tcatttatat    120
aataataatt tactaataat tggattatta attacaagat taattatata tcaatgatga    180
cgaga                                                                  185
```

<210> SEQ ID NO 116
<211> LENGTH: 661
<212> TYPE: DNA
<213> ORGANISM: Diabrotica virgifera virgifera

<400> SEQUENCE: 116

```
ggggaattgt caacctggaa aacgacttgt cgaagtcgca tagtttttat aagtttaaat      60
aaactaaatt aaatataaat acttcgagaa tgcaataatt attattcttt aactagaccc    120
acagcttatt aattagcaga agtagtagca gacttatact aactagcata aggagaaaca    180
tattaacata gcatggcaga cttcatagat tctgaagcag aagaaagtag tgaggaggag    240
gaattagatc ataggggatcg taaaaaagcc caaaaagcca aagttgtaga tagttcagat    300
gaagatgatg aagatgatga cgaaagactg agagaggaat taaaggattt gattgatgat    360
aatcctattg aagaaagtga tgctgagtct gatgcttcag gaagggaaaa acgtaagaaa    420
tctgacgacg aggatttgga tgatcgactg gaagatgaag attatgattt gcttgaagaa    480
aatttgggtg ttaaagttga aagaaggaaa ttcaagcgac tgcggcgttt tgaagatgaa    540
gaaagtgaag gagaagaaga acatgatcct gaacaagata gggaacaaat tgctatggat    600
atattttcag atgatgacga tgaaagacga tcagaacgaa gtcacaggcc tgccgtcgaa    660
c                                                                      661
```

<210> SEQ ID NO 117
<211> LENGTH: 488
<212> TYPE: DNA
<213> ORGANISM: Diabrotica virgifera virgifera

<400> SEQUENCE: 117

```
ggggccactt gatttttttgt tttagaaaaa ggcacgaaaa tggctggaga ctcagttgat      60
gcttcaaagt taaccggtat gagcaaaatt ttcaatggct ctaccatgag aggaagggca    120
aatgttgcct tagccacata tgccagtgtt ggactcctaa tcgcctattt ctcactgaaa    180
```

```
ccatcaaaac ccaaggcacc aaaaaattag tctagtagtc tattccgtaa tgttactcta    240
taactatgta catgtttaat aaacttaaa atctcaatgc ttaataagtt ttttagata       300 caatgttttt tgtagacata tgtaatgact caataaaatt gatgttgtat acaagggcaa    360
gatgaaaagt tctttgcctg gtagtgaaaa gtgagttttt tattcaaaac atgcctttat    420
ttacagtgca atctcacttt attgtaatat tatttgatat atttttccag taaagagatt    480
ccaccatc                                                             488
```

<210> SEQ ID NO 118
<211> LENGTH: 616
<212> TYPE: DNA
<213> ORGANISM: Diabrotica virgifera virgifera

<400> SEQUENCE: 118

```
ggggattgtc aaatagttgt cagcgttaca cagcgaatat tttcctcatc agttcaatat     60
taacaataaa ttgttttgtt gaaattgaaa tcacaaatta ctttataaaa tggtaactct    120
agaagacgtt gaaatgaaaa atgcagacag tcctccagga ttagaagctg gtgatacaaa    180
gaaagatacc gacctacaaa gtgtaataga gattcgtgaa catgcaagac aaatagaaaa    240
atcagtcaca agtaaagaaa accgtttcat cttacgagtt ttacgttgct tgcccaacac    300
tagaaggaag cttaatggac tggtgctgag aagcctcatt actcaaatat atcctgtagc    360
tgaacgtgat gccctcctta gtttcgtcga ggaagcttct ggagaactcg acgccaccca    420
gtcacgagca agatcagctg ttaagtcgcc tgttcccgag gtggatacat atataaatct    480
tttaatacta gtacgtttaa ttgataccaa taagttagtt gaagcagagc gctgttctca    540
agctcttatg aataaaataa ctaaccaaaa cagacgtact atagatcata ttgctgccaa    600
gtgttatttc tatcac                                                    616
```

<210> SEQ ID NO 119
<211> LENGTH: 609
<212> TYPE: DNA
<213> ORGANISM: Diabrotica virgifera virgifera

<400> SEQUENCE: 119

```
ggggacaag attttgcaat ggcggatgta gtagacgagg tgattatgga ctctgatgaa      60
aatgaggaaa tactatcaaa agcccagaaa gagatggctg aactcaaaaa ggaaaacggt    120
aaccagttat acaaaaccaa acagtacaga tctgcactcc ctctctatag cgaagccatc    180
aatctttgtc caaatgtagc cccttattat ggaaatagag ctgcctgcta catgatgctt    240
tacaggttta cagaagcttt ggaagatgtc aggaaaagtg tgcagctgga tccagaattc    300
gttaaaggat acatcagaat gttaaagtgt gctatagcaa tgggtgacac cactacagct    360
gattttgcca ttaagaagct tcaggacttg aaagttgacc aacaaacatt tgcaaatgaa    420
ttaaaatcgg ttcagcaatt gaagcagtac gagtcagatg gaaccaaagc gtacgataaa    480
aaagattatc gtttggttgt tttctgtatg gacagatgtc tcgataatgc ccctacttgc    540
taccgataca aaattgccaa agcagaatgc ctcacatatc tcggccgtta ccaagaagct    600
caggaaatt                                                            609
```

<210> SEQ ID NO 120
<211> LENGTH: 517
<212> TYPE: DNA
<213> ORGANISM: Diabrotica virgifera virgifera

<400> SEQUENCE: 120

```
ggggtcttga aggtggctcg ttgtagcaga tttgttgaaa accatggaaa tcgttcaaga      60
attatccagc caatatgttc tgtatattcc tgtagcttta gtaatcgttg gagctatttt     120
ggtgttcact tttggtttta aatctgcaga acaaccaccc ttcgacaaat tatcatttga     180
cgatagaaaa tctgctggga aaaagcgtaa aactaaggaa aagaaaccta ctgctaatgg     240
tcacatcagc aatgtagaaa atctgataa atccccatca aaggactcca agaagtcccc      300
ccagaaagaa gctgttgaag caaaacaaga aagaaggag aagaaactag acaaacaaaa      360
tgaaaagcct aaaaaacagg aaatcaaaaa gacagaggaa atcaaaaata gaaaaatttt     420
aaacaaagtg tcagagaagc cagtagattt tgatgatggc aactgggaga cagtacctct     480
taaatctgat aagaagaaga aagaccaatc gccagtt                              517

<210> SEQ ID NO 121
<211> LENGTH: 607
<212> TYPE: DNA
<213> ORGANISM: Diabrotica virgifera virgifera

<400> SEQUENCE: 121
ggggacagcg tgaaatctgt gcgcggacaa aaaaaacttg ttatcgccga tttattataa      60
tttatattta tgaagtgact gtgtcggtac ttaatagctt tatgtatatt gtgtttgttt     120
tcatttaaat tttaaatttc tataccaaag atatgagccg gttgaacata ttcagttttt     180
tgaaaatgct tcaagcattg tgttgtgtac tgggagttac atcagcatct tcagacccag     240
ttatagtctc cagagaagaa tggggggccc gcgctcctaa aaacatagaa atatggcga      300 acccagtacc ttacgtcgtt atccaccaca gttatctacc accagcttgt tacaatttaa     360
ccgattgttt caaagccatg cgttggatgc aagaccttca ccaagacacc aacggttggg     420
cggatattgg ctacaacttt ggtgttggcg agatggtag agcctacgaa ggaaggggat      480
ggtccagagt tggtgctcat gctccctatt acaacagcag aagtattgga atatgtataa     540
ttggagattg gacagttgaa cttccaccag aaaatcagct agcgacagtt catgagctaa     600
tacaaaa                                                              607

<210> SEQ ID NO 122
<211> LENGTH: 590
<212> TYPE: DNA
<213> ORGANISM: Diabrotica virgifera virgifera

<400> SEQUENCE: 122
gggggttgcc caatttgttt caatattgtt ctgattttat ttaaaagcgg cacttaaaca      60
tagtatataa ccatggttga gaacagtaca ttaactatag atgaaaaatt tcacctaata     120
tccagaaacc tgcaggaaat attaggtgaa gatagaatta aagcagtatt gaagaacgt      180 gatttgaagt tgtattgggg cacagctaca acgggtaaac ctcacattgc ctacttcgtt     240
ccaatgtcca aggtagcaga ctttctcaga gctggtgtag aagttactat tctttttgct     300
gatcttcatg cgtatttgga taatatgaag gcaccctggg aacttctagc gcttagagtt     360
cagtattacg aacattgcat taaagctatg cttcaatcta ttggagttcc tttggacaaa     420
cttaaatttg tgaagggaac agattatgaa ttgtctaaag aatacacact agatgtttac     480
aaaatgactt cagttgttac tgaacatgat gcaagaagg ctggagctga agttgttaaa      540
caagtagaaa atccctttact aagtggtctt ctatatccta gtttgcaagc                590

<210> SEQ ID NO 123
```

```
<211> LENGTH: 103
<212> TYPE: DNA
<213> ORGANISM: Diabrotica virgifera virgifera

<400> SEQUENCE: 123
gactcttacg aactcagata cttccagatt gacagtcaag aagacgatga tgaagaagat    60
aatgaataat ttattcagtt attttttta ttaaatagat tat                      103

<210> SEQ ID NO 124
<211> LENGTH: 381
<212> TYPE: DNA
<213> ORGANISM: Diabrotica virgifera virgifera

<400> SEQUENCE: 124
gggaactata aaatgcggtt acaacgttgt tccagcttag cattctagta tagatttcca    60
tttcagcata tcaagaacga tcacaattta gtgaaagtgt acatgggaat aacaacaact   120
ctatattgaa atattgttta atatttaata tgctaagtaa tattcagtta gaatattatc   180
atggatcatg gatgggtgaa atatcacagt tttaacaaaa aaaaaaagaa tgtgttgtat   240
tttgtacgcg cctaagaagt tatacttcta ttatgtgatt tcaatgaaat aaacatattt   300
taaacagttt atttgtattt tatttaaata ttaaactaat tttaataccct atttcttacc   360 aaatttgttt attaaaatag c                                             381

<210> SEQ ID NO 125
<211> LENGTH: 627
<212> TYPE: DNA
<213> ORGANISM: Diabrotica virgifera virgifera

<400> SEQUENCE: 125
ggggaacagt ttaattgcta gagttgtata gtcagtgtct ccagttgttt attatcaaac    60
aaaaatgtct ctgacaatga ttggtggtgt aaagatcccc atagtggggc taggaacatg   120
gcaggctacc aatgaagaag aattggaagg tgccgttgag gcagctctgg aaactggata   180
ccgccacata gatactgcat ctgcatacca aaacgagcat gtcatcggca agttctaaa    240 taaatggttg gcgtctggca aacttaagag agaagatatt tcattactaa ccaagcttcc   300
aatgacacac atccatcccg atctcgtcga aacagctctt aaagaatcct tacagaagct   360
tcagctggac tatgttgatt tgtacttggt gcattctccc atatacatga aatttgttga   420
agctggaaag ccaatggaac ctctacctac tgaccatctg gctgtttgga agaaaatgga   480
agagcaagta gatgcgaaaa gaaccagaac catcggtctc tccaacttca acgtaaacca   540
gatcgacaga atagtgaaga attgtagaat tcaaccagcc aacactcaag tggaactgca   600
cgtttactac cagcagaaaa aacttag                                       627

<210> SEQ ID NO 126
<211> LENGTH: 640
<212> TYPE: DNA
<213> ORGANISM: Diabrotica virgifera virgifera

<400> SEQUENCE: 126
ggggattgta ttttagtatt ttacaattct ttgaattgca gattatttag cggtttagta    60
caaaaacctg aagtaaattc tataacggaa agtgcttaaa ttttaatggt aaaatgtcca   120
ttctagctta caatggtggt gctatggtgg cgatgaaggg agaaaactgt gtagcaattg   180
cagcagatag gcggtttggt attcaagccc aaacagtagc tacaaatttc caaaaaatct   240
ttgaaatggg accacattta tatgtgggtc ttccaggatt agccacagat acccaaacag   300
```

```
ttatggaaaa actccgtttc cgaaaaaact tgtacgaact taaggaaaat cgaaaaatat        360
ctccaaaagt atttgcctct atgatatcaa atatgttgta tgaaaaaaga tttgggccat        420
tttttgtaga acctgtagta gctggacttc tacctaatac ttatgaaccc tttatctgta        480
atatggattt aattggttgt ataaaccaac cttcagactt tgttgttggt ggaacagcgt        540
cagcacagtt gtatggtatg tgtgaagcac tttgggggcc taacctagga cctgaggatc        600
tttttgaaac catctctcaa gctctcatca atgcctttga                              640

<210> SEQ ID NO 127
<211> LENGTH: 591
<212> TYPE: DNA
<213> ORGANISM: Diabrotica virgifera virgifera
<220> FEATURE:
<221> NAME/KEY: misc_feature
<222> LOCATION: 156, 241, 244
<223> OTHER INFORMATION: n = A,T,C or G

<400> SEQUENCE: 127
gtacattaaa atcgctaaaa acataaaaaa atacaatatg ggtacttgta tgtgataatg         60
ttacctgtta gttactaaat ttaaaacggt tgatattttg tatacttata tttagacatg        120
gcggtaaatg tttattccac gaacgttaca tctganaatc tatcccgtca tgatatgcta        180
gcatgggtga acgaatgttt gcagagtagt tttgcaaaaa ttgaagaatt atgtacaggc        240
nccngcatat tgccagttta tggacatgct ttttcctgga tctgtgcaat taaagagagt        300
taaatttaga accaatttgg aacatgagta catacaaaat ttcaagattc ttcaagctag        360
ttttaagaaa atgcaagtag ataagatcgt ccccatagat agactggtga aaggtagatt        420
ccaggataat tttgagttcc tacagtggtt caagaagttt tttgatgcca attacaaagg        480
gacggactac gatgcgctgg gagcacgtgc cggagagcaa ttggggcaag gaggatctaa        540
cgcccctaga ggtcaatctt tgatgttacg tcggccgaac gcgacgccct c                 591

<210> SEQ ID NO 128
<211> LENGTH: 614
<212> TYPE: DNA
<213> ORGANISM: Diabrotica virgifera virgifera

<400> SEQUENCE: 128
gggggaggag gttaagttaa acttcgtttg gtttggtttg gttgaccgag tgattttcca         60
gggtggagtt tttttgtgat gctaatttat ttatggccat ttcgcgttct ctgataaatg        120
aactataaag tattaaagca cataaattaa taatctttga ataacttaca ttgatattgc        180
gatcaacaag gtttttctaa acaaatattt agttaaaagt gcacaagttt ttatgcaggt        240
tgtcttgtaa ttgttttcaa ctgcttagag cttctatctc caccatgggc gatcaggttg        300
aaaattcgaa caataaagtg accgaaaatg atccacagcc aacagggac gaaatgataa         360 tggctcagca gaggcaaatt gaacaagagt atattgatgt cctcagaaga ctaaaagata        420
tagataatat tgatgaagcg cttaaagaat tatatagtgt atttaatgat caaggtttct        480
cagattattt ggtggtctac ctcagattgt taaccagtgg ccagttacaa aaggaacacg        540
aattttacag ttgtttcata gaaggtgata gaacggtagc tgattttgt caccaggaag         600 tagagcctat gtat                                                          614

<210> SEQ ID NO 129
<211> LENGTH: 639
<212> TYPE: DNA
```

<213> ORGANISM: Diabrotica virgifera virgifera

<400> SEQUENCE: 129

| | |
|---|---|
| ggggagtcga aaaatatggc agcgtttcta aggcatggcg ttttcaaaac aggacgagtt | 60 |
| gtctcttcaa aaacgtact tttgaggtcc tttgccacga aggctgagaa gaggaaagga | 120 |
| atcgacagaa aagttggccc aaaaatagac tccacagctc aatctttagc ttcaaaaggg | 180 |
| tttctgaggc aacaaagaga ttattctcca cctgaagatg ttaattccaa gttagaagca | 240 |
| atcttccaga ccgtcgtcgg tagttcagat atatctaccg aactcacaga tctgaatcaa | 300 |
| aagtttactt tattcatgca gtgtgaacag caactaggcc atagtattcc taattcgtta | 360 |
| cttcatcaca tgaaaacatt gaaggacgtt caaatattct ataacatgcc cgtagataca | 420 |
| agaacgccac tggaaagaat gaaatccatg gacttgccgg aaaatttaca tgttcagtac | 480 |
| gaatataaac gatttaatgc tgatactgat acgatgtttg gaggaaaaac agcattccct | 540 |
| aagagttcta caattgttac aggattaaaa tacaaagata agtacaaagg acaaaagcaa | 600 |
| ccattacctg atttctagtg tttttttcta gaaaataaa | 639 |

<210> SEQ ID NO 130
<211> LENGTH: 651
<212> TYPE: DNA
<213> ORGANISM: Diabrotica virgifera virgifera

<400> SEQUENCE: 130

| | |
|---|---|
| ggggatgttt taaaaggcgc tttaagttta agattcacac attgcataaa ataattttat | 60 |
| aactaaacta aatcatgggg aagaataaga agacaagaa aaagggaaaa ggggccgaga | 120 |
| aaacaacagc aaaaacagaa aagaaactgt caaacaaaat gaagaaagaa ctgcaagcta | 180 |
| agggagagga tgatatagaa tctattttat tacaaattga gaaggaagag aagaaaaggt | 240 |
| tgactgttac tgaagctata atcagtccac cttcaagaag attaaatttc acctttatgg | 300 |
| cccatccaga aaagaacag cttatttgt atggggagga atttttcaat ggacaaaaga | 360 |
| cttttgtgta tggtgactta ttttttctaca atataccaaa taacaaatgg acagtagtta | 420 |
| aggctcctaa tggcccaccc cctagatgtg gacatcaaat ggttgtctct tcagcaaata | 480 |
| aaggtcaatt atgggtgttt ggaggagagt ttactacacc cacacaatca caattttatc | 540 |
| actacagaga tctttgggtc ttccatttag ctactaaaca gtgggaaaaa attactgctc | 600 |
| cgaatggacc atcagcgaga agcgggcaca gaatggtatt aataaagaag c | 651 |

<210> SEQ ID NO 131
<211> LENGTH: 652
<212> TYPE: DNA
<213> ORGANISM: Diabrotica virgifera virgifera

<400> SEQUENCE: 131

| | |
|---|---|
| ggggaccta aatatccaga tattttaaat ccttgctgag caagacaatc ttcaacttca | 60 |
| taacattgaa tatttcttaa ttagttatct ggataactgc tgattcaata tcctccagga | 120 |
| gtttcatagg acaacacttg tcctcatgaa gtgtaaatca aaagtgatcg atatttaata | 180 |
| caccattcta cattcatgaa ccattctaca aaaatttgtc caaattgctc ttcttttctta | 240 |
| gatatcttca tacattttgt tctcttaatg ttttgtgaaa gttcatatct cttagactta | 300 |
| cttctatgat tctatttggc tccccacgtt gggcgccaaa tgttactctt cgccgatgtt | 360 |
| accagttttt ctataaggta tgcgaaggta attaactact tttatttct aacaaacgaa | 420 |
| agagaataat aataagaaat caaaaaaatc ggagaatcat acactattta ttcttattaa | 480 |

```
ccaaaattat aaaatttata ttaatcttaa ttgaagatat aaaaaaacca aaagaaaaag    540
gtaaaaagct taaataaagt ttatgcttgc ctctaagaat attcttttca gcgtacacac    600
atattaaaat tcttaaaact atgtaatatt atatttaggt actatttaca ag            652
```

<210> SEQ ID NO 132
<211> LENGTH: 658
<212> TYPE: DNA
<213> ORGANISM: Diabrotica virgifera virgifera

<400> SEQUENCE: 132

```
ggggacatta ttattccaag tatctttaag cagtgacatc gagtgttagg cttcaaagat     60
gaaggttttt ctaagtatta gtattggact ttttgtactt tgttcaatag aatcaaggtc    120
tctaaatagc aagcttttcta aaaagccaat atttaaagac ttttacggaa agctaaacat   180
agaagtaaga ggaaaccctg agagccact gatattaact gacttgatta aagcagggaa     240
gctggatgaa gctcagaacc aatcactcgt gcaaggattg gacacagagg ttaaaagtta    300
ttccggctat ttcactgtag ataaaaagca tgattctaat atcttcttct ggttttccc     360 ttcacaaagt gatcccagtt cggatccggt tgttctatgg ctccaaggag gaccaggatc    420
tacatccatg tttggacttt ttcaagaaaa tggacctctt acagtaaaag atggtgagct    480
gggtattaga ccaacgtctt ggaataggaa tcactcagtt atctcatcg atcagccagc     540 tggaactgga tggagttata ctaacggagg atacgccaag gatcaacata agtagccac    600 tgatttgtac gaagccttgc agcaatttt cacctcttc tatcaatacc aggagaga       658
```

<210> SEQ ID NO 133
<211> LENGTH: 638
<212> TYPE: DNA
<213> ORGANISM: Diabrotica virgifera virgifera

<400> SEQUENCE: 133

```
ggggatattg acattcgaca actttttgg gaggacaggt gaatgttgta gcgtttttca      60
aagtgtaagg tgtttatttt caaaaagttt ataaaataag caatcactat gggtaatgtg    120
tttgcaaatt tattcaaagg cctctctggc aaaaaggaaa tgaggatatt gatggtagga    180
ctcgatgcag ctggtaaaac cacaattta tataaactta aattaggaga aattgtaaca    240
actattccaa caattggatt taatgtggag actgtagaat ataagaacat tagttttaca   300
gtatgggatg taggtggtca agataaaatt aggccattgt ggagacacta tttccaaaac   360
acacaaggcc taattttcgt agtagacagt aacgacaggg aacgtatcac tgaggctaaa   420
gatgaattaa tgcgtatgtt ggccgaagat gaacttagag atgccgtact tctcattttc   480
gccaacaaac aagatttgcc caatgcaatg aacgctgcag aaatcaccga caaactcggt   540
ctccattcac tacgcaaccg caactggtac attcaagcta cctgtgcaac tagcggagat   600
ggtctctatg aaggtctgga ctggttgtcc aatcaatt                           638
```

<210> SEQ ID NO 134
<211> LENGTH: 192
<212> TYPE: DNA
<213> ORGANISM: Diabrotica virgifera virgifera

<400> SEQUENCE: 134

```
ggggaaaata cgtcaagctg tcattaatgt cgctatcctt ccttcctttt ccttttttaa     60
cttaacacac gtttgcatag gtaggtcaaa atgaccaaag gtacctcaag ttttggtaaa    120
```

```
cgtcgcaata agacccacac cctatgcagg aggtgcggta gatcttcata ccacatccaa    180
aagtcacaat gc                                                        192

<210> SEQ ID NO 135
<211> LENGTH: 576
<212> TYPE: DNA
<213> ORGANISM: Diabrotica virgifera virgifera

<400> SEQUENCE: 135
ggggattttt atttacttta acctaaattt attttagttg atcaacaatt ttttagttt     60 atttgacaaa ctttgtaatt ttaaattatg ccgaactgga atcagatcca ggctcaacta   120
aggcatccag ctaatcctgt agtattcttt gatgtatcag taggaactac agaaatcggt   180
aggatgatat ttgaacttttt tgccgatgta gttcccaaaa ccagtgaaaa ttttcgacag   240
ttttgtacag gagaatttag aaaagatgca gtacctcttg gttacaaagg agctagcttt   300
caccgtgtta ttaaagactt tatgatacaa ggggggagatt ttgtgaatgg tgatggaacg   360
ggtgtgatga gtatctatgg aggaagtaca tttgccgatg aaaactttag ttttaaaaca   420
tgatacacca ggactgttat ccatggcaaa tagtggaaaa gacacaaatg gttgtcagtt   480
ttttataact tgtgcaaaat gtaattttct tgatggaaaa catgttgttt ttgggagagt   540
tattgatgga cttttagtta tgagaaaaat tgaaaa                              576

<210> SEQ ID NO 136
<211> LENGTH: 618
<212> TYPE: DNA
<213> ORGANISM: Diabrotica virgifera virgifera

<400> SEQUENCE: 136
ggggaatatt tattttttatt taaacaagtt aactgatagt tattttaaac attttttatat   60 tcagcaacaa tggtgaaggt aaaaaaacaa aaaggcagta tcatctgagc gtgttcatgt   120
taaaaaagaa ccgaaaaaaa tgaacccctt cgaggttcat gtaaataggg aaaaactaca   180
agtgataggc aagaagcaaa agaatgacag aggtcttcca ggtgtctcca gagctaaagc   240
catcaaaaaa cgaaaatcta cgttactgga agaatacaag gtacaaaaca aaacaataa    300 attcgttgac agaagaattg gcgagaaagc tcacatggac agtgaagaaa aagctttggc   360
gaggtataca gctctaaaag taaaggccca taacagaaag agcattttca atcttgcaga   420
tgatgaaatt ttaactcata aaggtcaaac actgaacgaa atagagaaat tgatgatcc    480 tagatcggat gatgaagact tcgatgatag cgaaacaaag actggaaatt tggagtcaaa   540
ttttatagga gaagcacatt ttggcggagg attatttaca aacacaggaa agaaggtgc    600 tatgactcac aaagattt                                                  618

<210> SEQ ID NO 137
<211> LENGTH: 421
<212> TYPE: DNA
<213> ORGANISM: Diabrotica virgifera virgifera

<400> SEQUENCE: 137
ggggtaaaaa cgatgggaaa tgaaatatct ttggataaag aaattattac aggaaatgaa    60
tcaaaaaaat ctgtgtctct gtatcaaaca aattataaat gttatatatg ttctaaatac   120
ttttcagatg aatatatgtt gcgaaggcat attacgacag tgcataatga agaaaaattg   180
tttaagtgtg aagaatgtgg caaaagttta aaaactcgta actcattcag aaagcacatg   240
cgaacacata ccgaagaaga aatgtttgaa tgtaaagtat gttctaaaaa atttagagaa   300
```

```
aagtatgtgc acaatgatca tatgcggact catacaggag aaaaccatta tacatgtagc    360
ctttgttcag caacgtttag aaacaggacc ttgctaagaa atcatattgc atcaagtcac    420
g                                                                    421
```

<210> SEQ ID NO 138
<211> LENGTH: 508
<212> TYPE: DNA
<213> ORGANISM: Diabrotica virgifera virgifera

<400> SEQUENCE: 138

```
ggggttcacg aagacaaaaa tcgggtaccc ttcgtcaaag gggcaactga aaggtttgtc     60
tcaagccccg aagaagtatt cgaagctata gaagaaggaa atctaatag gcacatcgct    120 gtaacaaata tgaacgaaca ttcgtctagg tctcattcag tatttttaat aaatgttaaa    180
caagaaaatt tagaaaacca aaagaaacta tcagggaaac tttatttagt agatttggct    240
ggttccgaaa aagtgtcgaa aacaggcgcc gaaggtactg ttttggacga agctaaaaat    300
attaacaagt ctctgtcggc tttaggaaac gtaattagtg cattagcgga tggtaacaaa    360
actcacattc cttacagaga ctctaaacta accagaatcc ttcaggaatc gctcggagga    420
aacgccagga cgacgatcgt tatttgttgt tctcctgcta gctttaacga atctgaaact    480
aaatcgacgt tagaatttgg taaagagc                                       508
```

<210> SEQ ID NO 139
<211> LENGTH: 517
<212> TYPE: DNA
<213> ORGANISM: Diabrotica virgifera virgifera

<400> SEQUENCE: 139

```
gggtcagccc gatattccca aatttccttg gtacaagtct tgtagggctt ctagaaagta     60
cataacttct attattagag tacgattcgg gcacgcatgt tatccaaagc atttatttaa    120
aatacaggtt ttggataatg ataaatgtga gcattgtgaa gaggaaagtg atttagatca    180 tatattttt ggttgttcta aaaatacaat ttactcatct aaattaatga atgatttatt    240
aaaatgtaaa gtagcaactc cttggaatat actatattta ttatcacttg gttctgcaga    300
tgtataaaac tctttaatta acttttaaa agacagcaaa tcatcattat aattccctta    360
aacattttta attaatgcct ttggtagtta gttgttttag ctgttaagct tagtgttact    420 taatacctt tagttgttat ctttgttta aacctgtttt gtataacttg ataacttgta     480
ttccttatgt gtctggcagt atgacggtaa gtctaag                              517
```

<210> SEQ ID NO 140
<211> LENGTH: 585
<212> TYPE: DNA
<213> ORGANISM: Diabrotica virgifera virgifera

<400> SEQUENCE: 140

```
gggggtcggt aaaaagtatg tcaagtaaat gatttatcca atccaaaagt ccaatctgat     60
taaatacttt cctgtttggc tgagttgtga atctggtcga gcagggatta caaggaagaa    120
tagaacacta gttttattct cactatctcg ctactcttat ttcagatgta tcggtcgcca    180
tcgcatgata gaacgcacaa gagatgataa agtttcttcc tacctatagg cttagcgaat    240
acaagtgaac aaagccaaag ttaattaagt aatagatatg attatcagag acagagtacg    300
ttaaaataaa ttgccatgtt accggcggct cacagtggtt ccaaatgctg aaaacgtggt    360
```

```
catgagatgt catattctcc ctaaaattgg ataatactta atacaaaaaa agtgataata    420
tggtaagaaa tcagcttcta tggtatgacg gtgtgttgcg ttctcaccac tggcaaagag    480
agtttcatct tcattggtaa gataaaatgg gaaatagtac taaccatgca ttaagatata    540
acgcagaatt tcgactacgt cttctggttt ggcgatttaa acttt                    585

<210> SEQ ID NO 141
<211> LENGTH: 383
<212> TYPE: DNA
<213> ORGANISM: Diabrotica virgifera virgifera

<400> SEQUENCE: 141
gggtatatac ggatataaaa atttatattt ttaaatttaa gcggaagttc ggacacaatt     60 ctaacttta agtgaactcg tttaagatag tgtacacaca agtgttcaat tgttattata    120
acagtgtgac atgttttga atttgtaccc tttgaatgga gactatggaa tgaagaccgt    180
gatgcttgca gagttgtcag ccattagatt aacacaaaaa tgccacagat gacacccaca    240 aaaaaagaa tgtgtgtgta ctttgtacgc acgtaagaag ttatacttct attatatgat    300
ttcttaaaaa taatatact ttaaacagtt tgttttaatt ttttttttta acaccaaact    360
aattttgtgc ttaccgcctc cag                                          383

<210> SEQ ID NO 142
<211> LENGTH: 616
<212> TYPE: DNA
<213> ORGANISM: Diabrotica virgifera virgifera

<400> SEQUENCE: 142
gggggccata attatatctt aagccaagaa gttaatttta attatgaaaa taattttagt     60
agttttggtg attgtagctg cagctacagc atctacggac gaagaaaat ggagacaatt    120 taagattacc cacaacagag tatataacaa tattgaagag cataaacatc gatttgaaat    180
ctttaagaaa aatctgattc gtattaaaga gcaaaacgaa aaatacgaaa aaggggaatc    240
aacttttaac ttcggaatca ctcaatttgc agaccttacc gaagaagagt tccttagtcg    300
ttttaaactc gctggtagtt ctaagttaag caaaattaat agcaatgtct cttcttctaa    360
aagtagaagt aaaacctccg gtggatcaga tgatttgcca gaacaatatg actgggtccg    420
cactggtgca gtaacatctg taagagatgt tgcagattgt ggtgattgca cagctgaaag    480
cgtggtagcc gcagtagaag cgctgagtt tataaaaact ggaaatctaa tacagcgaag    540
tcccaagcag ctagaagact gcattccttt taacccagat gaatgttgga tatgttatga    600
gaaggtcctt aattac                                                   616

<210> SEQ ID NO 143
<211> LENGTH: 174
<212> TYPE: DNA
<213> ORGANISM: Diabrotica virgifera virgifera

<400> SEQUENCE: 143
gggttgataa gaacatgttt agttgttaaa gtccctaact ttttttatta cacaacatag     60
gcgaatgaat ggaaagcaga atgttaagaa aatatagcct gaggctatag ttgggtttta    120
atttcaatat tttataaatg ctagaatatt cctcagggtg ttgtgaaagt tgag          174

<210> SEQ ID NO 144
<211> LENGTH: 619
<212> TYPE: DNA
<213> ORGANISM: Diabrotica virgifera virgifera
```

<400> SEQUENCE: 144

```
ggggctacta cttcagttca gtgtgtaagt aagagagacg agaattcatg cttttcgtct      60
ctatgtatgt ttggaattgg aatttcatgt gggctgcgac acgacacgat attgctgtgg    120
tggtagggaa aggtgttgac gtttaaagtt cttacagcaa cagtgtggaa tttgtgatta    180
aacggcccaa tgggcgaact tttgtgaaat atcagaactg acaggcaata cttatcaaca    240
atgaagctca gcactcagga aaaacgggaa ttggataaat ttacaaaatt tttggcttta    300
aaatgtactc agatcatcgt acagtccaga cttggagaaa aagtaacaag caactgcaga    360
tcacaaacca caagcacgga ttggttcaac ttgaacatca gtgatctccc ggaagtcctt    420
gcggaaacga aaagagttct caacggcgaa atcctatcct caaatctgcc cttatgtgtc    480
gaaatttctt tgcgtacggt cgagggtgac catatggtcc tcgaaaattg gtgtctgggc    540
atgttgcccg aacaacagtg tgatcctacc acaagaatag tgcatacaat ctataatcgt    600
atggggactc tgctaaaat                                                  619
```

<210> SEQ ID NO 145
<211> LENGTH: 612
<212> TYPE: DNA
<213> ORGANISM: Diabrotica virgifera virgifera

<400> SEQUENCE: 145

```
ggggaacatt ttgcgattta taatagtttt gtcagttttg tttattatag atttaaatag     60
attataaatg ggtacattgc ttacatttga ttattttcat taacatatgt attttctaat    120
agtgtggcgc aattatataa ttatcaaaag tacgattat ttggaaaata gtaaatccaa     180
acaccaaata gcaaagatgc ctcatgaaca tattaaatac acaaattctg tatcttcggt    240
aaataattca gatgaagaag aagatgtgga agtaagact tctcccatga gctacaaaga    300
acgcaggaga gaagctcata cacaggccga acaaaaaaga cgtgatgcaa ttaaaaaagg    360
atatgataca ttacaagaac tggttccaac ttgccaacag cctgatgttt ctggctacaa    420
attgagtaaa gctactgtct tacaaaaatc catagactat attcagtatc tccaaatgca    480
aaagaagaag caagaggagg aacgaaatgc tttaagaaaa gaggtagtag cgttaagaat    540
aatgcagacc aactatgaac aaattgttaa ggcacaacaa tcacaaccgg gacacactgg    600
aactagaatt tc                                                         612
```

<210> SEQ ID NO 146
<211> LENGTH: 434
<212> TYPE: DNA
<213> ORGANISM: Diabrotica virgifera virgifera

<400> SEQUENCE: 146

```
gggtaataat aaaataaaat acactgcgaa tctcaacgca aagaaaataa acaacggctg     60
tgaactctga gcggcttgac gaaaacaagt agaatggtgg tgcgtggccg gattatctat    120
caccatcacc accaccacca tgtgattgtg cttgtgctac gacgttgccg gttgcattca    180
aaaggcgcgt aggttcgtag gtattcgacg tattatattt aatatcttag accatggtct    240
aagtttaata taatattatc tccataattt tgttttggt ttatatactt gtataatata     300
ccttttatgt caacgtaaag gtattaactt tttaggtttg agtacagaaa aatatacaaa    360
atagtaaaat ctcagggggg gccacgaccc cccctggcc cctctctgcg ggcgcccatg    420
gatggaaaga acac                                                      434
```

<210> SEQ ID NO 147
<211> LENGTH: 590
<212> TYPE: DNA
<213> ORGANISM: Diabrotica virgifera virgifera

<400> SEQUENCE: 147

| | | | | | | |
|---|---|---|---|---|---|---|
| gggaagcagt | ggtatcaacg | cagagtggtc | attacggccg | ggatattgat | acctacgaaa | 60 |
| gcctcctgaa | ttgtaaaaat | ggtcttcgag | ggggctgcgc | gtcgcatcta | agctatttga | 120 |
| ttatctgatt | ttgttgtacc | cacttcatta | tttaggattc | tggggctca | acaatcctat | 180 |
| atgtataatg | tagttatgga | gcgctgaaaa | ctacacctgc | atattttagg | ccaattgtgg | 240 |
| gatgcaacac | tctttgtatg | aggtatcaga | taatcaaata | gcttagatgt | gacgagaaga | 300 |
| caattttcac | gatttgggcg | cctttcgtag | gtataaataa | cccatatttc | tagtataata | 360 |
| tcataataat | agaaccagtg | gaaattgcta | cccacaaagc | aaaggcgctc | gagtcgtaaa | 420 |
| aagtcgaaaa | tttattataa | cggaaacagc | ggatattgat | acctacgaaa | ggtgccagaa | 480 |
| tggtaaaaat | ggtcttcgag | ggcgccgcgc | gtcctcggag | cggatattga | tacccacgac | 540 |
| gaaaggcgct | cgaatcctaa | aaaatctacg | acggcgcaca | gtggtccaaa | | 590 |

<210> SEQ ID NO 148
<211> LENGTH: 149
<212> TYPE: DNA
<213> ORGANISM: Diabrotica virgifera virgifera

<400> SEQUENCE: 148

| | | | | | | |
|---|---|---|---|---|---|---|
| ggggtgcggc | gcgctccatt | tcaaaaatct | cctattttca | tccgaaaaat | attttttata | 60 |
| gattctttgg | gacattctaa | ataaaataag | tttcttgaca | ttttctcaa | aagttaatag | 120 |
| ttttcaagtt | ataagcgatt | gaaaatccg | | | | 149 |

<210> SEQ ID NO 149
<211> LENGTH: 625
<212> TYPE: DNA
<213> ORGANISM: Diabrotica virgifera virgifera
<220> FEATURE:
<221> NAME/KEY: misc_feature
<222> LOCATION: 498, 499, 500
<223> OTHER INFORMATION: n = A,T,C or G

<400> SEQUENCE: 149

| | | | | | | |
|---|---|---|---|---|---|---|
| ggggaagata | aaataatttc | ctgaaataaa | gtattgccgt | tgaaaaatat | ctacaaaacc | 60 |
| actttggggg | gtgttcaaaa | tggacgtcat | tcttcatatt | cgctaattgc | cggtgaaaaa | 120 |
| tattgtctag | agttaaaatg | gaaacagtaa | attcacagtt | gttgaccaaa | gccataaact | 180 |
| ttcatggtca | acagctgcag | aagttgtggg | aaggagaatt | tggagaaaat | gatttgacaa | 240 |
| gaaaaaatgt | caaagatttg | aattacaatg | tgtatagtca | acgccagaag | aacctatctt | 300 |
| ttcaagatag | aggtaaacgg | ttgaaactcc | aacagttttt | gataaagaag | gctaatttta | 360 |
| tctatagttt | ggaacccacg | aagcaaaaga | acaatgagaa | agcgattact | gaagatatgt | 420 |
| atgctgttat | gcctcctttt | gaaacttaca | ccagtgtaga | caaacaaaaa | agagtggcat | 480 |
| tcttcatgga | gaatgtgnnn | taggtaatct | aatcctgggc | accattgtga | gcagacaaca | 540 |
| atcaggaatg | atgttgaaag | tgttgtgtac | tactggaaat | ggtaacactt | gtttatatgc | 600 |
| tgctgatatc | aacgtcaagg | cattc | | | | 625 |

<210> SEQ ID NO 150
<211> LENGTH: 594

```
<212> TYPE: DNA
<213> ORGANISM: Diabrotica virgifera virgifera

<400> SEQUENCE: 150 gggggtatg aggatgcagc acaatttgga gcaacagata caagcgagaa accagtccgg      60
tgtgagcgag gatgccctaa aagagttctc catgatgttc aagcacttcg acaaagaaaa    120
atccggaaaa ctcaaccatc aagagttcaa gagttgtcct cgagctcttg gatacgactt    180
acctatggtg gaagaaggcc aacctgatcc agagtttgat gctatactgg atgtagtgga    240
tccgaatagg gatggtcacg tttctctaca ggaatacatg gcctttatga taagcaaaga    300
aactgagaac gtccagagtt ccgaggaaat agaaaaggcg ttcagggcaa taacggcagg    360
agatcgtcca tatgtcacca agaagaatt atatgccaat cttaccaagg aaatggcgga     420
ctactgcgtg gcgaggatga agccttacgt agagccgaag acagaacggc ccatccaggg    480
cgctttggac tatatcgagt tcacacgcac acttttttcaa aattagttag gttaggttcc   540
gcattagtcg cttactcttg ctaaacgtta gatagacagt ataatattat tatt          594

<210> SEQ ID NO 151
<211> LENGTH: 627
<212> TYPE: DNA
<213> ORGANISM: Diabrotica virgifera virgifera

<400> SEQUENCE: 151
ggggttaagt ttgtaatcga agtcgtttcg ttttcgtttt gtcgtttgta ctttatttg     60 cactttattt gtgataattg ataataaaga caaattaata caaaatgaa acaaattttgg   120 aacaacagcg tcgttaccat gaagaaaaag aacgttaat tgatgccatg gtaaaagaaa   180
tgcttcacaa aaagacaact ttcagagaag caataaactc agaccaccga caaaagtacc   240
tgctggatag atatatggct tcaacagaaa gactaataga tctttatgat gatagagacg   300
gacagcgtaa ggctgaagta gccgctctta cgggccccaa cgagttccaa gaattctaca   360
gtaggttaaa attaatcaaa gacttttaca gaaggcatcc aaacgaaatc agtgttccta   420
tgtcagtgga atttgatgag tttgccaaag ccagggaaaa tcctaacgag gatatggcta   480
actttgtaga atttacagat gaggagggct acgggaagta tttggattta catgaatgtt   540
acgaaaagta tataaactta aaaggcatag aaaggtaga ttacattacc tatttgggta    600
tgtttgacca actatacgat attccga                                       627

<210> SEQ ID NO 152
<211> LENGTH: 526
<212> TYPE: DNA
<213> ORGANISM: Diabrotica virgifera virgifera

<400> SEQUENCE: 152
ggggggcatt gtctttata atcgttatc taaaagtttt cagtatgaag gtcgctttac      60
ttttactagt ttttatctgc tttgtaaata ggacctattc ccgaccaaat attttttaaat   120 tcaaagacgc caaacgaatc catgccgtat gtcaagcaaa ctcggaaaca catgtcaacg   180
agtaccttga aaggcttcaa gaatttggca agattgaagt tccaaatatg gcgaagcata   240
cactctgtat gaacattaat gccggactac aatacgaaaa cggtgatatt gcagttgaga   300
gattaagaag cgacttggaa gaagtttcaa acaacgaaaa taaaatcaaa gaaattgttg   360
atacttgtgg tgttcgagcc cctggaagcc ctgaagatgc agctatggct tttggcaaat   420
gtctatgcag tcaatggcct caacatgcag tatgtgtttg cagcacatag tagcagcgaa   480
```
aaatagtttt tatataaata tatatcaata aataaatttt atcttc         526

<210> SEQ ID NO 153
<211> LENGTH: 601
<212> TYPE: DNA
<213> ORGANISM: Diabrotica virgifera virgifera

<400> SEQUENCE: 153 acttttagt cttacacttt tcaaacaata aaatatatcg ccatgtttat taaaatatat    60
gtataaaaca tatgatgtac aaacatgaaa agtagtcgga accggcaaaa aatttaaaac   120
ttttttgttt atttgtgaag cataacgtaa acaattaacg taaaaagtct tattttttaaa  180
aattcttgta gttgatgcac taacaaaaaa tgacatgtga aattatcaac aaaaaaaaaa   240
aagaatctag aaacataaaa ttgtaatatt tttcgatata aaaaaatttg ggaggtacac   300
ccaaattttt caaggtatac accaacaact ccaaaaaaca aaccaaataa gattttgttt   360
aaaatttatc atcaaacttc ggagatatgt ttatatacac atttgtcaaa aaaaaaaacg   420
ataaatcgat attttttgat atattttcgc ttaaacataa aatatttaca catatgattg   480
aagggtttca aaaaacaaa atgagacttt ctaaattaaa atgaaaaaag tttatgccat    540
aattacaggg gaatagcgct actaaacgtt gcgtataaaa tacttgcagt acatataaaa   600
g                                                                   601

<210> SEQ ID NO 154
<211> LENGTH: 95
<212> TYPE: DNA
<213> ORGANISM: Diabrotica virgifera virgifera

<400> SEQUENCE: 154
aatgtgaaag ggcgcacttg atgaaaagga acccccgtaa agtaacatgg actgtcttgt    60
acagacgtaa acataagaag ggtcaggagg aagaa                              95

<210> SEQ ID NO 155
<211> LENGTH: 635
<212> TYPE: DNA
<213> ORGANISM: Diabrotica virgifera virgifera

<400> SEQUENCE: 155
ggggattctc gcgtcctttt ccccaagaga tcgtgacgaa aataactgtt tgttgaattt    60
ctccaattat ttgtgtaatt ttgccattaa tcgcgtttaa aatggcaacc cgagtgtttg   120
tgggtggtct tacttacaaa attcgcgaac gtgacttaga aaagttcttc agaaagtatg   180
gaagaatcaa ggaggtttcc atgaagaatg gttatgcatt tgtggaattc gacgatcgca   240
gagacgccga cgacgcttgc tatgagctaa acggtaagga cttaatgggg gaaagaatta   300
ctgtagaaag agcccgtggt acgccccgcg gaagtgatca atggcgggga agcggtcgag   360
atagaggtta ttcaggttat agcggtccac gcggtagaaa cgataattct agagctcgtg   420
acaaatatgg gcccccgacg cgtacagaat acagagttat tgttgaaaac ttgtctagcc   480
gttgtagctg gcaagatttg aaggattaca tgcgtaaagc cggtgaggta acctttgctg   540
atgctcataa actagttcca aacgagggag tcgtcgaatt tgtttcatac agcgatatga   600
aaaatgctat tgaaaagctt gatgatactg aaatt                              635

<210> SEQ ID NO 156
<211> LENGTH: 599
<212> TYPE: DNA
<213> ORGANISM: Diabrotica virgifera virgifera

<400> SEQUENCE: 156

```
gggggacctt ttctggttgc acctccaagg cttctaaaat ttgcaagcca taacggatgc    60
tgagactaaa aaagatgagg gaattttaca atttataatt cacgtctcat ctgctcagcg   120
cggtaaagtt ccaacgagaa tggttccctt agtactccaa tcagagtaaa catgttaatc   180
aaaaattaat aaccattttc aatttcgttg caacactaca gccgcatcat attctagttc   240
aatcagaggc cgcatcatat tctagttcaa tcagagagtg cagcaagcac ctctaccggt   300
ttcgaaactt attagtctct catcaggagg cacatctgct gctctctctg acccaaccag   360
gacaaaccct ggcgtgcagg tacgcattgc aacgaacgaa atggcaggga tgctctagcg   420
gcaactgcta gcaagagact aagttttcaa actaatagca cataaaataa tatcaaaaaa   480
attactctac atcccaccag attgaaaaca atgagaacct tctctgatta cacatacgag   540
gcttctaaaa tttgcaagcc ataacggatg ctgagactaa agaagatgag ggaatttta    599
```

<210> SEQ ID NO 157
<211> LENGTH: 167
<212> TYPE: DNA
<213> ORGANISM: Diabrotica virgifera virgifera
<220> FEATURE:
<221> NAME/KEY: misc_feature
<222> LOCATION: 85
<223> OTHER INFORMATION: n = A,T,C or G

<400> SEQUENCE: 157

```
agagtacgga atcaagtaga tgaaaagagg cgaatatttc aagcaatatc tgcgaatgtt    60
agttctgaag gtcagagatt gttcntagct atagctaaaa caattagtga ggttaggtgg   120
aacgattcgg aaattgtggt ttttaatcga gatgttataa ttagtcc                 167
```

<210> SEQ ID NO 158
<211> LENGTH: 650
<212> TYPE: DNA
<213> ORGANISM: Diabrotica virgifera virgifera

<400> SEQUENCE: 158

```
ggggaaatat gttagtatgt ggaaattact tgataaataa ataaaatatt gcaaaaagga    60
gcctaaaccg ccattaagaa agacaaaaaa atacacttta ttcaaataaa ctttttatc   120
ccacgcctag attttgtgtc acattggatc tactaaaaat cgattttcta taacaagaaa   180
tcgaacgtga ctgactcggc aacatttcgc gcctatgagt ataaaaatta ttgttttga   240
tagtataaaa atgtcattgt cagtgtcgaa ttaccgacgc actgttgcct cactgttgaa   300
agttcgcaga actttcgaaa aacaagaata ttgatgacgc gctactgttt actcttaata   360
ttaaatttgt aattctcttt tagcgttcct caataccttc ctctatgctt ggtgtccgct   420
caatttttg ttctagtatg ctggtcattt cttgttttac aatatcacat accatttctt   480
ctctatcaat aataactatt tgctttgtca cccatataat cttgtttaat ctcaatctga   540
tttttcctac aaaaatatgg tctccttgtt gccaatcctt aaatagtgca tgtcttctca   600
gttggttttg agttttggag atattattta caccaattgt aatttcaact              650
```

<210> SEQ ID NO 159
<211> LENGTH: 584
<212> TYPE: DNA
<213> ORGANISM: Diabrotica virgifera virgifera

<400> SEQUENCE: 159

```
ccactgaaaa ataaaaaaaa aaacttttag taaggggcta ttctggacta cggggcaatt      60
ctggacagtc aaaaaaatgc ctgtccagaa tggccccggt tgacaaatat acttataact     120 ttttttttggc tagaacaaaa aacacaacct caagggtcaa taataacaag ccatgtaaca    180
ttttgttaag gtgaaaaaca ttaccattac ttacttggaa atgagtgcag cacagaaagc     240
ttgaccgcta tattttttta acggtttttc cacgaaattt tgtttgcgcg ccaaaaggtg     300
aaaatgccca gcgcggacct tccaacagtt atcaaccaac tggctgaatt tctcgcgaaa    360
agttgtgaat atcacgccac ccgcaagtgc aggctttcgg cgcggttgcc acgtttacct     420
gagaaaacgc gttgtccaga attccccgc atgtccggat taaccccgtt atacggtacg     480 ttttttactta aaacttacgt aaaagttttc aaaaattgca tttttgcgtc atatcatttg    540
aattaaattt ttggcatttt tttgaatgaa acattgttta gtaa                      584
```

<210> SEQ ID NO 160
<211> LENGTH: 508
<212> TYPE: DNA
<213> ORGANISM: Diabrotica virgifera virgifera

<400> SEQUENCE: 160

```
ggggacattt gaattttttt ttggagaaga ctggactttg agaaattcag gttagttgag     60
gacaaatttt gcggacttac cttctagtga actagtcaaa ttgtcggtaa ggagtgttct    120
agggcggtac acagtggttc caaatgctga aaacgtggtc atgaggtaaa agagtgtggg    180
tacttatgta caattgtaca gctcccagaa agaatcatgg ccgatgacaa acgctgtcgt    240
cggtcgtaca cccacctaaa ctttagcaga gaggattct ctcgttggtc atggttcgct      300
ccgggagctg tacacacgta acaagttata cttctttggc gtcattaaaa agtagttttt    360
gattatatta tgtaaataat tacaataaaa taataaagt actggaaaac gatagtcaaa     420
gttcagttta aatttgaaaa attaaatatt taaatatttt tttatttatg tataaaattc    480
gttaatatac cagaaataaa acgaaaag                                        508
```

<210> SEQ ID NO 161
<211> LENGTH: 644
<212> TYPE: DNA
<213> ORGANISM: Diabrotica virgifera virgifera

<400> SEQUENCE: 161

```
gggttctgag aaatgttaat tggtttataa caattttttt aaacatttaa agattatgca     60
aaaaactgaa aaatttatat tttgtcgaca aaatattaaa taggcatcac accctttatca   120 tctttctaag tttgatcaat gtctcatgat tattttggtt gttattgcga ctgtaaattg    180
ttaattaaca attgaattgt tgctaaagta ttcgtttcat tttcaccggc ttctgaattt    240
ataatctata ccaagaaaga ttttatttct ccaagctata tactgataaa taattactgg    300
cccaaaaaaa ttatttgaaa attcgagatt tgttgggga aacccacatt ttccgaggaa     360
aattttcgtc ggagcaaatc gggaaaaaca tgcctctatg tagaattaaa ttggggtgaa    420 ttttttatttg agtgtttttg gtgtaaagtt aaaatcttcg gagttataga gcaataattg   480
aaaaaaatac gatttgtcgg cgcaatttg tttataaaaa agtagcacac tatctgcgga     540
cttttcaaac ctatattaat aatatatagg atcttataat tagattccag caataaaatg    600
gctggtaaat aacctttctt tgtacttaac taattagacc agcg                      644
```

<210> SEQ ID NO 162
<211> LENGTH: 659

```
<212> TYPE: DNA
<213> ORGANISM: Diabrotica virgifera virgifera

<400> SEQUENCE: 162
ggggcgtgta tatgtatata tttttatatt catgtaacgc cttggaaatc tcaatattta      60
attttatttt ataatctctt ggtattaaaa tttttggtat cggaactaat aaaagatagc     120
ggcttataca taattttgtc acgttttatc cttgatacat aacaagggtt ccaaaatctg     180
ccagtttata tcactaggta aaaagtttta gttcgacggt ccttctcact tttgttgtaa     240
aagccgtgaa tacctgtgtt ccagaggcgt gcggtccatg gaagcggggg aagcaccgct     300
tctctattat atacttcgat ataacaaaat atattattaa ctaatattta attatcaaaa     360
attttcccca atcccagtaa tctacatatt attacctagg caataggcat tgaaaaatat     420
taaaaattaa tcgcatagga aggaactcaa tatgcactat gcacacaatt caactattcg     480
gtccacccct gacagaagcg catctcaaaa tcgccgcttg tcatgcagtt gtcctgtata     540
aaaattggtc agggttcaat aaccgcaccc actagtcgcg cgaattttgg taccctgtag     600
aagcgattgt tcgatcgcct tccaagagtg ggatcatctg actgttactg cttctaagg      659

<210> SEQ ID NO 163
<211> LENGTH: 598
<212> TYPE: DNA
<213> ORGANISM: Diabrotica virgifera virgifera

<400> SEQUENCE: 163
gggggaagtt gcgctgtgct gtgagttaca accacgaatc tctcggccag gatgctggca      60
atttggtttt tatttgttgc tgtttcatcc tcaaatcaat ttgtcgttga taccgtgacg     120
gccaatgaag tctggcaagc tcctggttgc cataaagtgg gtcatactag aaaagtcagt     180
attccaaact gcgtagaatt cgtgataaca acaaacgctt gtcgcggatt ttgtgaaagt     240
tgggctatac cgtcattaat aaaaggatcc actatccaac cgataacatc cgttggccaa     300
tgctgcaata taatggagac agaaaatgtg ttagcaaagg ttatgtgcgt tgaaggaatg     360
aaagtattca cgttcaaatc ggccgtcaca tgttcttgtt accactgtaa gaaagattag     420
agcgactgct ggaaaggacc aaggcgagtt tattcaaaat ttatatgtaa catacttaaa     480
gttcattgat tatatttagg cgtaagtaaa aattacaata tactttctta attactgtat     540
atattgtact gactgactga ctgattgtag gaattatgtt cattaaattt tgtttccc        598

<210> SEQ ID NO 164
<211> LENGTH: 410
<212> TYPE: DNA
<213> ORGANISM: Diabrotica virgifera virgifera

<400> SEQUENCE: 164
gggagacagg taatagcaga gataaataga aaagggtag aataagagaa taatatataa       60
aggtaatgac acacagatag gagaagctat gctctaagtg aataaaatat atcttgaaaa     120
gctagaataa atggaatatg gagagaagta gaaagttgag agatatgtga agaaaattta     180
ttgaaaaagt tacttaaata cgaatgaaga acggtaggag attcatacag aaaacacaga     240
aacagcgtaa aaagactaat aagtgaaaca cagagaataa taattaaatg acagtttgga     300
aaataataat acatagttct gactatgaac tacaagattt aagaaaggga aaagtcgag      360
gtaatagcac ctatacaaaa aattacagta attacaaata aaagcaacac                410

<210> SEQ ID NO 165
```

<211> LENGTH: 646
<212> TYPE: DNA
<213> ORGANISM: Diabrotica virgifera virgifera

<400> SEQUENCE: 165

```
aaaaaatctt tacctaaaat aagagaatca aagaagattt ccccagtaga aatcagtaca      60
tttatcgaag aagaaagatc cgctatatta aaggaaaatg atcatgtcgt tgatagttct     120
tgggtcgtaa tagaagagga agaacttagt tatataccag aagtaatacc acctgtcatt     180
gttgaaccag aaaaaatgga tgcagatact actgaaaaag atgaacctat tcaagttaaa     240
cctgaagata gtttacctga agatcaaatt gaacatacag agtctatcaa aaagccaaga     300
aatcggtcta agtcaaaacg ccaaaaaacc cctaaagaac aggaattgtc tgaaactatt     360
gagcattcgc cacgtgtatt accagctata gctactgtcc aatctaacga acagtttgaa     420
gttaaatcaa ggtcccctag tagaacctac gcatcagttg tgaagtcgca tatagaagga     480
gttactcctg aatacattca gtataccaa gttattactt ctatcgataa taaaccccag     540
accgttgaaa gcattactga ttcaacgtc gaagaaacta cagaagagat aatatcagaa     600
aaagtagtgg agcaacccac agtgcaagaa ttgcaaacaa cagaga                    646
```

<210> SEQ ID NO 166
<211> LENGTH: 277
<212> TYPE: DNA
<213> ORGANISM: Diabrotica virgifera virgifera

<400> SEQUENCE: 166

```
gggggcctgg tacttactta tataatgtta agcttcttta aagtaacttt ttctacaacc      60
gtgttaaaaa tgcaatttt agcactccat acgagcgtta aaaatgctac tttaaggcac     120
tagtgcttta aaaaattta ggcagtgcag ttcatattga ccgtatacgc tgtgagctcg     180
tacgtagagg ggatgtttac aaattcgcga gcgccagtag tgacaagtcg gtaaacgttt     240
accggaaatt tgacataaat gtcaaagtgg ttaattc                              277
```

<210> SEQ ID NO 167
<211> LENGTH: 659
<212> TYPE: DNA
<213> ORGANISM: Diabrotica virgifera virgifera

<400> SEQUENCE: 167

```
gggagtgatg aagttttatt cagactggtt attcatccta tatttttttt gtaataatta      60
tggcgacatc aaaattaatg gtgtatctga agaaaaagta tcacaatcct gatgtagctt     120
atagagaaat aatcaacatc accacacaat acagaggttt acatccagaa cagagtgtct     180
acaccttcaa cgatggcaca agaatggatc tcattaactt aactggtaca attcctgtgc     240
gttacaaagg caatatttat aatattccaa tttgtatatg gttaattgac acgcatccag     300
agaatgctcc catttgctat gttaaaccga cttccgacat gtccataaaa gtttccatgt     360
ttgtagatca aaatggaaaa gttttatctgc catatttgca cgattgggtg ccgaatgaat     420
cagatttgct aggattaatc caagttatga ttgttacatt tggcgaacaa cctccagtgt     480
ttgctagggc caaagacaat gaatcgtatc cgtcaaattc attcatgcct caaccatctg     540
gtggttacat gcctccgtat cctaccccct acccaccagc atcaggaggt ttcggcgggt     600
accctccata tcctccaacc agcaacaatt cttttccaagg atatccaccc tacccttct     659
```

<210> SEQ ID NO 168
<211> LENGTH: 409

```
<212> TYPE: DNA
<213> ORGANISM: Diabrotica virgifera virgifera

<400> SEQUENCE: 168
ggggaggtta aggttaaaact tatgtcaaat caaattttaa atttgaacat gtggcctgtt      60
atatacacag cactcagaac atatgcaccc tatgtaactc ttcctgttgc tgctcttgta     120
ggagtcatag gttacaatct agaaagttgg atctctaata gatatacacc atacaacaaa     180
tctattaaag aacaacgaga agataggcta ttagttgaag caaaacttaa agaatctgat     240
aaagtagaga agttaaaata taaggctaat attctagaca caaatttatc tccttcctta     300
acttgaacat tagaatggtg cattggtata cacttaaatg ttaaataact ttaataaatt     360
ggagtatgta ttgttttagt tctctatatt aataaaaagt tgtgatatt                 409

<210> SEQ ID NO 169
<211> LENGTH: 253
<212> TYPE: DNA
<213> ORGANISM: Diabrotica virgifera virgifera

<400> SEQUENCE: 169
ggggacaaaa tatggagaaa taaaatatcg gaaaagaaat aaaaggcaga atttacaaaa      60
cagtcatcag accaataatg acatacgcgg cagaaatacg acccgacaca gagaggacca    120
aaagattgct cgaaacagag gagatgaaaa ccctaatata atcgacaagc tcatccggaa    180
aagagaatcc aatcgtcttc agcaactagc ttacaattca aacccagtca tcacaccaat    240
ctataggtcc ctc                                                         253

<210> SEQ ID NO 170
<211> LENGTH: 633
<212> TYPE: DNA
<213> ORGANISM: Diabrotica virgifera virgifera

<400> SEQUENCE: 170
ggggaaatac gaatatgaaa acatttcacc acatcaacac gtgaattaat attcgaaaat      60
ggagtacgaa aatacacaac aaaatataaa cttcgtaccg tgtgtaagat gggttaaacg    120
aggagtggcc aattcaagcc cagtaaaatt gcaactgtcg aaaaacgagc tggctcaaat    180
tattaatgac accaagatta aattacaaga atccaatgaa aatgaagatg agcctatgga    240
agaaggtgaa acgtctcaaa cagatgagtt tgccttagag gattacgata agaagacga    300 aaatgaggac actgcaaatg ctttaggaat tggatcattg gcagaactcg ataatgatgc    360
tgcagacaat ttttctgagt cagacgattc tgaaaaagaa gatgataaaa tcaaaccatc    420
tgacaatctc atactagtag gacatgtaga aggggatgca agtctattgg aagtctacat    480
atacaatgaa caagaagagt cattgtatgt tcatcatgat attatgttat catcctttcc    540
tctgtgttta gaaccgctaa actatgaacc gaagatgccc aaaggaaatt attgtgcagt    600
gggatcaatg tcacctgtta tagaggtctg gga                                  633

<210> SEQ ID NO 171
<211> LENGTH: 640
<212> TYPE: DNA
<213> ORGANISM: Diabrotica virgifera virgifera

<400> SEQUENCE: 171
gggccctgta tatacctcga tgcaataat ggacctgacg gatgtgctat tttttataga      60
aaggacaaat tcgaattact tgaggcacag accaaaattt tggagatatg gaaggttcaa    120
```

| | |
|---|---|
| agtaatcagg tcgttctact gacaatctta aagatgaaag aaacaggcca aaaaatctgc | 180 |
| gtcaccacaa cccacctcaa ggccaaaaaa ggagctctac tatccactct tcgcaacgaa | 240 |
| caaggtaaag atctcctcca gtttgtgaaa gcaaacagcc aggatcttcc tttgattcta | 300 |
| gccggagatt tcaacgcaga acctactgaa cctatctact caaccgtact cgacaatcct | 360 |
| ctgaagctgg gtagtgctta tgctgactgt gatattgatc ctacgatttc ctcagctgaa | 420 |
| agggaacctt cgtacacgac gtggaagatc agaggtgaag gagaggtctg ccataccata | 480 |
| gattacgtgt tttattccaa gaataagcta gaactagagg ccgtattaga tatgccgacg | 540 |
| ggagaggaaa ttggagagaa cagagtaccc agcttttctt acccatcgga tcacttttcc | 600 |
| ttagtgtgtg atttcaaaat aggccatagt taagtttagg | 640 |

<210> SEQ ID NO 172
<211> LENGTH: 651
<212> TYPE: DNA
<213> ORGANISM: Diabrotica virgifera virgifera

<400> SEQUENCE: 172

| | |
|---|---|
| gggggacaaa ttgatgaaag aatgatggtt ggtgcttttt tcaagtctat accaatggca | 60 |
| gcttttgcgc actgtagcga tctgaaataa gaaaaaaagt ttttttcgaa ccaccctatt | 120 |
| aagcagacaa attaataatt gtatcagaat catttattca ttgggagtta gtaaatatct | 180 |
| ctgctcataa tttaaaataa aatatttaaa aaatatcccg ggaagtcttg aagaattctc | 240 |
| ggtaatcggg attttcattt tttactgatt tcccgagaaa tttgtcccgg gaatgcagct | 300 |
| ctatttgtag gtactctact ggatgattga gaaaaaacaa cactaaaaag cttattgtaa | 360 |
| aaagttatga ccgagaaaat aaggccgact taaaagtacc attgggaagc aactgtcaaa | 420 |
| aaaaatctaa atgtgctgag agactaaggg ttaattatga tatacagatg tcgtttttcct | 480 |
| cctcacaact ttttctgttg tcccttggt ctactagctg ataactttgt aggttccttt | 540 |
| aaattcatgt gtaactggag tagttgaatt tggtttcact tctctttagt tcatataggt | 600 |
| cttgatcatt atcatcattc aatgatgatc ttgatcatca atcagttttg a | 651 |

<210> SEQ ID NO 173
<211> LENGTH: 667
<212> TYPE: DNA
<213> ORGANISM: Diabrotica virgifera virgifera

<400> SEQUENCE: 173

| | |
|---|---|
| ggggcctttt ccaaagtttc atataatttt taagatgagt actgttatta aaatcgtttt | 60 |
| aaaatggaac ggaaaagaat ttaatttaga atcatcggaa gatgacactg tatctgattt | 120 |
| aaagaaaacc atagaaaatg taacctcagt aaaatgtgga agacaaaagt tgttaaattt | 180 |
| aaaatacaaa gggaaaacgc ctgaagatga ttgtactctt ggtcttttga aacttaaacc | 240 |
| caactttaaa ctcatgatga tgggttcact tgaagaagac atagcagaag caaatactgc | 300 |
| acctgaaaac cttcctgatg ttgtcaatga tttagatata gaggaagagg aagttgccat | 360 |
| tgaaaatcag gatgtatatc ttgcaaaagt ggaaaaacgt atcaaagatt ataaaataaa | 420 |
| tatgttaaat gatctccggc ctgaaaaaaa gttgctagta ttagatatag attacacact | 480 |
| ttttgatcac agatctaccg cccaatctgg agcagaatta atgaggcctt atttacatga | 540 |
| gttttttaact acttcttatg aacactatga tattgttatt tggtctgcta caggaatgaa | 600 |
| atggatcgag gagaaaatga agctattagg tgtttctacg catcctgatt acaagattgc | 660 |
| cttttat | 667 |

<210> SEQ ID NO 174
<211> LENGTH: 623
<212> TYPE: DNA
<213> ORGANISM: Diabrotica virgifera virgifera

<400> SEQUENCE: 174

```
ggggagtctt gtgaaaaaag tcacagcgct cactggcgtt ttattaagat caaaatgcca      60
tcttcaccgg aggaaacaac ttttcctcaa agactgcagt caagcaacaa cttaggcgaa     120
caaaattcaa aagaccaaat aaaaaaaaat ggttatttcg agcaagattt ggtatggagg     180
aatgtaatta tatatatagt actccattat ctgttaattt ttgcaatatg gagacttttg     240
accggtcaaa tgaagcttgg aacttttatt tttcattgta tttacgctac ggcttctgtc     300
cttggtatca cagctggaaa tcgtcgtctc tgggctcata gaacctacaa agcaaaactg     360
ccattgcgaa tattttaat gttaatgcaa acaacgacca tccagaataa tatttacgtt     420
tgggccagag accatagact acatcacaaa tacacggaca ctgcagctga tcctcacaac     480
tcgaatagag gattcttctt ctctcacgtt ggatggctat aatgaagaa gaaccctgaa      540
gttaaaaaac aaaggaaaga atattgatat gagcgatgta gcagctgacc ctgtggttca     600
atttcagatc aagtattatg gaa                                              623
```

<210> SEQ ID NO 175
<211> LENGTH: 406
<212> TYPE: DNA
<213> ORGANISM: Diabrotica virgifera virgifera

<400> SEQUENCE: 175

```
gggatatgca gaagacataa ttcttatagg cagatacaag gaaagataaa acaagcagt      60
aacaatcctg gcaaatcaag tatgggaaag aggtctaaag gttaacgaaa taaaaacaaa     120
atatctactc tgctctagaa gagaagataa aagacgaga gaaatcaaga tagaaaacta     180
cacttttgaa agggttcaat aatttaaata tttgggagta attgtaaatg caaaaataa     240
gaaaagtgaa gaagtaatgg agcgaatact agcaggcaac gaaaatactg gagatatcat     300
aggctaatga aggaccagca cttatccaga aatacaaaac tgaaaatata cagatttgca     360
atcagaccag tatttacata cgcagctgag acaatgtgcc tcacag                    406
```

<210> SEQ ID NO 176
<211> LENGTH: 660
<212> TYPE: DNA
<213> ORGANISM: Diabrotica virgifera virgifera

<400> SEQUENCE: 176

```
gggggggaaga atttgtaggt taagaataaa ctgcatgttt ttgttttaat ttaaattttt      60
gaaagatcag taatacaaaa tggaaacaca ttcatctgaa agttcacaaa aaagaaataa     120
cagaaaaagg aagaagtctt ttctaaaaaa tgcaagaaaa tatgccaaaa aaggacattt     180
tggaagaggt tcccaattgg attctgatac atatcattat ttcgtaaaaa tattagaaac     240
atataaagaa ggttttgata cagatgaaga taaacaagtt tttgctaata atgtgtttgc     300
acaaccgaa gatcaagaag tgaattgttc ttgtaaccaa gtaggatgca gagttgtgga     360
aatgctatta ccttttgcca atgatgacat attgaagaaa ttcatggttg cctttagtga     420
agatatgagg cctctaatca gtgatagatt tgcaagccat gtattagaat gtcttgtttc     480
ggaaagttgt aaaaggactt taaataacaa agtgccagaa gaatcaagaa cagagtatca     540
```

```
gaaatttgct attaaagtta gcaagttctt gttaaacaat ctagaggatt atatttggga    600
tacttatggg aatcatgtta tacgaagttg tcttacacat ttaatacaga tgcctgttga    660
```

<210> SEQ ID NO 177
<211> LENGTH: 578
<212> TYPE: DNA
<213> ORGANISM: Diabrotica virgifera virgifera
<220> FEATURE:
<221> NAME/KEY: misc_feature
<222> LOCATION: 284
<223> OTHER INFORMATION: n = A,T,C or G

<400> SEQUENCE: 177

```
ggggcatgct ttgagcgtac agttgaactt ctctacaaat atgtagtacc taaaccacgt     60
gctgactgca ctaaaggcga acaattgatt gttacatttg ctgctggtta cattgcaggt    120
gtattctgtg ctattgtatc acatcctgct gatactgtcg tcagtaaatt gaaccaagaa    180
aagggatcaa ctgctctcga ggctgctaag aaattgggaa tggctggatt atggaaggga    240
ttgactccta ggattgtgat gattggtaca ttaactgctt tgcngtggtt catctatgat    300
gccttcaagg ttgccatgag aatgccacga ccaccaccac cagaaatgcc agaatcatta    360
aagaggaagt tggagggcaa atagagaatt aattattaa cactaatatg taatttatga    420
ctttatttcc agaaaaacga aatcgcagta tttccattag ttcgttatag ttattgattg    480
tcatcaactt tgcgaatttt gatgttttta agttcatacc agttatgtcc gatattttag    540
attgtaaata gataatcatc aatatacaac tggaactc                            578
```

<210> SEQ ID NO 178
<211> LENGTH: 678
<212> TYPE: DNA
<213> ORGANISM: Diabrotica virgifera virgifera

<400> SEQUENCE: 178

```
ggggagaatc aaattagaat ataaatttca aatgttttca aatttcaaa tatgaattat      60 taaaataaat agaaatgatt ttgtttaata acttctttct tcgacacgta aataagttaa    120
taaaacaagc atactgtaca aatataagta gtttgtcaaa agttgaaaga attaaattcc    180
taaggaaaat ggcccgtcct aacgcaaggg aaaacccggt gataatgaaa ctaaactcac    240
aagaattcca ctctatattc aacgaggaat tgcgaacttt agtatcctta tttaaagagt    300
atggctatga aattcgaatt gcaggtggag cagtaagaga tcttttaatg ggaatgcaac    360
ccaaagattt agattttgcc actacagcta ctccaaccca gatgaaagaa atgttcatat    420
cggaaaatgt tcgaatgata aatgccaatg gagaaaaaca tggcactatc acacccagaa    480
taaatgataa agaaaatttc gaggtaacta ctttaaggat agatgtggta actgacggta    540
ggcatgcaga agtacagttt acaacagatt ggctactaga tgcactgaga agagacttga    600
caatcaattc aatgttccta ggtctggatg gttctgttta tgattacttt tatggacatg    660
atgatcttca aaaacgaa                                                  678
```

<210> SEQ ID NO 179
<211> LENGTH: 647
<212> TYPE: DNA
<213> ORGANISM: Diabrotica virgifera virgifera

<400> SEQUENCE: 179

```
ggggctctgt catttaaaa tgggtagtgc aagaactctt tttggaattt taggctcaaa      60
acagatatta ctatgttcaa attcccagtt tactactaaa atttcaagaa catttcttca    120
```

```
tcaatgcttt agatgtcata aatctctact gctaaatacc tggtcagcta ataatttaac    180
tcaaaattct ttactccata aagaacgtt tcataagtca cacagtttca atgccgcaag    240
acgggattat tatgaattat taggagtagg taaaaatgct tcaaactctg atattaagaa    300
agcttattac aaattggcca aaagtatca tccagagtgta aataagaatg atccagaagc    360
atctaaaaag tttcaagaag tttctgaagc ctatgaaatt cttggagatg aaaataaaag    420
aaagcaatat gacacttggg gtgcaacagc tgatcaaatg ggaggcatgg gtggtggagg    480
aggccattca aaaggtccac aaggattcag tcagcaatgg caatatcaat caacaattga    540
tccagaagaa ttgtttagga aaattttcgg agatgctttt actcgaggct cttctcattt    600
tgaagatttt gcagaatcaa actatggatt tggcgaagct caagaga    647
```

```
<210> SEQ ID NO 180
<211> LENGTH: 204
<212> TYPE: DNA
<213> ORGANISM: Diabrotica virgifera virgifera

<400> SEQUENCE: 180
gggttgttag ataaattgaa aaaaaatgta cccacgaata tattcaaaca acattacatt    60
ttctcgagaa tgggcgggca tgatgacgta atcgatgatt tttattaaat gataatagga    120
ttcgtgtgat atctcactcg aaagtttatt caatgctcta ttcactaata taaacattta    180
tataattatt tataaagggt gccc    204
```

```
<210> SEQ ID NO 181
<211> LENGTH: 98
<212> TYPE: DNA
<213> ORGANISM: Diabrotica virgifera virgifera
<220> FEATURE:
<221> NAME/KEY: misc_feature
<222> LOCATION: 73
<223> OTHER INFORMATION: n = A,T,C or G

<400> SEQUENCE: 181
gtttggacag tctggagctg aaacaactg ggccaaggga cattacacag aaggtgctga    60
attagttgat tcngtattag atgttgtaag gaaagaag    98
```

```
<210> SEQ ID NO 182
<211> LENGTH: 174
<212> TYPE: DNA
<213> ORGANISM: Diabrotica virgifera virgifera

<400> SEQUENCE: 182
gtaaaattaa ctacttctgt gaaaacattt atgaaattat gtaagtagtc gtttttatat    60
tatattggta ttaagattat aataatattt ataaattagt attaaaaata gatggatgca    120
acaaaatgta ctcgtacagt gcgctggagt aagtgttagt gttaccccc cccc    174
```

```
<210> SEQ ID NO 183
<211> LENGTH: 577
<212> TYPE: DNA
<213> ORGANISM: Diabrotica virgifera virgifera

<400> SEQUENCE: 183
ggggagtagc tgataagcat ggatcataca cctattcaac agttttatag ggatgccaac    60
gtatttatca ctggagggac gggatttatg ggaaaaattc tcgtggaaaa gctgctgagg    120
tcaacggagg tgggaacttt gtatttgctt gtacgagaaa agaaagggaa gcacaaggat    180
```

```
gacagaatca cggaaatatt cgacgatgtg gttttaaaaa gacttaaatc agaaaaatcc    240
aaattcagac atcgagtaca agctatatcc ggagacttaa tgctaccgca tttgggatta    300
tcagagtcag atagacagct tttaatttca aaagttaacg taattatcca catgggagca    360
acaatcaaat tcaatgaaag catcatcagt gcattacatg ccaatgtata tagtaccaaa    420
ttagttatag acttagccaa agaaatgaaa catataaaat cgattgttta tgtatccact    480
gcctattcaa attgcacacg aagcgaagta gaggaaaggc tgtatgatcc accgatatcc    540
tatgagaaat cagtagagtt aatagaaaag ttgtcaa                            577

<210> SEQ ID NO 184
<211> LENGTH: 473
<212> TYPE: DNA
<213> ORGANISM: Diabrotica virgifera virgifera

<400> SEQUENCE: 184
gggattcctg aagttgattc cgttgtagaa cgatcagaca aaagtcgaag aacagccatg    60
ttgggtagtg tcggcgaaaa aagtgtatgt tcctagagaa aaactcgcag attttgtgc    120 ttgtgttgtg caatttgtta agtgtttgac ataatttgga ttatgaccgc cgtagcggag    180
aacctcaact ggggcaccga gctctgggac cagtatgaca acttgtccct gcacacgttg    240
aaaggaatag actttttgga aaatatggaa cagtttgtta gggatcgagc tagtatagaa    300
tgtgaatatg ctacaaaatt aaggagacta gtcaaaagtt atcagcctaa gaaaaaggac    360
gaagatgatt accaatttac ttcctgtaag gcatttcgag ccttaatgaa cgaagtaaac    420
gacttggcag gccagcatga gttagttgct gaagatttac aagcgaatgt gat           473

<210> SEQ ID NO 185
<211> LENGTH: 683
<212> TYPE: DNA
<213> ORGANISM: Diabrotica virgifera virgifera

<400> SEQUENCE: 185 gggggggattt tcaaaggtgt ttacaaattc aaattgttta ttacaagttt attacaatga    60
gagtgtatct ttgaaactgg aaatggcata gtccaagaag aaaaaggatt tttgaaaaac    120
gccggtacaa aggaagaagc tcaagtcgct caaggttttt cctcatatac ttcccccgaa    180
ggagtaaaaa tagaactccg gtacatcgca gacgaaaacg gtttccagcc aatcggagac    240
cacctaccga ctccgccacc aatccctgag gctattttac gagcgctaag tgtactgaaa    300
cagttgggta atttgaatga agaccaagaa gaaaataaca acattagatg aagagagagt    360
gtgatcaaat cgttattttg gataagtccc ttcatatttc aaaatggtac catactaact    420
atgaaatact tcaaagaatt aagatctttt taaaatacgt caacacttta gagtaggaaa    480
cagcggtgga acctcgcaaa atgtacacaa gttcggtttt attttttgc aggaaaatca    540 aggggtgctt ataatgaaac taacattttc ttaaaaaatt tcgcccctga acccccttt    600 ttatccctt aaggggggta tttgtggttt tgcgaaacg aggcccttcc tgtatacgtt    660
ttgcaaagaa atgtacttaa tgg                                            683

<210> SEQ ID NO 186
<211> LENGTH: 446
<212> TYPE: DNA
<213> ORGANISM: Diabrotica virgifera virgifera

<400> SEQUENCE: 186
gggttatttt agtatttgca cgaatctgcc gcacatgggt gcatgtgaag gtgagttgtg    60
```

```
catttattac atggtggttg acatagctaa aatgtttaaa atgtttccta aaaaatgttt      120
ttgcgctctt ttcaatggcg gtattaactt ttttaaaaat taatacatac agggtgaaag      180
aattaaaaaa aaaacaacat attttacat tctaggaaaa acacaacttc tggtaaaccg      240
attcttccgg ttcgacacct tgatcttaca cattaaataa agaacctata taccaaattt      300
ggtttgaata tgacgtctca ataaagaagt tatcgtgcta ttagtcacat atgtatagtc      360
agggccctcg ctacaatatg tgcaaagtgt gaaatgcaca cgggctccgt tctttagggg      420
cgccacaacc gagggtcaaa aagtac                                          446
```

<210> SEQ ID NO 187
<211> LENGTH: 148
<212> TYPE: DNA
<213> ORGANISM: Diabrotica virgifera virgifera

<400> SEQUENCE: 187

```
gggctgttct tcattcttgt tgctttactt aacacatctt caaattacaa agaccggatt       60
tctgtaactt ttgaaacgct cattttacc accgttaaaa atggtttatt ccattttcc      120 atgttgagat tgttgtttta tctacgtc                                        148
```

<210> SEQ ID NO 188
<211> LENGTH: 517
<212> TYPE: DNA
<213> ORGANISM: Diabrotica virgifera virgifera

<400> SEQUENCE: 188

```
gggggtttcg tttcatcatc atttgttgta attttttgtag taaagcacat taaaaaaaaa       60
atctgtttta aagccatggc tgatgaagaa tttgacgaaa atgatgtagc agatgatttc      120
gatgacgacg tagaggatga taatatcgaa gaactcgaac aacccgagga agatggagat      180
aacatcgata tccttgctcc aggacaagca ggaggtggtg taccaaaaaa caagaggata      240
acaactaaat atatgaccaa atatgagaga gccagagtat taggtactag agccttgcaa      300
atagccatgt gtgccccagt tatggttgaa ctagatggtg aaactgatcc tctgcaaatt      360
gccatgaagg aattaaaaca gagaaagatt ccaattatta ttagaagata tttacctgac      420
cattcctatg aagattgggg aatagacgag ctcattatta tagatcacta gattgtaatt      480
tttatgtgga tattatttaa tacataggtt tttataa                              517
```

<210> SEQ ID NO 189
<211> LENGTH: 654
<212> TYPE: DNA
<213> ORGANISM: Diabrotica virgifera virgifera

<400> SEQUENCE: 189

```
ggggacatac gtggaactta gctataagtt gtagttttgt agggtaaatt cgtaggtttt       60
agtgaaagaa aatgtcgtcg aaaagaaaaa gtaaagaaag cataattgct agggtgaatt      120
tcccactata tactcttcag atgttaacgt caaggcatgt aatcgttggt ggtggaggag      180
ggacatccaa aactggtgta cacaatggtt ttgaaatatt tgagattttt catgacggca      240
cacgctttgc agcaaaagaa gtaaccagac acgaaactgg aggcaatgtt gttatgaact      300
gttctgttta cagtgataga aaatattctc ttttggtagc tggacaagaa agtgagtgtc      360
aattgtacaa actgaatcct aaactagtcg aggaagtgga aatatcggt aataatactc      420 atctcaggca acggaataca aaaaacaaag aagttacaga tgcaacaaa aacgtgacaa      480
```

| | |
|---|---|
| aagagttata tttttgatgtt aatgcaatag aaaatgttca aactgacttt aatgggagtg | 540 |
| aaccattatc gagggtggta aaaattaatc atgatggtac attattagct acaggtggta | 600 |
| cagatggaga tgtacgaata tggaagtttc ctagtatgca acctctattt attc | 654 |

```
<210> SEQ ID NO 190
<211> LENGTH: 433
<212> TYPE: DNA
<213> ORGANISM: Diabrotica virgifera virgifera

<400> SEQUENCE: 190
```

| | |
|---|---|
| gggccacgtc acaatagaag acgcgtgtaa cggcgggtta acgaactccc ttacattaag | 60 |
| agccaatata tggtagaggt acattttcag ggtacaaggt ttctcccat gtaataatct | 120 |
| gacgcgctcg agtaactgca aaatccccg cttgggctcc cctactatat tgaatgtagc | 180 |
| aaatatttat tgaaatcttt tattttcaca aaatatttat ttagtattga tattttcaga | 240 |
| tagaaaatgt tctgtcagac atactgcata ataatataaa attgaggtat aggctgttga | 300 |
| ttatgtactt tagaaaggga ctacaatgtc aaaggtgttt tattgtttca tatagtcaaa | 360 |
| gggtccccaa atataaaaaa accgcggagt gctattactt aaagggctac gtttctaagg | 420 |
| aaagggtgaa tta | 433 |

```
<210> SEQ ID NO 191
<211> LENGTH: 316
<212> TYPE: DNA
<213> ORGANISM: Diabrotica virgifera virgifera

<400> SEQUENCE: 191
```

| | |
|---|---|
| tttaatactt cagaaagttg catttcagta tttctttaat ttaattttaa taaaattaat | 60 |
| tcacattgta ttcatttaaa tccttagaag caaaaatcca ataatggccc tatcaccatg | 120 |
| gttgaagtcc ccttttacag acttaacggg atctctagta aatcaccagt ggtacggaga | 180 |
| atgtgctgat atggaattaa aagttttaga ctgtctagat gcctatggat tggacagggg | 240 |
| cttaaaaaaa tgtgatgatc tgattgaaga cttcagagag tgtgctttaa aaacaaaaca | 300 |
| gttcaaaaga atgtac | 316 |

```
<210> SEQ ID NO 192
<211> LENGTH: 673
<212> TYPE: DNA
<213> ORGANISM: Diabrotica virgifera virgifera
<220> FEATURE:
<221> NAME/KEY: misc_feature
<222> LOCATION: 654
<223> OTHER INFORMATION: n = A,T,C or G

<400> SEQUENCE: 192
```

| | |
|---|---|
| gggggagcga cgtggtggcg acgtcagctg attatttcta tttccctatt tctatttctt | 60 |
| acccgttttg tagtttataa atttataaaa acaacgaatt tagaatgtag ttttctgtag | 120 |
| gtaggaacca taaacataaa aatcatatta tttgattttg cttttttggat gtaaacgtaa | 180 |
| aactgaaata cctctacaat aacgatctat ttatacataa atttattta aaaatcaaat | 240 |
| atggaaataa atcgagaagc tagtgaaaaa actgttgaaa taaagtaga aaacgaagac | 300 |
| acctgtgttg gtcccttgga tgctttcaaa attgaaatta cagaagaacc caagagagaa | 360 |
| cccagagaac ccgcatacga ggcatttggt tctttagact caaataaatt tctgttaaac | 420 |
| actgaagtaa aacaagacga atataaattt gcaccatttc aagaaaagca agaacagat | 480 |
| gaagaaaaat atattataca agttctaact actctatact gaaatcataa tgaagatgca | 540 |

```
ctagaaataa acaaaccaat atttatttat taagcgcaaa aggccttgta ggcctagggc      600
taaaatgttt acatttctga ttacataaat aatataataa ataacttagt atancttaca      660
taacttataa aag                                                         673

<210> SEQ ID NO 193
<211> LENGTH: 614
<212> TYPE: DNA
<213> ORGANISM: Diabrotica virgifera virgifera

<400> SEQUENCE: 193
ggggtcatca agttcttgtt ttgtctcgag gagttgattc gttttgttgg cagtacattt       60
tataattatt ggagtcggaa tatttaatta atgtgattag aaagtgtata gttttagaac      120
tagccatcac ttacttaaat ttctttaata gactcattgt tttaatatag tttggtcagt      180
tagttaataa agtgtaatta aaaatgagtg accccacaaa tcctactgga ctacctagaa      240
gtttaaatta tgaagcatta aaggctcata taatatcgca caaataaat tgcggcctat       300 ggttaattag ggtcataggc attctctgct ccatagctta cttcattcca attttggaa       360 atccttacaa ctactattac aaagtactcc tagcaaatgc agctatcagc gcattgagat      420
tacatcaaag gataggcaga gtgcaattca cgagacaatt tgctgcagaa ttactttcag      480
aagatagttg tcactatctt ttctattcgt tgatattttt atacgtatcg ccagtatcat      540
tggtactcgt accaattatc ctcttctgcg tactccattc agctagttat tcactcacat      600
tgttagatac atta                                                        614

<210> SEQ ID NO 194
<211> LENGTH: 396
<212> TYPE: DNA
<213> ORGANISM: Diabrotica virgifera virgifera

<400> SEQUENCE: 194
gggataatca ttagtttttt tattgaaagc tggaatgaag ggttggatga aaaaaaaaac       60
tgtctttatt taatttataa agaatttat ttttaagtta aaaagcttaa attttttta        120 aagacgagaa gaccctatag agtttttataa aattattaat aagtttttt agtattaaat      180 ttatttatat aataaattta tttaattggg gtgattaaaa aataaattta acttttttta     240
tattattata ttaattaata atttttttgat ccaattttt tgattataag aataaattac      300
cttagggata acagcgtaat tttattggag agttcaaatc ggtaataaag attgcgacct      360
cgatgttgga ttaaagttta taattggtgt agcagc                                396

<210> SEQ ID NO 195
<211> LENGTH: 533
<212> TYPE: DNA
<213> ORGANISM: Diabrotica virgifera virgifera

<400> SEQUENCE: 195
ggggaggtta taaaatattt gattttttgct ttttgcaacg gggattttttg atttattatt     60 tatttataat tcataggatt tatttgaggg aaaatttgaa aatttggcac agatttgggg      120
atgcctgttg tgttaagtgt tggtagagag taatcagtta ctatttatca tgggaaaagt     180
aaagaaacca aaagcgaaag cgctaggtgc gtttgaatcc aaaaataata gtgctccaat      240
aaaggaatcc atttcagcca actttgattt tagtataaaa caaggaaaat cagttgtggc      300
agatgatgta aaaagtgttc tttcatataa atccattaag tcccataatc caattaacag      360
```

| | |
|---|---|
| gattataaag aaaaaagaaa aagtgaattt aaaacgaaag ttactgatga aaaaaattga | 420 |
| tttaggcaat gtactaaaga aagaacaaaa gatcagggac aagagaaaaa atacatcact | 480 |
| tattggtgac actaatgcac tgcatgatgc tttaccttca ctggattcat tat | 533 |

<210> SEQ ID NO 196
<211> LENGTH: 655
<212> TYPE: DNA
<213> ORGANISM: Diabrotica virgifera virgifera

<400> SEQUENCE: 196

| | |
|---|---|
| ggggatttgt aattgagata tctgttggta tgtgttggtt ttctatacac ttgagtctca | 60 |
| tatccagtat ccttctttaa gactaaagca tcgaggaaag gcagggtgtt attatattcc | 120 |
| ttttccattg taaattttat tgtctctttt atttattta ttgtctattc tattatctct | 180 |
| aacgcgagag ttttagtgtc accgttgcat gtggttgtct ttttgaagac agatcgcatg | 240 |
| ctatgatttt tttttgtgac ggatgttctt gagttggggt tgatttcatg tggtcgagtg | 300 |
| agctatcttt cagtggagtc gtcccaggaa cgcgactcat aaatgttggc agtatcattt | 360 |
| taaagtcttc tactttggaa tgtgtcatat gtatctgaat tgccgatgtg aatgagtcgg | 420 |
| attaagtaaa ttattggaag attttttac taagcaacaa catttttgtt tatattagtg | 480 |
| gtattttgta ttttgacagc ggcgcccgat ttgggcgtcg aaacgttagt aaaaatcatt | 540 |
| ttttaatgat attgtggttt atttcccatt ctaaatagtt aaaaatgatt tctttgattt | 600 |
| gtgtctgatg aataattatt taggtatttt taaatgctac ttaaattata ttttt | 655 |

<210> SEQ ID NO 197
<211> LENGTH: 602
<212> TYPE: DNA
<213> ORGANISM: Diabrotica virgifera virgifera

<400> SEQUENCE: 197

| | |
|---|---|
| gggtattcgc tttaaactcc agtttttta aaaactaatc attctaagcc agtcaaactt | 60 |
| ctagaatcta ttaataatac ataaataaag aagaataaat aagtccaatg actgaaaaca | 120 |
| ccgccaactt acattattat gcttccaatt ggatttctct ttttttttc aaaaaaatat | 180 |
| attgattttt taaccgtaac ttttttaaatt tttatcttag aaagttcgtt aaataagaat | 240 |
| tttgtaggtt tttacaaggt ttataatgct attaacatta aatccttta aaattctcag | 300 |
| tcacaaaaag aggtggcatt gaaagggttg gtaaaggtgg ttttttgcgtg atattacaag | 360 |
| ttttaattgt caatagctca ctcaatttt gtcgtaaaaa aatttttgca aactaaattc | 420 |
| ttgggaatta ataagttac aatttcatat ttaaatattt ttttttcgta tctctgatgc | 480 |
| tactcttct attctgaaga aaaggcattt tttaacaaac tacaaaaact cgttattcgc | 540 |
| ttttaactca attttttaa aagctgatca ttcgaagccg atcaaacttc tagaacctat | 600 |
| ta | 602 |

<210> SEQ ID NO 198
<211> LENGTH: 557
<212> TYPE: DNA
<213> ORGANISM: Diabrotica virgifera virgifera

<400> SEQUENCE: 198

| | |
|---|---|
| gggacatggc ttgctgtatg ttgtacagag gggatgttgt accaaaggat gtaaatgctg | 60 |
| ctattgcaac cattaagacc aaacgtacca tccaattcgt agactggtgt ccaactggtt | 120 |
| tcaaagtagg tatcaactac caaccaccaa ctgttgtacc tggaggtgat ttggctaaag | 180 |

```
tacaacgtgc cgtatgcatg ttgtccaaca ctacagctat tgctgaagcc tgggcaagat    240
tggaccacaa attcgatctt atgtatgcca agagagcttc cgtccactgg tatgtaggag    300
agggtatgga agaaggtgaa ttctctgaag ctcgtgaaga tttggctgct ttggagaaag    360
attatgaaga agttggtatg gactccggag aaggtgaggg tgaaggagct gaagaatatt    420
aaatttgatt ccaaacatga caaatcactt gttttttaaga caaaaaattc ctttcaattt    480
ttttacactt tttcattact tttctgtgaa acgattattt aaagtctgat ttaacttaat    540
acagaatttt ttacgag                                                   557
```

<210> SEQ ID NO 199
<211> LENGTH: 630
<212> TYPE: DNA
<213> ORGANISM: Diabrotica virgifera virgifera
<400> SEQUENCE: 199

```
gggagttact cggtattcgg tatcaataat gttattaaca gactcgttta atattttatc     60
agttttctcc tcgacaatga gcagctagta tggtcgttcg gaaatacttg tatataaact    120
ttttgatatt aatggagttg tcctatttct acgcgacttt ctgaacgtgt tagagaatat    180
agttgatcta acatttggta atagtatttt ttagagtgtt tattagtgtg ttcaagatgg    240
ttaactttac gaagagacag tggtcaacgt tgatcgttat tggtattgct gattttttgta    300 acgctgtttg tgtgtcgctg caagctccat tttatccaca agttgccgaa agtaagcatt    360
gcacagcgac ggagtatgga ttggtgtttg gaatttttga atttgttgtg ttcttgatta    420
gtcctatata tggagcaaac ctgaatagaa ttggacctaa actcatgttt aatgttggag    480
gctacactat tggtgtgtgt gctatattgt ttggagctga gacaaaaact gagcatcgga    540
atctgaagct agcggggttt aatgtaagtt ccaataaata attttagaca atagattgta    600
ttttagttga gtgattgctg aataaatagt                                     630
```

<210> SEQ ID NO 200
<211> LENGTH: 615
<212> TYPE: DNA
<213> ORGANISM: Diabrotica virgifera virgifera
<400> SEQUENCE: 200

```
ggggagtgaa aaccccctcac cacaacgcac cgacaccgag tatgattcaa cttcaacaag     60
agtgcaacca ttcgatatag aatcacaatc tcatatcgat tttgcaccag taaataatca    120
gaatcagaac aactgtgata gtttagacgc gaaagaaatg agtgcaacga agaacaaca    180 aagtacattg gggggagccg ataaagtgaa aaaacacaag aaaggccctc gacctccgcc    240 tcccctgga ttaaaagatg atctaacaac aattgcacat gttctgtgg tgattttcgt    300 agggcttatc ttgtatttat gttttgcacg gccgtttgaa ttcttcacgt ggcatccttt    360
gttgatgtct gtagggtaga tgcttatgat gatagaaggc gttctcttca tatccaaaga    420
aaacccgata ggaagaagac taaacttggg ccgccttta aaagttcgtt tccattggat    480
agctttaaca ataagttcta ttttagttac gatcggtttc gtaatagtag ttataagcaa    540
aaacaaccac ggcaaggaac attttaaatc cttacatgcg attttcggtc tcataggttt    600
attagggtgt atacc                                                     615
```

<210> SEQ ID NO 201
<211> LENGTH: 587
<212> TYPE: DNA

<213> ORGANISM: Diabrotica virgifera virgifera

<400> SEQUENCE: 201

```
ggggatttta ttttttgaa agtttagtac atgtacatta tatttaaaaa cagtattgtt      60
taaatataaa ataaattctt gacgattgtc agacgtagaa aatgttacaa agtgtaaaaa    120
agtacgatac tattatcaga accattgatg atgatgaaga agttgaagat ttatcagaaa    180
acagtgatga ggaaatagag tttcaaccat ccaaacaaaa aactcgaagt aaggaggatt    240
ttgatacgga atttaatttt gtcagttccg tagaagaata taataaagat gtttggaatg    300
atttgactaa atacgttaaa aggaaagcaa acaaaaaac tgatgacaaa attaaaaaag     360
tcagaggcac acaagctgat gaggatcaaa caaacactga aatggtaca aatgatcttg     420
tcgattccga tatatctctt tcagaagatg aactaaaaca tgataggatt aaacttaaag    480
aaaagaaaaa gaaaaaagta aaagctgaca atgatacaga agaattttt gaagaggttg     540
aattaaattc tggagaaact gttagttttt atcagatgaa tctgtca                  587
```

<210> SEQ ID NO 202
<211> LENGTH: 559
<212> TYPE: DNA
<213> ORGANISM: Diabrotica virgifera virgifera

<400> SEQUENCE: 202

```
ggggacactt cctttcggtc cggctctgca tatcaaaggt gcgaatttag tcattaaatt     60
gccaaatttt ccatttgtat tctctaaatc attcgtttgg taagaagatg cagacttag    120
atgatttctt tgccaaaaaa gaccgcgaga agtccaaaag tacaaaaaaa tatgctacca    180
ctgaagaagt tgccaagaag ctagaagaca ctgcaaaaaa gactgacaaa ttaaagaaag    240
aacgtgttaa tgagggcgaa gatagtatag ttactgaaca agaccaagac gaatggaagg    300
acttcgagga agaaaagaaa gactacacag ggttaaagat aggaaactta gccatcggtc    360
aaaattcgga aagcagtact acgggagcta aggaaagtac cgaacagcaa caagaagatg    420
agcctggaca agatgtagac aagaaatctg gaccttggaa acgcatcgac gtcggggaag    480
cagcggaagt ggagaaagtt gaatataaac cggaaccgat acttcctaat gtatctaaga    540
ctggcactta tatacccc                                                  559
```

<210> SEQ ID NO 203
<211> LENGTH: 631
<212> TYPE: DNA
<213> ORGANISM: Diabrotica virgifera virgifera

<400> SEQUENCE: 203

```
gggggattga cgtgaagtta gcagctgcac gcagtgacag ctcagtgttt accgtcagaa     60
aattttaaat taaaagaaat aaaatttaga atatgttgaa attgttcaaa gaaatatctt    120
caagtttggg gaaatctctt accaaaaggg gacttcaaac tacttccact ttacaacatg    180
atagcttatt tgtacatcga gatactcctg aagataatcc agatattgtc tttgaattca    240
ccccggaaaa taaaagagg gctgaagcta ttctagccat atatccagaa ggccacaaga    300
gggctgcaat gattccatta cttgatttag ctcaaagaca gtatggatgg ttaccaatt     360
ctgctatgca taaagtggct gaaattttaa acttgccaag aatgagggtg tatgaagtag    420
ctactttcta cactatgttt atgaggaaac ccacaggtaa atatcatgtt caaatttgta    480
ctacaactcc ttgctggtta agaggatcag atgagattct ggaagctatt aagaaaaatc    540
ttaagttaga agttggagag acaagcaaag acatgttatg gaccttatct ggggttgaat    600
```

```
gtctgggagc atgtgttaat gcccccatgg t                                    631
```

<210> SEQ ID NO 204
<211> LENGTH: 93
<212> TYPE: DNA
<213> ORGANISM: Diabrotica virgifera virgifera

<400> SEQUENCE: 204

```
taggattttt cgtaaaacta atccacatcc ccatcaacaa cattatagtg ggatcataaa     60
tatattttc atatttatgt cagttcatac aat                                   93
```

<210> SEQ ID NO 205
<211> LENGTH: 614
<212> TYPE: DNA
<213> ORGANISM: Diabrotica virgifera virgifera

<400> SEQUENCE: 205

```
gggaataaaa aatttatttt atttatattt ttatttattt taaaataata aaatattttt     60
tagtaaaagt aaagaaaaat tttatttaat gatagttaat tagtattgtg agagaatatt    120
ttatttttat aaagaaaaa tttatttttt gtaccttgtg tatcagggat tattaattaa     180
taattatata tttattattt tcgaatttaa aagagctaaa aaattaaaat ttttattgta    240
aaataaaat tttaaataat tttttgtaa tgaaatgtta ttcgttttta aatatatcta      300
atttttaag aaataaatta aatttattta ttaacaatat atttataatt aaatattttt     360
atattattaa tattaaatat ttttagggat gagcttaaaa ataaaattt attaaaattt     420
aatttttaaa taaaaattag gattaaaaat tttcatattt taaaatatgt tattatttat    480
ttttatatat tattattttt atttttata aatttttat taaaatataa atttaaatta      540
tttaaattta gtaatgatga taatattagt attaaaaaat tgtatattta gtaaaaatat    600
ataggtttaa taaa                                                      614
```

<210> SEQ ID NO 206
<211> LENGTH: 621
<212> TYPE: DNA
<213> ORGANISM: Diabrotica virgifera virgifera

<400> SEQUENCE: 206

```
ggggcttctc tgtgcatgtt tcaccatttt taataattta aaaacccgct attcgtaatt     60
ttgttggttg tctttacgga ttacttacaa ttttggaaat aaaatgactc ccggccgatc    120
atcaacgact acaaaagtgt tgtaggaag tttgcctcca gacgctaccc cagaggattt     180
gaagaaactt ttcgagccct acgggaacat tgcagaatgc gacatcgcga acaaatgtgg    240
attcctccac ttggaggatg gcgaattggc aatgaaggcc attgacgaac taatggtat     300
ggaatttatg ggttccaaaa tttcagtgga aaaggggcga gttaagccgc gaaggagtgg    360
cggtggaccc agaggtggaa gagaacgagg aggcccgtat tcaagagtta tggtggatcc    420
aacggatacg gcgcttctgc cggttacggt cgcgacgccg gtggctacgg cgccgcctat    480
ggagatcgcg cagccgccga tccgtacgct gcagctgatc catacagagg ggcttcagcc    540
ggtggtggct atcaggatag aggtgataga ggatacggtg ggcgacctgc tgagggttat    600
ggaaactcat acgctgctgc a                                              621
```

<210> SEQ ID NO 207
<211> LENGTH: 624
<212> TYPE: DNA

<213> ORGANISM: Diabrotica virgifera virgifera

<400> SEQUENCE: 207

```
gggggagtgt gtggtgagtg tcagttaaac gttaacgtta acaagtatt ttattacatg    60
gtaacacacg tgttgtagga attcccttta aaaacgatgg atgtccttag tcgtcctgcg   120
gaagaatttg aaaatgacca acagtggaa actatgtggg ctataaaagc cttcgaacat   180
gccgaagttt actttaacat tttatgttca gttgatccaa aattgctcaa actaacacca   240
gtagacgatt taatctataa agtctttaga gaagaattcc caaaactaga gtcgaagta   300
ataatagaaa atgaattgaa gagcacaaaa gaaaaaagca agtggagacc ttttttgtgaa  360
cgatttaaga ccattgcaga agactatagt tatggtactt tactgagagc agatgccaaa   420
gatgattata agaggagaa caccatatta gttactagga ttcaatttta tgccatcgaa   480
ctggccagga atagggaggg agtcaatgac attctaagga aaaagttctg gcctgaagcc   540
aaggaagaga aagacgatta ggaagtattt aataaatctc agttttttta tacattttag   600
ttatttataa gttttttgta agtc                                          624
```

<210> SEQ ID NO 208
<211> LENGTH: 574
<212> TYPE: DNA
<213> ORGANISM: Diabrotica virgifera virgifera

<400> SEQUENCE: 208

```
ggggagcctt tatttttttg tttcgacatg tcgcatgtcg agatcccctg tatatcgggg    60
gcccctttta attgatacgt cggtagctac gcctctgctc ataccagacg gaaaagttga   120
tttaagcgct ccgtacctat cttgtttaaa agggtgtgca acaaagtttc gaagccacgg   180
taatccggaa atcacatata tcgaagaact tacgaaattt ggcaactatt acaacagaca   240
atttgttatt tcaagtataa tgcaacatcg gaatcattaa tttgttgctg ttcgtttagt   300
agttttttat aaaaatgggt ttgggaagaa gaaatggtag tagctgttgt agaaaatggc   360
ttataggaac ttgtttgtat atatttgttt tattactatt aatattttta atagtatttg   420
ttgtagtccc agtcgttttt aaatatagtg ttggaatcca aagaagtata atatttccgt   480
catgggtaat cgacccgaaa aactattcaa acatcgacca atttgggatc aaaggggtga   540
aaaacttcta cgcgaacttg caagaagatg acaa                                574
```

<210> SEQ ID NO 209
<211> LENGTH: 600
<212> TYPE: DNA
<213> ORGANISM: Diabrotica virgifera virgifera

<400> SEQUENCE: 209

```
ggggagatg atgagcaacc aaaacaaaac attaacattt taatttaaca cacccatttg    60
attactaata acattttaaa aacggctctt aagacacgat gaattacgta tatctttgta   120
ttcttattgt aatattagtg ttagttaaga aaagtgaagc agtaagatgc tatcaatgcg   180
gatcagatga agatggcaaa tatgaagaca actgtggtgc ctatcaaaaa tttgacaaat   240
tgaatcacat tgccattgaa tgtaatagtg aggaaagtca tatgcctggt tctttttgta   300
tgaaatttac tcaacaaagt cctagaggtt ttatttggga tggcagatgg agacaagtaa   360
taagaagatg tgcatctgta gctgacacgg gagtaacagg agtatgtaac tggggggtgt   420
atgaaaatgg catttactgg gaagaatgtt attgttcaga agatgaatgt aatagtgcac   480
atatgactaa aatatcaata ttttcagtta ttagttttat catttaccca attgtgaggt   540
```

```
atatttggaa ctaaaagata tattatctta ttagtttgtt gactaatgaa agtagtcaga    600
```

<210> SEQ ID NO 210
<211> LENGTH: 574
<212> TYPE: DNA
<213> ORGANISM: Diabrotica virgifera virgifera

<400> SEQUENCE: 210

```
gggatcccgg tatatacacg acacgatttc taagtttacg ctcaatacac gcgtgaatcg     60
agtcacactc catttgagta tgacccttt ctagataata ttgaaatatt tctacacctg    120
atgttcttga taagtaagaa agagcattcg aaagcgtaac atttcgagtt tggtagcagc    180
atccgtcgct gaagcaaaca acggatttag tagcaggaga taaatttctt ttgatataat    240
ctatgataat ggaagtgaac tcgtttgctt caacccacc tgaaccctca tgccatacat    300
agcaatggcc tttgccagtg gataaattat agaagctata gttgtgaaca tttagcttca    360
ttttataata tgcagctgat acttgtaatc ttggtgctgt taatattgcc tgtgcatcca    420
tagtcaaaac aagtttactg ttgtccttac tagcctcttc ttttagtttt tccttttcag    480
cacgagctaa atttttttc tccaaatgct gctgaaactg ttcatcattt attttgccga    540
cagaataccc agtgcaagtg tcgcactgat cttt                                574
```

<210> SEQ ID NO 211
<211> LENGTH: 227
<212> TYPE: DNA
<213> ORGANISM: Diabrotica virgifera virgifera

<400> SEQUENCE: 211

```
gggacttaga ttttattcat catctcgtta aactgtacaa tgagaaacgg tcagatctgg     60
aggagcaaca gttgcatttg aacgttggtc tgaataagat cgccgaaact gtagaacagg    120
ttgaagaaat gcagaagagt ttggccgtca atctcagga gccacaggcc aaaaatgaag    180
ctgccaacgc taaactcagg cagatggtga agatcaaca agaagcc                   227
```

<210> SEQ ID NO 212
<211> LENGTH: 631
<212> TYPE: DNA
<213> ORGANISM: Diabrotica virgifera virgifera

<400> SEQUENCE: 212

```
ggggattatt tctgattttc gtttgctgct ttgttgtcta tacatattgt aaaaatacag     60
ctaaaaactt ttaaaaatga gcgaagccaa ggaagcaatg gaagttgaag tggaaacagc    120
cccggtggct gaaaattcaa aatcttccat ggaggtaacc acagatacag gcaaaaatgt    180
aatggccccg ggagctgttg gatcaatcac ttgttcccctt catcctcttg taataatgaa    240
tgtatcagaa cattggacta gggaaagggc ccaagaagga gctgtgcaac aagtcattgg    300
agctttgatc ggcaaacaaa agggtagaaa tattgaagta atgaactcat ttgagctagt    360
atttacactt ataggaggtg atatagttat tgataaggat tattacaaca tgaaagaaga    420
gcaatttaaa caagtcttca gtgatttaga tttcattggc tggtacacaa caggtgacgc    480
cccaagtgaa atggatatca aggtccacaa gcaaatttgt gaaatcaatg agtctccccat    540
tttattgaag ctcaacccctt atgataaaaa tattgaacat ttaccagtaa acttatagga    600
atctgtgata gacttagtaa atggtgaagc c                                   631
```

<210> SEQ ID NO 213

```
<211> LENGTH: 611
<212> TYPE: DNA
<213> ORGANISM: Diabrotica virgifera virgifera

<400> SEQUENCE: 213
ggggaagaga tgacaatatg gcgtcaaggt attagttgct aggacgtttt attttcatt      60
cgagagtttt acagtaataa atgagaaagt tgtaccgaaa ttattgtgat ttcgacgtaa    120
tatttctcag tctaactttg gattatgaac attatcacga aagttgatgg agaacatagg    180
cagagacaag aggactatgg agcatctaga atagcagtag agccaattca acacaagcat    240
ggatgacatg gataacatga ggaagaggac tttgttcagc agtggacctt tgaggctgga    300
tgataatgga ctccatcaat gaggatgtaa aggatatcac tttcatgtac tggagtacaa    360
tgtaacattg tgtaggcata atattttact cttttatt gacaaatatt taccaactcc      420
cttacatggg ggttgactaa tatttgacca cttctgaaaa tctcatttta tgttttttgc    480
atcaactgta ggcaatttgc tatacaattg caatattgtt tgaacgtcaa tattttgtta    540
aagtaaatta ttatctggtt tgagtggta tactttttaa atgaattcca aaaattactt     600
tattagccta a                                                          611

<210> SEQ ID NO 214
<211> LENGTH: 569
<212> TYPE: DNA
<213> ORGANISM: Diabrotica virgifera virgifera

<400> SEQUENCE: 214
ggggatttca tttttcattt gtttgtaaac aaatttatgt aaaattgaca gtttgtgcaa     60
aagattatta tattctttgg ttttttgttg gctgaaaatg ttaaaaaatg ttgtattaaa    120
taataaatga atgacattat accttttcttg caaggatttc gtagattgtt tggaacaatg    180
tcccgatcta aagttagata gtttgttaac ccaaaagaag actatagaga atctagtcaa    240
attgtgattc cagtaccaga tataatacaa catttaaatg atactgttgt caaaatagaa    300
agtggtgtta agccagcaga agagaatgct ggagatggaa tttatttagg tactgctggg    360
atagcatata tgttctacca ccttagcaag gttccaacac tttcatcaaa gcaatctcag    420
tatttaagac aagctgtaac ttacctaaat ccggcaataa cagtagcaag ctgcaacaaa    480
acagatagta tcccctcttt catattagga aatgctggaa tttatgctgt agcagccaca    540
gttttcaaca gtttaggaga tctgaatca                                      569

<210> SEQ ID NO 215
<211> LENGTH: 630
<212> TYPE: DNA
<213> ORGANISM: Diabrotica virgifera virgifera

<400> SEQUENCE: 215
gggataatat agagataatt tcttcaccca gtgtgtactc tatactcagg ttttttgactt    60
tatcaataat ttcatccatg atgaggtgaa actgtagcag gcttgacgta tgcctctttc    120
cacttgtatc ggcagcttct tattaataat ttcggcctgc atattatttc tcctgtatat    180
gttttcggta gtcttgataa tatctgatgg tatgttttga ttacgtgaca ggtgaattac    240
gtcattcagc tctacgcggt cgaatgactt ttgtagatct atgaagcaac agtaaggcgg    300
gacgttgtat tcagtgccgg atttaccact aggccgacta ggccgcggcc tagtgccgca    360
agcaaaaggg ggccgcagcg ctttgtaaaa aaaacttat tggtaaaaaa attgtcacaa     420
cattgtcaaa aatagcaata acgataagaa actccttcca aaaagagtaa acgttacaag    480
```

```
acgggctgcc aaatggcatg ctgtaaaagc tattttactt aactactggg agctactacg    540
atgcaattaa aaaaaatatc agccgataca ggggaaacaa atgtgagccg agctgaagct    600
aatggaatca gtaaacaatt tttaaaatta                                     630
```

<210> SEQ ID NO 216
<211> LENGTH: 624
<212> TYPE: DNA
<213> ORGANISM: Diabrotica virgifera virgifera

<400> SEQUENCE: 216

```
ggggacagca atcgcagctg ttttaaaaga aagaaaattg ttccccttct tcgactgtgc     60
ctaccaaggt ttcgcctctg gtaacttggt caaagatgct gctgtggtaa gaaaattcgc    120
cgccgaaggc taggagttct tctgtgccca gagttttgcc aagaacttcg gtctctacaa    180
tgaacgtgtt ggaaacctaa cagtagcggt tagcaaacca gaccttatgg cacctgtaaa    240
atcgcagctt actctcatcg tcagaggaat gtactcaaac ccacctagtc acggagccag    300
gatagtatct tttgtgctca ataacccaga tttggcaaag cagtggcaag ataatatcac    360
tacgatgtct tcaagaataa ttgaaatgag accctgttg agaaacgcat tagaggagtt     420
gggcactcca ggagactgga gccatttaac taaacacatc ggaatgttct cttacacagg    480
tctaaatgaa atccagtcag agcacttggt gaagaaacat catgtctacc tgctgcgttc    540
tggaagaatt agtataagtg gttttgaacaa tgacaacgtg aactatgttg ctaaagccat    600
ccatgaaaca gtaaccaccc tacc                                            624
```

<210> SEQ ID NO 217
<211> LENGTH: 362
<212> TYPE: DNA
<213> ORGANISM: Diabrotica virgifera virgifera

<400> SEQUENCE: 217

```
ggggacagtc gacatctgac agtttctaca gtatagttac agtgttcagt ggaaaatatt     60
caattaagac tgcgattata cgacacactt tcactgtcaa ggccgtcttt cttgcatccc    120
taaaacgtac atttgcgaca aaaaaattga ctgctgggac ggcagcgatg aagaaaactg    180
ctactacgaa catatctgcc aagagggga ataccattgt aataatggtt attgtataaa    240
atcggagcaa ttgtgtgatg ctttccgga ttgttctgat aactcagacg aaccatctgg    300
gtgtttagag tattatttgt caacaactac tgatgttaca agtccggaaa atgattatga    360
gc                                                                    362
```

<210> SEQ ID NO 218
<211> LENGTH: 644
<212> TYPE: DNA
<213> ORGANISM: Diabrotica virgifera virgifera

<400> SEQUENCE: 218

```
ggggttcgtg gggtagaatt tcagactttt gacaaattaa aattttgaac aatttatttt     60
attaatttca atcacattgc agttttaaaa agaattaaaa atggtatccc taaatcccgt    120
aagaattctc aagcaagaag ccgaggaaga aagggcagag attgcccgac tcagtagttt    180
tgtaggtgct atagctatag gagatttggt tagaagcacc ttgggaccaa aaggaatgga    240 taaaattttta gtatccagtg gtagatctgc aggatcagtt gaagttacta acgacggagc    300
aactatccta aaatcggtgg gtgttgataa tcctgctgct aaaattttgg tggatatgtc    360
```

```
aaaagtccag gatgatgaag taggagatgg caccacatca gtgacagtat tagcatctga        420
actacttaaa gaagcagaaa aacttgtaga acagaaaatt cacccacaaa caatcattgc        480
cggttggagg aaagcagtag atattgccag aaaagctctt ctagaaactg ccaaagacaa        540
cagctctgat tcggaaaagt tcagagaaga tctgatgaac attgccagaa ctacactcag        600
ctcaaagatt ctttcacaac ataaagaata ttttgccaaa ctgg                         644
```

<210> SEQ ID NO 219
<211> LENGTH: 637
<212> TYPE: DNA
<213> ORGANISM: Diabrotica virgifera virgifera

<400> SEQUENCE: 219

```
ggggagtgac agatgacaat aagaaagaat gaatgaaggg caaaatagct tttcatttta        60
atattatgtt caaaaataaa tttacttaga caatccataa aattaaggca actccgtaat       120
tatgacagaa acattagcag ccgaagaaaa acctttaaca acaatggac gagcagcttt         180 tagtcccgta ccaactaaaa gaacatctgg aggactgatg aaactatcca gttatgtgct       240
agctcttcga ccatggtctc ttagtgcaag tttaattcca actctattag gatcgacaat       300
agcttacaaa tatccagggt cttcggattt taattatata actctatttt ttacgatatt      360
aacaattata tcagtgcatg gggctggtaa tgtagtgaat acatactttg actatgtaaa      420
gggcatagac aatcgaaaat cagacgtatg aattcttgta gatcatatat tatcgaagga     480
tgaagttgta tcgttgggtg ctatcttata tttcgcagga tgtattggat ttattatatt     540
agcgaacata tctccagcaa aatggaacat tttagcttta gtgtattttg ggggcttatc     600
gtcaagtttt ttatacaccg ggggcattgg ttttaaa                                637
```

<210> SEQ ID NO 220
<211> LENGTH: 271
<212> TYPE: DNA
<213> ORGANISM: Diabrotica virgifera virgifera

<400> SEQUENCE: 220

```
ggggactcca acgaaattaa tacgtacttt aaacggttta tttatatttt atttaatatt        60
aaactaattt taatacttac tactttccaa aaattttat taaaacaata ccaaaaatta       120
aaaaaataaa agaataaaac acacacaaac acattgaaaa atgccacaaa taatgattt       180 ctgaacaata attgttggca aaaatctaac caaatacgca ttttctgaaa aaaaattata      240
taacaaatat acttacaatc ataaaatgta c                                       271
```

<210> SEQ ID NO 221
<211> LENGTH: 80
<212> TYPE: DNA
<213> ORGANISM: Diabrotica virgifera virgifera

<400> SEQUENCE: 221

```
taaagctttg gataaaagac aagccgtact ttgtgtgctc gctgaaaact gtgacgagcc        60
tatgtataag aaactagtct                                                    80
```

<210> SEQ ID NO 222
<211> LENGTH: 657
<212> TYPE: DNA
<213> ORGANISM: Diabrotica virgifera virgifera

<400> SEQUENCE: 222

```
gggggctctt taaattgtgg ttatgttgat ttatttataa agaaataaat ttattttaaa        60
```

```
tatgttaaag aattggaatg atttagatgt agaacttcac tcagaggtaa aatgtggaat    120
tgaatcacta aaatttccta ctatgacacc agtgcaagcg tacactatac ctcagctttt    180
aaagaagaaa gatgttgcag ctgaagcagt tactggttct ggaaagactc tggcattcct    240
aataccaata ttacaaataa tgaagcaaag agaaactgaa gaaaaatggg ggaaacatca    300 agtagggggca gttgtcttat ctccaacaag agaattagcc ttgcaaacaa gagatgtact    360
tgataaactg ttagtcgatg ttaaaaatat atccaatatt ttattggttg gaggaaatag    420
tgttgaagaa gatgtaaata atttcaaatc acatggagga aatattataa tttgtactcc    480
tggcagacta gaagatttgt taactaggaa atatgattta aaccttccaa atcattaaa    540 gagtttggaa atccttattt tagatgaggc tgatagactt ttagatttag ctttcaaaa    600 gtccattgac acaattttaa gttatttgcc taggcaacga aggacaggct tattctc      657

<210> SEQ ID NO 223
<211> LENGTH: 541
<212> TYPE: DNA
<213> ORGANISM: Diabrotica virgifera virgifera

<400> SEQUENCE: 223
atatataact cggattacca cagtcaaagt gcataaaact taacaatacg caaaaaccgt    60
agcagtccgt ttatttcttt cctgcggcct tggctggagc cttcttggcc ttcttaggtt   120
ttgatttctt atcttttcaag atttgtgccc ttctcctttc ttgcaatttt ctggatctaa   180
tcacgacgtt gtcggcactc acggtaatac cacgtttctt ggccaaaagt tcttccctgt   240
ttaactgtct cttttgattc ttcaaaatgg cttcacgttt gagtacagca gcatatggat   300
tcaacttaag catggcctta gcgttggtca atggattgag acgacgtaca cgacgtacaa   360
ccttcttttg aggagcacgt aatacagctt tgatttcatc agccttcaac aatctagata   420
gatcagtgtt ggccatttta ggctggggta gattgtaacc cttcttttcc aatgatgctg   480
ttttccatgt gccgaacaat ttatctaaac gttggaaagc tgattcagtc caaataacaa   540
a                                                                    541

<210> SEQ ID NO 224
<211> LENGTH: 650
<212> TYPE: DNA
<213> ORGANISM: Diabrotica virgifera virgifera

<400> SEQUENCE: 224
ggggacattt acgactgatg tgttgatatc ttcactgagg gttacctata atggatatca    60
tagagaaaac cttatcgtat aataacaaac taatagaacc cccacctgat aacattgtgg   120
tccaaaatga agataacgaa gaagttcact atgtaaatat tcatgaggtg cacgtcaaca   180
aagtcatcga gaaaaactg ggcaccaatc atttcgttct acttaattat gagcttaaac    240
ctataactga ccgtcttggt cttcttggag accacagtat tttgttcgta acattcctca    300
ataatattgg atccaaagaa catttgcaat ttttcgttaa gtattttcct tttactgaat   360
ctcaagcaca attcgctgat ggcatcggag catttgaaaa agaagcactg gtttataaat   420
tgttcaaaga gttttataag caaggtatca ctcaagccag taatgttgtc ccctactgct   480
atgtagtagc tcccaaaaaa tattttatat aaatgatct tactctcgag agttatcaaa   540
ttttaaataa acatatttgc ttagaatacg atgtcgttgt agttgtttta caagctttag   600
cccagttaca ttccggtagt atagcgtacg aagaaaaatt aaagaagaat               650
```

<210> SEQ ID NO 225
<211> LENGTH: 655
<212> TYPE: DNA
<213> ORGANISM: Diabrotica virgifera virgifera

<400> SEQUENCE: 225

```
gggcattgag ctcctgcata caaaaaacac tggaaagaat gataaaactt aggctcgaaa      60
gttggctaga aaaaaaacaa taaattatca caaacacaat ttggatttcg aaaaaaatca     120
ttctactgtg gaagctgtga gtcatttggt aacagatata aatttagcgt ttacgaaaaa     180
ttcttcagta atcgctcttt tattagatgt tgaagcagca tacgacaacg ttaatttaaa     240
tatactatat aacaaaatga tacaaatagg tctgccagaa tgcttctgtc aaaaaataat     300
aaaattgtat gactgtagaa aaatttatat atcggtaaat aataacacat ttggtccaag     360
agtagcgatg ggtggtttac ctcaaggagg aatattaagc cctttgttat atttaattta     420
cacttctgat atagaaaaaa atttaaactc aacaaaaatt ttacaatttg cagatgatgt     480
agttatttat caagaaaaca ttaaaataga aaatgcagtc aaatccattg aagaggaga      540 caaacatatt aaaatatgga gtgaattaca tggactaaat atatctgatt ccaaaaccaa     600
attatgtatt tttacaagaa aacgaaaaga atacccaat cacatcttaa taaac           655
```

<210> SEQ ID NO 226
<211> LENGTH: 521
<212> TYPE: DNA
<213> ORGANISM: Diabrotica virgifera virgifera

<400> SEQUENCE: 226

```
gggggaaacg atgacagttt tgaaagaagt aaaaaagcaa agagaacaca acagaaaaat      60
gaagcagaca aagatacaaa tgcagtcatg attagaatga tgaaagaact tatggagaaa     120
aatgaagaaa tgatgaatga aataaaacag gtcaggaagg aacaagccga aaacaataag     180
caattaatgg aaatgaggca agagaatcag aacttgaaaa gagaagtaaa gcaactacag     240
gaaagaatcg aatacataga aaaatacagt aagaagaaaa gcctgataat atcaggatta     300
aaaatggaca caaacgacga tagaaacatt agagaagaaa tggaaaattt cctagtcaga     360
gaactgcaag ttaaagtgaa attaaggaac gccacaaaaa ttggagagaa tctctgtgtt     420
atagaaacgg aaacaacgac tgaaaaaatg gagatattga aaaacaagag aaagttaaaa     480
aaccacaacg aacgcattta cataaacagt gacctaacga c                         521
```

<210> SEQ ID NO 227
<211> LENGTH: 627
<212> TYPE: DNA
<213> ORGANISM: Diabrotica virgifera virgifera

<400> SEQUENCE: 227

```
ggggagttcg ttcctgtacg tctgtctgtt cgttcgtgcg tgaccatttt tgatttctac      60
aattattgcc accgccatca ggagagtagc taaactcgga taacttaaat agtgttgtgc     120
ggattgtgat tttcgacatg ggagataaca agaataacga ttctcgaaga aaggtaaaga     180
aagtaaggaa agcggaagat ttagacgatt taaaacagga attagacatc gactatcata     240
agatctcacc agaagaacta tatcaaaggt ttcaaacaca cccagaaaac ggtcttagtc     300
atgcaaaagc gaaagaaaat ttggacaggg acggacccaa tgccctcaca ccaccaaaaa     360
caactcccga atgggtgaaa ttctgtaaaa atctcttcgg gggtttcgca ctcttacttt     420
ggattggtgc aatcatttgt ttcatcgcct actccataca ggctagtact gtagaagaac     480
```

```
cagcagatga taatctatat cttggcatcg tattagctgc cgttgttatc gttacaggta    540
tattttctta ttatcaagaa agcaaaagtt caaaaattat ggaatctttc aagaacatgg    600
tgccccagtt cgcgaccgtt cttaggg                                        627
```

<210> SEQ ID NO 228
<211> LENGTH: 643
<212> TYPE: DNA
<213> ORGANISM: Diabrotica virgifera virgifera

<400> SEQUENCE: 228

```
aggggtgaca acagaaaaat atagaaaatc atcctctgtg tttccgtttt gaacttaact     60
tgtatttagt ttaaaaaata atcatgtcta gaggaagcag tgcaggtttt gaccgacaca    120
taacaatttt ctcgcccgaa ggccgactct atcaagtaga gtatgctttt aaagccatta    180
accaagccgg ccccacttcg gtagcagtcc gaggagtaga tgctgcggcg tgtgtgaccc    240
agagaaagat cccggataag ctgattgatc ccaacacaat tacacatctg ttccagttaa    300
cagaacacac tggatgtgtg atgactggca tgattgctga cagcaagtcc caggtgcaga    360
gagctagata tgaggctgcc gagttcaaat ataagtttgg atatgagatg ccaatcgatg    420
ccttgtgtag gagagtatcg gatatttccc aggtttatac gcagaatgct gagatgagac    480
ctttgggttg ctccatgctt ctgataggat atgaccaaga aatgggacca tgtgtccaca    540
aagctgaccc tgctggctat tactgtggct acagagcagt aagtgtagga tccaaacaaa    600
ctgaagccaa cagctaccta gagaagaagc taaagaagaa aac                      643
```

<210> SEQ ID NO 229
<211> LENGTH: 639
<212> TYPE: DNA
<213> ORGANISM: Diabrotica virgifera virgifera

<400> SEQUENCE: 229

```
gataacgatc acaaggcaat aaataatcat tagcaatttc aactgttaca ttttcattat     60
cattagcaaa aaccaggtca agtaaaactc cgttacaatt tgtgatgtga ttaagctgaa    120
ataggttgta aaatgcaaaa gtatcaacta aagtatcagt agcagtgtta ctattattac    180
taaagacacc tcttttatca tggtaccatt cgctatttgg cagattgtag tctcctgtta    240
gaatgaactt gtgttcagga aaattgttac agacagattc tatactaata caatgattct    300
cataggatat taaggctgaa ttaggaggaa gatagactgt accaaatata taacattcat    360
tcagagtgca aacttcaaca aacagttcct ccaacttaca cgaacataag gcaatacaat    420
taaaattgaa aaatgtatcc attaatatat tataacaccc tgtaaattta gataataagt    480
attcttagat attaatttaa aattgttatt gtaataccat acaaaaaaaa acaaatagtc    540
tggctaattg gctatgtcaa agccattaat aaaaaaaatc cttatgggag ttttttagcgt   600 ggcgatgccg attttcttca aaataatttt caatcggac                           639
```

<210> SEQ ID NO 230
<211> LENGTH: 238
<212> TYPE: DNA
<213> ORGANISM: Diabrotica virgifera virgifera
<220> FEATURE:
<221> NAME/KEY: misc_feature
<222> LOCATION: 139
<223> OTHER INFORMATION: n = A,T,C or G

<400> SEQUENCE: 230

```
gggtattaac ttttattatt aatttgtata tcgtcgtaat taaatatttt tttagaatta    60
aaatatttaa aattttata  aaaaaattaa tcagatcaag gtgcagtgag agccaaattc   120
aataggaatt taccagccna ggctatggga catcgtattc gtattatgct gtacccatct   180
aagatatagt tgttttata  aatataaata agaaataaaa aatacgtttt ccaacccg    238
```

<210> SEQ ID NO 231
<211> LENGTH: 116
<212> TYPE: DNA
<213> ORGANISM: Diabrotica virgifera virgifera

<400> SEQUENCE: 231

```
gaaagttgtg tcttgaaaag tagaaatgac gtctaaagta tctcgtgata ctctatacga    60
gtgtgtgaat ggagtcttgg aaaatgccaa ggagaagaaa aggaactttt tggaaa       116
```

<210> SEQ ID NO 232
<211> LENGTH: 491
<212> TYPE: DNA
<213> ORGANISM: Diabrotica virgifera virgifera

<400> SEQUENCE: 232

```
cttatgtatt tagttatggt agtgtagtca tcttaacacc ccttcacccc tccctaacga    60
atctacgacc tagctcccgc acaacaaatg agctgccgtc ccgcaacgag gctttatgtg   120
tctgcttctt cttctttagc cccattctta cccccagta  tctctataga tagtcttcc   180 ttgttcccat atgagcagac atgtaaaacg catcaaactt tgggactcac ccatttcctt   240
acgccccgct caaatcgtca gatttttgaa atatacactc ctttccatgt acttaactta   300
ccttatctta atctgacaat ttcgagtttt ttttaaggat agagtttttt tttcgagccc   360
cccttaacga actcccctgt gttaagagcc aatatatggt agaggtacat ctgcagggta   420
ccaggtttct ccccatatga taatctgacg cgctcgagta actgcaaaaa tccccgcttg   480 ggctcccctac                                                         491
```

<210> SEQ ID NO 233
<211> LENGTH: 645
<212> TYPE: DNA
<213> ORGANISM: Diabrotica virgifera virgifera

<400> SEQUENCE: 233

```
ggggatgttg tgatggattt tttgagatgt caattttata aatttaaaat ttaattaaaa    60
atcaaaaggg attttatttt atgtctgata gttactggta tattaaaact ataaaaaata   120
ttttaagttt gaaatgaata atgtatttat gttctatatt aaaaggaaga ccaaaacact   180
tacagagaag ttttactca  gtgaaaaaat taattaaaga tgaagataac ttaggccgaa   240
gactttatca acaaattaaa gtcaaaggtc ctataactgt agctgattat atgaaggaag   300
tacttactaa ttctacaatg ggatattaca tgcataaaga tgttttttgga gtctcgggtg   360 attttatcac atctccagaa atcactcaga tgtttggaga aattgtagct gtttggttaa   420
taaatgagtg acaaaaaatg gggtctccaa agccgctaca gatagttgaa ctgggaccag   480
gaagaggaac tttggccagt gatatcctga gagtgtttaa tcattttaaa gtactagagc   540
aaacacgctt acagcttgtt gagattagta caacgttaag tgaaattcaa gctaaaaagt   600
tgtgtaatca aaataatgta atcgatgaga atcagcctat ctaca                   645
```

<210> SEQ ID NO 234
<211> LENGTH: 662

<212> TYPE: DNA
<213> ORGANISM: Diabrotica virgifera virgifera

<400> SEQUENCE: 234

```
ggggataata agttcgattt tttacgaaaa tgacaagtat cgagactgtg gggaccattg      60
tcctgaaatt gctgaagttg gtgatcaatt tgatatgtct catcttgtac cgaaccggat     120
atcaaggcta cttcttggga gtaggaggaa cctggaatct aaacgaagaa aaaaatcccg     180
atgcagaaat tgtggcttcc ggcgtattcg taggatttat gatttacaca ttcgtctcgc     240
tgatcagcct ttgcttcgct agtggagatc acaaaacgac attcactgat attctgatga     300
atatagtagg gattttttatg tggatagctg ctggagctac agctcttcat tattggcttg     360
ggtacttgtc cgaatacaaa tacacgacaa tagattctga acgacaagtt ggtttggcgt     420
taggagcgat gtgtataata aatggagcgg tctatcttgt agacggagta ctttccgcaa     480
tctttatcct caaagccaaa atgcaataac tttcatcgta atataaatat atttatttag     540
gttatatact ttactttaag cagctcaagt ataccgtgac atcccactca tacatcaatg     600
tctataattg tttcatgaca aatcatttaa tagtatttta aagcattcat tcgttcaaca     660
cc                                                                    662
```

<210> SEQ ID NO 235
<211> LENGTH: 677
<212> TYPE: DNA
<213> ORGANISM: Diabrotica virgifera virgifera

<400> SEQUENCE: 235

```
ggggaggttg gtgtggtttt gtcaacaaat aggttgatct attttttgtgt tctttaataa     60
taattgagaa ataattcgat aaaatgggta aaaaggcaga agtaggtact cccaagtacc    120
tggcaaataa aatgaaagcc aaaggtctgc aaaagcttcg atggtattgt caaatgtgtc    180
agaaacagtg cagagatgaa aatggtttca agtgccatac aacctctgaa tctcaccaaa    240
gacaactact gttgtttgca gacaactcca aaagtatat agatgacttc tcatttgatt     300
tcgcgaaggg atatatggag atccttcgaa gacaatttgg tacaaaaaga gtcaatgcta    360
acagagtcta tcaagaatac atacatgaca gggatcatgt ccacatgaat ggtactagat    420
gggtgacact tactggattt gttaaatggt taggtaaaac tggacaagct gttgttgacg    480
aaacagagaa aggttggtac atcacttaca tagatagaag tcccgagacg gtagaaaagg    540
cagaatcgaa aaagaaaaaa gagaaatgg ataagaacga tgaagagaag caaatagagt     600
ttgtagagaa gcaggctaga ttagcacaag agaaggcagg gccatcagtg gaaccaatct    660
atacagaatt agtgagg                                                   677
```

<210> SEQ ID NO 236
<211> LENGTH: 600
<212> TYPE: DNA
<213> ORGANISM: Diabrotica virgifera virgifera

<400> SEQUENCE: 236

```
ggggtacacg ctgggacccg aaagatggtg aactatgcct ggtcaggacg aagtcagggg     60
aaaccctgat ggaggtccgt agcgattctg acgtgcaaat cgatcgtcgg aactgggtat    120
aggggcgaaa gactaatcga accatctagt agctggttcc ctccgaagtt tccttcagga    180
tagctggcgc tcgttccgta cgagtttcat ccggtaaagc gaatgattag aggcattggg    240
gtcgaaacga cctcaaccta ttctcaaact ttaaatgggt gagatcttcg gcttgctcga    300
```

```
acttatgaag ccgtgagaaa cgaatcagag tgccaagtgg gccattttg gtaagcagaa      360 ctggcgctgt gggatgaacc aaacgttgag ttaaagcgcc aaaatcgacg cttatgggat      420
accatgaaag gcgttggtaa cttaagacag caggacggtg gccatggaag tcggaatccg      480
ccaaggagtg tgtaacaact cacctgccga agttactagc cctgaaaatg gatggcgcta      540
aagcgtcgtg cttatactca accgtcagcg gcatgtgcgg ttcgttaata gcgactatga      600
```

<210> SEQ ID NO 237
<211> LENGTH: 3928
<212> TYPE: DNA
<213> ORGANISM: Diabrotica virgifera virgifera

<400> SEQUENCE: 237

```
tgcagcgtga cccggtcgtg cccctctcta gagataatga gcattgcatg tctaagttat       60
aaaaaattac cacatatttt ttttgtcaca cttgtttgaa gtgcagttta tctatcttta      120
tacatatatt taaactttac tctacgaata atataatcta tagtactaca ataatatcag      180
tgttttagag aatcatataa atgaacagtt agacatggtc taaaggacaa ttgagtattt      240
tgacaacagg actctacagt tttatctttt tagtgtgcat gtgttctcct ttttttttgc      300
aaatagcttc acctatataa tacttcatcc attttattag tacatccatt tagggtttag      360
ggttaatggt ttttatagac taattttttt agtacatcta ttttattcta ttttagcctc      420
taaattaaga aaactaaaac tctattttag tttttttatt taataattta gatataaaat      480
agaataaaat aaagtgacta aaaattaaac aaataccctt taagaaatta aaaaaactaa      540
ggaaacattt ttcttgtttc gagtagataa tgccagcctg ttaaacgccg tcgacgagtc      600
taacggacac caaccagcga accagcagcg tcgcgtcggg ccaagcgaag cagacggcac      660
ggcatctctg tcgctgcctc tggacccctc tcgagagttc cgctccaccg ttggacttgc      720
tccgctgtcg gcatccagaa attgcgtggc ggagcggcag acgtgagccg gcacggcagg      780
cggcctcctc ctcctctcac ggcaccggca gctacggggg attccttttcc caccgctcct      840 tcgctttccc ttcctcgccc gccgtaataa atagacaccc cctccacacc ctctttcccc      900
aacctcgtgt tgttcggagc gcacacacac acaaccagat ctcccccaaa tccacccgtc      960
ggcacctccg cttcaaggta cgccgctcgt cctccccccc cccctctctct accttctcta     1020 gatcggcgtt ccgtccatg catggttagg gcccggtagt tctacttctg ttcatgtttg     1080
tgttagatcc gtgtttgtgt tagatccgtg ctgctagcgt tcgtacacgg atgcgacctg     1140
tacgtcagac acgttctgat tgctaacttg ccagtgtttc tctttgggga atcctgggat     1200
ggctctagcc gttccgcaga cgggatcgat ttcatgattt ttttttgttc gttgcatagg     1260
gtttggtttg ccctttttcct ttatttcaat atatgccgtg cacttgtttg tcgggtcatc     1320
ttttcatgct ttttttttgtc ttggttgtga tgatgtggtc tggttgggcg gtcgttctag     1380
atcggagtag aattctgttt caaactacct ggtggattta ttaattttgg atctgtatgt     1440
gtgtgccata catattcata gttacgaatt gaagatgatg gatggaaata tcgatctagg     1500
ataggtatac atgttgatgc gggttttact gatgcatata cagagatgct ttttgttcgc     1560
ttggttgtga tgatgtggtg tggttgggcg gtcgttcatt cgttctagat cggagtagaa     1620
tactgtttca aactacctgg tgtatttatt aattttggaa ctgtatgtgt gtgtcataca     1680
tcttcatagt tacgagttta agtggatgg aaatatcgat ctaggatagg tatacatgtt     1740
gatgtgggtt ttactgatgc atatacatga tggcatatgc agcatctatt catatgctct     1800
aaccttgagt acctatctat tataataaac aagtatgttt tataattatt ttgatcttga     1860
```

| | |
|---|---|
| tatacttgga tgatggcata tgcagcagct atatgtggat ttttttagcc ctgccttcat | 1920 |
| acgctattta tttgcttggt actgtttctt ttgtcgatgc tcaccctgtt gtttggtgtt | 1980 |
| acttctgcag accggtctct acgtacagtc cggactggcg ccttggcgcg gtaccacatg | 2040 |
| gttcgatatc aacaagtttg tacaaaaaag caggggcttt tctgattttt gacagcttct | 2100 |
| atagaagttt atcaagatgt tgatgccaaa aagaataga gtatgtattt acgaatacct | 2160 |
| cttcaaagag ggagtcatgg tagctaaaaa agattaccat gccccaaaac acctcgaact | 2220 |
| agaaactatc cctaaccttc aagtaattaa ggctttacaa tcacttaaat caaaaggtta | 2280 |
| cgtaaaggaa caattcgcct ggaggcatta ttattggtat ttgactaact ctggcatcga | 2340 |
| atacctccgc acattcttac acttacctgg agaaattgtc ccatctacct tgaaacgccc | 2400 |
| agcaaggaca gaaccaccc gtcctagacc agctgctctc agatctgaga catctaaacc | 2460 |
| ttcagaagac cgtgcaggat acagaaggac tcctggaggc cctggagctg acaagaaagc | 2520 |
| tgatgttggt ccaggaactg agatgttga gttcaggcaa ggattcggac gtggacgggc | 2580 |
| accacaataa atttattgat aagttaattt ttataaattg atcagccaat aaaaagtttg | 2640 |
| gttaaaaaaa aaaaaaaaaa aaaaaaaaaa aaacagcttt cttgtacaaa gtggtcgata | 2700 |
| tcaggtccgc cttgtttctc ctctgtctct tgatctgact aatcttggtt tatgattcgt | 2760 |
| tgagtaattt tggggaaagc ttcgtccaca gttttttttc gatgaacagt gccgcagtgg | 2820 |
| cgctgatctt gtatgctatc ctgcaatcgt ggtgaactta tttcttttat atcctttact | 2880 |
| cccatgaaaa ggctagtaat cttttctcgat gtaacatcgt ccagcactgc tattaccgtg | 2940 |
| tggtccatcc gacagtctgg ctgaacacat catacgatct atggagcaaa aatctatctt | 3000 |
| ccctgttctt taatgaagga cgtcattttc attagtatga tctaggaatg ttgcaacttg | 3060 |
| caaggaggcg tttctttctt tgaatttaac taactcgttg agtggccctg tttctcggac | 3120 |
| gtaaggcctt tgctgctcca cacatgtcca ttcgaatttt accgtgttta gcaagggcga | 3180 |
| aaagtttgca tcttgatgat ttagcttgac tatgcgattg cttttcctgga cccgtgcagc | 3240 |
| tgcccatcga ccactttgta caagaaagct gttttttttt ttttttttttt ttttttttt | 3300 |
| taaccaaact ttttattggc tgatcaattt ataaaaatta acttatcaat aaatttattg | 3360 |
| tggtgcccgt ccacgtccga atccttgcct gaactcaaca tctccagttc ctggaccaac | 3420 |
| atcagctttc ttgtcagctc cagggcctcc aggagtcctt ctgtatcctg cacggtcttc | 3480 |
| tgaaggttta gatgtctcag atctgagagc agctggtcta ggacgggtgg tttctgtcct | 3540 |
| tgctgggcgt ttcaaggtag atgggacaat ttctccaggt aagtgtaaga atgtgcggag | 3600 |
| gtattcgatg ccagagttag tcaaatacca ataataatgc ctccaggcga attgttcctt | 3660 |
| tacgtaacct tttgatttaa gtgattgtaa agccttaatt acttgaaggt tagggatagt | 3720 |
| ttctagttcg aggtgttttg gggcatggta atctttttta gctaccatga ctccctcttt | 3780 |
| gaagaggtat tcgtaaatac atactctatt cttttttggc atcaacatct tgataaactt | 3840 |
| ctatagaagc tgtcaaaaat cagaaagccc cctgcttttt tgtacaaact tgttgatggg | 3900 |
| gttaggccgc caccgcggtg gagctcga | 3928 |

<210> SEQ ID NO 238
<211> LENGTH: 4181
<212> TYPE: DNA
<213> ORGANISM: Diabrotica virgifera virgifera

<400> SEQUENCE: 238

```
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc tttttttttg     300
caaatagctt cacctatata atacttcatc cattttatta gtacatccat ttagggttta     360
gggttaatgg tttttataga ctaattttt tagtacatct atttattct atttagcct        420
ctaaattaag aaaactaaaa ctctatttta gttttttat ttaataattt agatataaaa       480
tagaataaaa taaagtgact aaaaattaaa caaatacct ttaagaaatt aaaaaaacta       540
aggaaacatt tttcttgttt cgagtagata atgccagcct gttaaacgcc gtcgacgagt     600
ctaacggaca ccaaccagcg aaccagcagc gtcgcgtcgg gccaagcgaa gcagacggca     660
cggcatctct gtcgctgcct ctggaccct ctcgagagtt ccgctccacc gttggacttg      720
ctccgctgtc ggcatccaga aattgcgtgg cggagcggca gacgtgagcc ggcacggcag     780
gcggcctcct cctcctctca cggcaccggc agctacgggg gattcctttc ccaccgctcc     840
ttcgcttcc cttcctcgcc cgccgtaata aatagacacc ccctccacac cctctttccc      900
caacctcgtg ttgttcggag cgcacacaca cacaaccaga tctcccccaa atccacccgt     960
cggcacctcc gcttcaaggt acgccgctcg tcctcccccc ccccctctc taccttctct     1020
agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gccctttcc tttatttcaa tatatgccgt gcacttgttt gtcgggtcat     1320
cttttcatgc ttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
gataggtata catgttgatg cgggttttac tgatgcatat acagagatgc ttttgttcg     1560
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920
tacgctattt atttgcttgg tactgttttct tttgtcgatg ctcaccctgt tgtttggtgt    1980
tacttctgca gaccggtctc tacgtacagt ccggactggc gccttggcgc ggtaccacat    2040
ggttcgatat caacaagttt gtacaaaaaa gcagggggct ttttcacaat gcaggcacca    2100
acgacaaagc caaaagagga tccaatccac tctgtccaag tttttggcag aaagaaatca    2160
gctacagccg tagcttattg caaaagaggt agaggagtct tgagggtaaa tggcagacct    2220
ctcagccaag tggagcctaa aatgctccaa gacaaacttc aagaacccat tcttcttctt    2280
ggaaaggaca aattctctgc tgttgacatc agagttagag taaatggtgg tggacatgtt    2340
tcccaaattt atgctattag acaagctatc tcaaaggctt tggtagctta ttaccaaaaa    2400
```

| | |
|---|---|
| tatgttgatg aagcatcaaa gaaggaattg aaggatatcc ttatccaata tgaccgtacc | 2460 |
| ttgttggtag ccgatcccag acgctgcgaa cccaagaaat tcggtggtcc aggtgctcgt | 2520 |
| gcccgctacc aaaaatctta ccgttaagtt cttttttaga tttaatgttg tgtttcttgt | 2580 |
| atgtattaag atatcaacaa taaacacaat tttttcccgc aaaaaaaaaa aaaaaaaaaa | 2640 |
| aaaaaaaaaa cagctttctt gtacaaagtg gtcgatatca ggtccgcctt gtttctcctc | 2700 |
| tgtctcttga tctgactaat cttggtttat gattcgttga gtaattttgg ggaaagcttc | 2760 |
| gtccacagtt ttttttcgat gaacagtgcc gcagtggcgc tgatcttgta tgctatcctg | 2820 |
| caatcgtggt gaacttattt cttttatatc ctttactccc atgaaaaggc tagtaatctt | 2880 |
| tctcgatgta acatcgtcca gcactgctat taccgtgtgg tccatccgac agtctggctg | 2940 |
| aacacatcat acgatctatg gagcaaaaat ctatcttccc tgttctttaa tgaaggacgt | 3000 |
| cattttcatt agtatgatct aggaatgttg caacttgcaa ggaggcgttt ctttctttga | 3060 |
| atttaactaa ctcgttgagt ggccctgttt ctcggacgta aggcctttgc tgctccacac | 3120 |
| atgtccattc gaattttacc gtgtttagca agggcgaaaa gtttgcatct tgatgattta | 3180 |
| gcttgactat gcgattgctt tcctggaccc gtgcagctgc ccatcgacca ctttgtacaa | 3240 |
| gaaagctgtt tttttttttt tttttttttt tttttttgc gggaaaaaat tgtgtttatt | 3300 |
| gttgatatct taatacatac aagaaacaca acattaaatc taaaaaagaa cttaacggta | 3360 |
| agattttggg tagcgggcac gagcacctgg accaccgaat ttcttgggtt cgcagcgtct | 3420 |
| gggatcggct accaacaagg tacggtcata ttggataagg atatccttca attccttctt | 3480 |
| tgatgcttca tcaacatatt tttggtaata agctaccaaa gcctttgaga tagcttgtct | 3540 |
| aatagcataa atttgggaaa catgtccacc accatttact ctaactctga tgtcaacagc | 3600 |
| agagaatttg tccttttccaa gaagaagaat gggttcttga agtttgtctt ggagcatttt | 3660 |
| aggctccact tggctgagag gtctgccatt taccctcaag actcctctac ctcttttgca | 3720 |
| ataagctacg gctgtagctg atttctttct gccaaaaact tggacagagt ggattggatc | 3780 |
| tcttttttggc tttgtcgttg gtgcctgcat tgtgaaaaag cccctgctt ttttgtacaa | 3840 |
| acttgttgat ggggttaggc cgccaccgcg gtggagctcg aattccggtc cgggtcacct | 3900 |
| ttgtccacca agatggaact gcggccgctc attaattaag tcaggcgcgc ctctagttga | 3960 |
| agacacgttc atgtcttcat cgtaagaaga cactcagtag tcttcggcca gaatggccat | 4020 |
| ctggattcag caggcctaga aggccattta atcctgagg atctggtctt cctaaggacc | 4080 |
| cgggatatcg gaccgattaa actttaattc ggtccgaagc ttgaagttcc tattccgaag | 4140 |
| ttcctattct ccagaaagta taggaacttc gcatgcctgc a | 4181 |

<210> SEQ ID NO 239
<211> LENGTH: 5247
<212> TYPE: DNA
<213> ORGANISM: Diabrotica virgifera virgifera

<400> SEQUENCE: 239

| | |
|---|---|
| gtgcagcgtg acccggtcgt gcccctctct agagataatg agcattgcat gtctaagtta | 60 |
| taaaaaatta ccacatatt ttttttgtcac acttgtttga agtgcagttt atctatcttt | 120 |
| atacatatat ttaaacttta ctctacgaat aatataatct atagtactac aataatatca | 180 |
| gtgtttaga gaatcatata aatgaacagt tagacatggt ctaaaggaca attgagtatt | 240 |
| ttgacaacag gactctacag ttttatcttt ttagtgtgca tgtgttctcc ttttttttg | 300 |

```
caaatagctt cacctatata atacttcatc cattttatta gtacatccat ttagggttta   360
gggttaatgg ttttttataga ctaattttttt tagtacatct attttattct attttagcct   420
ctaaattaag aaaactaaaa ctctatttta gttttttttat ttaataattt agatataaaa   480
tagaataaaa taaagtgact aaaaattaaa caaataccct ttaagaaatt aaaaaaacta   540
aggaaacatt tttcttgttt cgagtagata atgccagcct gttaaacgcc gtcgacgagt   600
ctaacggaca ccaaccagcg aaccagcagc gtcgcgtcgg gccaagcgaa gcagacggca   660
cggcatctct gtcgctgcct ctggacccct ctcgagagtt ccgctccacc gttggacttg   720
ctccgctgtc ggcatccaga aattgcgtgg cggagcggca gacgtgagcc ggcacggcag   780
gcggcctcct cctcctctca cggcaccggc agctacgggg gattcctttc ccaccgctcc   840 ttcgcttttcc cttcctcgcc cgccgtaata aatagacacc ccctccacac cctctttccc   900
caacctcgtg ttgttcggag cgcacacaca cacaaccaga tctcccccaa atccacccgt   960
cggcacctcc gcttcaaggt acgccgctcg tcctccccccc ccccctctc taccttctct   1020 agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gcccttttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc ttttttgttcg   1560 cttggttgtg atgatgtggt gtggttgggc ggtcgttcat tcgttctaga tcggagtaga   1620
atactgtttc aaactacctg gtgtatttat taatttggga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttttagc cctgccttca   1920 tacgctattt atttgcttgg tactgtttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcagggggga gtagttgttt ttattgtgag   2100
atgatttcga agttcaccct ggttttcttg gtttgcattg tcgcaccagc gataggtgat   2160
ccaccagttc cagaatggag tgacacttat agcgtagaag gaactatcca tttgccttat   2220
gcagaaatag tagagccttt ccatgcttgg tatgatggaa aatctaaaaa ttcgcgcatt   2280
gattactaca atgggacggc taagacatac caacttggag gaaatggaaa tggtgtccaa   2340
ctgaaagtag ttccattcac tacagaggag gtcctaaacc aaataacgtg cttccagatc   2400
aatggaactg aagacgatcc agtgactcct caatcgattt tgccagattt agaaggattt   2460
gaatatcaag gcatacagga gtatggagat agagaactag aggtatggtt tctaaaaact   2520
gtccagttag aaaagaaaa cgaatacact ctatgggttg tccgagatga gcatggtaaa   2580
gctattccag ttaaatatga tatgagagga tacaattcgt tattgggaag ccactacgat   2640
cattactatt tgctatacac atcgaagtct tacaggactc acaagattga tccctccgtt   2700
```

```
tttgaagtag aaactaatag tgaatgcaga agttttcctg acccggaaaa tcaacatgtt    2760
cacatcatga accccatggc cgaatacatt cgtcccgaaa aaagtgagca cgtggactca    2820
agctttggcg attttataaa taaccacaac aaaaattacg cagacacaaa agaacacgtt    2880
tttagaaaag aggttttccg tcaaaacgtc aggttcatcg aatctgtcaa ccgacaaaat    2940
aaaggtaagt gttatagtag gggagcaaag taggtgtgct aaatttgcag tcactcgaga    3000
gttatggcga cctattgggt tgtgattatt aggtcctaaa accaaaaaaa gttaagtaaa    3060
attttccatt tccaacaatc gttttttccg attatagcgt catctatcca taattcgaaa    3120
aaatgtctct aataaaagtt gcttattttt acgaaaaaaa aaaaaaaaaa aaaaaaaaa    3180 aaacagcttt cttgtacaaa gtggtcgata tcaggtccgc cttgtttctc ctctgtctct    3240
tgatctgact aatcttggtt tatgattcgt tgagtaattt tggggaaagc ttcgtccaca    3300
gttttttttc gatgaacagt gccgcagtgg cgctgatctt gtatgctatc ctgcaatcgt    3360
ggtgaactta tttcttttat atccttact cccatgaaaa ggctagtaat ctttctcgat    3420
gtaacatcgt ccagcactgc tattaccgtg tggtccatcc gacagtctgg ctgaacacat    3480
catacgatct atggagcaaa aatctatctt ccctgttctt taatgaagga cgtcattttc    3540
attagtatga tctaggaatg ttgcaacttg caaggaggcg tttctttctt tgaatttaac    3600
taactcgttg agtggccctg tttctcggac gtaaggcctt tgctgctcca cacatgtcca    3660
ttcgaatttt accgtgttta gcaagggcga aaagtttgca tcttgatgat ttagcttgac    3720
tatgcgattc ctttcctgga cccgtgcagc tgcccatcga ccactttgta caagaaagct    3780 gtttttttt ttttttttt tttttttttt tcgtaaaaat aagcaacttt tattagagac    3840
attttttcga attatggata gatgacgcta taatcgaaaa aaacgattgt tggaaatgga    3900 aaatttttact taactttttt tggttttagg acctaataat cacaacccaa taggtcgcca    3960
taactctcga gtgactgcaa atttagcaca cctactttgc tcccctacta taacacttac    4020
cttttatttg tcggttgaca gattcgatga acctgacgtt ttgacggaaa acctcttttc    4080
taaaaacgtg ttcttttgtg tctgcgtaat ttttgttgtg gttatttata aaatcgccaa    4140
agcttgagtc cacgtgctca cttttttcgg gacgaatgta ttcggccatg gggttcatga    4200
tgtgaacatg ttgatttccg ggtccaggaa aacttctgca ttcactatta gtttctactt    4260
caaaaacgga gggatcaatc ttgtgagtcc tgtaagactt cgatgtgtat agcaaatagt    4320
aatgatcgta gtggcttccc aataacgaat tgtatcctct catatcatat ttaactggaa    4380
tagctttacc atgctcatct cggacaaccc atagagtgta ttcgttttct ttttctaact    4440
ggacagtttt tagaaaccat acctctagtt ctctatctcc atactcctgt atgccttgat    4500
attcaaatcc ttctaaatct ggcaaaatcg attgaggagt cactggatcg tcttcagttc    4560
cattgatctg gaagcacgtt atttggttta ggacctcctc tgtagtgaat ggaactactt    4620
tcagttggac accatttcca tttcctccaa gttggtatgt cttagccgtc ccattgtagt    4680
aatcaatgcg cgaattttta gattttccat cataccaagc atggaaaggc tctactattt    4740
ctgcataagg caaatggata gttccttcta cgctataagt gtcactccat tctggaactg    4800
gtggatcacc tatcgctggt gcgacaatgc aaaccaagaa aaccagggtg aacttcgaaa    4860
tcatctcaca ataaaaacaa ctactccccc ctgctttttt gtacaaactt gttgatgggg    4920
ttaggccgcc accgcggtgg agctcgaatt ccggtccggg tcacctttgt ccaccaagat    4980
ggaactgcgg ccgctcatta attaagtcag gcgcgcctct agttgaagac acgttcatgt    5040
```

```
cttcatcgta agaagacact cagtagtctt cggccagaat ggccatctgg attcagcagg    5100
cctagaaggc catttaaatc ctgaggatct ggtcttccta aggacccggg atatcggacc    5160
gattaaactt taattcggtc cgaagcttga agttcctatt ccgaagttcc tattctccag    5220
aaagtatagg aacttcgcat gcctgca                                        5247
```

<210> SEQ ID NO 240
<211> LENGTH: 4939
<212> TYPE: DNA
<213> ORGANISM: Diabrotica virgifera virgifera

<400> SEQUENCE: 240

```
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc ttttttttg      300 caaatagctt cacctatata atacttcatc cattttatta gtacatccat ttagggttta    360
gggttaatgg ttttatagaa ctaatttttt tagtacatct attttattct attttagcct    420
ctaaattaag aaaactaaaa ctctatttta gtttttttat ttaataattt agatataaaa    480
tagaataaaa taaagtgact aaaaattaaa caaatacct ttaagaaatt aaaaaaacta     540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccct ctcgagagtt ccgctccacc gttggacttg     720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840 ttcgcttttcc cttcctcgcc cgccgtaata aatagacacc cctccacac cctctttccc     900 caacctcgtg ttgttcggag cgcacacaca cacaaccaga tctcccccaa atccacccgt    960
cggcacctcc gcttcaaggt acgccgctcg tcctccccc ccccctctc taccttctct      1020 agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gccccttttcc tttatttcaa tatatgccgt gcacttgttt gtcgggtcat    1320
cttttcatgc ttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
gataggtata catgttgatg cgggttttac tgatgcatat acagagatgc ttttgttcg      1560 cttggttgtg atgatgtggt gtggttgggc ggtcgttcat tcgttctaga tcggagtaga    1620
atactgtttc aaactacctg gtgtatttat taatttggga actgtatgtg tgtgtcatac    1680
atcttcatag ttacgagttt aagatggatg gaaatatcga tctaggatag gtacacatgt    1740
tgatgtgggt tttactgatg catatacatg atggcatatg cagcatctat tcatatgctc    1800
taaccttgag tacctatcta tttataataaa caagtatgtt ttataattat ttgatcttg    1860 atatacttgg atgatggcat atgcagcagc tatatgtgga ttttttttagc cctgccttca    1920
```

```
tacgctattt atttgcttgg tactgtttct tttgtcgatg ctcaccctgt tgtttggtgt    1980
tacttctgca gaccggtctc tacgtacagt ccggactggc gccttggcgc ggtaccacat    2040
ggttcgatat caacaagttt gtacaaaaaa gcagggggat tacaaactga actcaacaac    2100
ctcttttcat cttcgacccg tttgccggcg ttagcttgta aaacattcct gttaaaatca    2160
cgaaccatcc gttaaaagaa atggcagatg aatattttt tgctttaacc ctcaaaggta    2220
aaaacagtga aatctgggat ccagaagcga agggagcaga ggattaccaa ggggacaca    2280
aattgatcat taaacaagct tgttgggac ccgaagccca agaaggtgaa gtaaatgttg    2340
tacaagtaga agctatgacg tggaaagact cagttaaaat cccaattgcc acactaaaag    2400
ccggaggccc aaataaccaa gtattgttag atctgtcatt cccagaccca ccagtcacat    2460
tttcacttat acaaggtaat ggaccagttc acattgtagg ccatcattta attggtagtc    2520
cgatggaaga attcgatgaa atggatgaat tagaagagga aatgttggat gatgaagaag    2580
gggaagaagg agccgaggaa gatgaggatg aagatgaacc caaagccaaa aaagcaaaat    2640
cagcgactaa cgccaagggc aaaactcccg taaaaaacaa ttcaaaggct gcaaagaaat    2700
aaacaagttc atctaatccc caaaccacct cctttgtaat gttaagttag ttttttaatg    2760
tatctcggga gttgttatac atccattaac agatcaaccg taacaatttc tcttaaatat    2820
aagtataata tttatgttt cttgacgtca taagattttg tgaaagtttc ttttattcca    2880
ggtgtaactc ttagtttaa tgtgatcaat attttaagc tggaaacgta tttatttcct    2940
ttgaaatcat ccaattttgt tgtaaatatg cagccctcat taaaccatttt tttgtagcaa    3000
aaaaaaaaaa aaaaaaaaa aaaaaaaaac agctttcttg tacaaagtgg tcgatatcag    3060
gtccgccttg tttctcctct gtctcttgat ctgactaatc ttggtttatg attcgttgag    3120
taattttggg gaaagcttcg tccacagttt tttttcgatg aacagtgccg cagtggcgct    3180
gatcttgtat gctatcctgc aatcgtggtg aacttatttc ttttatatcc tttactccca    3240
tgaaaaggct agtaatcttt ctcgatgtaa catcgtccag cactgctatt accgtgtggt    3300
ccatccgaca gtctggctga acacatcata cgatctatgg agcaaaaatc tatcttccct    3360
gttcttaat gaaggacgtc attttcatta gtatgatcta ggaatgttgc aacttgcaag    3420
gaggcgtttc tttctttgaa tttaactaac tcgttgagtg gccctgtttc tcggacgtaa    3480
ggccttttgct gctccacaca tgtccattcg aattttaccg tgtttagcaa gggcgaaaag    3540
tttgcatctt gatgatttag cttgactatg cgattgcttt cctggacccg tgcagctgcc    3600
catcgaccac tttgtacaag aaagctgttt tttttttt tttttttttt tttttttgc    3660
tacaaaaaat ggtttaatga gggctgcata tttacaacaa aattggatga tttcaaagga    3720
aataaatacg tttccagctt aaaaatattg atcacattaa aactaagagt tacacctgga    3780
ataaagaaa ctttcacaaa atcttatgac gtcaagaaac ataaatatt atacttatat    3840
ttaagagaaa ttgttacggt tgatctgtta atggatgtat aacaactccc gagatacatt    3900
aaaaaactaa cttaacatta caaggaggt ggtttgggga ttagatgaac ttgtttatttt    3960
ctttgcagcc tttgaattgt ttttacggg agttttgccc ttggcgttag tcgctgattt    4020
tgctttttg gctttgggtt catcttcatc ctcatcttcc tcggctcctt cttcccttc    4080
ttcatcatcc aacatttcct cttctaattc atccatttca tcgaattctt ccatcggact    4140
accaattaaa tgatggccta caatgtgaac tggtccatta ccttgtataa gtgaaaatgt    4200
gactggtggg tctgggaatg acagatctaa caatacttgg ttatttgggc ctccggcttt    4260
```

```
tagtgtggca attgggattt taactgagtc tttccacgtc atagcttcta cttgtacaac   4320
atttacttca ccttcttggg cttcgggtcc caacaaagct tgtttaatga tcaatttgtg   4380 tccccccttgg taatcctctg ctcccttcgc ttctggatcc cagatttcac tgtttttacc   4440
tttgagggtt aaagcaaaaa aatattcatc tgccatttct tttaacggat ggttcgtgat   4500
tttaacagaa atgttttaca agctaacgcc ggcaaacggg tcgaagatga aaagaggttg   4560
ttgagttcag tttgtaatcc ccctgctttt ttgtacaaac ttgttgatgg ggttaggccg   4620
ccaccgcggt ggagctcgaa ttccggtccg ggtcaccttt gtccaccaag atggaactgc   4680
ggccgctcat taattaagtc aggcgcgcct ctagttgaag acacgttcat gtcttcatcg   4740
taagaagaca ctcagtagtc ttcggccaga atggccatct ggattcagca ggcctagaag   4800
gccatttaaa tcctgaggat ctggtcttcc taaggacccg ggatatcgga ccgattaaac   4860
tttaattcgg tccgaagctt gaagttccta ttccgaagtt cctattctcc agaaagtata   4920
ggaacttcgc atgcctgca                                                4939
```

<210> SEQ ID NO 241
<211> LENGTH: 4661
<212> TYPE: DNA
<213> ORGANISM: Diabrotica virgifera virgifera

<400> SEQUENCE: 241

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg tttttataga ctaatttttt tagtacatct attttattct attttagcct    420
ctaaattaag aaaactaaaa ctctatttta gtttttttat ttaataattt agatataaaa    480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc ccccctctc taccttctct    1020 agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttttcc tttatttcaa tatatgccgt gcacttgttt gtcgggtcat  1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
```

```
tgtgtgccat acatattcat agttacgaat tgaagatgat ggatggaaat atcgatctag    1500
gataggtata catgttgatg cgggttttac tgatgcatat acagagatgc tttttgttcg    1560
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgtttct tttgtcgatg ctcaccctgt tgtttggtgt    1980
tacttctgca gaccggtctc tacgtacagt ccggactggc gccttggcgc ggtaccacat    2040
ggttcgatat caacaagttt gtacaaaaaa gcaggggtc taattctaat agcccgtatc    2100
tgccaagaga tttgtcaagt aggttttttc tgttttttt ttcttatcaa gtctaaagat    2160
attcagttac gaggtattag atgactggta ttagaggttc ctagaatttt ttgtttagat    2220
cagagttttg tgtatagatg gataactgtt ttgttagtcg tttgccacga aaattggaaa    2280
ttaagttttt ttgcagatac ggggtataga attagactgt caatatggaa acaatgagtt    2340
ttgtaaacat attgatgacg acaatgtatg ttcatgtcat atttcatatg catctataga    2400
tgtagtttga atatgcacaa ttcgttattt taaaaatgtc atctagacgt ttcaatggaa    2460
attagacatc tatagatgtt atgtctgtca acatgttaat atttgaggct atcagcaaca    2520
gtggcataag ctcaaaaact aagttttgag ataaatgcaa tctttgcatt catattttca    2580
ttatgtttat gagataaagc tacaaattat gtagcatcat ctagccaaat atagaggtag    2640
gttgtgtagg tccctgttaa tcggaagatt taattttgct gcttttattg atatattaat    2700
ctaaaaatgc tgaatttgtg acttagtcca ctgttgttct gagggcccca tttaaatgtt    2760
ttcaaaatat gtatagtcaa aactcctttt acatgatgat aagaacgtag ggacatgtga    2820
ataaataccc tgattattta cgttgatggg aatctctctg aaaaaaaaaa aaaaaaaaaa    2880
aaaaaaaaaa cagctttctt gtacaaagtg gtcgatatca ggtccgcctt gtttctcctc    2940
tgtctcttga tctgactaat cttggtttat gattcgttga gtaattttgg ggaaagcttc    3000
gtccacagtt tttttcgat gaacagtgcc gcagtgcgc tgatcttgta tgctatcctg    3060
caatcgtggt gaacttattt cttttatatc ctttactccc atgaaaaggc tagtaatctt    3120
tctcgatgta acatcgtcca gcactgctat taccgtgtgg tccatccgac agtctggctg    3180
aacacatcat acgatctatg gagcaaaaat ctatcttccc tgttctttaa tgaaggacgt    3240
cattttcatt agtatgatct aggaatgttg caacttgcaa ggaggcgttt ctttctttga    3300
atttaactaa ctcgttgagt ggccctgttt ctcggacgta aggcctttgc tgctccacac    3360
atgtccattc gaattttacc gtgtttagca agggcgaaaa gtttgcatct tgatgattta    3420
gcttgactat gcgattgctt tcctggaccc gtgcagctgc ccatcgacca ctttgtacaa    3480
gaaagctgtt tttttttttt tttttttttt tttttttttca gagagattcc catcaacgta    3540
aataatcagg gtatttattc acatgtccct acgttcttat catcatgtaa aaggagtttt    3600
gactatacat attttgaaaa catttaaatg gggccctcag aacaacagtg gactaagtca    3660
caaattcagc attttagat taatatatca ataaaagcag caaaattaaa tcttccgatt    3720
aacagggacc tacacaacct acctctatat ttggctagat gatgctacat aatttgtagc    3780
```

| | |
|---|---|
| tttatctcat aaacataatg aaaatatgaa tgcaaagatt gcatttatct caaaacttag | 3840 |
| tttttgagct tatgccactg ttgctgatag cctcaaatat taacatgttg acagacataa | 3900 |
| catctataga tgtctaattt ccattgaaac gtctagatga cattttttaaa ataacgaatt | 3960 |
| gtgcatattc aaactacatc tatagatgca tatgaaaatat gacatgaaca tacattgtcg | 4020 |
| tcatcaatat gtttacaaaa ctcattgttt ccatattgac agtctaattc tatacccccgt | 4080 |
| atctgcaaaa aaacttaatt tccaattttc gtggcaaacg actaacaaaa cagttatcca | 4140 |
| tctatacaca aaactctgat ctaaacaaaa aattctagga acctctaata ccagtcatct | 4200 |
| aatacctcgt aactgaatat ctttagactt gataagaaaa aaaaaacaga aaaaacctac | 4260 |
| ttgacaaatc tcttggcaga tacgggctat tagaattaga ccccctgctt ttttgtacaa | 4320 |
| acttgttgat ggggttaggc cgccaccgcg gtggagctcg aattccggtc cgggtcacct | 4380 |
| ttgtccacca agatggaact gcggccgctc attaattaag tcaggcgcgc ctctagttga | 4440 |
| agacacgttc atgtcttcat cgtaagaaga cactcagtag tcttcggcca gaatggccat | 4500 |
| ctggattcag caggcctaga aggccattta aatcctgagg atctggtctt cctaaggacc | 4560 |
| cgggatatcg gaccgattaa actttaattc ggtccgaagc ttgaagttcc tattccgaag | 4620 |
| ttcctattct ccagaaagta taggaacttc gcatgcctgc a | 4661 |

<210> SEQ ID NO 242
<211> LENGTH: 5116
<212> TYPE: DNA
<213> ORGANISM: Diabrotica virgifera virgifera

<400> SEQUENCE: 242

| | |
|---|---|
| gtgcagcgtg acccggtcgt gcccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag ttttatcttt ttagtgtgca tgtgttctcc tttttttttg | 300 |
| caaatagctt cacctatata atacttcatc cattttatta gtacatccat ttagggttta | 360 |
| gggttaatgg ttttttataga ctaatttttt tagtacatct attttattct attttagcct | 420 |
| ctaaattaag aaaactaaaa ctctatttta gtttttttat ttaataattt agatataaaa | 480 |
| tagaataaaa taaagtgact aaaaattaaa caaataccct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggaccccct ctcgagagtt ccgctccacc gttggacttg | 720 |
| ctccgctgtc ggcatccaga aattgcgtgg cggagcggca gacgtgagcc ggcacggcag | 780 |
| gcggcctcct cctcctctca cggcaccggc agctacgggg gattccttttc ccaccgctcc | 840 |
| ttcgctttcc cttcctcgcc cgccgtaata aatagacacc ccctccacac cctctttccc | 900 |
| caacctcgtg ttgttcggag cgcacacaca cacaaccaga tctcccccaa atccacccgt | 960 |
| cggcacctcc gcttcaaggt acgcgctcg tcctcccccc ccccctctc taccttctct | 1020 |
| agatcggcgt tccggtccat gcatggttag ggcccggtag ttctacttct gttcatgttt | 1080 |
| gtgttagatc cgtgtttgtg ttagatccgt gctgctagcg ttcgtacacg gatgcgacct | 1140 |
| gtacgtcaga cacgttctga ttgctaactt gccagtgttt ctctttgggg aatcctggga | 1200 |
| tggctctagc cgttccgcag acgggatcga tttcatgatt tttttttgttt cgttgcatag | 1260 |

```
ggtttggttt gccctttttcc tttatttcaa tatatgccgt gcacttgttt gtcgggtcat    1320
cttttcatgc ttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
dataggtata catgttgatg cgggttttac tgatgcatat acagagatgc tttttgttcg    1560
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgttttct tttgtcgatg ctcaccctgt tgtttggtgt    1980
tacttctgca gaccggtctc tacgtacagt ccggactggc gccttggcgc ggtaccacat    2040
ggttcgatat caacaagttt gtacaaaaaa gcaggggag tcgtcaacat caatttcaag    2100
tttcaagaaa aagcaaatca ctacgacttg ccggattttg tagtagtgtt aattttgtat    2160
taaaaaatca aaatgagttc tattggaact gggtacgatt tatcagcttc ccaattctct    2220
cctgatggaa gagtatttca agttgaatat gcaatgaaag cagttgaaaa tagtggcacc    2280
gtaataggcc tccgaggtac agatggcatt gtattggctg ctgaaaagct cattatgtca    2340
aaattgcatg aaccaagtac aaataaacga attttcaaca ttgataaaca cataggaatg    2400
gcattttcag gcttaatagc tgatgcaagg caaatcgttg agattgctag aaaagaagca    2460
tcaaattata gacatcaata tggttcaaat attcctctta aatacctaaa tgatagagta    2520
agcatgtaca tgcatgcata cactttatac agtgctgtta gaccatttgg ttgcagtgtc    2580
atcttggcca gttatgaaga tagtgaccca tctatgtatc tgattgatcc atctggagtt    2640
agctatggat actttggatg tgctacaggt aaagcaaaac agtctgcaaa gactgaaata    2700
gaaaaattga agatggggaa tctaacatgc aaagaacttg ttaaagaagc agccaaaatc    2760 attatttgg tccatgatga gctgaaggat aagaattttg aactggaact ttcatgggta    2820
tgcaaagata cgaatggttt acataccaaa gtgcctgaat cagtgttgc tgatgcagaa    2880 aaagctgcca acaagcaat ggaagcagat tcagaatcag atacagaaga tatgtaataa    2940
ctacatttag tttttaatat ttcgctgatg gtggctgttc ttacaatatt tcgtgtgtta    3000
tgttcatata ttatgtaata ctgtgagaat ttccatttca aggataggtt tataacttt    3060 ttttctaata aatacataac tttatgtcaa aaaaaaaaaa aaaaaaaaa aaaaaaacag    3120 ctttcttgta caaagtggtc gatatcaggt ccgccttgtt tctcctctgt ctcttgatct    3180
gactaatctt ggtttatgat tcgttgagta attttgggga aagcttcgtc cacagttttt    3240
tttcgatgaa cagtgccgca gtggcgctga tcttgtatgc tatcctgcaa tcgtggtgaa    3300
cttatttctt ttatatcctt tactcccatg aaaaggctag taatctttct cgatgtaaca    3360
tcgtccagca ctgctattac cgtgtggtcc atccgacagt ctggctgaac acatcatacg    3420
atctatggag caaaaatcta tcttccctgt tctttaatga aggacgtcat tttcattagt    3480
atgatctagg aatgttgcaa cttgcaagga ggcgttctt tctttgaatt taactaactc    3540
gttgagtggc cctgtttctc ggacgtaagg cctttgctgc tccacacatg tccattcgaa    3600
```

```
ttttaccgtg tttagcaagg gcgaaaagtt tgcatcttga tgatttagct tgactatgcg    3660
attgctttcc tggacccgtg cagctgccca tcgaccactt tgtacaagaa agctgttttt    3720
tttttttttt tttttttttt ttttgacata aagttatgta tttattagaa aaaaaagtta    3780
taaacctatc cttgaaatgg aaattctcac agtattacat aatatatgaa cataacacac    3840
gaaatattgt aagaacagcc accatcagcg aaatattaaa actaaatgt agttattaca     3900 tatcttctgt atctgattct gaatctgctt ccattgcttg tttggcagct tttctgcat     3960 cagcaaacac tgattcaggc actttggtat gtaaaccatt cgtatctttg catacccatg    4020
aaagttccag ttcaaaattc ttatccttca gctcatcatg gaccaaataa atgattttgg    4080
ctgcttcttt aacaagttct tgcatgttta gattccccat cttcaatttt tctatttcag    4140
tctttgcaga ctgttttgct ttacctgtag cacatccaaa gtatccatag ctaactccag    4200
atggatcaat cagatacata gatgggtcac tatcttcata actggccaag atgacactgc    4260
aaccaaatgg tctaacagca ctgtataaag tgtatgcatg catgtacatg cttactctat    4320
catttaggta tttaagagga atatttgaac catattgatg tctataattt gatgcttctt    4380
ttctagcaat ctcaacgatt tgccttgcat cagctattaa gcctgaaaat gccattccta    4440
tgtgtttatc aatgttgaaa attcgttat ttgtacttgg ttcatgcaat tttgacataa      4500
tgagcttttc agcagccaat acaatgccat ctgtacctcg gaggcctatt acggtgccac    4560
tattttcaac tgctttcatt gcatattcaa cttgaaatac tcttccatca ggagagaatt    4620
gggaagctga taaatcgtac ccagttccaa tagaactcat tttgattttt taatacaaaa    4680
ttaacactac tacaaaatcc ggcaagtcgt agtgatttgc ttttcttga aacttgaaat      4740 tgatgttgac gactcccct gcttttttgt acaaacttgt tgatggggtt aggccgccac      4800
cgcggtggac ctcgaattcc ggtccgggtc acctttgtcc accaagatgg aactgcggcc    4860
gctcattaat taagtcaggc gcgcctctag ttgaagacac gttcatgtct tcatcgtaag    4920
aagacactca gtagtcttcg gccagaatgg ccatctggat tcagcaggcc tagaaggcca    4980
tttaaatcct gaggatctgg tcttcctaag gacccgggat atcggaccga ttaaacttta    5040
attcggtccg aagcttgaag ttcctattcc gaagttccta ttctccagaa agtataggaa    5100
cttcgcatgc ctgcag                                                    5116
```

<210> SEQ ID NO 243
<211> LENGTH: 4995
<212> TYPE: DNA
<213> ORGANISM: Diabrotica virgifera virgifera

<400> SEQUENCE: 243

```
gtgcagcgtg acccggtcgt gcccctctct agagataatg agcattgcat gtctaagtta      60
taaaaaatta ccacatattt ttttgtcac acttgtttga agtgcagttt atctatcttt      120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc tttttttttg      300
caaatagctt cacctatata atacttcatc catttttatta gtacatccat ttagggttta    360
gggttaatgg ttttatatag ctaatttttt tagtacatct attttattct atttttagcct    420 ctaaattaag aaaactaaaa ctctatttta gtttttttat ttaataattt agatataaaa     480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt     600
```

-continued

```
ctaacggaca ccaaccagcg aaccagcagc gtcgcgtcgg gccaagcgaa gcagacggca    660
cggcatctct gtcgctgcct ctggaccect ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtt ttgttcggag cgcacacaca cacaaccaga tctcccccaa atccacccgt    960
cggcacctcc gcttcaaggt acgccgctcg tcctcccccc ccccctctc taccttctct    1020
agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gcccttttcc tttatttcaa tatatgccgt gcacttgttt gtcgggtcat    1320
cttttcatgc ttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
gataggtata catgttgatg cgggttttac tgatgcatat acagagatgc ttttgttcg     1560
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920
tacgctattt atttgcttgg tactgtttct tttgtcgatg ctcaccctgt tgtttggtgt    1980
tacttctgca gaccggtctc tacgtacagt ccggactggc gccttggcgc ggtaccacat    2040
ggttcgatat caacaagttt gtacaaaaaa gcagggggct ttttcagcag ttgtcaaagc    2100
actgccacaa tgggtaaaat aatgaaatca ggaaaagtcg tattggtcct cggggggcga    2160
tacgccggca gaaaagccgt agtcgtcaaa acctacgatg aaggtacatc agataaacaa    2220
tacggacatg ccttagtagc tggaattgat aggtacccaa ggaaaatcca caaacgcatg    2280
ggcaaaggca aaatgcacaa gaggtccaag atcaagcctt ttatcaaagt attgaactac    2340
aaccatctca tgcccactag atactctgta gatttggcat cagacttgaa agttgtaccc    2400
aaggacctca agatgccat gaagaggaag aaggctagat ccagacccg tgtcaaattt    2460
gaggaaaggt ataagcaagg aaagaacaaa tggttcttcc aaaaattgag gttctaggct    2520
gtagatttaa ttttataatt gtacactttt tattttgaga ataaaatgtg gataaatgca    2580
aaaaaaaaa aaaaaaaaa aaaaaaaaac agctttcttg tacaaagtgg tcgatatcag    2640
gtccgccttg tttctcctct gtctcttgat ctgactaatc ttggtttatg attcgttgag    2700
taattttggg gaaagcttcg tccacagttt ttttcgatg aacagtgccg cagtggcgct    2760
gatcttgtat gctatcctgc aatcgtggtg aacttatttc ttttatatcc tttactccca    2820
tgaaaaggct agtaatcttt ctcgatgtaa catcgtccag cactgctatt accgtgtggt    2880
ccatccgaca gtctggctga acacatcata cgatctatgg agcaaaaatc tatcttccct    2940
```

```
gttctttaat gaaggacgtc attttcatta gtatgatcta ggaatgttgc aacttgcaag    3000
gaggcgtttc tttctttgaa tttaactaac tcgttgagtg gccctgtttc tcggacgtaa    3060
ggcctttgct gctccacaca tgtccattcg aattttaccg tgtttagcaa gggcgaaaag    3120
tttgcatctt gatgatttag cttgactatg cgattgcttt cctggacccg tgcagctgcc    3180
catcgaccac tttgtacaag aaagctgttt ttttttttt ttttttttt ttttttttgca    3240
tttatccaca ttttattctc aaaataaaaa gtgtacaatt ataaaattaa atctacagcc    3300
tagaacctca attttggaa gaaccatttg ttctttcctt gcttatacct ttcctcaaat    3360
ttgacacggg tctggaatct agccttcttc ctcttcatgg catctttgag gtccttgggt    3420
acaactttca agtctgatgc caaatctaca gagtatctag tgggcatgag atggttgtag    3480
ttcaatactt tgataaaagg cttgatcttg gacctcttgt gcattttgcc tttgcccatg    3540
cgtttgtgga ttttccttgg gtacctatca attccagcta ctaaggcatg tccgtattgt    3600
ttatctgatg taccttcatc gtaggttttg acgactacgg cttttctgcc ggcgtatcgg    3660
cccccgagga ccaatacgac ttttcctgat ttcattattt tacccattgt ggcagtgctt    3720
tgacaactgc tgaaaagcc ccctgctttt ttgtacaaac ttgttgatgg ggttaggccg    3780
ccaccgcggt ggagctcgaa ttccggtccg ggtcaccttt gtccaccaag atggaactgc    3840
ggccgctcat taattaagtc aggcgcgcct ctagttgaag acacgttcat gtcttcatcg    3900
taagaagaca ctcagtagtc ttcggccaga atggccatct ggattcagca ggcctagaag    3960
gccatttaaa tcctgaggat ctggtcttcc taaggacccg ggatatcgga ccgattaaac    4020
tttaattcgg tccgaagctt gaagttccta ttccgaagtt cctattctcc agaaagtata    4080
ggaacttcgc atgcctgcag tgcagcgtga cccggtcgtg ccctctctct agataatga    4140
gcattgcatg tctaagttat aaaaaattac cacatatttt ttttgtcaca cttgtttgaa    4200
gtgcagttta tctatcttta tacatatatt taaactttac tctacgaata atataatcta    4260
tagtactaca ataatatcag tgttttagag aatcatataa atgaacagtt agacatggtc    4320
taaaggacaa ttgagtattt tgacaacagg actctacagt tttatctttt tagtgtgcat    4380
gtgttctcct ttttttttgc aaatagcttc acctatataa tacttcatcc atttttattag    4440
tacatccatt tagggtttag ggttaatggt ttttatagac taattttttt agtacatcta    4500
ttttattcta ttttagcctc taaattaaga aaactaaaac tctattttag ttttttatt    4560
taataattta gatataaaat agaataaaat aaagtgacta aaaattaaac aaatacccctt   4620
taagaaatta aaaaaactaa ggaaacattt ttcttgtttc gagtagataa tgccagcctg    4680
ttaaacgccg tcgacgagtc taacggacac caaccagcga accagcagcg tcgcgtcggg    4740
ccaagcgaag cagacggcac ggcatctctg tcgctgcctc tggacccctc tcgagagttc    4800
cgctccaccg ttggacttgc tccgctgtcg gcatccagaa attgcgtggc ggagcggcag    4860
acgtgagccg gcacggcagg cggcctcctc ctcctctcac ggcaccggca gctacggggg    4920
attcctttcc caccgctcct tcgctttccc ttcctcgccc gccgtaataa atagacaccc    4980
cctccacacc ctctt                                                    4995

<210> SEQ ID NO 244
<211> LENGTH: 7112
<212> TYPE: DNA
<213> ORGANISM: Diabrotica virgifera virgifera

<400> SEQUENCE: 244
gtgcagcgtg acccggtcgt gccctctctct agagataatg agcattgcat gtctaagtta       60
```

```
taaaaaatta ccacatattt tttttgtcac acttgtttga agtgcagttt atctatcttt      120
atacatatat ttaaacttta ctctacgaat aatataatct atagtactac aataatatca      180
gtgttttaga gaatcatata aatgaacagt tagacatggt ctaaaggaca attgagtatt      240
ttgacaacag gactctacag ttttatcttt ttagtgtgca tgtgttctcc ttttttttg       300 caaatagctt cacctatata atacttcatc cattttatta gtacatccat ttagggttta      360
gggttaatgg ttttataga ctaattttt tagtacatct attttattct attttagcct        420
ctaaattaag aaaactaaaa ctctatttta gttttttat ttaataattt agatataaaa        480
tagaataaaa taaagtgact aaaaattaaa caaatacccct ttaagaaatt aaaaaaacta     540
aggaaacatt tttcttgttt cgagtagata atgccagcct gttaaacgcc gtcgacgagt      600
ctaacggaca ccaaccagcg aaccagcagc gtcgcgtcgg gccaagcgaa gcagacggca      660
cggcatctct gtcgctgcct ctggacccct ctcgagagtt ccgctccacc gttggacttg      720
ctccgctgtc ggcatccaga aattgcgtgg cggagcggca gacgtgagcc ggcacggcag      780
gcggcctcct cctcctctca cggcaccggc agctacgggg gattcctttc ccaccgctcc      840
ttcgctttcc cttcctcgcc cgccgtaata aatagacacc ccctccacac cctctttccc      900
caacctcgtg ttgttcggag cgcacacaca cacaaccaga tctcccccaa atccacccgt      960
cggcacctcc gcttcaaggt acgccgctcg tcctccccccc ccccctctc taccttctct     1020 agatcggcgt tccggtccat gcatggttag ggcccggtag ttctacttct gttcatgttt     1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga     1200
tggctctagc cgttccgcag acgggatcga tttcatgatt tttttgttt cgttgcatag      1260 ggtttggttt gcccttttcc tttatttcaa tatatgccgt gcacttgttt gtcgggtcat     1320
cttttcatgc ttttttttgt cttggttgtg atgatgtggt ctggttgggc ggtcgttcta     1380
gatcggagta gaattctgtt tcaaactacc tggtggattt attaattttg gatctgtatg     1440
tgtgtgccat acatattcat agttacgaat tgaagatgat ggatggaaat atcgatctag     1500
gataggtata catgttgatg cgggttttac tgatgcatat acagagatgc tttttgttcg     1560
cttggttgtg atgatgtggt gtggttgggc ggtcgttcat tcgttctaga tcggagtaga     1620
atactgtttc aaactacctg gtgtatttat taattttgga actgtatgtg tgtgtcatac     1680
atcttcatag ttacgagttt aagatggatg gaaatatcga tctaggatag gtatacatgt     1740
tgatgtgggt tttactgatg catatacatg atggcatatg cagcatctat tcatatgctc     1800
taaccttgag tacctatcta ttataataaa caagtatgtt ttataattat tttgatcttg     1860
atatacttgg atgatggcat atgcagcagc tatatgtgga tttttttagc cctgccttca     1920
tacgctattt atttgcttgg tactgtttct tttgtcgatg ctcaccctgt gtttggtgt      1980 tacttctgca gaccggtctc tacgtacagt ccggactggc gccttggcgc ggtaccacat     2040
ggttcgatat caacaagttt gtacaaaaaa gcaggggag ataaaacgaa gaatggcact      2100
agaacaagac ataatcaact acatcgaaga aaaacgttca atttggtatg gacatgtgag    2160
aagagcagat catacaaggt ggatatcaaa gattacggat tggagcccaa taggaaagag    2220
aagaagaggt agaccccgaa tatcgtggag ggatgaagtg tacgaagcca tggaaagacg    2280
agacgttaaa gatggagaat ggtagaacag gaaggactgc agacgttggc tgaaaaaagg    2340
atagatagat agatatagaa atagaaatat ataggtgttt attagcgcgc tatggttatt    2400
```

```
atatgggaa tatataatga gaaaagcact cgacaaatgg aatggcggta tttctatcgc    2460
aggaaagaag atctcaaatc tcagatatgc agatgataca ccattaataa ctgcatccga    2520
agaagaaatg tccagtctgc tgcagctagt ggaagccgaa agcaatagat gtggtctcaa    2580
gatcaataaa caaaaaacaa aaattatgat agtagaatat ttaaattcat agtcccagga    2640
acgcaactca tcaatattgg caatatcatt ttaaagtcgt ctactttaaa atgtataata    2700
cgtgtctgaa ttgccgatat aaatgagtca gattaaataa attattggaa gaattttta    2760
ctaggcaaca ccattttgt ttatttagta ttattttgta ttttgagaac gacacccgac    2820
ttgggcgtcg aaacgttaat aaaatcattt ttaggtaaaa ttgtggctta tttcccattt    2880
gaatatactt aataacaata tttaaattca cttcagacaa cacgggcctt agaccagttt    2940
gaagtggtta acgagttcga ttatctagga tcctacatca gtaatacagg atgttgtgaa    3000
acagaaatac gtaggagaat aggcattgcc aaaaacgcta tgagtcgatt atcgaaaatc    3060
tggaaagatc gctccttgtc gaagaacacc aaaataagat tagtacgtgc attaattttt    3120
cccatatta attagggatc cgaaacatgg acaatgaaat cggacgacag aaaaaggat    3180
gacgccttg aaatgtggtg ctggagaaga atgcttcgga tctcatggac ggaacagaga    3240
acaaatcact caatcttcca agagcttaat attcagactc gactttcctc tacttgcctc    3300
tccaccgcct taaaattttt cggccatatt gcaagaagtg atgataatct ggagagactt    3360
ataatttcgg aaaaggttga agagcgcaga agtagaggtc gctcacctgc tcgatggacg    3420
gaccaagtac aggaagccag tggaaaaaca ttctctgaat ccatgaggga agctcaggac    3480
agaagccgac ggaaagagat agttgatcgt attataggga atcacgacac tcagaaatga    3540
ggaaacgact gaggaggaga aggaggagga gcgtgctcat cactgtatat tattatacaa    3600
tttaattatt actatttaaa aatgtgatga aacaaatttt tcaatactgt gtttaagcaa    3660
tggtaatatc gacctcagtc atcccatcga taatgttatt gctgaataac attagcaact    3720
atttagcata gctctgtgat gtatcaaagc atcttgttaa taattggttt ccaatattcc    3780
gtaattcggg attacgagct ttacccacca aacgacacgt atttggtcaa gtagcggttt    3840
cgagcatttc aatcatcgcc acatccatca gcatttgtgt agtgaagtaa tctccttaa    3900
tggagaaggt ggtaaaagac tctattttt ttgttagtgg tttattttg gtttgattga    3960
atacaaaaac attacaaaat tatatacaca atgaaattta ctgttttta tttgaatga    4020
gccataactt tactttgaaa ttaagttttt ttgacatttc gatttccact ttagaaatcg    4080
ttatcaaaaa aaaaaaaaa aaaaaaaaaa aaaacagct tcttgtaca agtggtcga    4140
tatcaggtcc gccttgtttc tcctctgtct cttgatctga ctaatcttgg tttatgattc    4200
gttgagtaat tttggggaaa gcttcgtcca cagttttttt tcgatgaaca gtgccgcagt    4260
ggcgctgatc ttgtatgcta tcctgcaatc gtggtgaact tatttctttt atatcccttta   4320
ctcccatgaa aaggctagta atcttctcg atgtaacatc gtccagcact gctattaccg    4380
tgtggtccat ccgacagtct ggctgaacac atcatacgat ctatggagca aaaatctatc    4440
ttccctgttc tttaatgaag gacgtcattt tcattagtat gatctaggaa tgttgcaact    4500
tgcaaggagg cgtttctttc tttgaattta actaactcgt tgagtggccc tgtttctcgg    4560
acgtaaggcc tttgctgctc cacacatgtc cattcgaatt ttaccgtgtt tagcaagggc    4620
gaaaagtttg catcttgatg atttagcttg actatgcgat tgcttcctg gacccgtgca    4680
gctgcccatc gaccactttg tacaagaaag ctgttttttt ttttttttt ttttttttt    4740
tttgataacg atttctaaag tggaaatcga aatgtcaaaa aaacttaatt tcaaagtaaa    4800
```

```
gttatggctc attccaaata aaaaacagta aatttcattg tgtatataat tttgtaatgt    4860
ttttgtattc aatcaaacca aaaataaacc actaacaaaa aaaatagagt cttttaccac    4920
cttctccatt aaaggagatt acttcactac acaaatgctg atggatgtgg cgatgattga    4980
aatgctcgaa accgctactt gaccaaatac gtgtcgtttg gtgggtaaag ctcgtaatcc    5040
cgaattacgg aatattggaa accaattatt aacaagatgc tttgatacat cacagagcta    5100
tgctaaatag ttgctaatgt tattcagcaa taacattatc gatgggatga ctgaggtcga    5160
tattaccatt gcttaaacac agtattgaaa atttgtttc atacattatt taaatagtaa     5220
taattaaatt gtataataat atacagtgat gagcacgctc ctcctccttc tcctcctcag    5280
tcgtttcctc atttctgagt gtcgtgattc cctataatac gatcaactat ctctttccgt    5340
cggcttctgt cctgagcttc cctcatggat tcagagaatg tttttccact ggcttcctgt    5400
acttggtccg tccatcgagc aggtgagcga cctctacttc tgcgctcttc aacctttcc     5460 gaaattataa gtctctccag attatcatca cttcttgcaa tatggccgaa aaattttaag    5520
gcggtggaga ggcaagtaga ggaaagtcga gtctgaatat taagctcttg gaagattgag    5580
tgatttgttc tctgttccgt ccatgagatc cgaagcattc ttctccagca ccacatttca    5640
aaggcgtcaa tcctttttct gtcgtccgat ttcattgtcc atgtttcgga tccctaatta    5700
aatatgggaa aaattaatgc acgtactaat cttattttgg tgttcttcga caaggagcga    5760
tctttccaga ttttcgataa tcgactcata gcgttttgg caatgcctat tctcctacgt      5820
atttctgttt cacaacatcc tgtattactg atgtaggatc ctagataatc gaactcgtta    5880
accacttcaa actggtctaa ggcccgtgtt gtctgaagtg aatttaaata ttgttattaa    5940
gtatattcaa atgggaaata agccacaatt ttacctaaaa atgattttat taacgtttcg    6000
acgcccaagt cgggtgtcgt tctcaaaata caaaataata ctaaataaac aaaaatggtg    6060
ttgcctagta aaaattcttt ccaataattt atttaatctg actcattat atcggcaatt      6120 cagacacgta ttatacattt taaagtagac gactttaaaa tgatattgcc aatattgatg    6180
agttgcgttc ctgggactat gaatttaaat attctactat cataatttt gtttttgtt       6240 tattgatctt gagaccacat ctattgcttt cggcttccac tagctgcagc agactggaca    6300
tttcttcttc ggatgcagtt attaatggtg tatcatctgc atatctgaga tttgagatct    6360
tctttcctgc gatagaaata ccgccattcc atttgtcgag tgcttttctc attatatatt    6420
ccccatataa taaccatagc gcgctaataa acacctatat atttctattt ctatatctat    6480
ctatctatcc tttttcagc caacgtctgc agtccttcct gttctaccat tctccatctt     6540
taacgtctcg tctttccatg gcttcgtaca cttcatccct ccacgatatt cggggtctac    6600
ctcttcttct ctttcctatt gggctccaat ccgtaatctt tgatatccac cttgtatgat    6660
ctgctcttct cacatgtcca taccaaattg aacgttttc ttcgatgtag ttgattatgt     6720
cttgttctag tgccattctt cgttttatct cccctgctt ttttgtacaa acttgttgat     6780
ggggttaggc cgccaccgcg gtggagctcg aattccggtc cgggtcacct tgtccacca    6840 agatggaact gcggccgctc attaattaag tcaggcgcgc ctctagttga agacacgttc    6900
atgtcttcat cgtaagaaga cactcagtag tcttcggcca gaatgccat ctggattcag     6960 caggcctaga aggccattta aatcctgagg atctggtctt cctaaggacc cgggatatcg    7020
gaccgattaa actttaattc ggtccgaagc ttgaagttcc tattccgaag ttcctattct    7080
ccagaaagta taggaacttc gcatgcctgc ag                                  7112
```

<210> SEQ ID NO 245
<211> LENGTH: 4076
<212> TYPE: DNA
<213> ORGANISM: Diabrotica virgifera virgifera

<400> SEQUENCE: 245

| | | | | | |
|---|---|---|---|---|---|
| gtgcagcgtg | acccggtcgt | gccctctct | agagataatg | agcattgcat | gtctaagtta | 60 |
| taaaaaatta | ccacatattt | ttttgtcac | acttgtttga | agtgcagttt | atctatcttt | 120 |
| atacatatat | ttaaacttta | ctctacgaat | aatataatct | atagtactac | aataatatca | 180 |
| gtgttttaga | gaatcatata | aatgaacagt | tagacatggt | ctaaaggaca | attgagtatt | 240 |
| ttgacaacag | gactctacag | ttttatcttt | ttagtgtgca | tgtgttctcc | ttttttttg | 300 |
| caaatagctt | cacctatata | atacttcatc | cattttatta | gtacatccat | ttagggttta | 360 |
| gggttaatgg | tttttataga | ctaatttttt | tagtacatct | attttattct | attttagcct | 420 |
| ctaaattaag | aaaactaaaa | ctctatttta | gtttttttat | ttaataattt | agatataaaa | 480 |
| tagaataaaa | taaagtgact | aaaaattaaa | caaataccct | ttaagaaatt | aaaaaaacta | 540 |
| aggaaacatt | tttcttgttt | cgagtagata | atgccagcct | gttaaacgcc | gtcgacgagt | 600 |
| ctaacggaca | ccaaccagcg | aaccagcagc | gtcgcgtcgg | gccaagcgaa | gcagacggca | 660 |
| cggcatctct | gtcgctgcct | ctggaccct | ctcgagagtt | ccgctccacc | gttggacttg | 720 |
| ctccgctgtc | ggcatccaga | aattgcgtgg | cggagcggca | gacgtgagcc | ggcacggcag | 780 |
| gcggcctcct | cctcctctca | cggcaccggc | agctacgggg | gattcctttc | ccaccgctcc | 840 |
| ttcgctttcc | cttcctcgcc | cgccgtaata | aatagacacc | cctccacac | cctctttccc | 900 |
| caacctcgtg | ttgttcggag | cgcacacaca | cacaaccaga | tctcccccaa | atccacccgt | 960 |
| cggcacctcc | gcttcaaggt | acgccgctcg | tcctcccccc | cccccctctc | taccttctct | 1020 |
| agatcggcgt | tccggtccat | gcatggttag | ggcccggtag | ttctacttct | gttcatgttt | 1080 |
| gtgttagatc | cgtgtttgtg | ttagatccgt | gctgctagcg | ttcgtacacg | gatgcgacct | 1140 |
| gtacgtcaga | cacgttctga | ttgctaactt | gccagtgttt | ctctttgggg | aatcctggga | 1200 |
| tggctctagc | cgttccgcag | acgggatcga | tttcatgatt | ttttttgttt | cgttgcatag | 1260 |
| ggtttggttt | gcccttttcc | tttatttcaa | tatatgccgt | gcacttgttt | gtcgggtcat | 1320 |
| cttttcatgc | tttttttgt | cttggttgtg | atgatgtggt | ctggttgggc | ggtcgttcta | 1380 |
| gatcggagta | gaattctgtt | tcaaactacc | tggtggattt | attaattttg | gatctgtatg | 1440 |
| tgtgtgccat | acatattcat | agttacgaat | tgaagatgat | ggatggaaat | atcgatctag | 1500 |
| gataggtata | catgttgatg | cgggttttac | tgatgcatat | acagagatgc | ttttgttcg | 1560 |
| cttggttgtg | atgatgtggt | gtggttgggc | ggtcgttcat | tcgttctaga | tcggagtaga | 1620 |
| atactgtttc | aaactacctg | gtgtatttat | taattttgga | actgtatgtg | tgtgtcatac | 1680 |
| atcttcatag | ttacgagttt | aagatggatg | gaaatatcga | tctaggatag | gtatacatgt | 1740 |
| tgatgtgggt | tttactgatg | catatacatg | atggcatatg | cagcatctat | tcatatgctc | 1800 |
| taaccttgag | tacctatcta | ttataataaa | caagtatgtt | ttataattat | tttgatcttg | 1860 |
| atatacttgg | atgatggcat | atgcagcagc | tatatgtgga | ttttttagc | cctgccttca | 1920 |
| tacgctattt | atttgcttgg | tactgtttct | tttgtcgatg | ctcaccctgt | tgtttggtgt | 1980 |
| tacttctgca | gaccggtctc | tacgtacagt | ccggactggc | gccttggcgc | ggtaccacat | 2040 |
| ggttcgatat | caacaagttt | gtacaaaaaa | gcagggggg | gtagcttcc | gcagcaaaaa | 2100 |
| gataggtggt | taggcattat | tttctaaaaa | ccacatggat | gaattgttgg | caaattcagc | 2160 |

```
cctagaggct gaaaaattta agccaaccgt agtaaataag cttattgatc taaattatga    2220
cttaggaagc cttttagcac aagacacaaa tgaatttgat acaaatttat taaggaggca    2280
gaaggaagat tatttgctta atttagctag agataacacc caattactat taaatcaaat    2340
atgggactta actacagaac gcctagaaga agctattgta gtgaaattac cacttcaaat    2400
aactttatta cctaggatga aaccactacc taagcccaaa cctttaacaa agtgggaaca    2460
gtttgccaaa acgaaaggta tacagaaaaa gaaaaatcc aagttatcat gggaccagca    2520
actcaaaaag tgggtaccct tatatggatt taagcgagca caagctgaaa aaaaaaaaa    2580 aaaaaaaaaa aaaaaaacag ctttcttgta caaagtggtc gatatcaggt ccgccttgtt    2640
tctcctctgt ctcttgatct gactaatctt ggtttatgat tcgttgagta attttgggga    2700
aagcttcgtc cacagttttt tttcgatgaa cagtgccgca gtggcgctga tcttgtatgc    2760
tatcctgcaa tcgtggtgaa cttatttctt ttatatcctt tactcccatg aaaaggctag    2820
taatctttct cgatgtaaca tcgtccagca ctgctattac cgtgtggtcc atccgacagt    2880
ctggctgaac acatcatacg atctatggag caaaaatcta tcttccctgt tctttaatga    2940
aggacgtcat tttcattagt atgatctagg aatgttgcaa cttgcaagga ggcgtttctt    3000
tctttgaatt taactaactc gttgagtggc cctgtttctc ggacgtaagg cctttgctgc    3060
tccacacatg tccattcgaa ttttaccgtg tttagcaagg gcgaaaagtt tgcatcttga    3120
tgatttagct tgactatgcg attgctttcc tggacccgtg cagctgccca tcgaccactt    3180
tgtacaagaa agctgttttt tttttttttt tttttttttt tttttcagct tgtgctcgct    3240
taaatccata taagggtacc cacttttttga gttgctggtc ccatgataac ttggattttt    3300
tctttttctg tataccttc gttttggcaa actgttccca ctttgttaaa ggtttgggct    3360
taggtagtgg tttcatccta ggtaataaag ttatttgaag tggtaatttc actacaatag    3420
cttcttctag gcgttctgta gttaagtccc atatttgatt taatagtaat tgggtgttat    3480
ctctagctaa attaagcaaa taatcttcct tctgcctcct taataaattt gtatcaaatt    3540
catttgtgtc ttgtgctaaa aggcttccta agtcataatt tagatcaata agcttattta    3600
ctacggttgg cttaaatttt tcagcctcta gggctgaatt tgccaacaat tcatccatgt    3660 ggttttaga aaataatgcc taaccaccta tcttttttgct gcggaaagct acacccccct    3720
gcttttttgt acaaacttgt tgatgggggtt aggccgccac cgcggtggag ctcgaattcc    3780
ggtccgggtc acctttgtcc accaagatgg aactgcggcc gctcattaat taagtcaggc    3840
gcgcctctag ttgaagacac gttcatgtct tcatcgtaag aagacactca gtagtcttcg    3900
gccagaatgg ccatctggat tcagcaggcc tagaaggcca tttaaatcct gaggatctgg    3960
tcttcctaag gacccgggat atcggaccga ttaaacttta attcggtccg aagcttgaag    4020
ttcctattcc gaagttccta ttctccagaa agtataggaa cttcgcatgc ctgcag        4076
```

<210> SEQ ID NO 246
<211> LENGTH: 4415
<212> TYPE: DNA
<213> ORGANISM: Diabrotica virgifera virgifera

<400> SEQUENCE: 246

```
gtgcagcgtg acccggtcgt gcccctctct agagataatg agcattgcat gtctaagtta     60
taaaaaatta ccacatattt ttttgtcac acttgtttga agtgcagttt atctatcttt    120
atacatatat ttaaacttta ctctacgaat aatataatct atagtactac aataatatca    180
```

-continued

```
gtgttttaga gaatcatata aatgaacagt tagacatggt ctaaaggaca attgagtatt      240
ttgacaacag gactctacag ttttatcttt ttagtgtgca tgtgttctcc tttttttttg      300
caaatagctt cacctatata atacttcatc cattttatta gtacatccat ttagggttta      360
gggttaatgg tttttataga ctaattttt tagtacatct attttattct attttagcct       420
ctaaattaag aaaactaaaa ctctatttta gttttttat ttaataattt agatataaaa       480
tagaataaaa taaagtgact aaaaattaaa caaatacccct ttaagaaatt aaaaaaacta     540
aggaaacatt tttcttgttt cgagtagata atgccagcct gttaaacgcc gtcgacgagt     600
ctaacggaca ccaaccagcg aaccagcagc gtcgcgtcgg ccaagcgaa gcagacggca      660 cggcatctct gtcgctgcct ctggaccccct ctcgagagtt ccgctccacc gttggacttg    720
ctccgctgtc ggcatccaga aattgcgtgg cggagcggca gacgtgagcc ggcacggcag     780
gcggcctcct cctcctctca cggcaccggc agctacgggg gattcctttc ccaccgctcc     840
ttcgctttcc cttcctcgcc cgccgtaata aatagacacc ccctccacac cctcttccc     900 caacctcgtg ttgttcggag cgcacacaca cacaaccaga tctccccaa atccaccgt      960 cggcacctcc gcttcaaggt acgccgctcg tcctccccccc cccccctctc taccttctct    1020
agatcggcgt tccggtccat gcatggttag ggcccggtag ttctacttct gttcatgttt     1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga    1200
tggctctagc cgttccgcag acgggatcga tttcatgatt tttttgttt cgttgcatag     1260 ggtttggttt gcccttttcc tttatttcaa tatatgccgt gcacttgttt gtcgggtcat     1320
cttttcatgc ttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
gataggtata catgttgatg cgggttttac tgatgcatat acagagatgc ttttgttcg      1560 cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgtttct tttgtcgatg ctcaccctgt tgtttggtgt    1980
tacttctgca gggggcagt tatttcgact tttcatgctt gtcataaaat aaaattaaaa     2040
tatatccggc gaggtgttga ctagcggatt ttttagatt caacaatctt attttataaa     2100
ataattagtt aaaatgatgc aaacagctaa taatgcatat tatcccgatt attccactgc    2160
tccaatgcaa cgtcaaatta acccctatgc agataatgga gggagtgtag tagcaatagc    2220
aggtgaagac tttgtaataa ttggtgcaga tacacgtttg agtactggat tttccattta    2280
taccagagaa caaaacaaac ttttcccact atcaggcact actgttttgg gttgtgcagg    2340
atgttggtgt gacactctaa cattaaccag aatccttaaa tctcgcatgc agatgtacca    2400
acaagagcat aacaaaacaa tgtctacaac tgcatgtgcc cagatgttgt caaccatgct    2460
ctactacaag agattctttc cttattatat atcaaacatt ctagtaggtt tagataatga    2520
aggaaagggc tgtgtttaca gctatgatcc tattggacat tgtgaaaaag ctacgtatag    2580
```

```
agcaggtggt tcagctggag ctcttcttca gcctctgttg gacaatcaaa ttggacagaa    2640
gaacatgctt aaaacatctg gggaacctct tagtcaggag aaagctctgt ctacccttaa    2700
agatgtattt atttctgctg ctgaaagaga catctacact ggagatagcg tacttataaa    2760
tattattact aaagatggag taaaggaaga gtccttccag ttgagacggg attagaagca    2820
agtggttttg tttatatttt cttatgtgta attcaaatat actttctaaa taaacaaaaa    2880
aaaaaaaaaa aaaaaaaaa aaaacagctt tcttgtacaa agtggtcgat atcaggtccg     2940
ccttgtttct cctctgtctc ttgatctgac taatcttggt ttatgattcg ttgagtaatt    3000
ttggggaaag cttcgtccac agttttttt cgatgaacag tgccgcagtg gcgctgatct     3060
tgtatgctat cctgcaatcg tggtgaactt atttctttta tatcctttac tcccatgaaa    3120
aggctagtaa tctttctcga tgtaacatcg tccagcactg ctattaccgt gtggtccatc    3180
cgacagtctg gctgaacaca tcatacgatc tatggagcaa aaatctatct tccctgttct    3240
ttaatgaagg acgtcatttt cattagtatg atctaggaat gttgcaactt gcaaggaggc    3300
gtttctttct ttgaatttaa ctaactcgtt gagtggccct gtttctcgga cgtaaggcct    3360
ttgctgctcc acacatgtcc attcgaattt taccgtgttt agcaagggcg aaaagtttgc    3420
atcttgatga tttagcttga ctatgcgatt gctttcctgg acccgtgcag ctgcccatcg    3480
accactttgt acaagaaagc tgtttttttt tttttttt tttttttttt tgtttattta      3540
gaaagtatat ttgaattaca cataagaaaa tataaacaaa accacttgct tctaatcccg    3600
tctcaactgg aaggactctt cctttactcc atctttagta ataatattta taagtacgct    3660
atctccagtg tagatgtctc tttcagcagc agaaataaat acatctttaa gggtagacag    3720
agctttctcc tgactaagag gttccccaga tgtttaagc atgttcttct gtccaatttg     3780
attgtccaac agaggctgaa gaagagctcc agctgaacca cctgctctat acgtagcttt    3840
ttcacaatgt ccaataggat catagctgta aacacagccc tttccttcat tatctaaacc    3900
tactagaatg tttgatatat aataaggaaa gaatctcttg tagtagagca tggttgacaa    3960
catctgggca catgcagttg tagacattgt tttgttatgc tcttgttggt acatctgcat    4020
gcgagattta aggattctgg ttaatgttag agtgtcacac caacatcctg cacaacccaa    4080
aacagtagtg cctgatagtg ggaaaagttt gttttgttct ctggtataaa tggaaaatcc    4140
agtactcaaa cgtgtatctg caccaattat tacaaagtct tcacctgcta ttgctactac    4200
actccctcca ttatctgcat aggggttaat ttgacgttgc attggagcag tggaataatc    4260
gggataatat gcattattag ctgtttgcat cattttaact aattatttta taaaataaga    4320
ttgttgaatc taaaaaaatc cgctagtcaa cacctcgccg gatatatttt aattttattt    4380
tatgacaagc atgaaaagtc gaaataactg ccccc                               4415
```

<210> SEQ ID NO 247
<211> LENGTH: 3389
<212> TYPE: DNA
<213> ORGANISM: Diabrotica virgifera virgifera

<400> SEQUENCE: 247

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatccatata aatgaacagt tagacatggt ctaaaggaca attgagtatt    240
```

```
ttgacaacag gactctacag ttttatctttt ttagtgtgca tgtgttctcc tttttttttg    300
caaatagctt cacctatata atacttcatc cattttatta gtacatccat ttagggttta    360
gggttaatgg tttttataga ctaattttttt tagtacatct attttattct attttagcct    420
ctaaattaag aaaactaaaa ctctatttta gttttttttat ttaataattt agatataaaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattccttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctccccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt tttttgttt cgttgcatag   1260
ggtttggttt gccctttcc tttattttcaa tatatgccgt gcacttgttt gtcgggtcat   1320
cttttcatgc tttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat gaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat ttgatcttg    1860
atatacttgg atgatggcat atgcagcagc tatatgtgga ttttttttagc cctgccttca   1920
tacgctattt atttgcttgg tactgttcct tttgtcgatg ctcaccctgt tgtttggtgt   1980
tacttctgca gggggattt tctctagttt gcaggaagca ggaatttcag taaagaaata   2040
agattaaaat ggcagacaaa gtagaaaagg ttgccagacc aatgaaattc ccttacacat   2100
tcagtgcaaa aattgcacaa ttcccaatca agcactactt gaagaaccaa tggatctgga   2160
aatactatgc tatttctctt gtagtatgtc ttccagtctt caactcgatt agtaaactgg   2220
ccaactctcc tggaaacgtt gctaaatggg cagagattcg cagaagagaa gctgctgaac   2280
atcatcacta agaaaatttt ttttatagta attagtctgc caattgtttt gttctaattt   2340
aatttctatt aaatacatgt agaaaaaaaa aaaaaaaaa aaaaaaaaaa acagctttct   2400
tgtacaaagt ggtcgatatc aggtccgcct tgtttctcct ctgtctcttg atctgactaa   2460
tcttggttta tgattcgttg agtaattttg gggaaagctt cgtccacagt ttttttcga    2520
tgaacagtgc cgcagtggcg ctgatcttgt atgctatcct gcaatcgtgg tgaacttatt   2580
tctttttatat cctttactcc catgaaaagg ctagtaatct ttctcgatgt aacatcgtcc   2640
```

| agcactgcta | ttaccgtgtg | gtccatccga | cagtctggct | gaacacatca | tacgatctat | 2700 |
| ggagcaaaaa | tctatcttcc | ctgttcttta | atgaaggacg | tcattttcat | tagtatgatc | 2760 |
| taggaatgtt | gcaacttgca | aggaggcgtt | tctttctttg | aatttaacta | actcgttgag | 2820 |
| tggccctgtt | tctcggacgt | aaggcctttg | ctgctccaca | catgtccatt | cgaattttac | 2880 |
| cgtgtttagc | aagggcgaaa | agtttgcatc | ttgatgattt | agcttgacta | tgcgattgct | 2940 |
| ttcctggacc | cgtgcagctg | cccatcgacc | actttgtaca | agaaagctgt | tttttttttt | 3000 |
| tttttttttt | tttttttttct | acatgtattt | aatagaaatt | aaattagaac | aaaacaattg | 3060 |
| gcagactaat | tactataaaa | aaaatttttct | tagtgatgat | gttcagcagc | ttctcttctg | 3120 |
| cgaatctctg | cccatttagc | aacgtttcca | ggagagttgg | ccagtttact | aatcgagttg | 3180 |
| aagactggaa | gacatactac | aagagaaata | gcatagtatt | tccagatcca | ttggttcttc | 3240 |
| aagtagtgct | tgattgggaa | ttgtgcaatt | tttgcactga | atgtgtaagg | gaatttcatt | 3300 |
| ggtctggcaa | ccttttctac | tttgtctgcc | attttaatct | tatttcttta | ctgaaattcc | 3360 |
| tgcttcctgc | aaactagaga | aaatccccc | | | | 3389 |

<210> SEQ ID NO 248
<211> LENGTH: 3349
<212> TYPE: DNA
<213> ORGANISM: Diabrotica virgifera virgifera

<400> SEQUENCE: 248

| gtgcagcgtg | acccggtcgt | gcccctctct | agagataatg | agcattgcat | gtctaagtta | 60 |
| taaaaaatta | ccacatattt | tttttgtcac | acttgtttga | agtgcagttt | atctatcttt | 120 |
| atacatatat | ttaaacttta | ctctacgaat | aatataatct | atagtactac | aataatatca | 180 |
| gtgttttaga | gaatcatata | aatgaacagt | tagacatggt | ctaaaggaca | attgagtatt | 240 |
| ttgacaacag | gactctacag | ttttatcttt | ttagtgtgca | tgtgttctcc | ttttttttg | 300 |
| caaatagctt | cacctatata | atacttcatc | cattttatta | gtacatccat | ttagggttta | 360 |
| gggttaatgg | tttttataga | ctaattttt | tagtacatct | attttattct | attttagcct | 420 |
| ctaaattaag | aaaactaaaa | ctctatttta | gttttttat | ttaataattt | agatataaaa | 480 |
| tagaataaaa | taaagtgact | aaaaattaaa | caaatacccct | ttaagaaatt | aaaaaaacta | 540 |
| aggaaacatt | tttcttgttt | cgagtagata | atgccagcct | gttaaacgcc | gtcgacgagt | 600 |
| ctaacggaca | ccaaccagcg | aaccagcagc | gtcgcgtcgg | gccaagcgaa | gcagacggca | 660 |
| cggcatctct | gtcgctgcct | ctggaccccct | ctcgagagtt | ccgctccacc | gttggacttg | 720 |
| ctccgctgtc | ggcatccaga | aattgcgtgg | cggagcggca | gacgtgagcc | ggcacggcag | 780 |
| gcggcctcct | cctcctctca | cggcaccggc | agctacgggg | gattcctttc | ccaccgctcc | 840 |
| ttcgctttcc | cttcctcgcc | cgccgtaata | aatagacacc | ccctccacac | cctcttttccc | 900 |
| caacctcgtg | ttgttcggag | cgcacacaca | cacaaccaga | tctcccccaa | atccaccgt | 960 |
| cggcacctcc | gcttcaaggt | acgccgctcg | tcctccccccc | cccccctctc | taccttctct | 1020 |
| agatcggcgt | tccggtccat | gcatggttag | ggcccggtag | ttctacttct | gttcatgttt | 1080 |
| gtgttagatc | cgtgtttgtg | ttagatccgt | gctgctagcg | ttcgtacacg | gatgcgacct | 1140 |
| gtacgtcaga | cacgttctga | ttgctaactt | gccagtgttt | ctctttgggg | aatcctggga | 1200 |
| tggctctagc | cgttccgcag | acgggatcga | tttcatgatt | ttttttgttt | cgttgcatag | 1260 |
| ggtttggttt | gccctttcc | tttatttcaa | tatatgccgt | gcacttgttt | gtcgggtcat | 1320 |

| | | | | |
|---|---|---|---|---|
| cttttcatgc | ttttttttgt | cttggttgtg | atgatgtggt | ctggttgggc | ggtcgttcta | 1380 |
| gatcggagta | gaattctgtt | tcaaactacc | tggtggattt | attaattttg | gatctgtatg | 1440 |
| tgtgtgccat | acatattcat | agttacgaat | tgaagatgat | ggatggaaat | atcgatctag | 1500 |
| gataggtata | catgttgatg | cgggttttac | tgatgcatat | acagagatgc | ttttttgttcg | 1560 |
| cttggttgtg | atgatgtggt | gtggttgggc | ggtcgttcat | tcgttctaga | tcggagtaga | 1620 |
| atactgtttc | aaactacctg | gtgtatttat | taattttgga | actgtatgtg | tgtgtcatac | 1680 |
| atcttcatag | ttacgagttt | aagatggatg | gaaatatcga | tctaggatag | gtatacatgt | 1740 |
| tgatgtgggt | tttactgatg | catatacatg | atggcatatg | cagcatctat | tcatatgctc | 1800 |
| taaccttgag | tacctatcta | ttataataaa | caagtatgtt | ttataattat | tttgatcttg | 1860 |
| atatacttgg | atgatggcat | atgcagcagc | tatatgtgga | ttttttttagc | cctgccttca | 1920 |
| tacgctattt | atttgcttgg | tactgttctt | tttgtcgatg | ctcaccctgt | tgtttggtgt | 1980 |
| tacttctgca | gggggggggg | ggaggttaag | ggaataaagc | ccctataaaa | ttttatcgg | 2040 |
| ctgtgaaaat | tcactacta | ttttttttaaa | gattttccta | ccataataat | gtcaaatgcc | 2100 |
| cattttaacc | tctaatatt | ttcgatattc | tcgattttta | ttttataagc | tcaaagagtt | 2160 |
| ataacttttt | ttatgtgcac | cttttgtacta | aggtaactta | ggttcaatgg | aactattttt | 2220 |
| attcccagaa | tattttattt | tattcatgac | ccaccttttt | actacaccttt | gtgcaattgt | 2280 |
| tatttatttt | caaatagata | tttaataatg | aaaattgtaa | ttcttcctcc | aatccaaagg | 2340 |
| agtgtaaaat | ttttagcaga | attacttccc | ccagctttct | tgtacaaagt | ggtcgatatc | 2400 |
| aggtccgcct | tgtttctcct | ctgtctcttg | atctgactaa | tcttggttta | tgattcgttg | 2460 |
| agtaattttg | gggaaagctt | cgtccacagt | tttttttttcga | tgaacagtgc | cgcagtggcg | 2520 |
| ctgatcttgt | atgctatcct | gcaatcgtgg | tgaacttatt | tcttttatat | cctttactcc | 2580 |
| catgaaaagg | ctagtaatct | ttctcgatgt | aacatcgtcc | agcactgcta | ttaccgtgtg | 2640 |
| gtccatccga | cagtctggct | gaacacatca | tacgatctat | ggagcaaaaa | tctatcttcc | 2700 |
| ctgttcttta | atgaaggacg | tcattttcat | tagtatgatc | taggaatgtt | gcaacttgca | 2760 |
| aggaggcgtt | tctttctttg | aatttaacta | actcgttgag | tggccctgtt | tctcggacgt | 2820 |
| aaggcctttg | ctgctccaca | catgtccatt | cgaatttttac | cgtgtttagc | aagggcgaaa | 2880 |
| agtttgcatc | ttgatgattt | agcttgacta | tgcgattgct | ttcctggacc | cgtgcagctg | 2940 |
| cccatcgacc | actttgtaca | agaaagctgg | gggaagtaat | tctgctaaaa | attttacact | 3000 |
| cctttggatt | ggaggaagaa | ttacaatttt | cattattaaa | tatctatttg | aaaataaata | 3060 |
| acaattgcac | aaggtgtagt | aaaaaggtgg | gtcatgaata | aaataaaata | ttctgggaat | 3120 |
| aaaaatagtt | ccattgaacc | taagttacct | tagtacaaag | gtgcacataa | aaaaagttat | 3180 |
| aactctttga | gcttataaaa | taaaaatcga | gaatatcgaa | aaatattaga | ggttaaaatg | 3240 |
| ggcatttgac | attattatgg | taggaaaatc | tttaaaaaaa | tagtagtgaa | attttcacag | 3300 |
| ccgataaaaa | ttttataggg | gctttattcc | cttaacctcc | cccccccc | | 3349 |

<210> SEQ ID NO 249
<211> LENGTH: 3953
<212> TYPE: DNA
<213> ORGANISM: Diabrotica virgifera virgifera

<400> SEQUENCE: 249

| | | | | |
|---|---|---|---|---|
| gtgcagcgtg | acccggtcgt | gcccctctct | agagataatg | agcattgcat | gtctaagtta | 60 |
| taaaaaatta | ccacatattt | tttttgtcac | acttgtttga | agtgcagttt | atctatcttt | 120 |

```
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg     300 caaatagctt cacctatata atacttcatc cattttatta gtacatccat ttagggttta    360
gggttaatgg ttttatagaa ctaatttttt tagtacatct attttattct attttagcct    420
ctaaattaag aaaactaaaa ctctatttta gttttttat ttaataattt agatataaaa     480
tagaataaaa taaagtgact aaaaattaaa caaatacccct ttaagaaatt aaaaaaacta   540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccccct ctcgagagtt ccgctccacc gttggacttg   720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtt tgttcggag cgcacacaca cacaaccaga tctcccccaa atccacccgt     960
cggcacctcc gcttcaaggt acgccgctcg tcctccccccc cccccctctc taccttctct   1020
agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gcccttttcc tttatttcaa tatatgccgt gcacttgttt gtcgggtcat    1320
cttttcatgc tttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
gataggtata catgttgatg cgggttttac tgatgcatat acagagatgc ttttgttcg     1560 cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat ttgatcttg     1860 atatacttgg atgatggcat atgcagcagc tatatgtgga ttttttttagc cctgccttca    1920 tacgctattt atttgcttgg tactgttcct tttgtcgatg ctcaccctgt tgtttggtgt    1980
tacttctgca gcacgaacta acttggtttt taatacttca ataataaagc tttcaacttc    2040
gtctggtttc atctgtaact ccttttcgat gacatcaaaa gatatttcag gattactctc    2100
agcaagctgc atgaaggaaa gcagtctcat tttttgcata ttctgttcat gatttaaacc    2160
ttgtgcactc acaaattcct tatgttcatt gtaaaacttg aggtaggtgg acaaattttc    2220
actaacaaag atgtttaaaa ggtcatgtat taaatcaccc tccaaaaatc tgacaggttt    2280
tagtgataac aatggatcaa gaaggaatgt gttgggatca gctagtgctg atacaatgca    2340
acggatggcg tcttctctgg catgagaagc attttttgtca gtgtatgtac caagaagttc    2400
aatcatcact aaagcagcct gctcactttg atttgattta accagtactt catgtaaaag    2460
```

| | |
|---|---:|
| cctataaagc ttttgaagct gttcattaga cggaaggcaa ttggcaaact gttgctttag | 2520 |
| atggttgata tcttgaaaca ctaattttac agattctgtc tgtttcgcaa tttgtattaa | 2580 |
| gtggtaatat acaggatacc gcattggaga acgatcatcc aatgattgga agagtaacca | 2640 |
| taatgctcta agacatacta aaccccagct ttccttgtaca aagtggtcga tatcaggtcc | 2700 |
| gccttgtttc tcctctgtct cttgatctga ctaatcttgg tttatgattc gttgagtaat | 2760 |
| tttggggaaa gcttcgtcca cagtttttt tcgatgaaca gtgccgcagt ggcgctgatc | 2820 |
| ttgtatgcta tcctgcaatc gtggtgaact tatttctttt atatccttta ctcccatgaa | 2880 |
| aaggctagta atctttctcg atgtaacatc gtccagcact gctattaccg tgtggtccat | 2940 |
| ccgacagtct ggctgaacac atcatacgat ctatggagca aaaatctatc ttccctgttc | 3000 |
| tttaatgaag acgtcatttt tcattagtat gatctaggaa tgttgcaact tgcaaggagg | 3060 |
| cgtttctttc tttgaattta actaactcgt tgagtggccc tgtttctcgg acgtaaggcc | 3120 |
| tttgctgctc cacacatgtc cattcgaatt ttaccgtgtt tagcaagggc gaaaagtttg | 3180 |
| catcttgatg atttagcttg actatgcgat tgctttcctg gacccgtgca gctgcccatc | 3240 |
| gaccactttg tacaagaaag ctggggacgg ttttacgtgg ggtttagtat gtcttagagc | 3300 |
| attatggtta ctcttccaat cattggatga tcgttctcca atgcggtatc ctgtatatta | 3360 |
| ccacttaata caaattgcga aacagacaga atctgtaaaa ttagtgtttc aagtatcaa | 3420 |
| ccatctaaag caacagtttg ccaattgcct tccgtctaat gaacagcttc aaaagcttta | 3480 |
| taggctttta catgaagtac tggttaaatc aaatcaaagt gagcaggctg ctttagtgat | 3540 |
| gattgaactt cttggtacat acactgacaa aaatgcttct catgccagag aagacgccat | 3600 |
| ccgttgcatt gtatcagcac tagctgatcc caacacattc cttcttgatc cattgttatc | 3660 |
| actaaaacct gtcagatttt tggagggtga tttaatacat gacctttaa acatctttgt | 3720 |
| tagtgaaaat ttgtccacct acctcaagtt ttacaatgaa cataaggaat tgtgagtgc | 3780 |
| acaaggttta aatcatgaac agaatatgca aaaaatgaga ctgctttcct tcatgcagct | 3840 |
| tgctgagagt aatcctgaaa tatcttttga tgtcatcgaa aaggagttac agatgaaacc | 3900 |
| agacgaagtt gaaagcttta ttattgaagt attaaaaacc aagttagttc gtg | 3953 |

<210> SEQ ID NO 250
<211> LENGTH: 3433
<212> TYPE: DNA
<213> ORGANISM: Diabrotica virgifera virgifera

<400> SEQUENCE: 250

| | |
|---|---:|
| gtgcagcgtg acccggtcgt gcccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgtttaga gaatcatata aatgaacagt tagacatggt ctaaaggaca attgagtatt | 240 |
| ttgacaacag gactctacag ttttatcttt ttagtgtgca tgtgttctcc tttttttttg | 300 |
| caaatagctt cacctatata atacttcatc cattttatta gtacatccat ttagggttta | 360 |
| gggttaatgg ttttttataga ctaatttttt tagtacatct atttattct attttagcct | 420 |
| ctaaattaag aaaactaaaa ctctatttta gttttttat ttaataattt agatataaaa | 480 |
| tagaataaaa taaagtgact aaaaattaaa caaataccct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |

```
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840 ttcgcttttcc cttcctcgcc cgccgtaata aatagacacc ccctccacac cctctttccc    900
caacctcgtg ttgttcggag cgcacacaca caaccagat ctcccccaa atccacccgt    960 cggcacctcc gcttcaaggt acgccgctcg tcctccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt tttttgttt cgttgcatag   1260 ggtttggttt gccctttttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc ttttgttcg   1560 cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttagc cctgccttca   1920 tacgctatt atttgcttgg tactgtttct tttgtcgatg ctcaccctgt tgtttggtgt   1980
tacttctgca gggggggaaat atatactaca atgaagtttt taagatcgac agtgtgctac   2040
attgccatct tggcaattct ctttacccctc tgtgccgatg aggttgaagg aaggagaaaa   2100
attttgatgg ggcgaaaaag cattaccagg acatatcttc gtggaaatgc tgttcctgcg   2160
tatgtgataa taatccttgt aggaattggt caactcatcc tgggagggat attgtacgtt   2220
gcattgagga agaagatcat tgctgcacct gtaacggcat catatgcagt ggctagacaa   2280
gaaccataaa ttttattgt ctagaatatt attttctaaa tatgcatctt ttttaaatta   2340
ttgtctacgt aaataataag tctagaaata tataaaaatt gtcaaaaaaa aaaaaaaaa   2400 aaaaaaaaa aaacagcttt cttgtacaaa gtggtcgata tcaggtccgc cttgtttctc   2460
ctctgtctct tgatctgact aatccttggtt tatgattcgt tgagtaattt tggggaaagc   2520
ttcgtccaca gttttttttc gatgaacagt gccgcagtgg cgctgatctt gtatgctatc   2580
ctgcaatcgt ggtgaactta tttcttttat atcctttact cccatgaaaa ggctagtaat   2640 cttttctcgat gtaacatcgt ccagcactgc tattaccgtg tggtccatcc gacagtctgg   2700
ctgaacacat catacgatct atggagcaaa aatctatctt ccctgttctt taatgaagga   2760
cgtcattttc attagtatga tctaggaatg ttgcaacttg caaggaggcg tttctttctt   2820
tgaatttaac taactcgttg agtggccctg tttctcggac gtaaggcctt gctgctcca   2880 cacatgtcca ttcgaatttt accgtgttta gcaagggcga aaagtttgca tcttgatgat   2940
ttagcttgac tatgcgattg ctttcctgga cccgtgcagc tgcccatcga ccactttgta   3000
```

| | |
|---|---|
| caagaaagct gtttttttt tttttttttt tttttttttt tgacaatttt tatatatttc | 3060 |
| tagacttatt atttacgtag acaataattt aaaaaagatg catatttaga aaataatatt | 3120 |
| ctagacaaat aaaatttatg gttcttgtct agccactgca tatgatgccg ttacaggtgc | 3180 |
| agcaatgatc ttcttcctca atgcaacgta caatatccct cccaggatga gttgaccaat | 3240 |
| tcctacaagg attattatca catacgcagg aacagcattt ccacgaagat atgtcctggt | 3300 |
| aatgcttttt cgccccatca aaattttct ccttccttca acctcatcgg cacagagggt | 3360 |
| aaagagaatt gccaagatgg caatgtagca cactgtcgat cttaaaaact tcattgtagt | 3420 |
| atatatttcc ccc | 3433 |

<210> SEQ ID NO 251
<211> LENGTH: 3121
<212> TYPE: DNA
<213> ORGANISM: Diabrotica virgifera virgifera

<400> SEQUENCE: 251

| | |
|---|---|
| gtgcagcgtg acccggtcgt gcccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag tttatctttt ttagtgtgca tgtgttctcc ttttttttg | 300 |
| caaatagctt cacctatata atacttcatc cattttatta gtacatccat ttagggttta | 360 |
| gggttaatgg ttttatataga ctaatttttt tagtacatct attttattct attttagcct | 420 |
| ctaaattaag aaaactaaaa ctctattta gtttttttat ttaataattt agatataaaa | 480 |
| tagaataaaa taaagtgact aaaaattaaa caaatacccct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggacccct ctcgagagtt ccgctccacc gttggacttg | 720 |
| ctccgctgtc ggcatccaga aattgcgtgg cggagcggca gacgtgagcc ggcacggcag | 780 |
| gcggcctcct cctcctctca cggcaccggc agctacgggg gattcctttc ccaccgctcc | 840 |
| ttcgcttttcc cttcctcgcc cgccgtaata aatagacacc ccctccacac cctctttccc | 900 |
| caacctcgtg ttgttcggag cgcacacaca cacaaccaga tctcccccaa atccacccgt | 960 |
| cggcacctcc gcttcaaggt acgccgctcg tcctcccccc ccccccctctc taccttctct | 1020 |
| agatcggcgt tccggtccat gcatggttag ggcccggtag ttctacttct gttcatgttt | 1080 |
| gtgttagatc cgtgtttgtg ttagatccgt gctgctagcg ttcgtacacg gatgcgacct | 1140 |
| gtacgtcaga cacgttctga ttgctaactt gccagtgttt ctctttgggg aatcctggga | 1200 |
| tggctctagc cgttccgcag acgggatcga tttcatgatt ttttttgttt cgttgcatag | 1260 |
| ggtttggttt gcccttttcc tttatttcaa tatatgccgt gcacttgttt gtcgggtcat | 1320 |
| cttttcatgc ttttttttgt cttggttgtg atgatgtggt ctggttgggc ggtcgttcta | 1380 |
| gatcggagta gaattctgtt tcaaactacc tggtggattt attaattttg gatctgtatg | 1440 |
| tgtgtgccat acatattcat agttacgaat tgaagatgat ggatggaaat atcgatctag | 1500 |
| gataggtata catgttgatg cgggttttac tgatgcatat acagagatgc ttttttgttcg | 1560 |
| cttggttgtg atgatgtggt gtggttgggc ggtcgttcat tcgttctaga tcggagtaga | 1620 |
| atactgtttc aaactacctg gtgtatttat taattttgga actgtatgtg tgtgtcatac | 1680 |

```
atcttcatag ttacgagttt aagatggatg gaaatatcga tctaggatag gtatacatgt      1740
tgatgtgggt tttactgatg catatacatg atggcatatg cagcatctat tcatatgctc      1800
taaccttgag tacctatcta ttataataaa caagtatgtt ttataattat tttgatcttg      1860
atatacttgg atgatggcat atgcagcagc tatatgtgga ttttttttagc cctgccttca      1920 tacgctattt atttgcttgg tactgtttct tttgtcgatg ctcaccctgt tgtttggtgt      1980
tacttctgca gctgttagtt tcatcgtatt attttttaaaa tctaccacta catgtttttc      2040
tgccaattcg tccactccta ctatcatgtc atgtgacatg tttggcatta ttacacattg      2100
tagtgcatac atattcttgc ccagtcgtac cattactcgt atgccttcat ttatagttgc      2160
caatgtccgt ttgtttgcgc ccactaaatt taccctaggt attttataaa ttaaatttgt      2220
taagttatct tcttctatta gttttctgtt gaccaatcag ctttcttgta caaagtggtc      2280
gatatcaggt ccgccttgtt tctcctctgt ctcttgatct gactaatctt ggtttatgat      2340
tcgttgagta attttgggga aagcttcgtc cacagttttt tttcgatgaa cagtgccgca      2400
gtggcgctga tcttgtatgc tatcctgcaa tcgtggtgaa cttatttctt ttatatcctt      2460
tactcccatg aaaaggctag taatctttct cgatgtaaca tcgtccagca ctgctattac      2520
cgtgtggtcc atccgacagt ctggctgaac acatcatacg atctatggag caaaaatcta      2580
tcttccctgt tctttaatga aggacgtcat tttcattagt atgatctagg aatgttgcaa      2640
cttgcaagga ggcgtttctt tctttgaatt taactaactc gttgagtggc cctgtttctc      2700
ggacgtaagg cctttgctgc tccacacatg tccattcgaa ttttaccgtg tttagcaagg      2760
gcgaaaagtt tgcatcttga tgatttagct tgactatgcg attgctttcc tggacccgtg      2820
cagctgccca tcgaccactt tgtacaagaa agctgattgg tcaacagaaa actaatagaa      2880
gaagataact taacaaattt aatttataaa ataccctaggg taaatttagt gggcgcaaac      2940
aaacggacat tggcaactat aaatgaaggc atacgagtaa tggtacgact gggcaagaat      3000
atgtatgcac tacaatgtgt aataatgcca aacatgtcac atgacatgat agtaggagtg      3060
gacgaattgg cagaaaaaca tgtagtggta gattttaaaa ataatacgat gaaactaaca      3120
g                                                                    3121
```

<210> SEQ ID NO 252
<211> LENGTH: 3758
<212> TYPE: DNA
<213> ORGANISM: Diabrotica virgifera virgifera

<400> SEQUENCE: 252

```
gtgcagcgtg acccggtcgt gcccctctct agagataatg agcattgcat gtctaagtta       60
taaaaaatta ccacatattt ttttgtcac acttgtttga agtgcagttt atctatcttt      120
atacatatat ttaaacttta ctctacgaat aatataatct atagtactac aataatatca      180 gtgtttaga gaatcatata aatgaacagt tagacatggt ctaaaggaca attgagtatt      240
ttgacaacag gactctacag ttttatcttt ttagtgtgca tgtgttctcc ttttttttg       300 caaatagctt cacctatata atacttcatc cattttatta gtacatccat ttagggttta      360
gggttaatgg ttttttataga ctaatttttt tagtacatct attttattct attttagcct      420
ctaaattaag aaaactaaaa ctctatttta gttttttttat ttaataattt agatataaaa      480
tagaataaaa taaagtgact aaaaattaaa caaatacccct ttaagaaatt aaaaaaacta      540
aggaaacatt tttcttgttt cgagtagata atgccagcct gttaaacgcc gtcgacgagt      600
```

```
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gccctttttcc tttatttcaa tatatgccgt gcacttgttt gtcgggtcat   1320
cttttcatgc tttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc ttttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta tttataataaa caagtatgtt ttataattat tttgatcttg   1860
atatacttgg atgatggcat atgcagcagc tatatgtgga ttttttttagc cctgccttca   1920
tacgctattt atttgcttgg tactgttcct tttgtcgatg ctcaccctgt tgtttggtgt   1980
tacttctgca ggcaaattct atgttaattt gacgattatt ttaaaataac aaggaatgta   2040
gagttgtagg ttaaaaaaatt agaataaaat ataatttaca accagtgaac actgatgagt   2100
tgtataaaat acataatata taaatattgt ttttgcaaga acttttcatg catggatgac   2160
caccattccc aatacagtcc ggagtgttta tagaaatgct cttttccaaa ttatttttttc   2220
tcttaaacac aacacaatgt gcgagtaata tctaacttga aactgaacgt ttgactcaca   2280
ctgaattgca gtaacgcttg aaacgccact gtggtctata tcgggaatct gtgggcacgt   2340
tttgcgacag ttacttgtta gtacgcgata ctttgctctg tagaatgttt ccgattcaga   2400
gaggcaaaaa atcgcgtcgg tctcaaggtt cagagcgcca atcacagaag ttttttctaa   2460
acttaaaatc tagaaggagg catctagtgc gtcaataaaa gatttctaaa atattgttac   2520
ggaaggttgt cagtttagtt gtagtgtttt gggctgttcc cacgtaaaac cgtcccagct   2580
ttcttgtaca aagtggtcga tatcaggtcc gccttgtttc tcctctgtct cttgatctga   2640
ctaatcttgg tttatgattc gttgagtaat tttggggaaa gcttcgtcca cagttttttt   2700
tcgatgaaca gtgccgcagt ggcgctgatc ttgtatgcta tcctgcaatc gtggtgaact   2760
tatttctttt atatccttta ctcccatgaa aaggctagta atctttctcg atgtaacatc   2820
gtccagcact gctattaccg tgtggtccat ccgacagtct ggctgaacac atcatacgat   2880
ctatggagca aaaatctatc ttccctgttc tttaatgaag acgtcatttt tcattagtat   2940
gatctaggaa tgttgcaact tgcaaggagg cgtttctttc tttgaattta actaactcgt   3000
```

```
tgagtggccc tgtttctcgg acgtaaggcc tttgctgctc cacacatgtc cattcgaatt    3060
ttaccgtgtt tagcaagggc gaaaagtttg catcttgatg atttagcttg actatgcgat    3120
tgctttcctg gacccgtgca gctgcccatc gaccactttg tacaagaaag ctggggacgg    3180
ttttacgtgg gaacagccca aaacactaca actaaactga caaccttccg taacaatatt    3240
ttagaaatct tttattgacg cactagatgc ctccttctag attttaagtt tagaaaaaac    3300
ttctgtgatt ggcgctctga accttgagac cgacgcgatt ttttgcctct ctgaatcgga    3360
aacattctac agagcaaagt atcgcgtact aacaagtaac tgtcgcaaaa cgtgcccaca    3420
gattcccgat atagaccaca gtggcgtttc aagcgttact gcaattcagt gtgagtcaaa    3480
cgttcagttt caagttagat attactcgca cattgtgttg tgtttaagag aaaaaataat    3540
ttggaaaaga gcatttctat aaacactccg gactgtattg ggaatggtgg tcatccatgc    3600
atgaaaagtt cttgcaaaaa caatatttat atattatgta ttttatacaa ctcatcagtg    3660
ttcactggtt gtaaattata ttttattcta atttttttaac ctacaactct acattccttg    3720
ttattttaaa ataatcgtca aattaacata gaatttgc                            3758
```